(12) United States Patent
Jung et al.

(10) Patent No.: US 9,502,662 B2
(45) Date of Patent: Nov. 22, 2016

(54) COMPOUND FOR AN ORGANIC OPTOELECTRONIC DEVICE, ORGANIC LIGHT-EMITTING ELEMENT COMPRISING SAME, AND DISPLAY DEVICE COMPRISING THE ORGANIC LIGHT-EMITTING ELEMENT

(71) Applicant: CHEIL INDUSTRIES INC., Gyeongsangbuk-do (KR)

(72) Inventors: Sung-Hyun Jung, Uiwang-si (KR); Dong-Wan Ryu, Uiwang-si (KR); Han-Ill Lee, Uiwang-si (KR); Young-Kyoung Jo, Uiwang-si (KR); Mi-Young Chae, Uiwang-si (KR); Dal-Ho Huh, Uiwang-si (KR); Jin-Seok Hong, Uiwang-si (KR)

(73) Assignee: CHEIL INDUSTRIES, INC., Gumi-Si, Kyeongsangbuk-Do (KR)

( * ) Notice: Subject to any disclaimer, the term of this patent is extended or adjusted under 35 U.S.C. 154(b) by 360 days.

(21) Appl. No.: 14/359,196

(22) PCT Filed: Dec. 21, 2012

(86) PCT No.: PCT/KR2012/011264
§ 371 (c)(1),
(2) Date: May 19, 2014

(87) PCT Pub. No.: WO2013/095039
PCT Pub. Date: Jun. 27, 2013

(65) Prior Publication Data
US 2015/0263291 A1    Sep. 17, 2015

(30) Foreign Application Priority Data

Dec. 23, 2011 (KR) .................. 10-2011-0141437

(51) Int. Cl.
*H01L 51/50* (2006.01)
*H01L 51/00* (2006.01)
(Continued)

(52) U.S. Cl.
CPC ......... *H01L 51/0061* (2013.01); *C07D 498/10* (2013.01); *C07D 513/10* (2013.01);
(Continued)

(58) Field of Classification Search
None
See application file for complete search history.

(56) References Cited

U.S. PATENT DOCUMENTS

| 6,872,824 B2 | 3/2005 | Wong et al. |
| 7,892,658 B2 * | 2/2011 | Yoon ............... C07D 221/20 252/301.16 |

(Continued)

FOREIGN PATENT DOCUMENTS

| JP | 4647660 B2 | 3/2011 |
| KR | 2006-0051606 A | 5/2006 |

(Continued)

OTHER PUBLICATIONS

Kim, et al., "Study of Deep Blue Organic Light-Emitting Diodes Using Doped BCzVBi with Various Blue Host Materials", Transactions on Electrical and Electronic Materials, vol. 11, No. 2, pp. 85-88, Apr. 25, 2010.

(Continued)

*Primary Examiner* — Gregory Clark
(74) *Attorney, Agent, or Firm* — Lee & Morse, P.C.

(57) ABSTRACT

Disclosed are a compound for an organic optoelectronic device, an organic light emitting diode including the same, and a display device including the organic light emitting diode. The compound for an organic optoelectronic device represented by the following Chemical Formula ad-1 provides an organic light emitting diode having life-span characteristics due to excellent electrochemical and thermal stability, and high luminous efficiency at a low driving voltage.

19 Claims, 3 Drawing Sheets

(51) Int. Cl.
*C09K 11/06* (2006.01)
*C07D 498/10* (2006.01)
*C07D 513/10* (2006.01)
*H01L 51/42* (2006.01)

(52) U.S. Cl.
CPC ............ *C09K 11/06* (2013.01); *H01L 51/006* (2013.01); *H01L 51/0067* (2013.01); *H01L 51/0071* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *H01L 51/0052* (2013.01); *H01L 51/0053* (2013.01); *H01L 51/0058* (2013.01); *H01L 51/0072* (2013.01); *H01L 51/0073* (2013.01); *H01L 51/0081* (2013.01); *H01L 51/42* (2013.01); *H01L 51/5012* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5096* (2013.01); *H01L 2251/308* (2013.01); *Y02E 10/549* (2013.01)

(56) References Cited

U.S. PATENT DOCUMENTS

2004/0147742 A1   7/2004   Wong et al.
2004/0219386 A1*  11/2004  Thoms ................. C07D 221/20
                                                       428/690
2009/0295275 A1   12/2009  Parham et al.

FOREIGN PATENT DOCUMENTS

| KR | 10-2007-0078200 A | 7/2007 |
| KR | 10-2011-0000006 A | 1/2011 |
| KR | 10-2011-009964 A | 9/2011 |
| WO | WO-2004/013080 A1 | 2/2004 |
| WO | WO-2006/056465 A1 | 6/2006 |
| WO | WO-2006/080640 A1 | 8/2006 |
| WO | WO-2007/040847 A1 | 12/2007 |
| WO | WO-2007/140847 A1 | 12/2007 |

OTHER PUBLICATIONS

Extended European Search Report for 12859017.1 dated May 20, 2015; Jung, et al.

* cited by examiner

COMPOUND FOR AN ORGANIC OPTOELECTRONIC DEVICE, ORGANIC LIGHT-EMITTING ELEMENT COMPRISING SAME, AND DISPLAY DEVICE COMPRISING THE ORGANIC LIGHT-EMITTING ELEMENT

TECHNICAL FIELD

A compound for an organic optoelectronic device being capable of providing an organic optoelectronic device having excellent life-span, efficiency, electrochemical stability, and thermal stability, an organic light emitting diode including the compound, and a display device including the organic light emitting diode are disclosed.

BACKGROUND ART

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a currant source (a voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer includes a multi-layer including different materials, for example a hole injection layer, a hole transport layer, an emission layer, an electron transport layer, and an electron injection layer, in order to improve efficiency and stability of an organic light emitting diode.

In such an organic light emitting diode, when a voltage is applied between an anode and a cathode, holes from the anode and electrons from the cathode are injected to an organic materiel layer and recombined to generate excitants having high energy. The generated excitons generate light having certain wavelengths while shifting to a ground state.

Recently, it has become known that a phosphorescent fight emitting material may be used for a light emitting material of an organic light emitting diode in addition to the fluorescent light emitting material. Such a phosphorescent material emits lights by transporting the electrons from a ground state to an exiled state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

The low molecular organic light emitting diode is manufactured as a thin film in a vacuum deposition method and can have good efficiency and life-span performance. A polymer organic light omitting diode is manufactured in an inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristics compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Based on these advantages, they have been remarkably developed to have 80 times efficiency and more than 100 times lifespan since they come out for the first time in the late 1980s. Recently, they keep being rapidly larger such as a 40-inch organic light emitting diode panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons. Accordingly, while increasing electron injection and mobility from a cathode and simultaneously preventing movement of holes is required.

In order to improve life-span, a material crystallization caused by Joule heats generated during device operating is required to be prevented. Accordingly, there has been a strong need for an organic compound having excellent electron injection and mobility, and high electrochemical stability.

DISCLOSURE

Technical Problem

A compound for an organic optoelectronic device that may act as a hole injection and transport material or an electron injection and transport material, and also act as a light emitting host along with an appropriate dopant is provided.

An organic light emitting diode having excellent lifespan, efficiency, driving voltage, electrochemical stability, and thermal stability and a display device including the same are provided.

Technical Solution

In one embodiment of the present invention, a compound for an organic optoelectronic device represented by the following Chemical Formula ad-1 is provided.

[Chemical Formula ad-1]

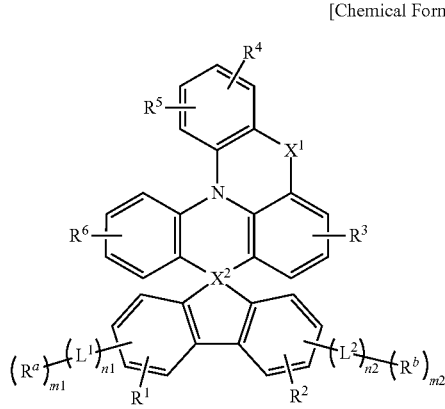

In the above Chemical Formula ad-1, $X^1$ is —O— or —S—, $X^2$ is —C— or —Si—, $Ar^1$ to $Ar^4$ are independently a substituted or unsubstituted C6 to C30 aryl group or a substituted or unsubstituted C2 to C30 heteroaryl group. $L^1$ and $L^2$ are independently a substituted or unsubstituted C2 to C10 alkenylene group, a substituted or unsubstituted C2 to C10 alkynylene group, a substituted or unsubstituted C8 to C30 arylene group, or a substituted or unsubstituted C2 to C30 heteroarylene group, m1 and m2 are independently integers of 0 or 1, n1 and n2 are independently integers ranging from 0 to 3, and $R^1$ to $R^6$ are independently hydrogen, deuterium, a substituted or unsubstituted C1 to C10 alkyl group, a substituted or unsubstituted C8 to C30 aryl group, or a substituted or unsubstituted C2 to C30 heteroaryl group, $R^a$ and $R^b$ are each independently, hydrogen, deuterium, a substituted or unsubstituted silyl group, a substituted or unsubstituted C4 to C60 amine group, a substituted or unsubstituted C6 to C30 aryl group, or a substituted or unsubstituted C2 to C30 heteroaryl group.

At least one of the $R^a$ and $R^b$ may be a substituted or unsubstituted pyridine group, a substituted or unsubstituted pyrimidinyl group, or a substituted or unsubstituted triazinyl group.

At least one of the $R^a$ and $R^b$ may be a substituted or unsubstituted phenyl group, a substituted or unsubstituted biphenyl group, a substituted or unsubstituted naphthyl group, a substituted or unsubstituted anthracenyl group, or a substituted of unsubstituted phenanthrenyl group.

The compound for an organic optoelectronic device may be represented by the following Chemical Formula 1.

[Chemical Formula 1]

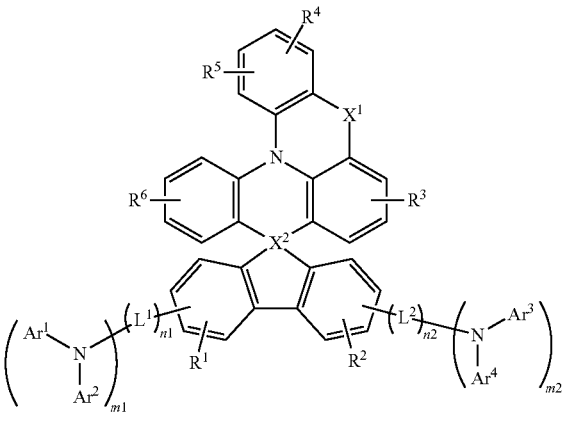

In the above Chemical Formula 1, $X^1$ is —O— or —S—, $X^2$ is —C— or —Si—, $Ar^1$ to $Ar^4$ are independently a substituted or unsubstituted C6 to C30 aryl group, or a substituted or unsubstituted C2 to C30 heteroaryl group, $L^1$ and $L^2$ are independently a substituted or unsubstituted C2 to C10 alkenylene group, a substituted or unsubstituted C2 to C10 alkynylene group, a substituted or unsubstituted C8 to C30 arylene group, or a substituted or unsubstituted C2 to C30 heteroarylene group, m1 and m2 are independently integers of 0 or 1, one of m1 and m2 is 1, n1 and n2 are independently integers ranging from 0 to 3, and $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

The compound for an organic optoelectronic device may be represented by the following Chemical Formula 2.

[Chemical Formula 2]

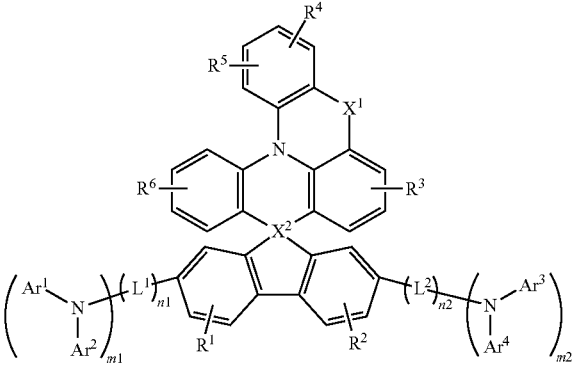

In the above Chemical Formula 2, $X^1$ is —O— or —S—, $X^2$ is —C— or —Si—, $Ar^1$ to $Ar^4$ are independently a substituted or unsubstituted C6 to C30 aryl group, or a substituted or unsubstituted C2 to C30 heteroaryl group, $L^1$ and $L^2$ are independently a substituted or unsubstituted C2 to C10 alkynylene group, a substituted or unsubstituted C2 to C10 alkynylene group, a substituted or unsubstituted C8 to C30 arylene group, or a substituted or unsubstituted C2 to C30 heteroarylene group m1 and m2 are independently integers of 0 or 1, one of m1 and m2 is 1, n1 and n2 are independently integers ranging from 0 to 3, and $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

The compound for an organic optoelectronic device may be represented by the following Chemical formula 3.

[Chemical Formula 3]

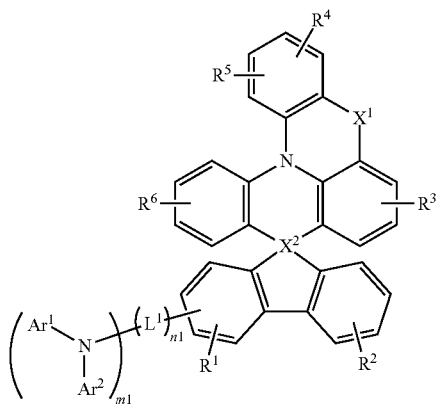

In the above Chemical Formula 3 $X^1$ is —O— or —S—, $X^2$ is —C— or —Si—, $Ar^1$ and $Ar^2$ are independently a substituted or unsubstituted C6 to C30 aryl group, or a substituted or unsubstituted C2 to C30 heteroaryl group, $L^1$ is a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 is 1, n1 is integers ringing from 0 to 3, and $R^1$ to $R^6$ are independently hydrogen, deuterium, a substituted or unsubstituted C1 to C10 alkyl group, a substituted or unsubstituted C8 to C30 aryl group, or a substituted or unsubstituted C2 to C30 heteroaryl group.

The compound for an organic optoelectronic device may be represented by the following Chemical Formula 4.

[Chemical Formula 4]

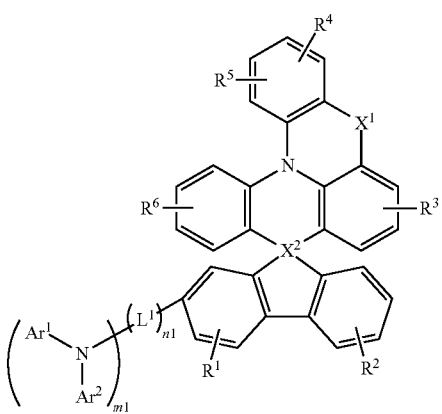

In the above Chemical Formula 4, $X^1$ is —O— or —S—, $X^2$ is —C— or —Si—, $Ar^1$ and $Ar^2$ are independently a substituted or unsubstituted C6 to C30 aryl group, or a substituted or unsubstituted C2 to C30 heteroarylene group, V is a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 is 1, n1 is integers ranging from 0 to 3, and $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

The $X^2$ may be —C—.

The $Ar^1$ to $Ar^4$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiopheneyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiopheneyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

The compound for an organic optoelectronic device may be represented by one of the following Chemical Formulae A-1 to A-26.

A-1

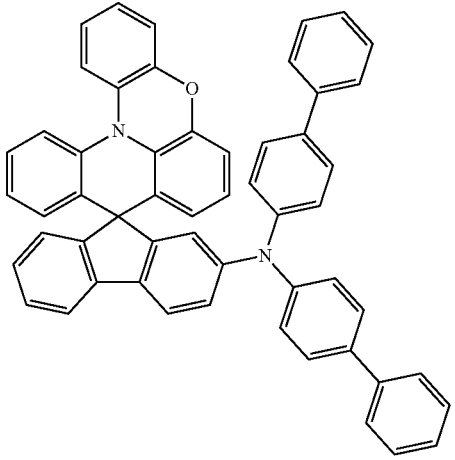

A-2
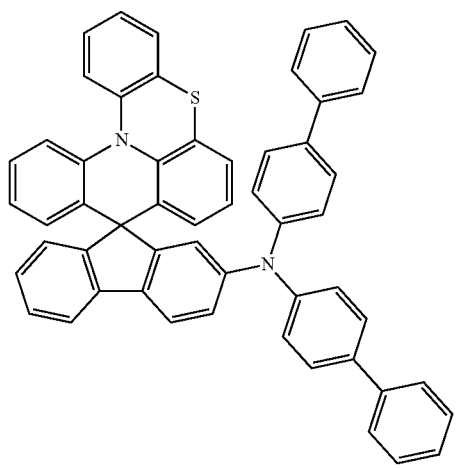
A-5
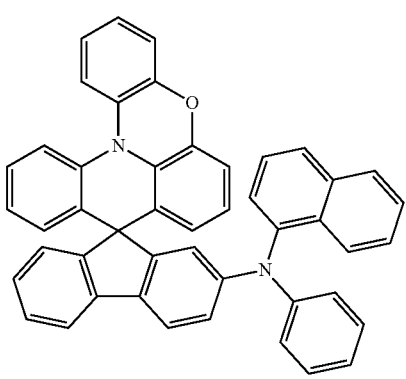
A-3
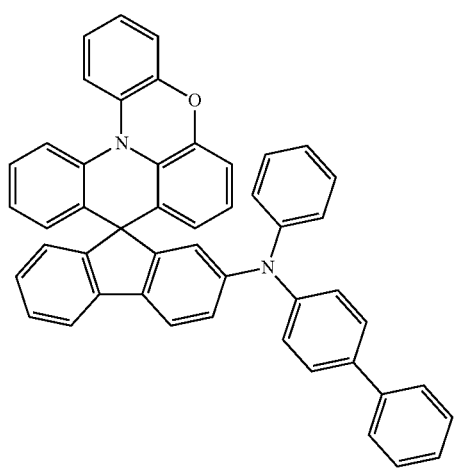
A-6
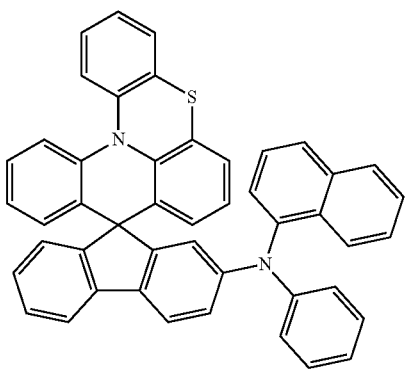
A-4
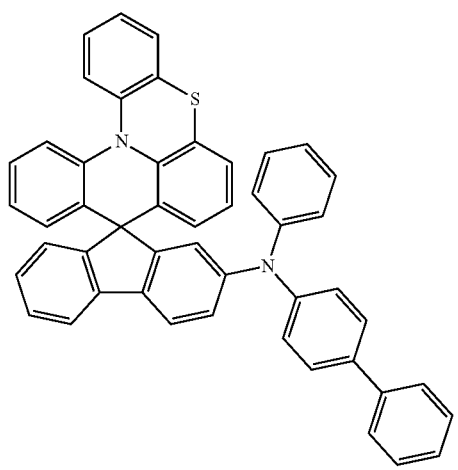
A-7
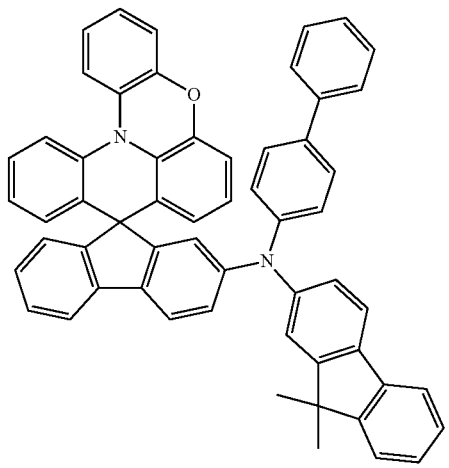

A-8
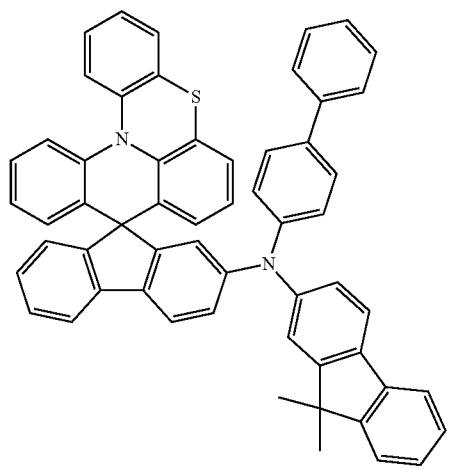
A-9
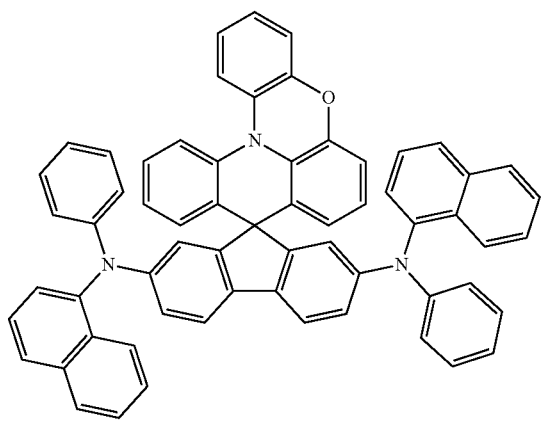
A-10
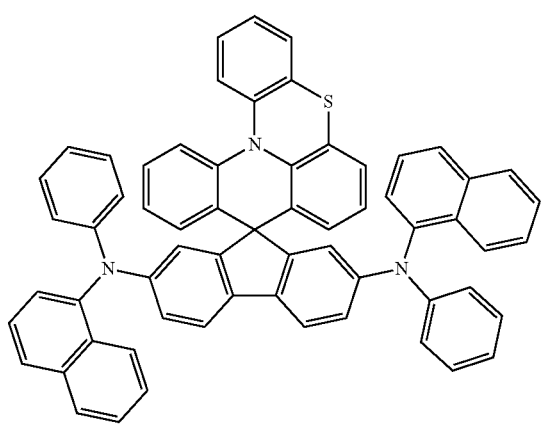
A-11
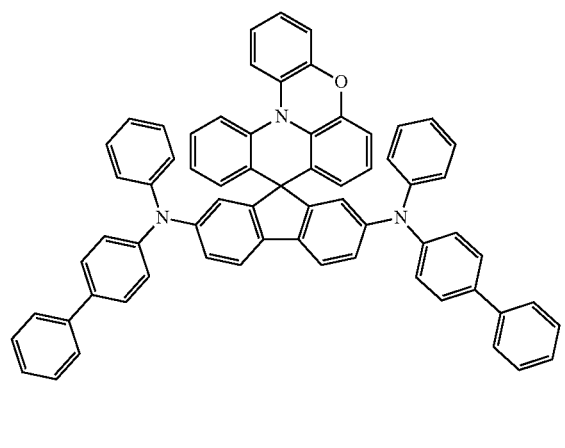
A-12
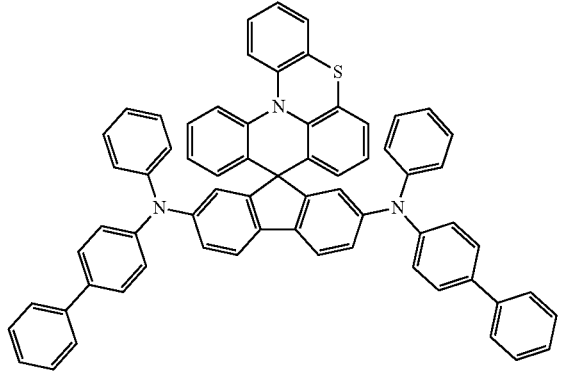
A-13
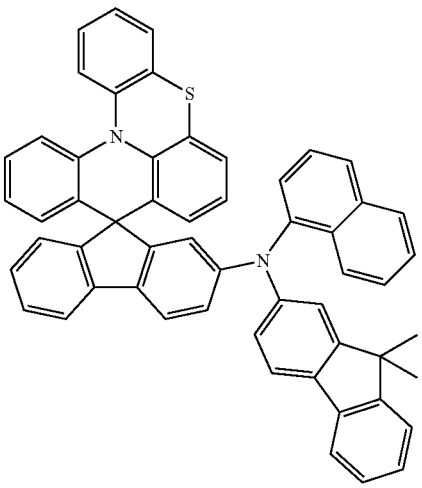

A-14
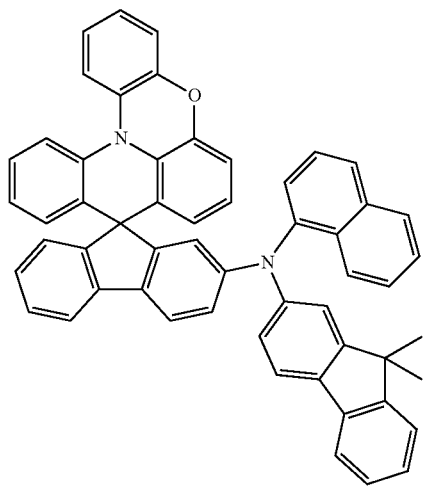
A-17
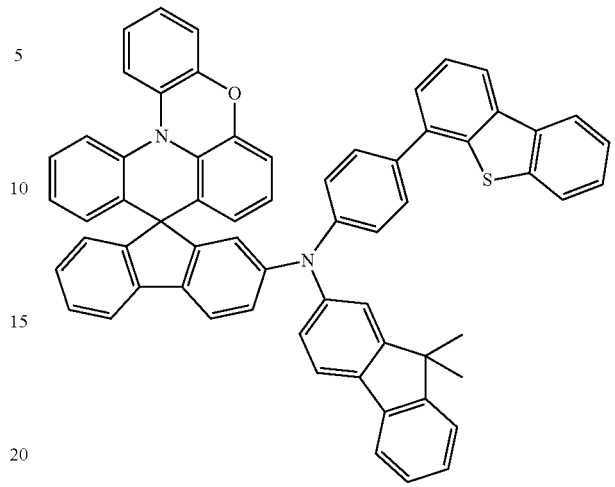
A-15
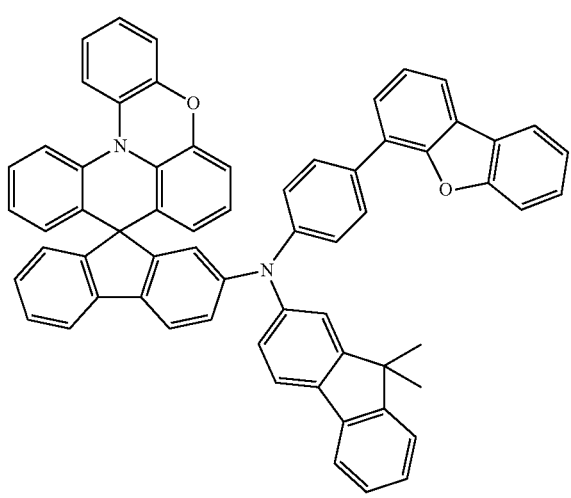
A-18
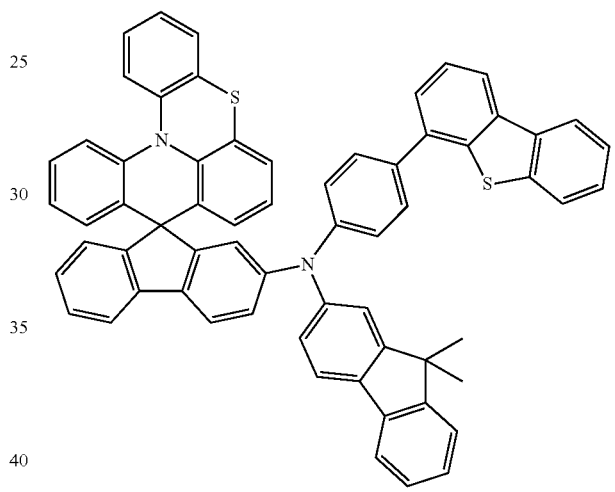
A-16
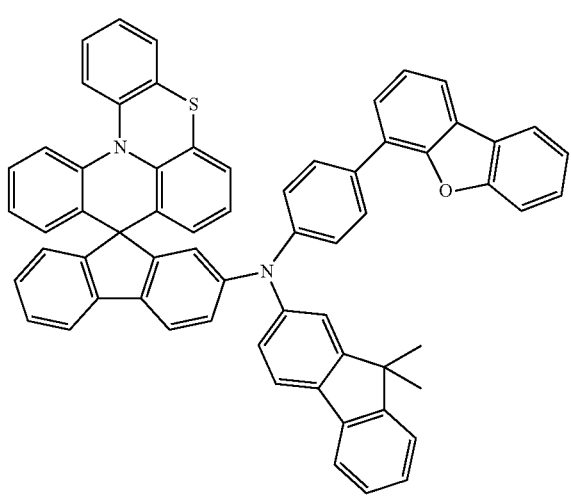
A-19
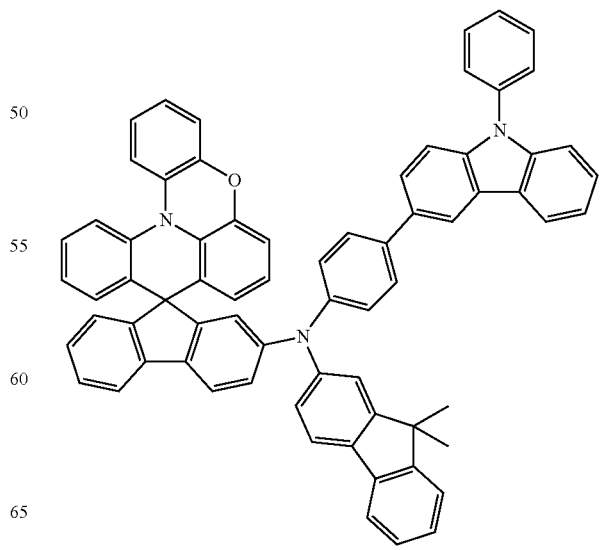

A-20
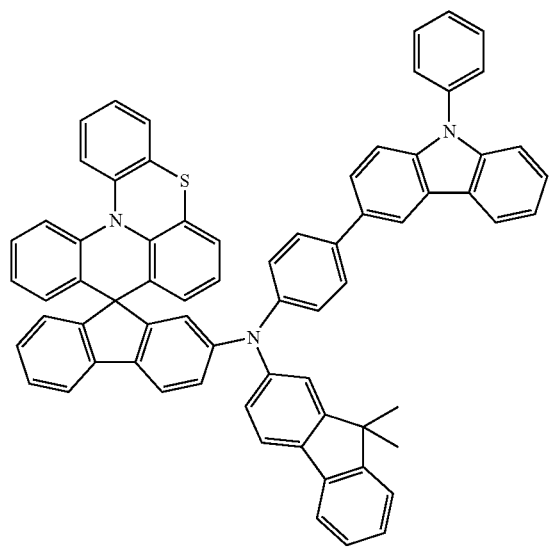
A-22
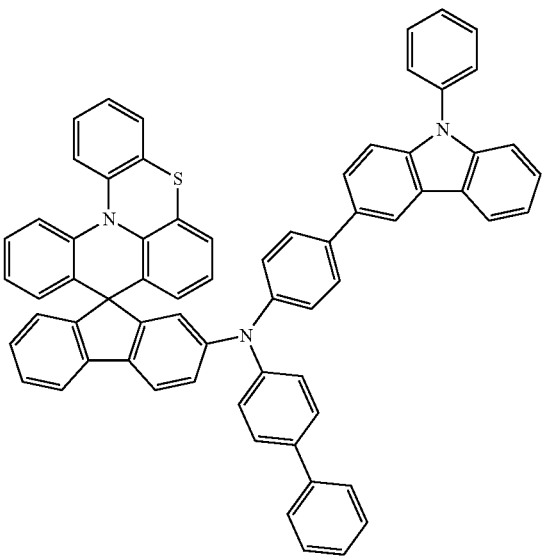
A-21
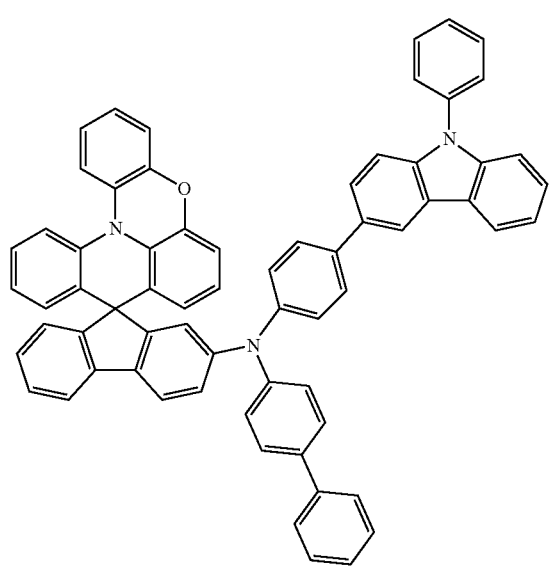
A-23
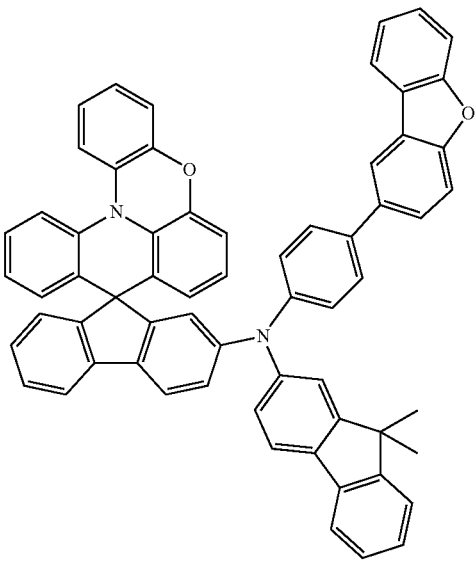

A-24
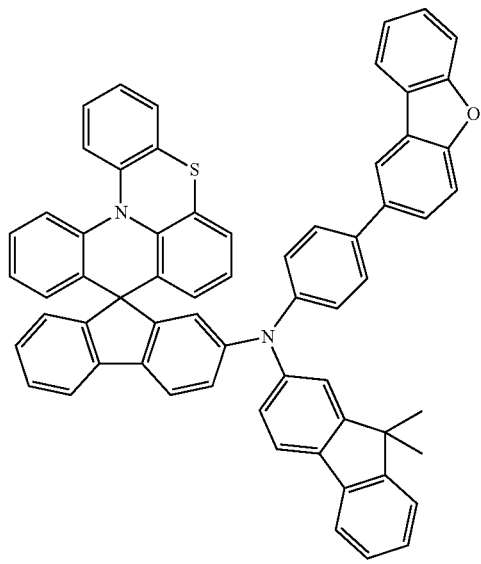
A-26
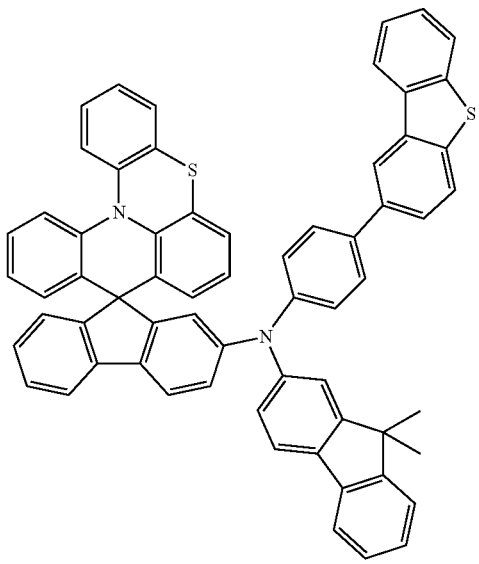
The compound for an organic optoelectronic device may be represented by one of the following Chemical formulae B-1 to 8-10.
[B-1]
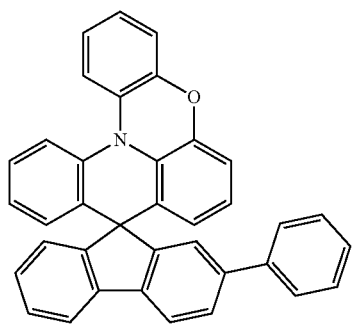
A-25
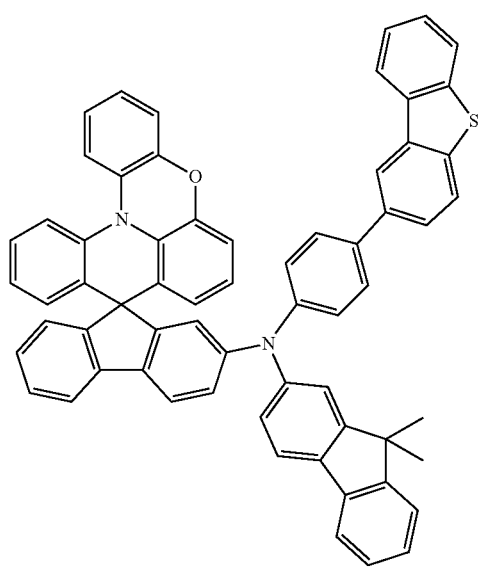
[B-2]
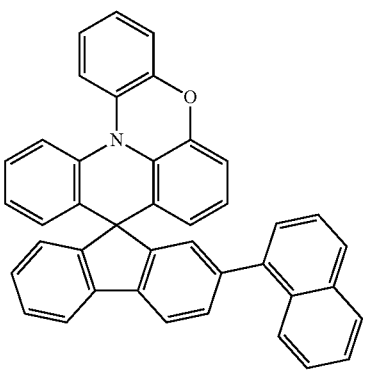

-continued

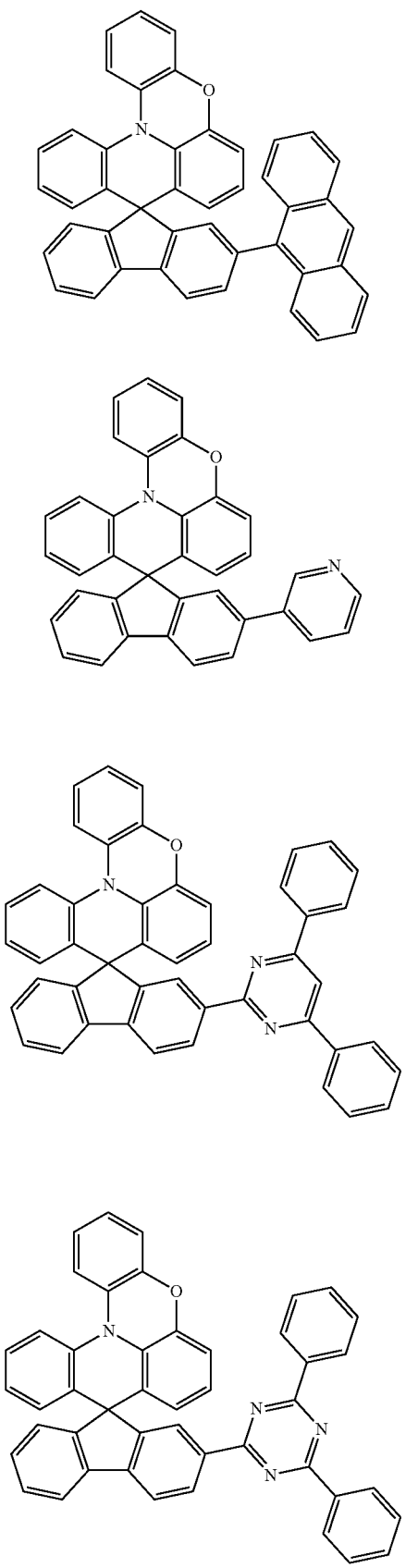

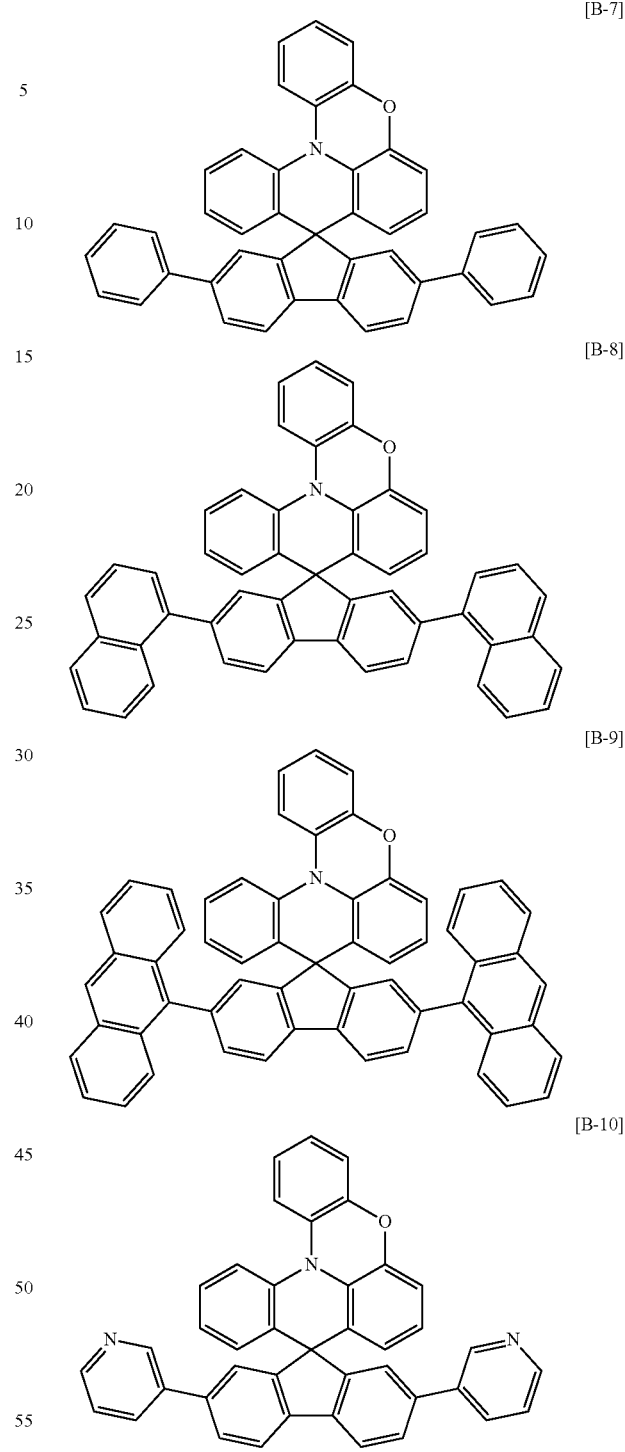

The compound for an organic optoelectronic device may have triplet exciton energy (T1) of greater than or equal to about 2.0 eV.

The organic optoelectronic device may be selected from an organic photoelectric device, an organic light emitting diode, an organic solar cell, an organic transistor, an organic photo-conductor drum, and an organic memory device.

In another embodiment of the present invention, provided is an organic light emitting diode including an anode, a cathode, and at least one organic thin layer interposed between the anode and cathode, wherein at least one of the organic thin layers includes the above compound for an organic optoelectronic device.

The organic thin layer may be selected from an emission layer, a hole transport layer, a hole injection layer, an electron transport layer, an electron injection layer, a hole blocking layer, and a combination thereof.

The compound for an organic optoelectronic device may be included in a hole transport layer (HTL) or a hole injection layer (HIL).

The compound for an organic optoelectronic device may be included in an emission layer.

The compound for an organic optoelectronic device may be used as a phosphorescent or fluorescent host material in an emission layer.

Advantageous Effects

In yet another embodiment of the present invention, a display device including the above organic light emitting diode is provided.

A compound having high hole or electron transport properties, film stability, thermal stability, and high triplet exciton energy may be provided.

Such a compound may be used as a hole injection/transport material, host material, or electron injection/transport material of an emission layer. An organic optoelectronic device using the same has improved life-span characteristics, and high luminous efficiency at a low driving voltage due to excellent electrochemical and thermal stability.

Figure 1:
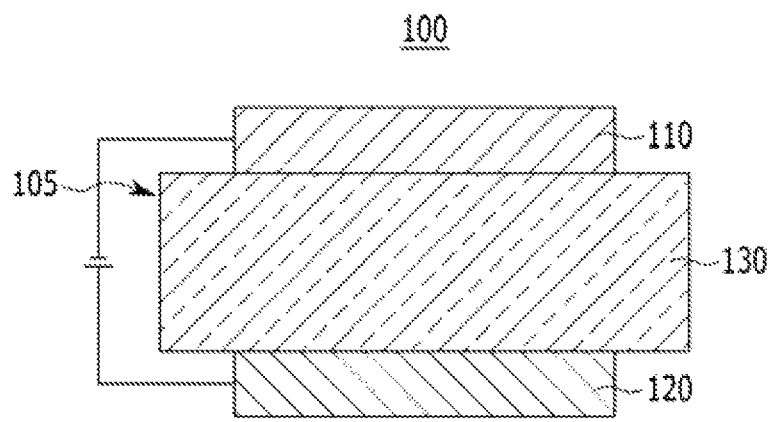
FIGS. 1 to 5 are cross-sectional views showing organic light emitting diodes according to various embodiments of the present invention including the compound for an organic optoelectronic device according to one embodiment of the present invention.

| <Description of Symbols> | |
|---|---|
| 100: organic light emiting diode | 110: cathode |
| 120: anode | 105: organic thin film |
| 130: emission layer | 140: hole transport layer (HTL) |
| 150: electron transport layer (ETL) | 160: electron injection layer (EIL) |
| 170: hole injection layer (HIL) | 230: emission layer + electron transport layer (ETL) |

BEST MODE

Hereinafter, embodiments of the present invention are described in detail. However, these embodiments ere exemplary, and this disclosure is not limited thereto.

As used herein, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

The two adjacent substituent selected from the substituted a halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group, and the like, or cyano group may be fused to form a ring.

In the present specification, when specific definition is not otherwise provided, "hetero" refers to one including 1 to 3 hetero atoms selected from N, O, S, and P, and remaining carbons in one compound or substituent.

In the present specification, when a definition is not otherwise provided, the term "combination thereof" refers to at least two substituents bonded with each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond. The alkyl group may be branched, linear or cyclic.

The "alkenylene group" refers to a functional group of at least one carbon-carbon double bond of at least two carbons, and the "alkynylene group" refers to a functional group of at least one carbon-carbon triple bond of at least two carbons.

The alky; group may be a C1 to C20 alkyl group. More specifically, the alkyl group may be a C1 to C10 alkyl group or a C1 to C6 alkyl group.

For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

"Aromatic group" refers to a cyclic functional group where all elements have p-orbitals, and these p-orbitals forms conjugation. Specific examples are aryl group and a heteroaryl group.

"Aryl group" includes monocyclic or fused ring polycystic (i.e., rings sharing adjacent pairs of carbon atoms) groups.

"Heteroaryl group" refers to aryl group including 1 to 3 hetero atoms selected from N, O, S, and P, and remaining carbons. When the heteroaryl group is a fused ring, each ring may include 1 to 3 hetero atoms.

As used herein, the carbazole-based derivative may refer to a substituted structure where a nitrogen atom of a substituted or unsubstituted carbazolyl group is substituted with a hetero atom or carbon except nitrogen. Specific examples may be dibenzofuran (a dibenzofuranyl group), dibenzothiophene (a dibenzothipheneyl group), fluorine (a fluorenyl group) and the like.

In the present specification, hole characteristics refer to characteristics that holes formed in the anode is easily injected into the emission layer and transported in the emission layer due to conductive characteristics according to HOMO level. Specifically, it is similar to electron-repelling characteristics.

Electron characteristics refer to characteristics that electron formed in the cathode is easily injected into the emission layer and transported in the emission layer due to conductive characteristics according to LUMO level. Specifically, it is similar to electron-withdrawing characteristics.

A compound for an organic optoelectronic device according to one embodiment of the present invention, for example, may have a core that phenoxazine and spirofluorene are formed as a fused ring.

Selectively, at least one aryl amine (or heteroaryl amine) may be combined with the core structure.

Accordingly, the core structure may be used as a light emitting material, a hole injection material, or a hole transport material for an organic optoelectronic device. In particular, the core structure may be appropriately used as a hole injection material or a hole transport material.

The compound for an organic optoelectronic device includes a core part and various substituents for a substituent for substituting the core part and thus may have various energy bandgaps.

When the compound having an appropriate energy level depending on a substituent is used for an organic optoelectronic device, the compound may reinforce hole transport capability or electron transport capability of the organic optoelectronic device, have excellent effects on efficiency and a driving voltage, and also, have excellent electrochemical and thermal stability and thus, improve life-span characteristics during operation of the organic optoelectronic device.

In one embodiment of the present invention, a compound for an organic optoelectronic device represented by the following Chemical Formula ad-1 is provided.

[Chemical Formula ad-1]

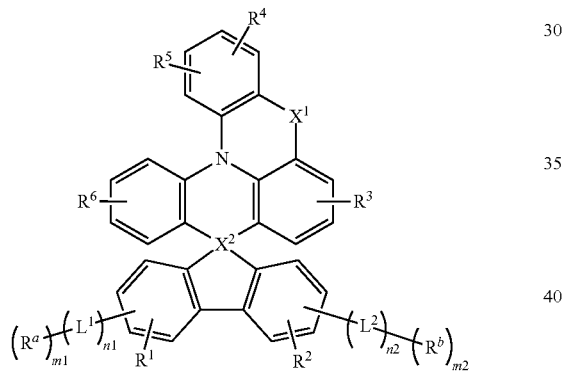

In the above Chemical Formula ad-1, $X^1$ is —O— is —S—, $X^2$ is —C— or —Si—, $AR^1$ to $Ar^4$ are independently a substituted or unsubstituted C6 to C30 aryl group, or a substituted or unsubstituted C2 to C30 heteroaryl group, $L^1$ and $L^2$ are independently a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 and m2 are independently integers of 0 or 1, n1 and n2 are independently integers ranging from 0 to 3, $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, $R^a$ and $R^b$ are each independently, hydrogen, deuterium, a substituted or unsubstituted silyl group, a substituted or unsubstituted C4 to C60 amine group, a substituted or unsubstituted C6 to C30 aryl group, or a substituted of unsubstituted C2 to C30 heteroaryl group.

At least one of the $R^a$ and $R^b$ may be a substituted or unsubstituted pyridinyl group, a substituted or unsubstituted pyrimidinyl group, or a substituted or unsubstituted triazinyl group. Herein, the substituent may additionally apply electron characteristics to the compound, and thus, the compound may have bipolar characteristics.

At least one of the $R^a$ and $R^b$ may be a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group. However, it is not limited thereto.

The substituted or unsubstituted C4 to C60 amine group may be anyone of the following substituents. A linking group at the left of the following amine substituents indicates a linking position with the core.

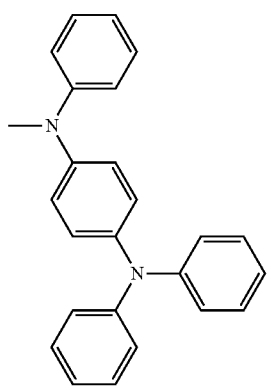

1

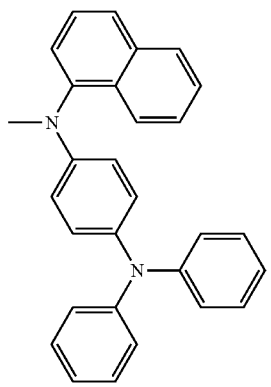

2

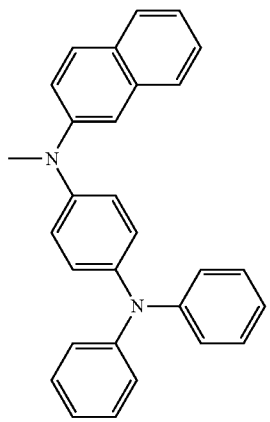

3

4
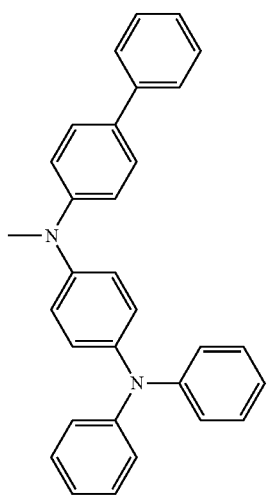
5
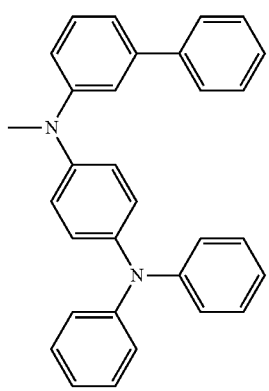
6
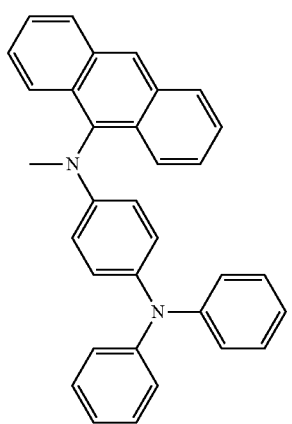
7
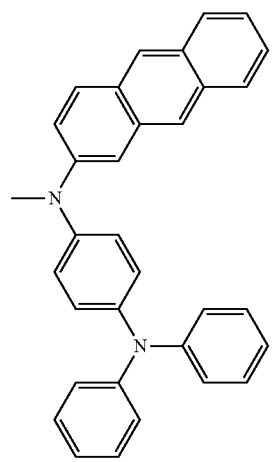
8
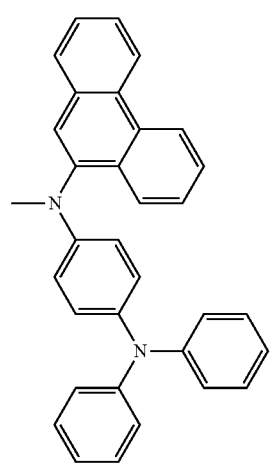
9
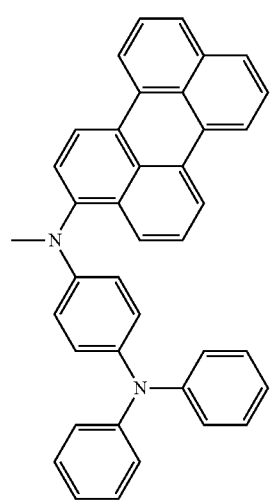

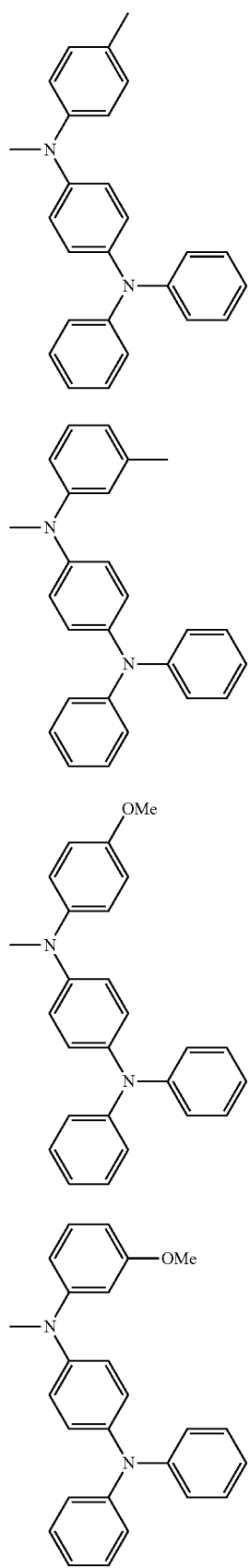
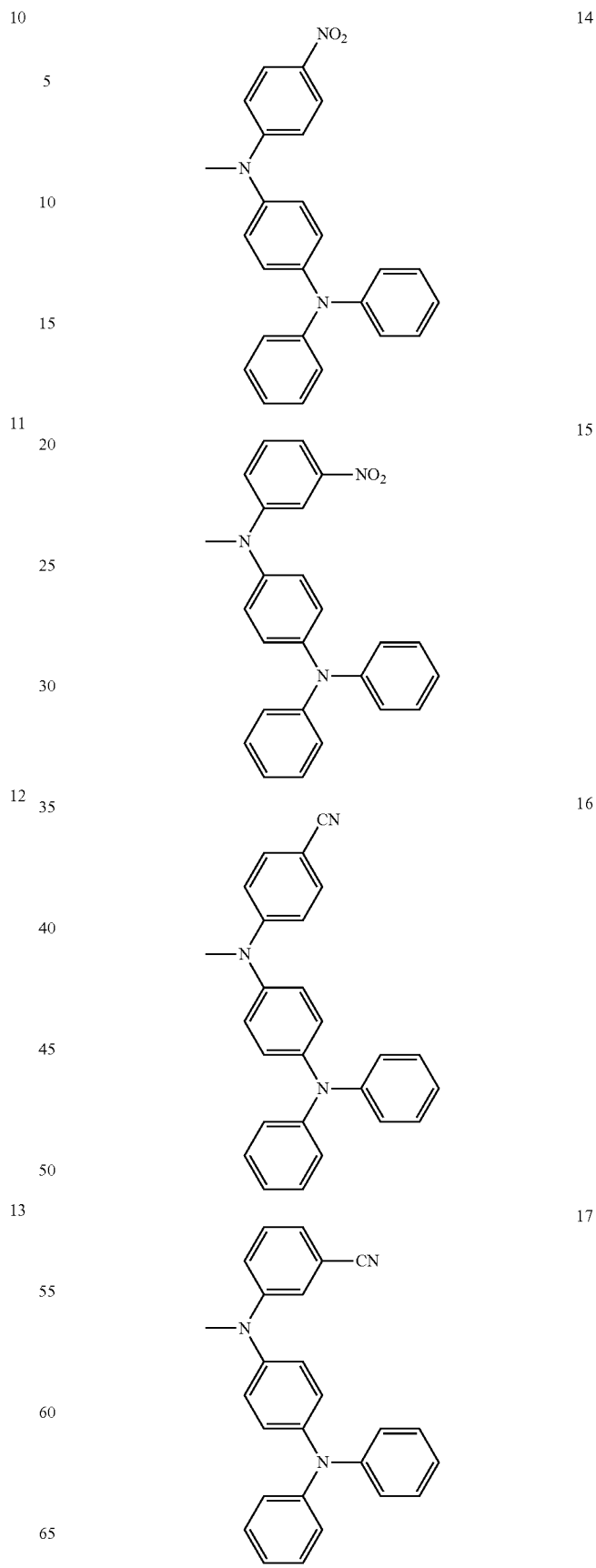

-continued
18
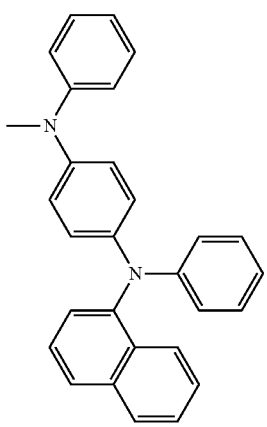
19
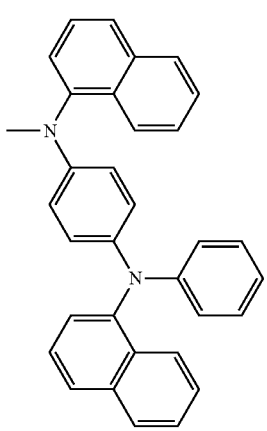
20
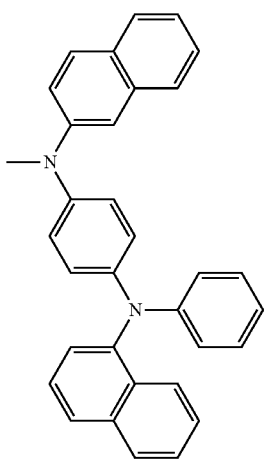
-continued
21
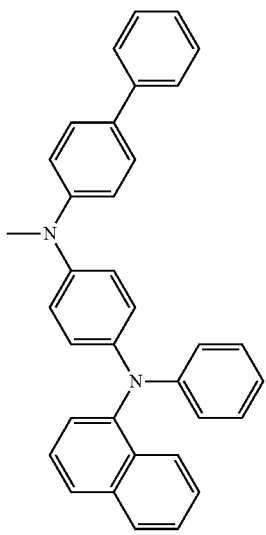
22
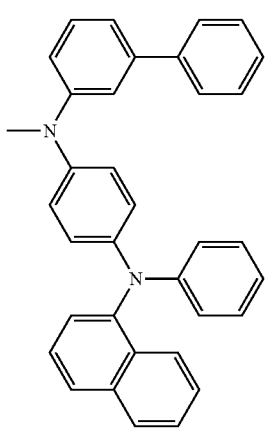
23
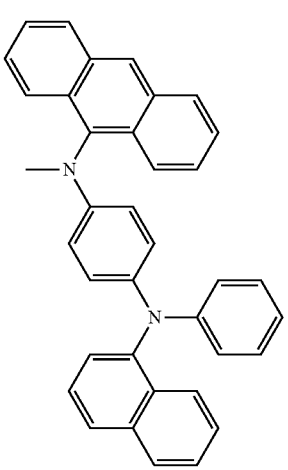

24
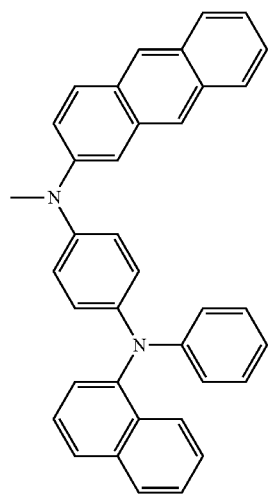
25
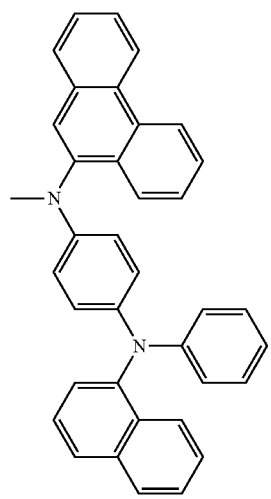
26
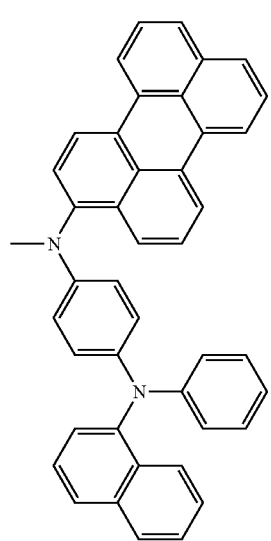
27
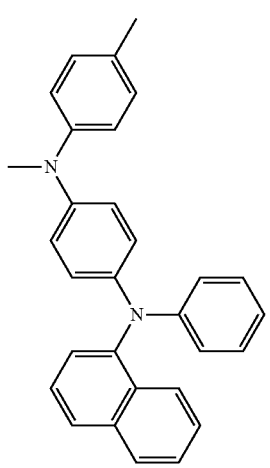
28
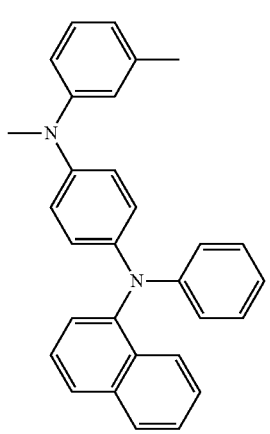
29
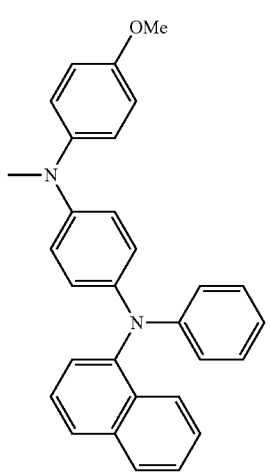

30
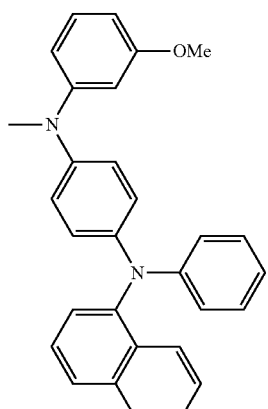
31
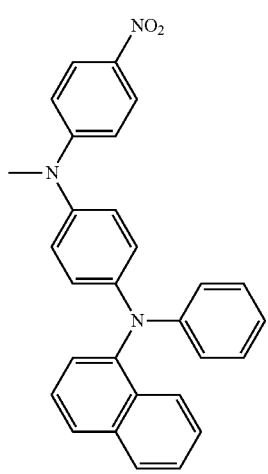
32
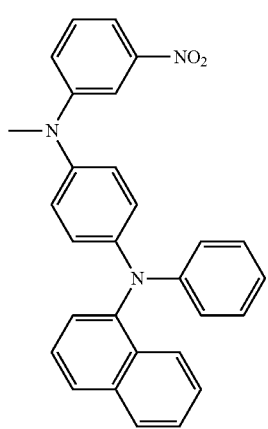
33
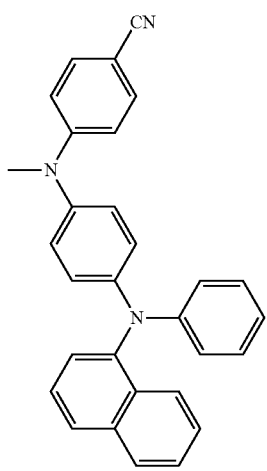
34
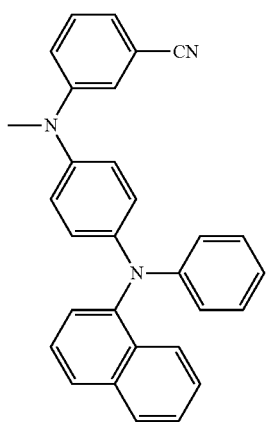
35
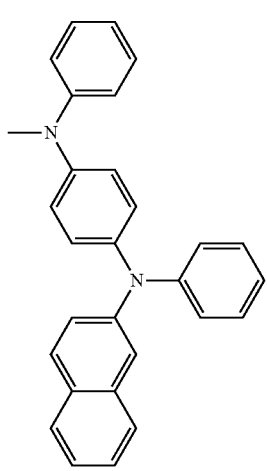

36
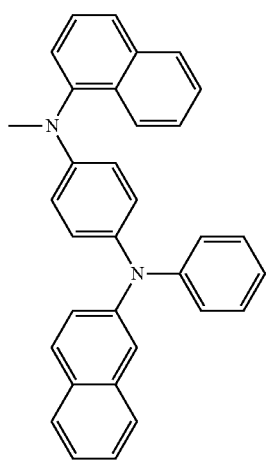
37
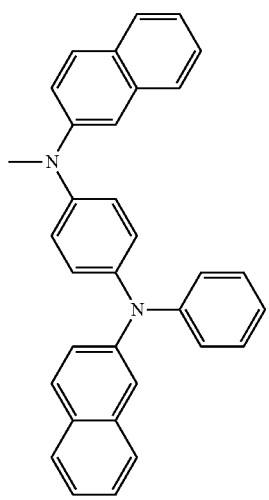
38
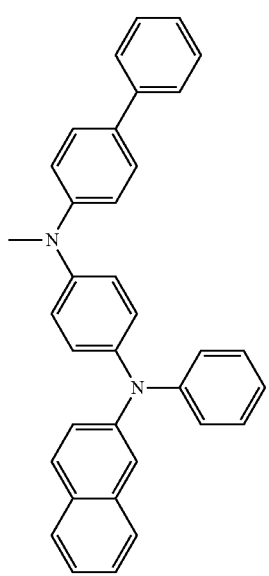
39
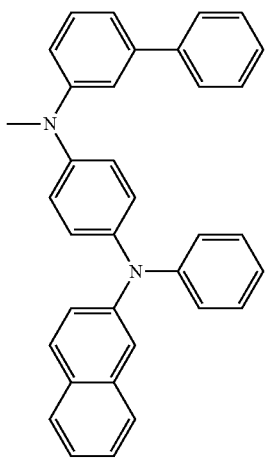
40
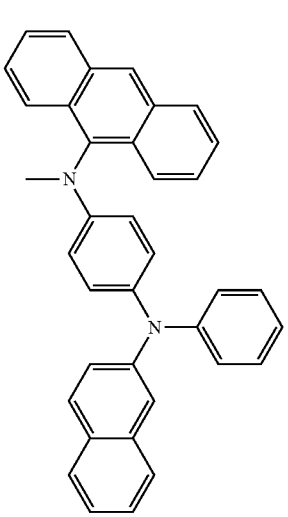
41
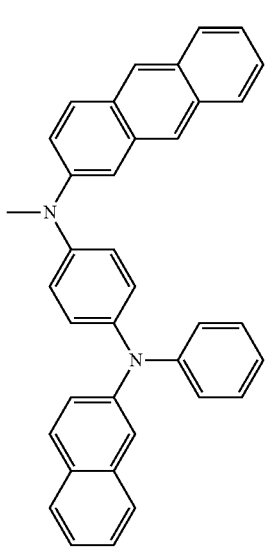

42 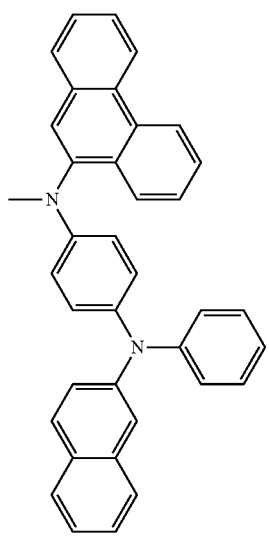
43 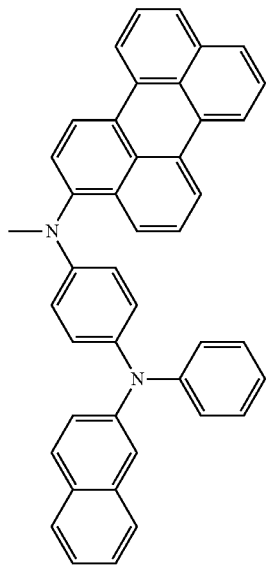
44 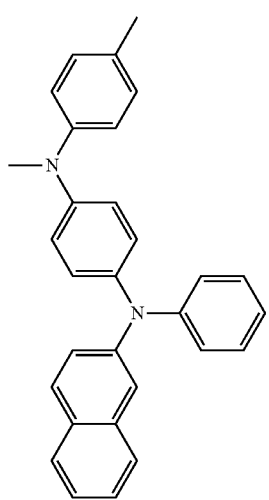
45 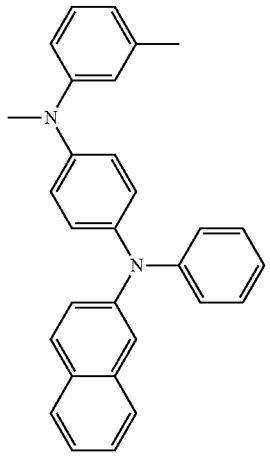
46 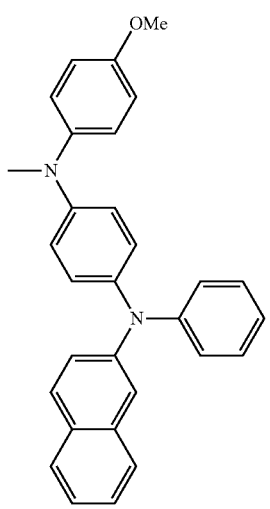
47 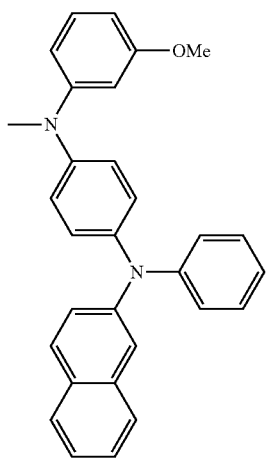

48
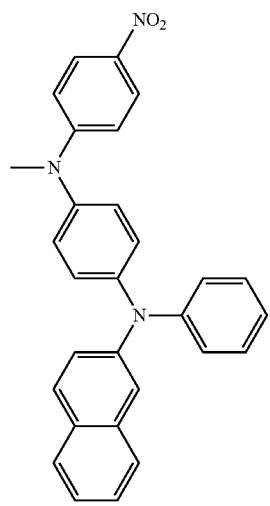
49
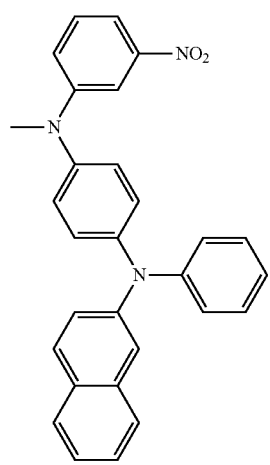
50
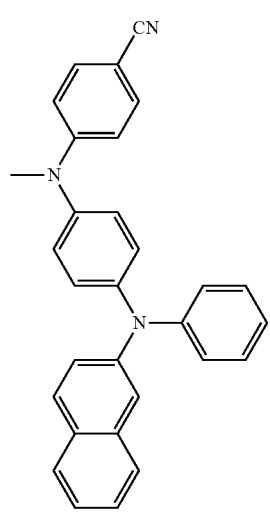
51
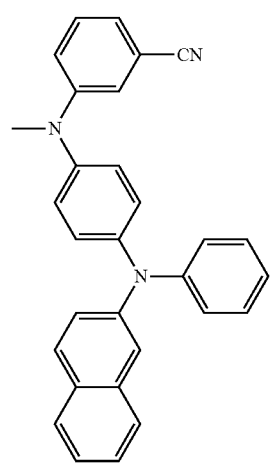
52
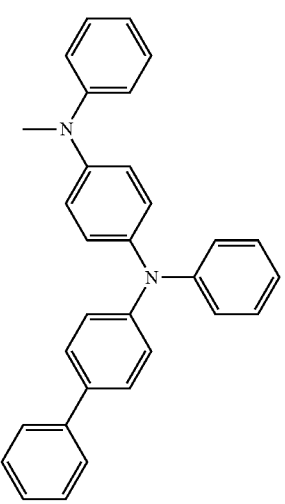
53
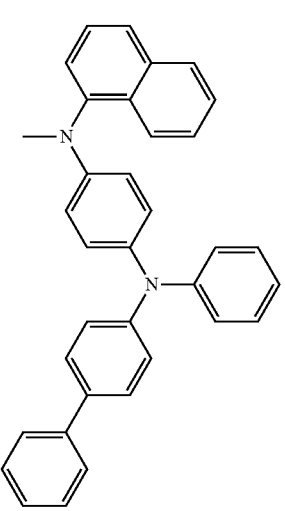

54
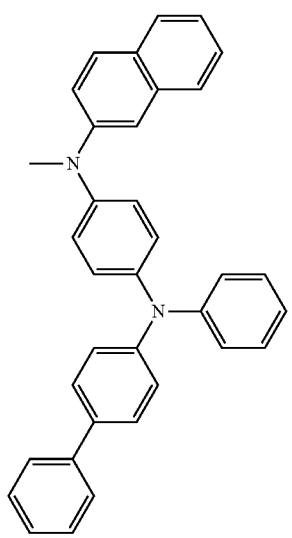
55
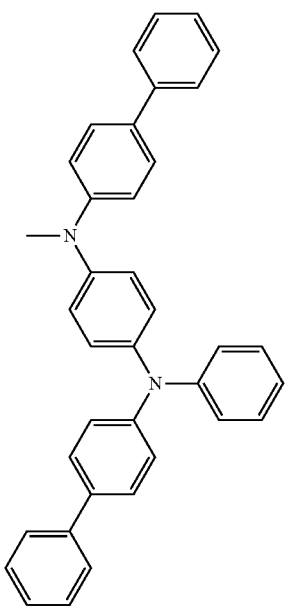
56
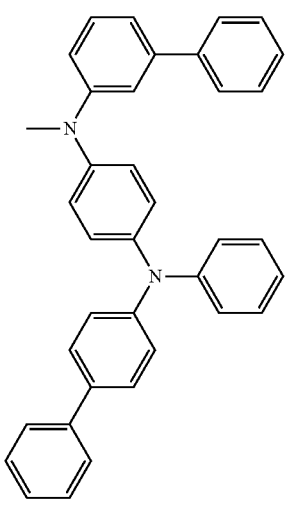
57
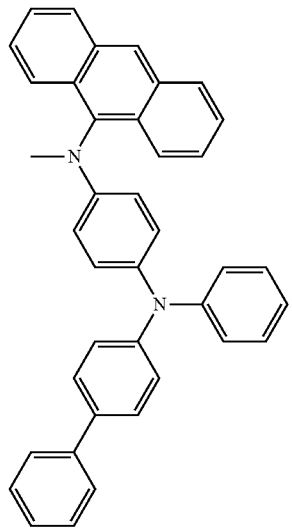
58
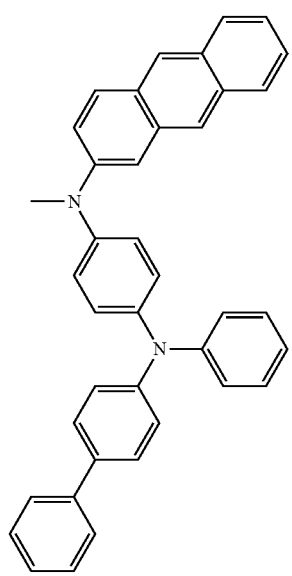
59
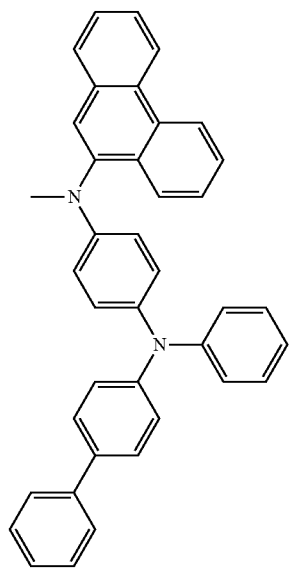

60
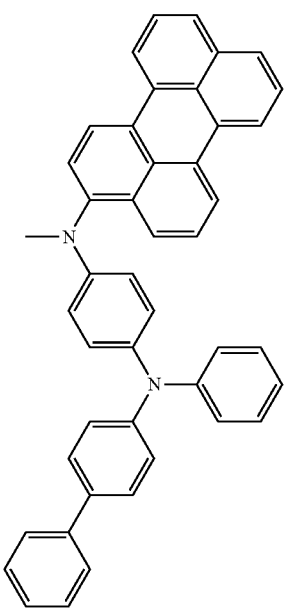
61
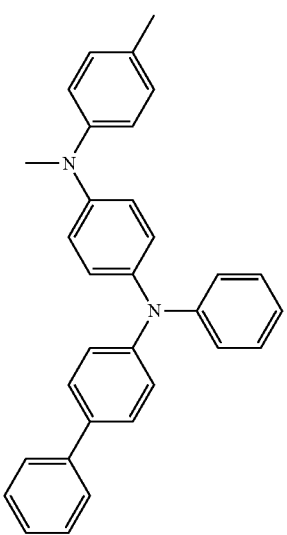
62
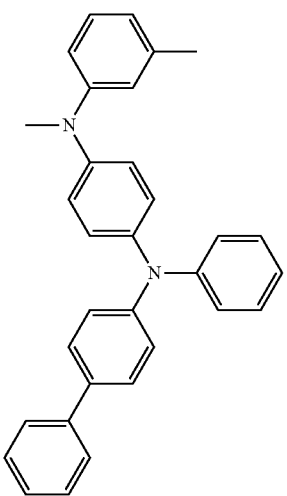
63
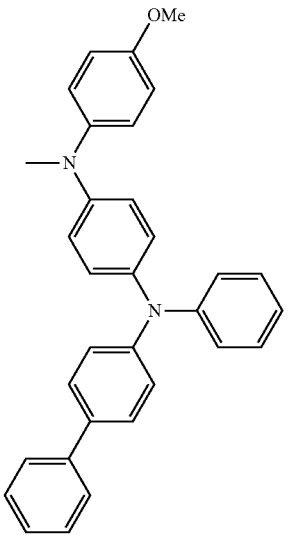
64
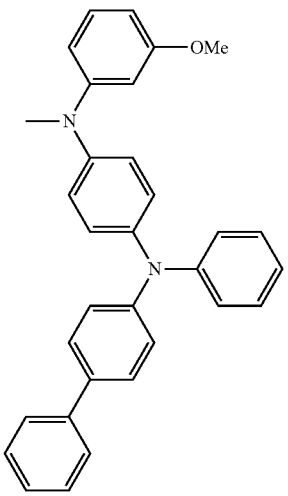
65
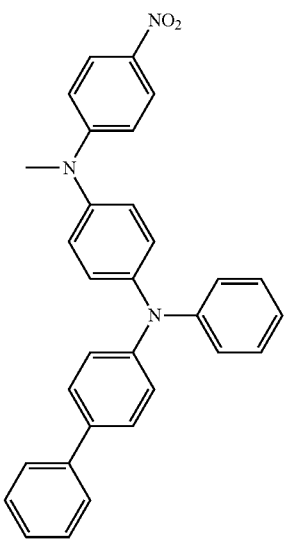

66
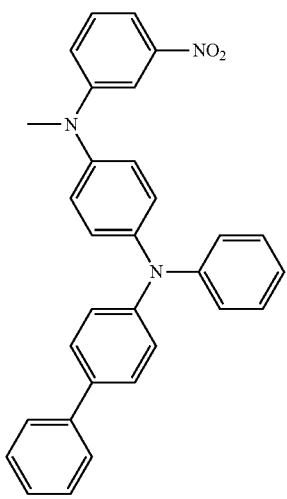
67
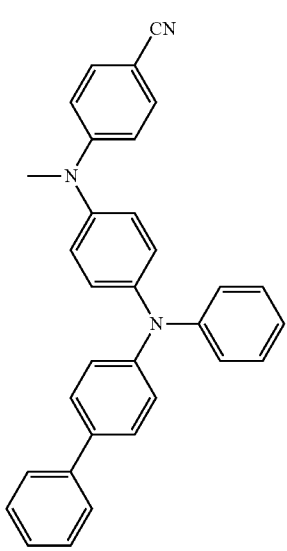
68
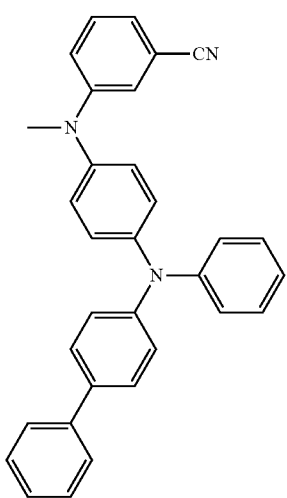
69
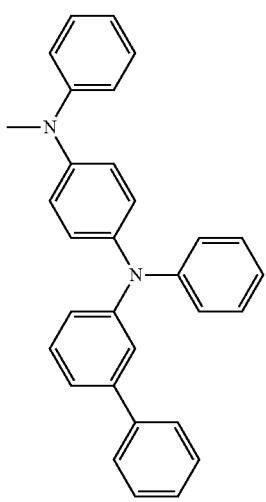
70
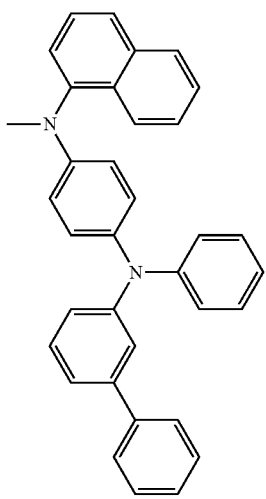
71
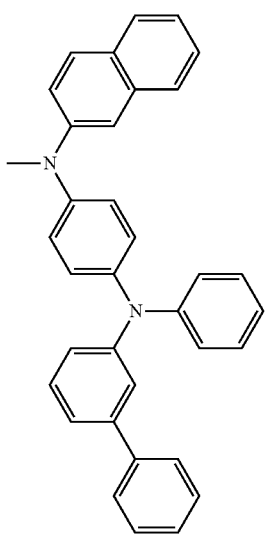

72
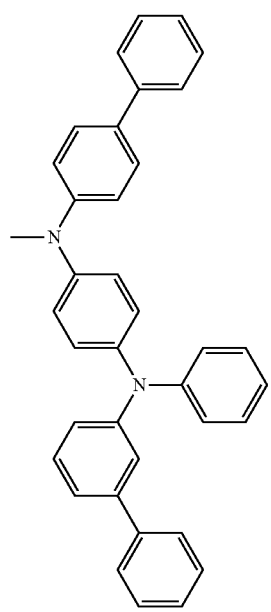
73
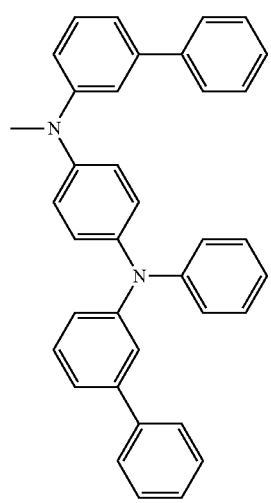
74
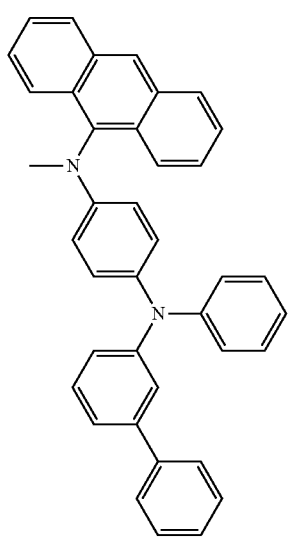
75
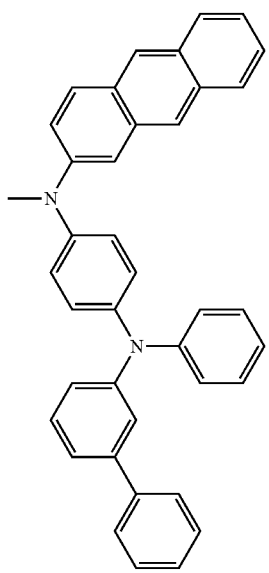
76
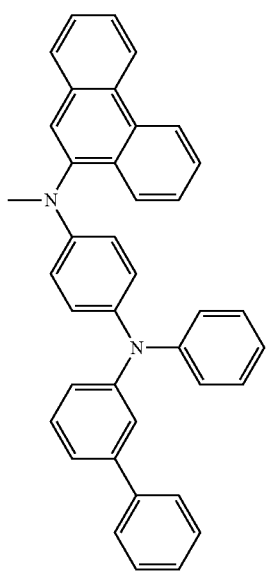

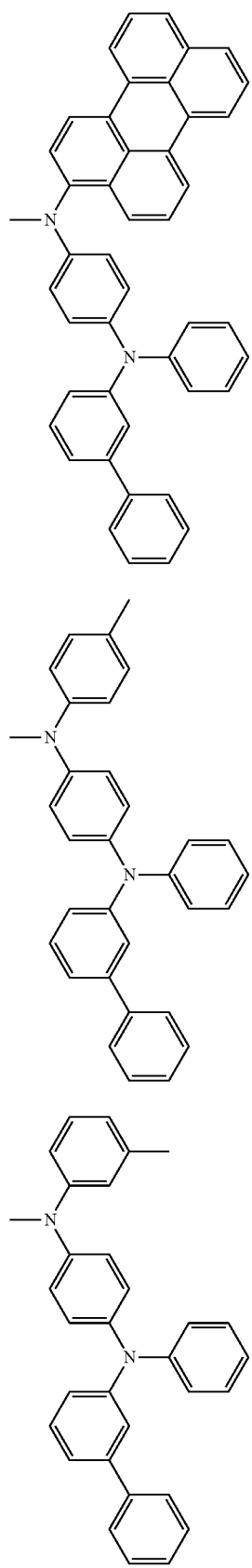
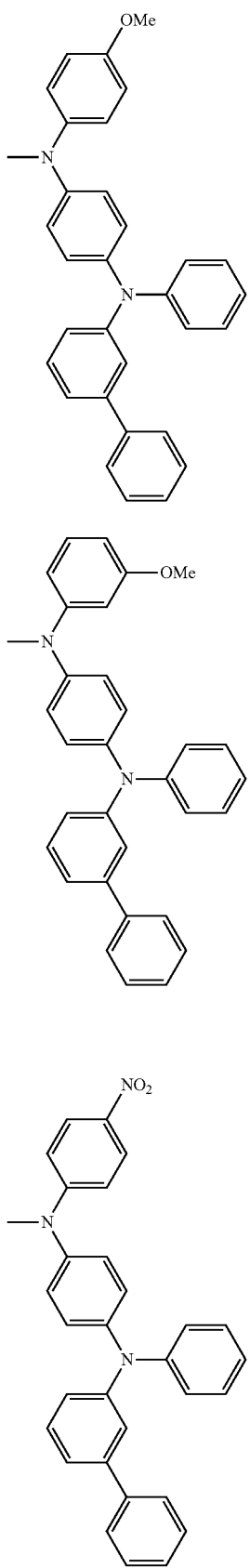

83
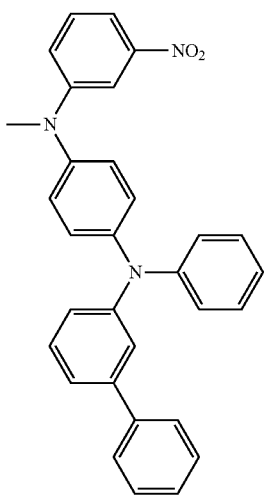
84
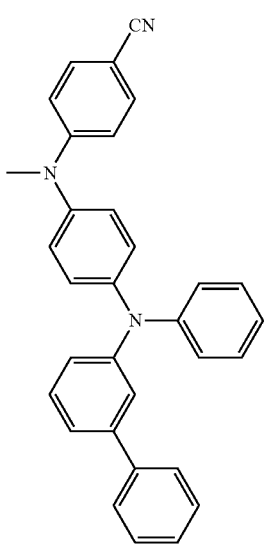
85
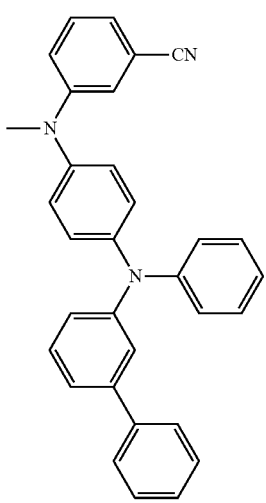
86
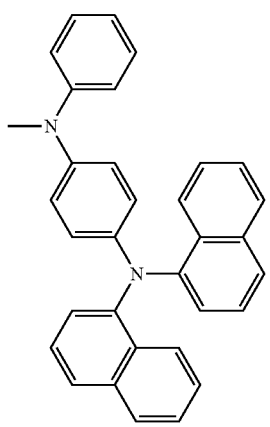
87
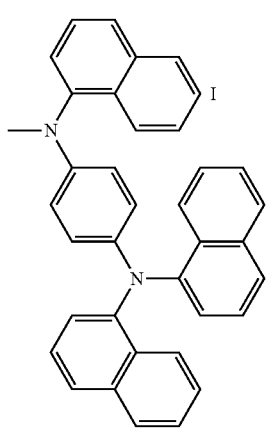
88
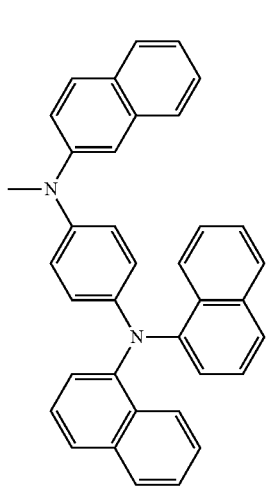

89
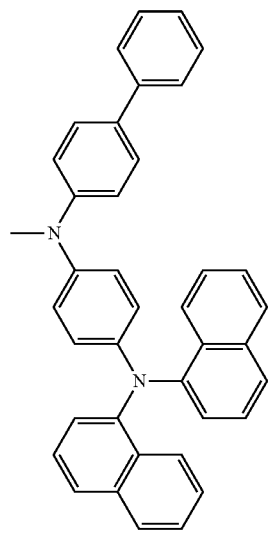
90
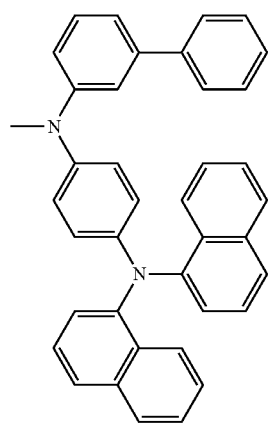
91
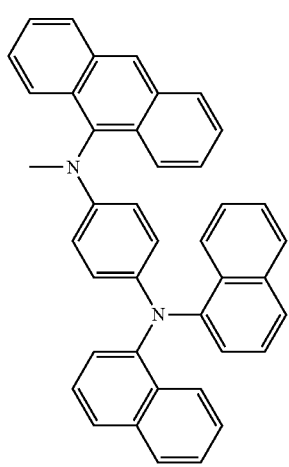
92
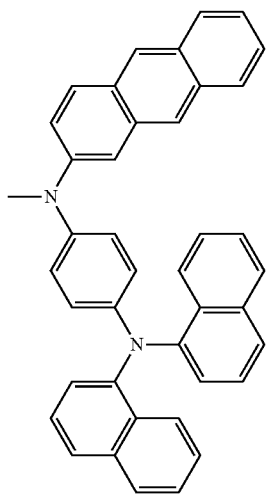
93
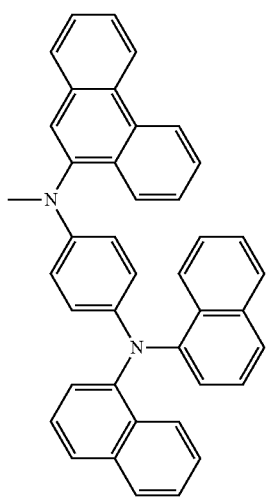
94
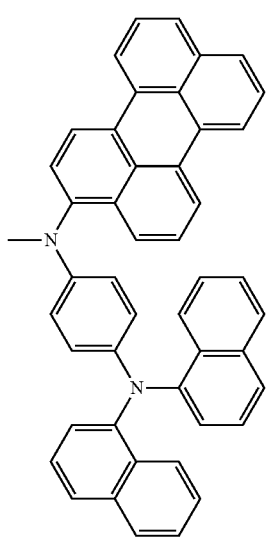

95
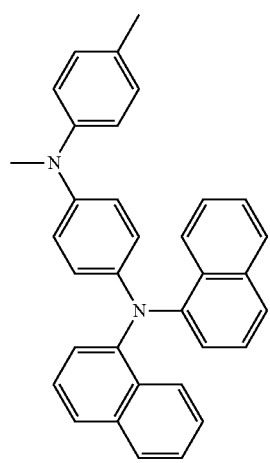
96
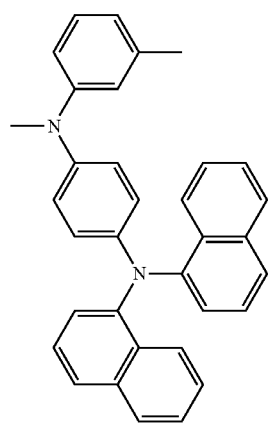
97
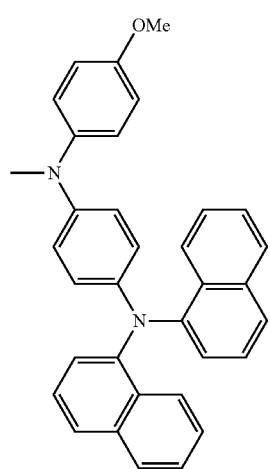
98
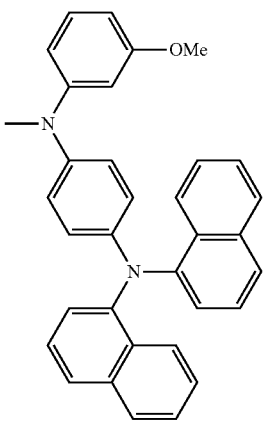
99
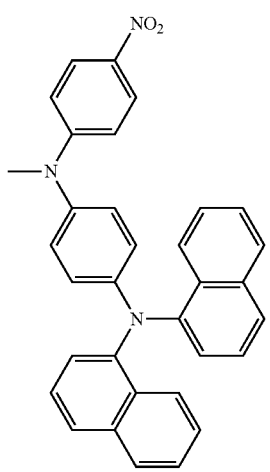
100
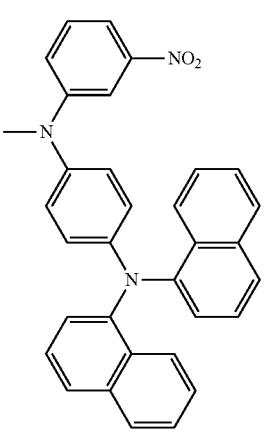

101
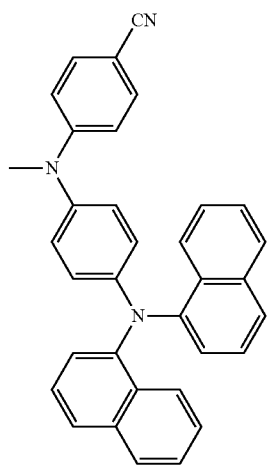
102
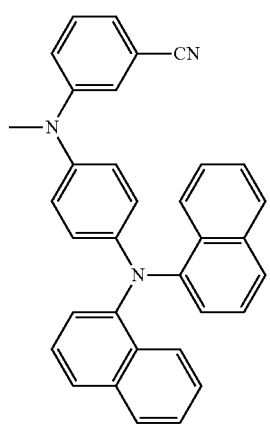
103
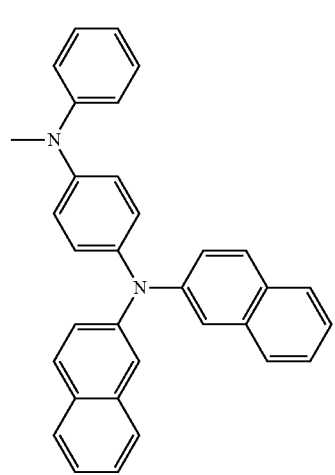
104
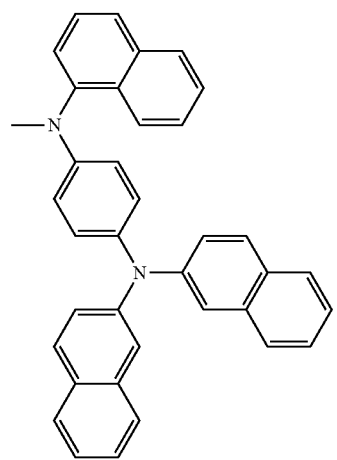
105
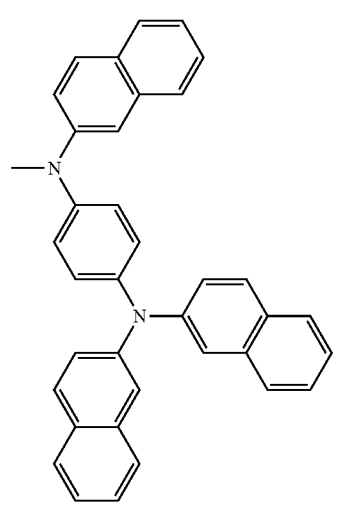
106
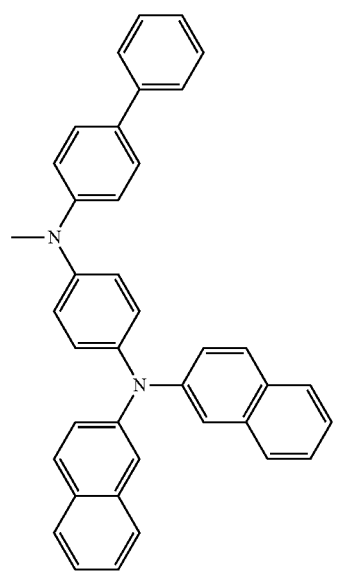

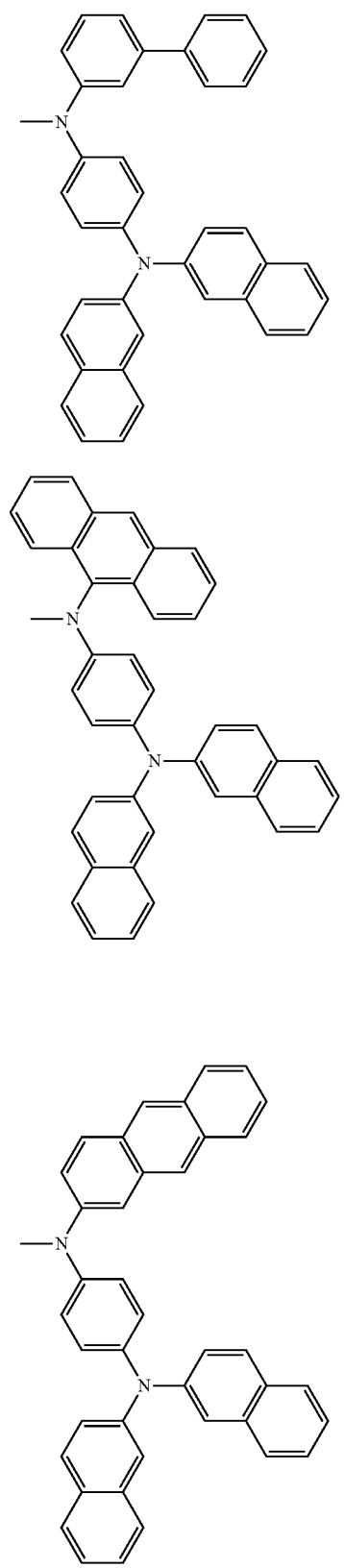
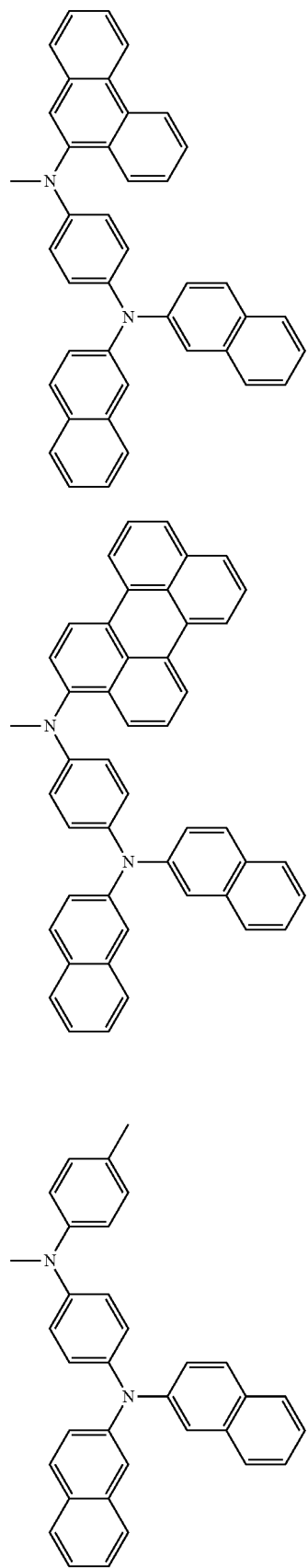

113
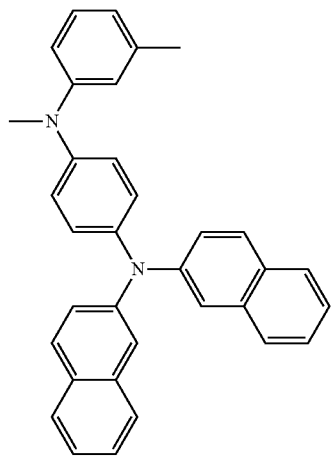
114
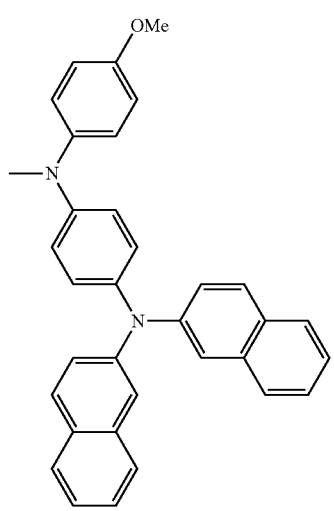
115
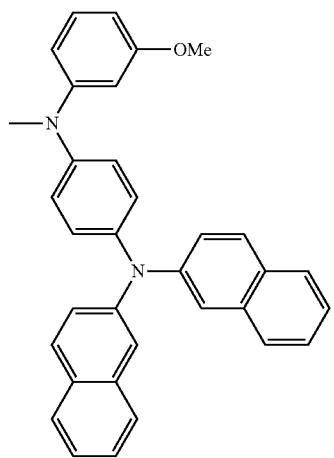
116
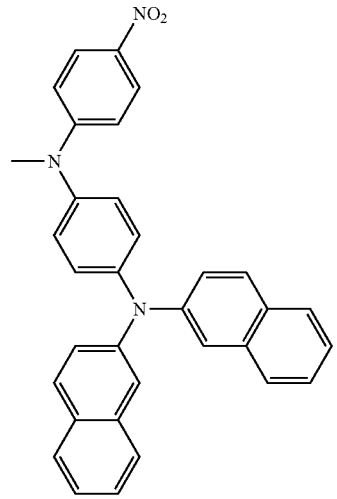
117
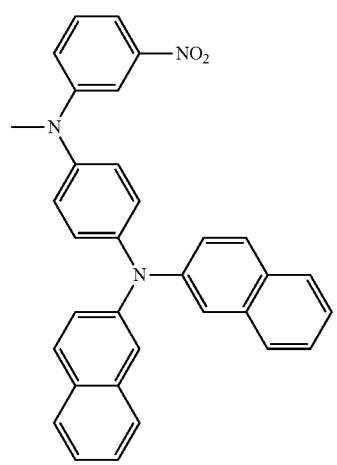
118
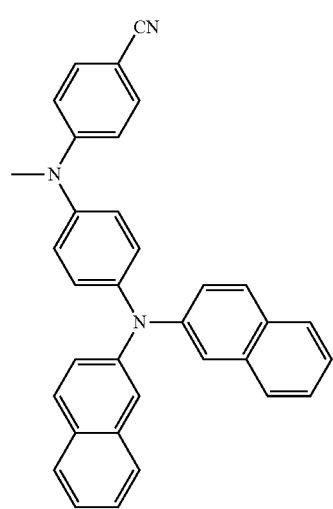

119 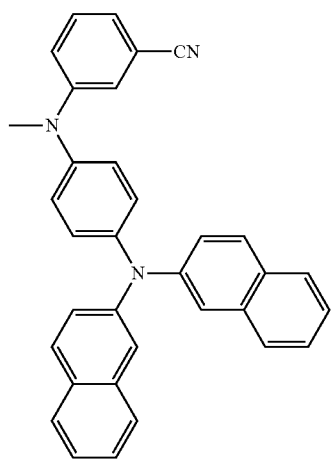
120 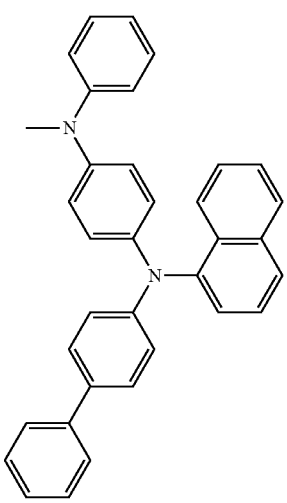
121 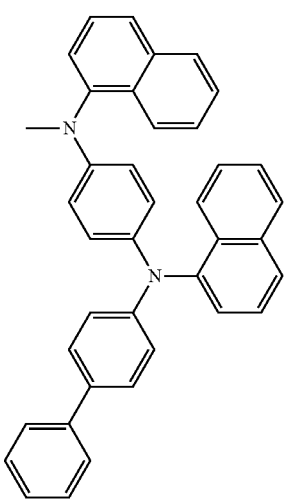
122 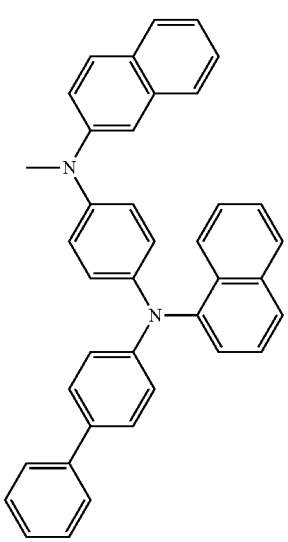
123 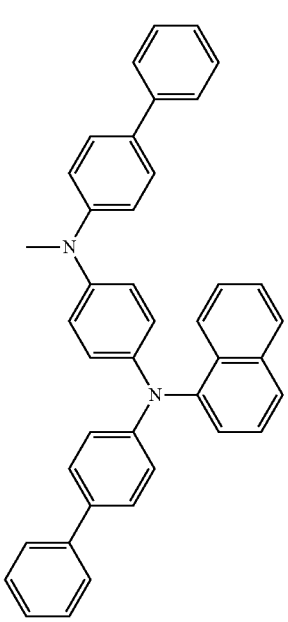
124 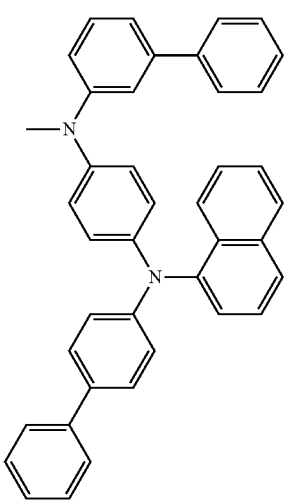

125
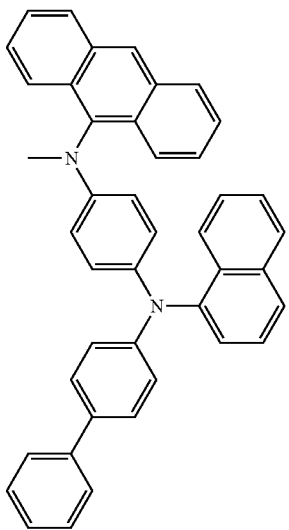
126
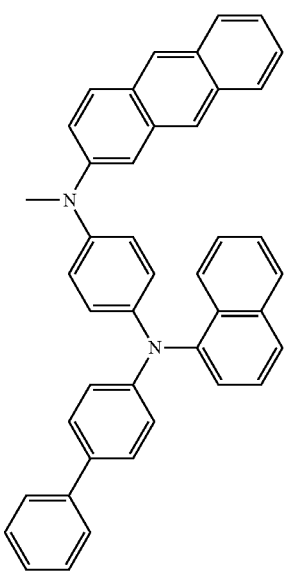
127
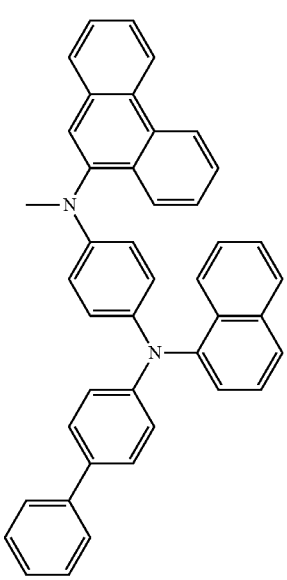
128
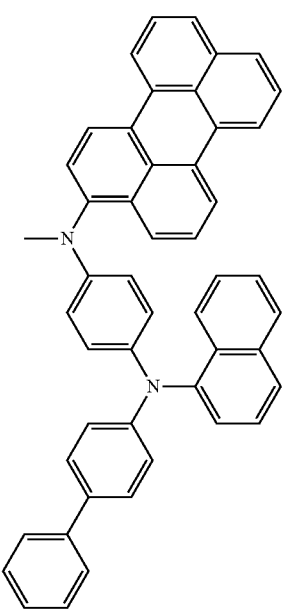
129
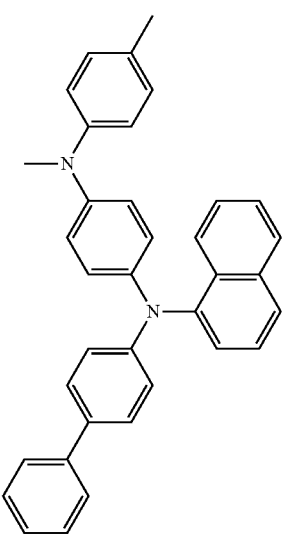
130
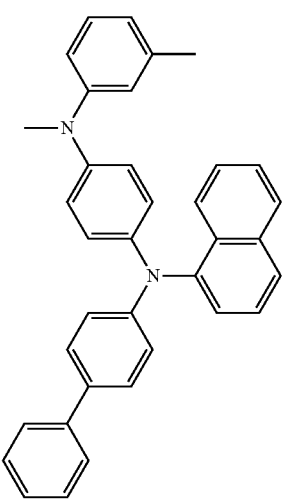

131 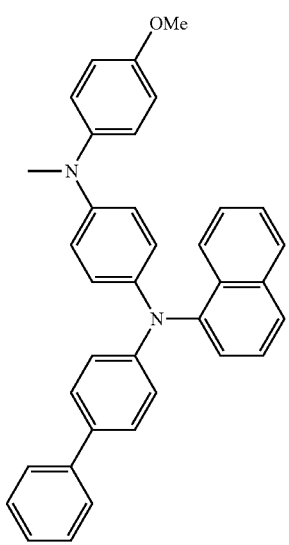
132 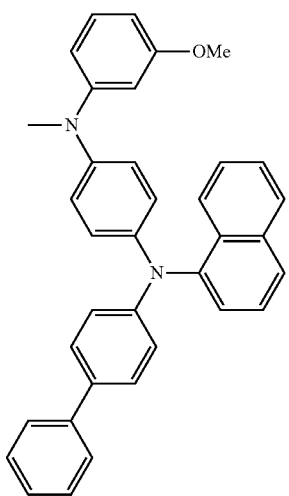
133 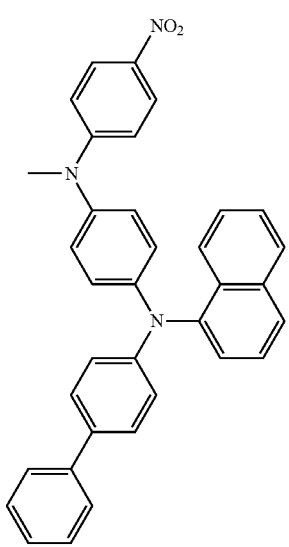
134 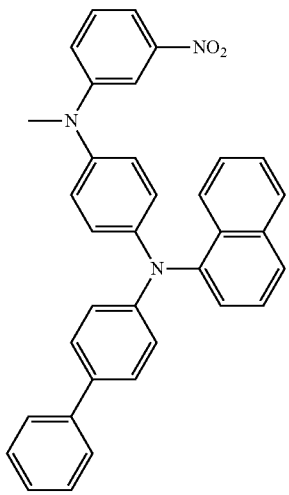
135 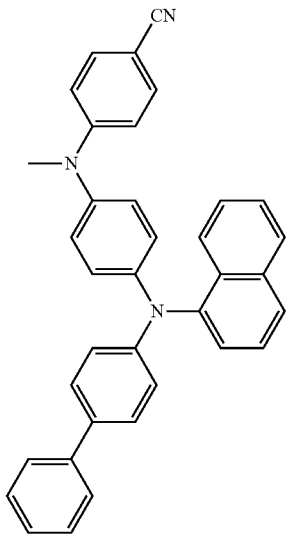
136 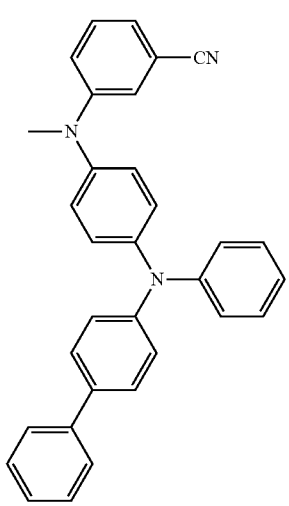

137
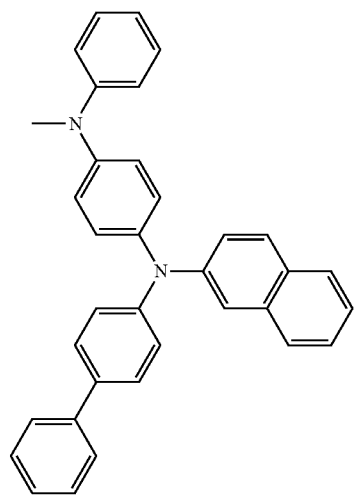
138
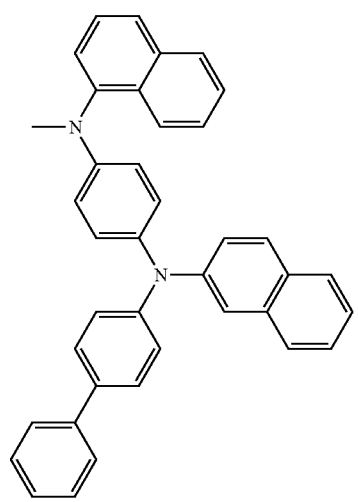
139
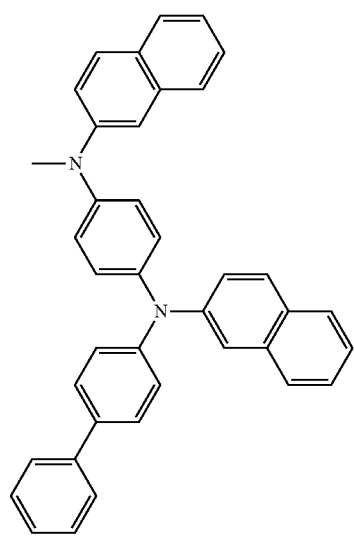
140
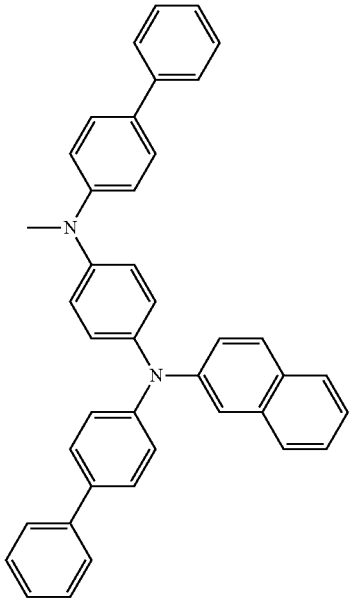
141
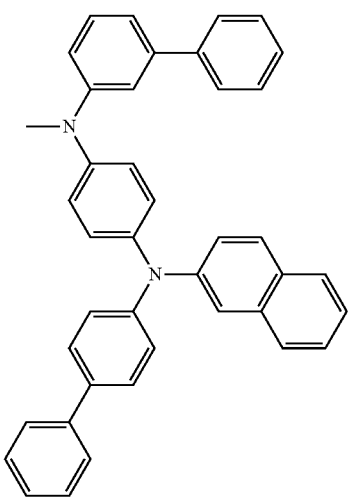
142
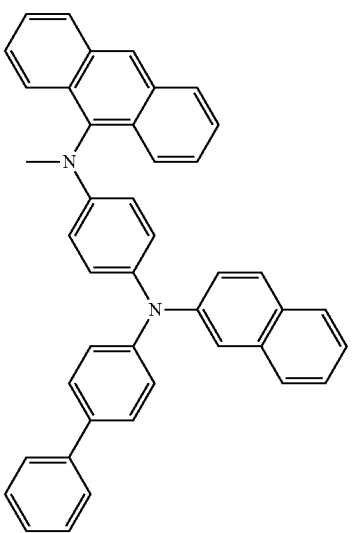

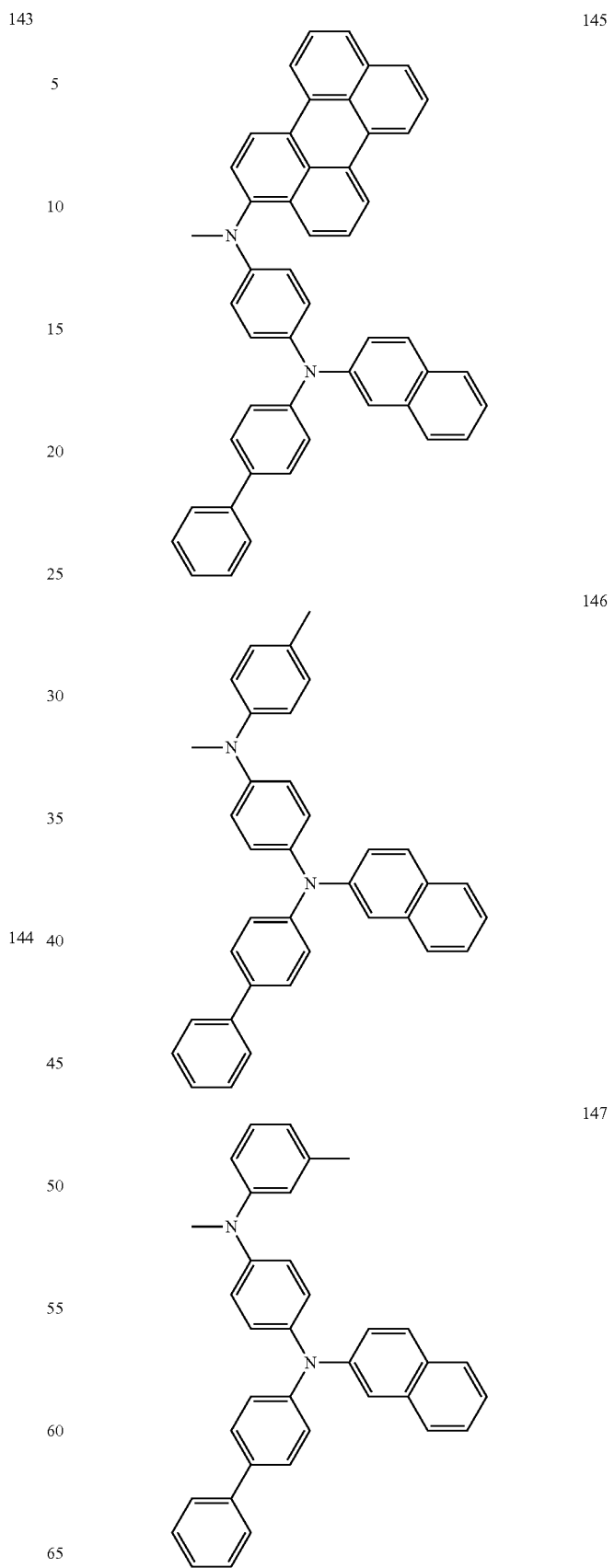

148
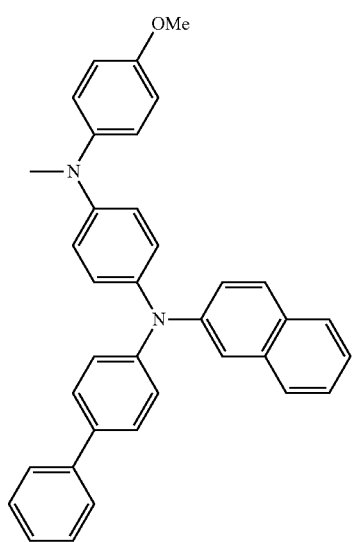
149
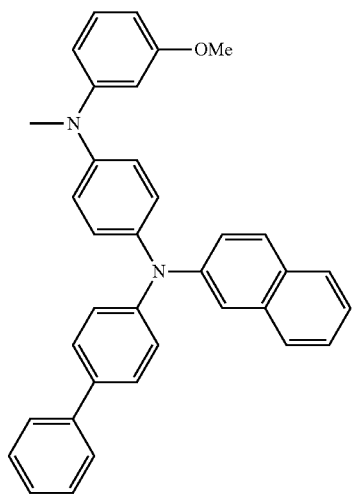
150
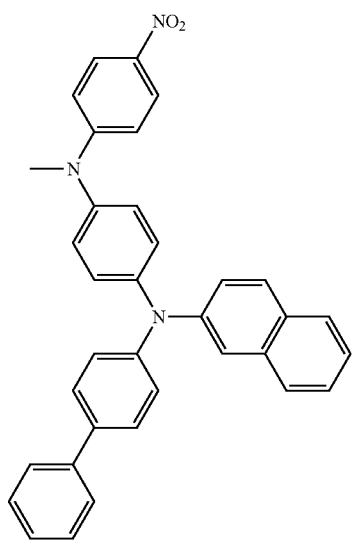
151
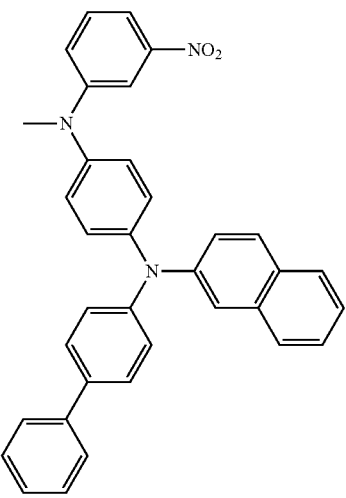
152
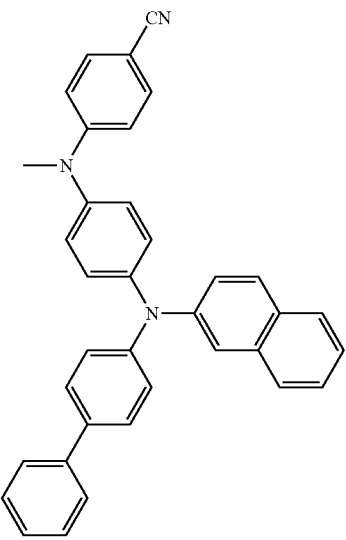
153
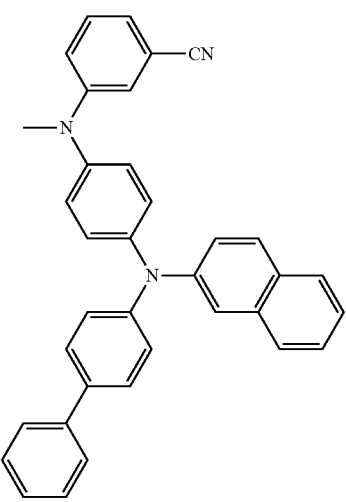

154
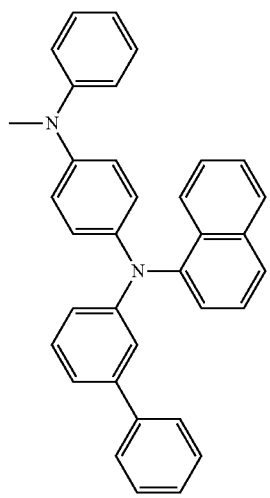
155
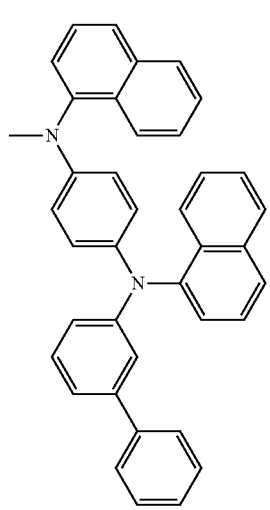
156
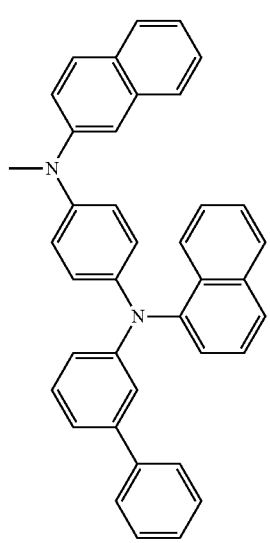
157
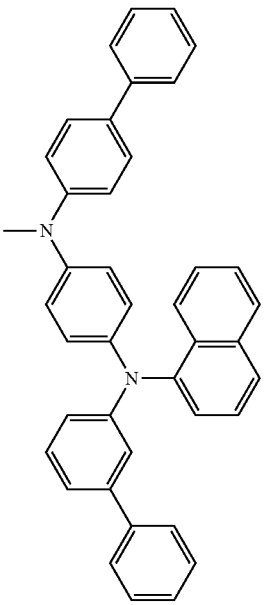
158
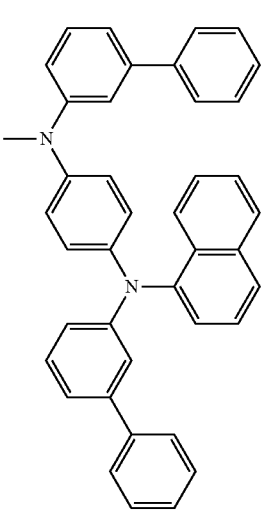
159
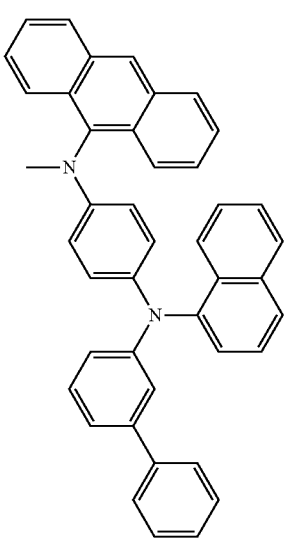

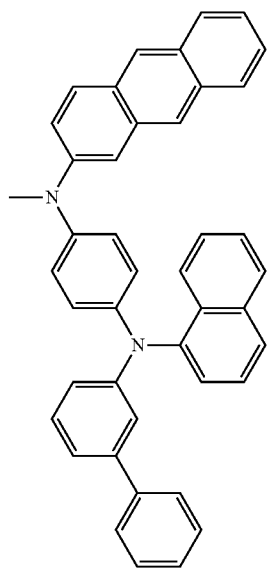
160
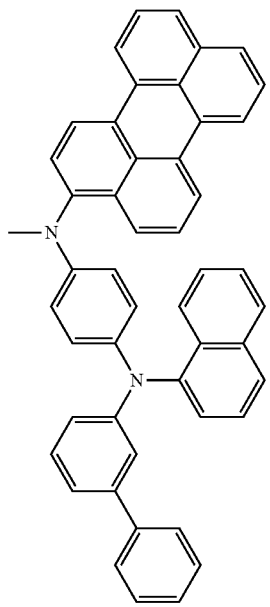
162
161
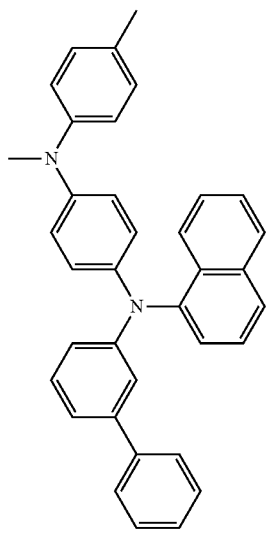
163
164
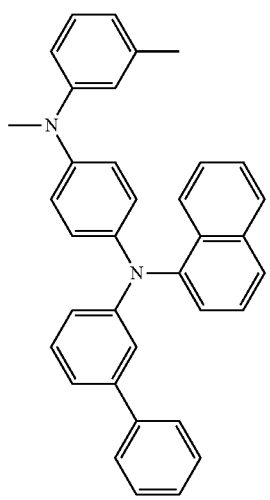

165 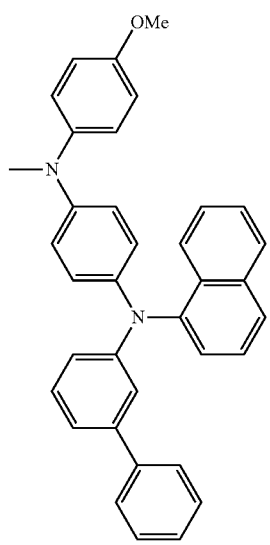
166 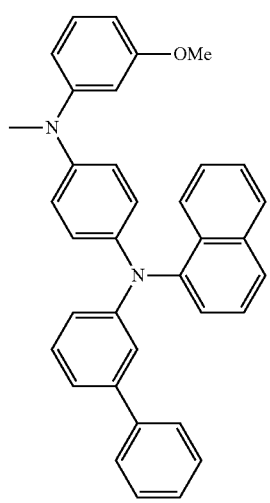
167 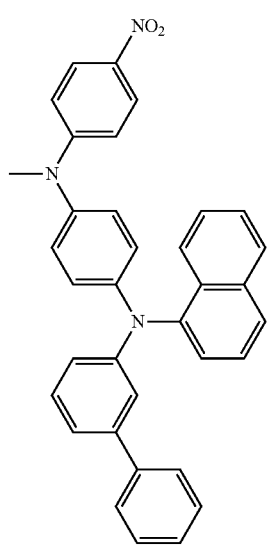
168 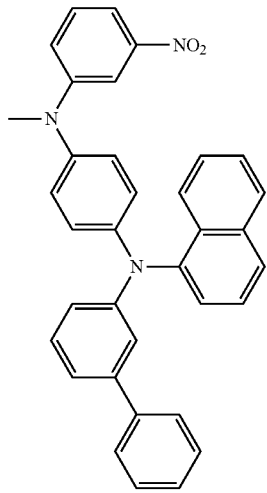
169 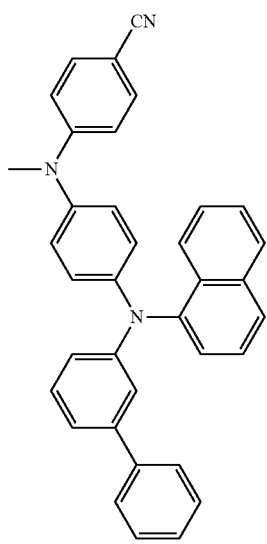
170 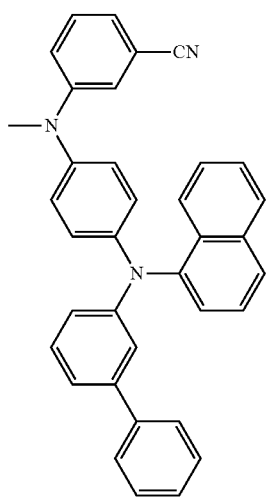

171
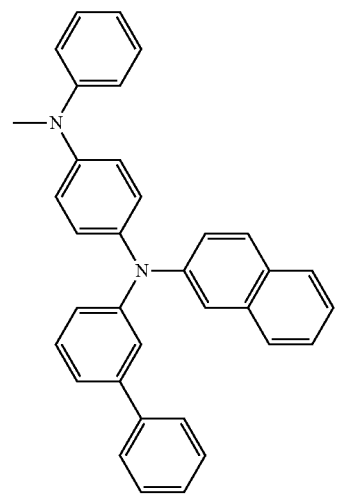
172
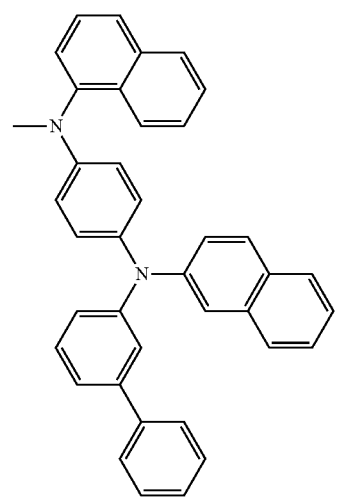
173
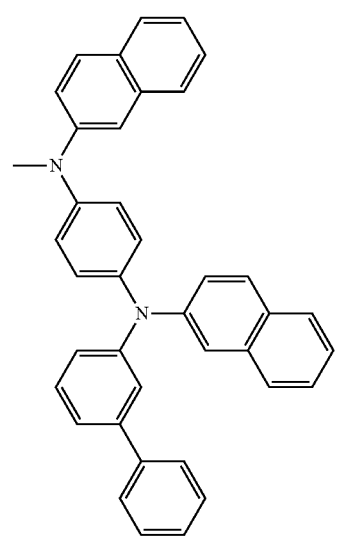
174
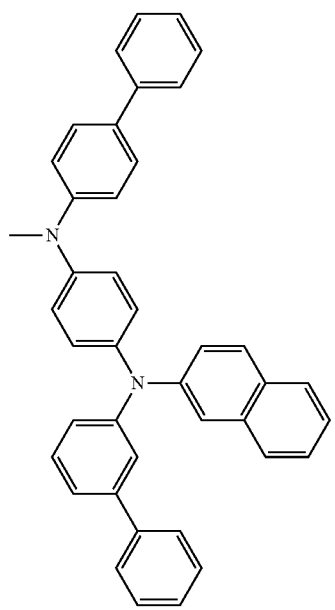
175
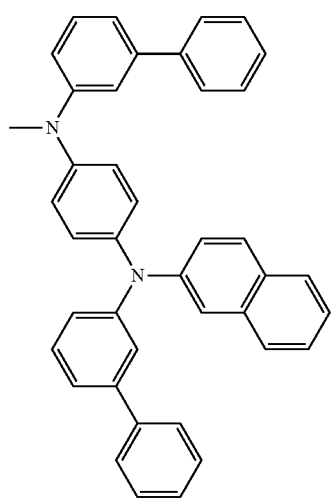
176
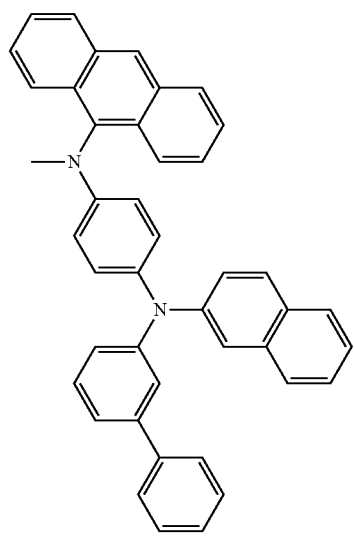

177
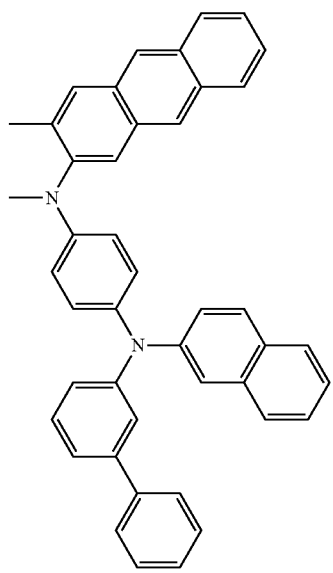
178
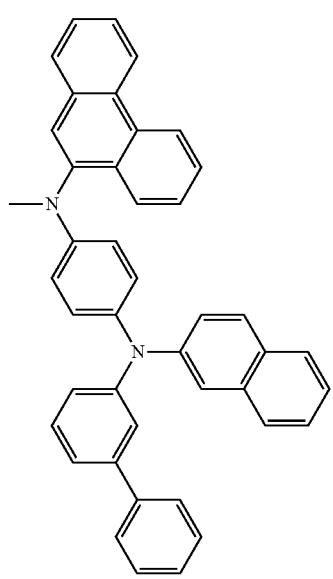
179
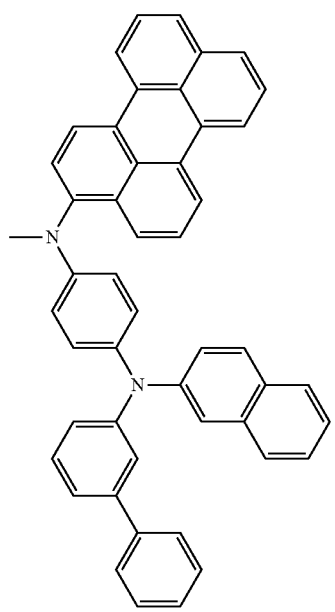
180
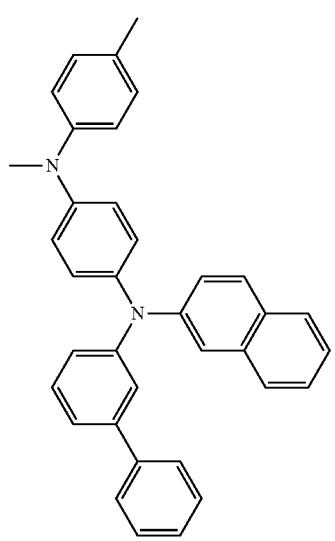
181
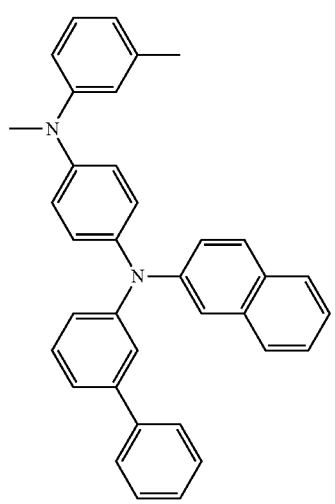

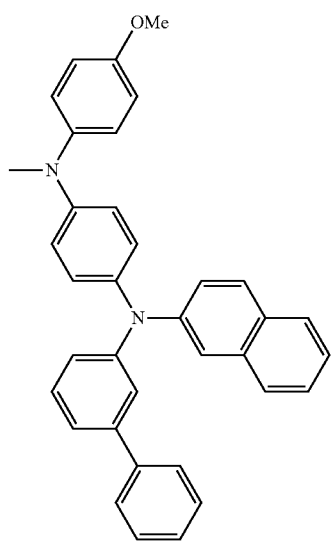
182
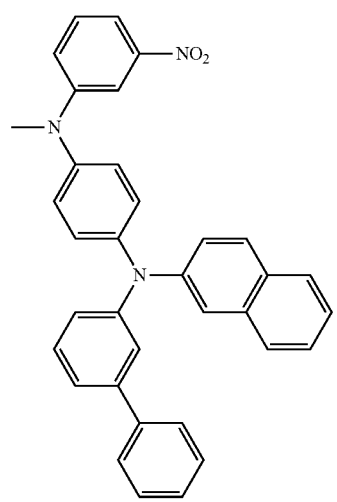
185
183
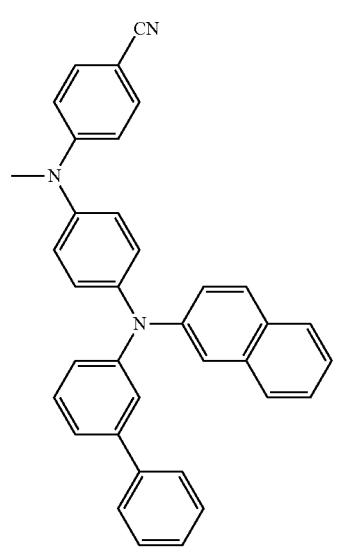
186
184
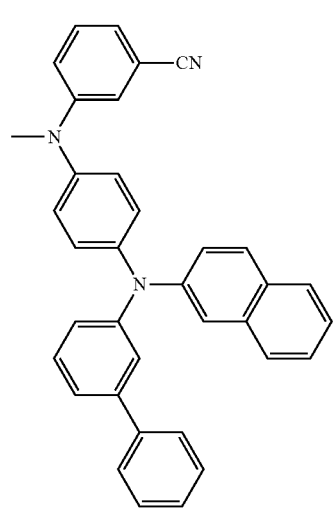
187

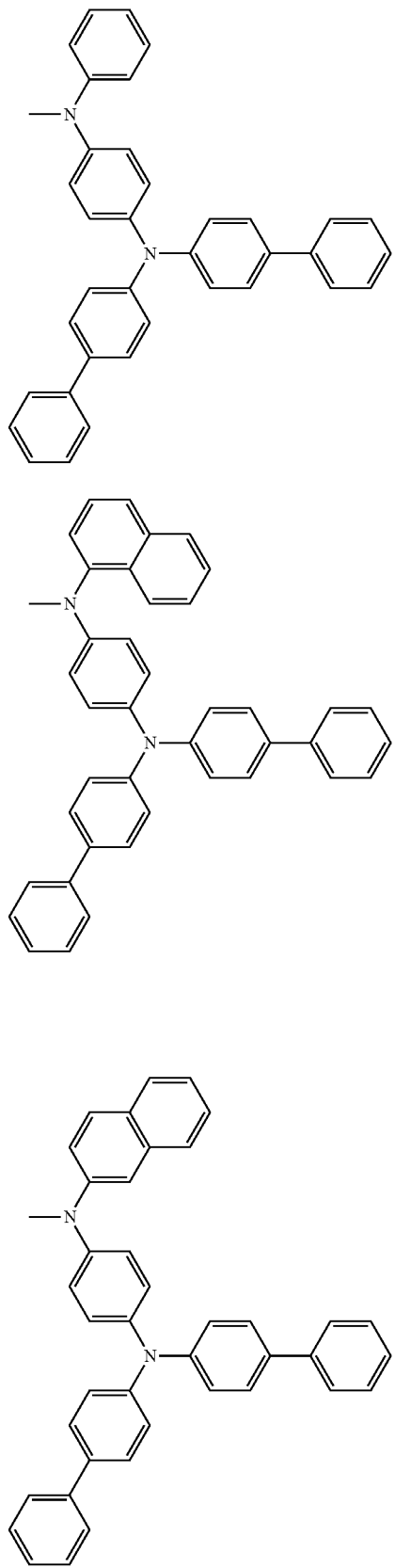
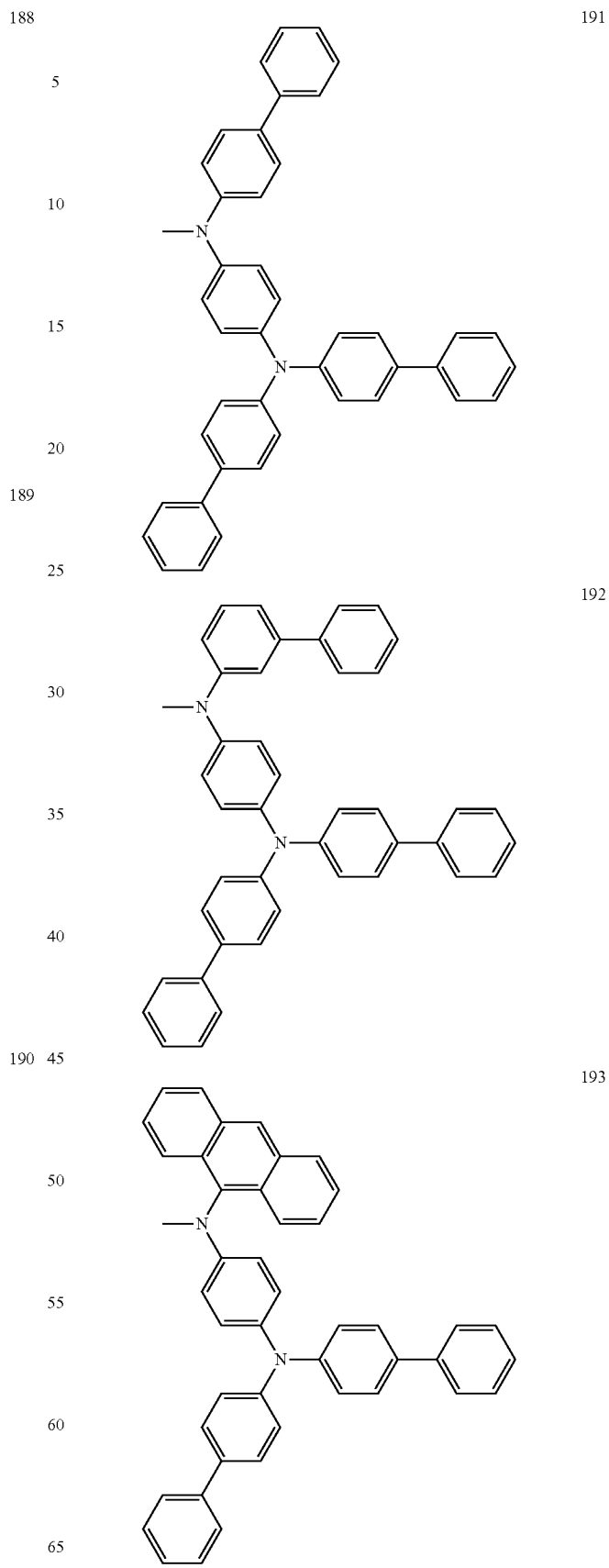

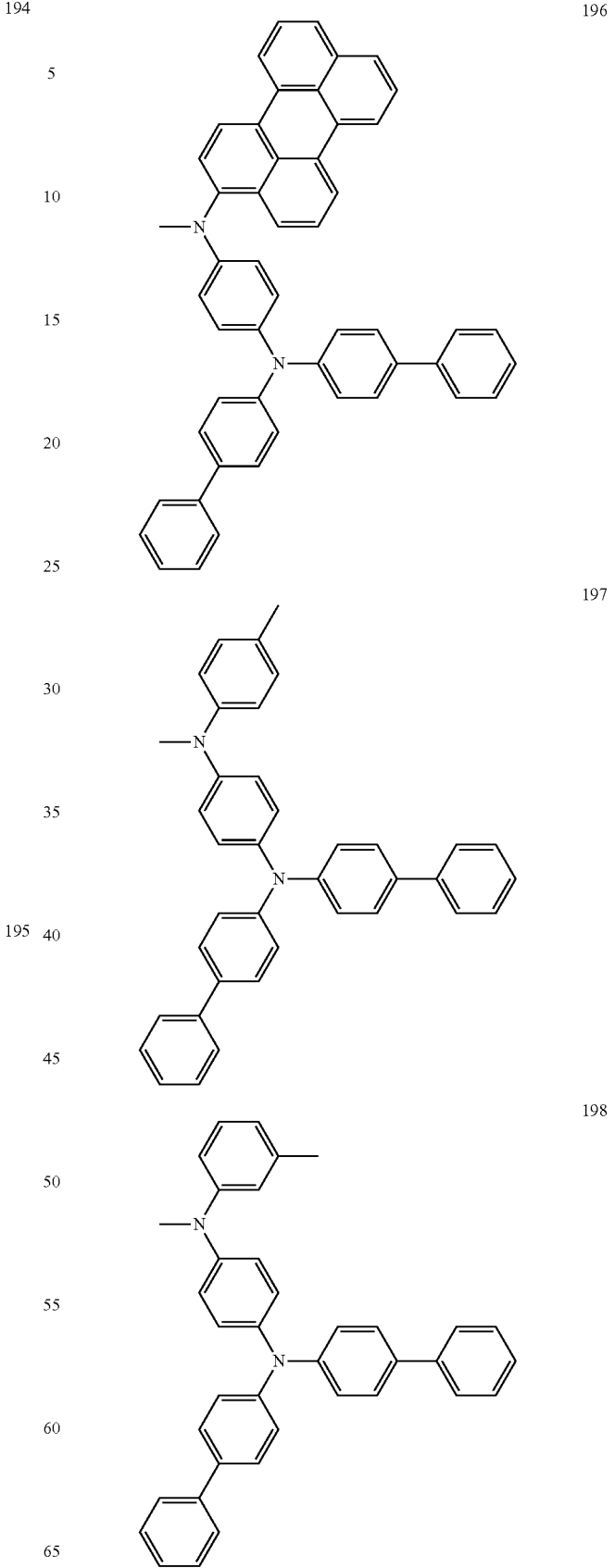

199
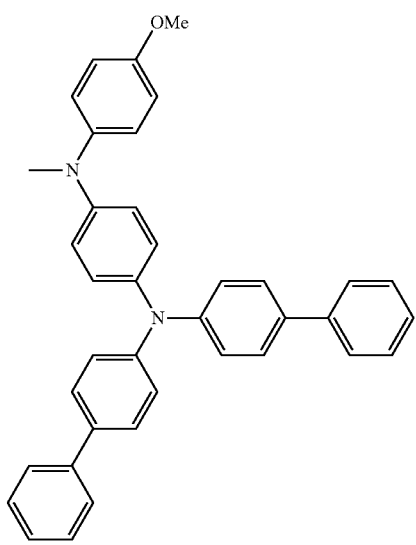
200
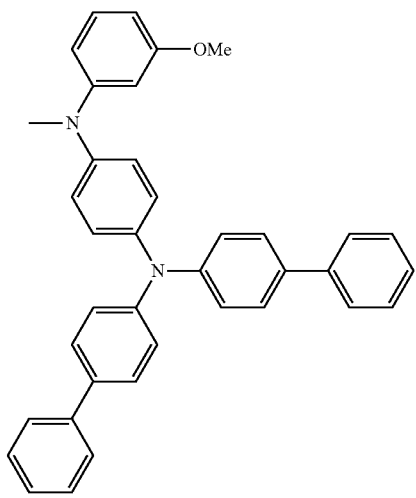
201
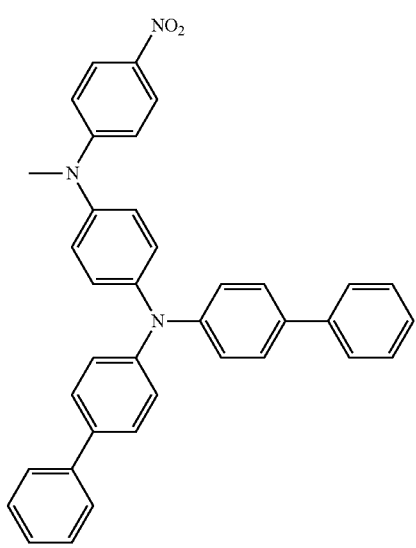
202
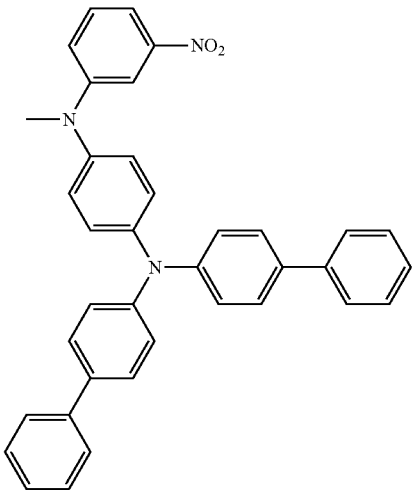
203
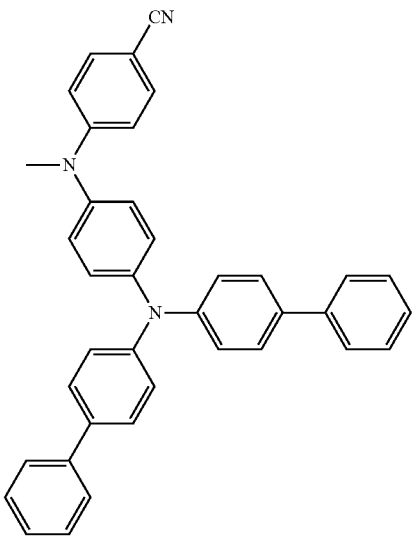
204
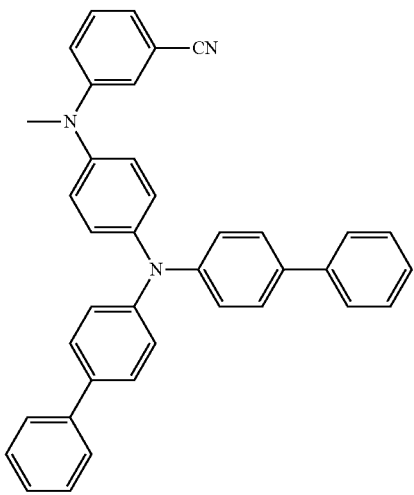

91
-continued
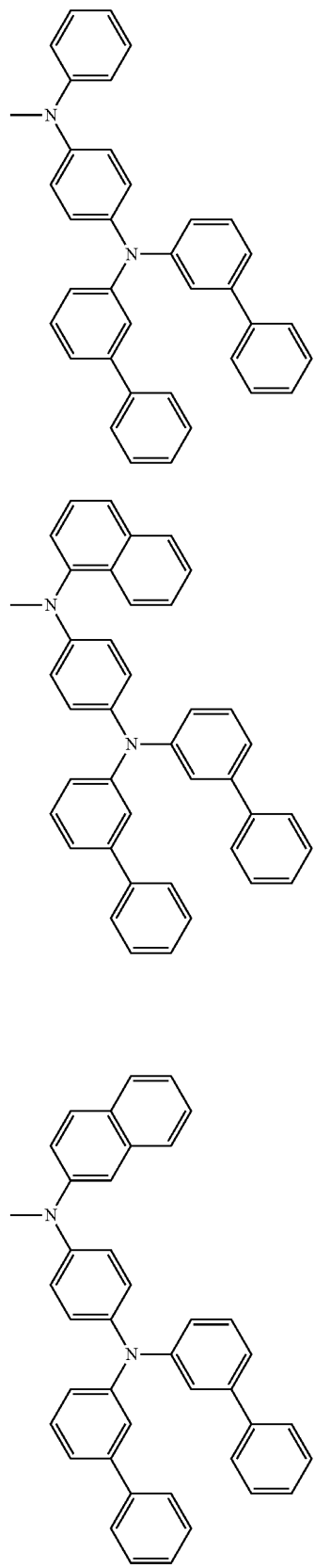
205
206
207
92
-continued
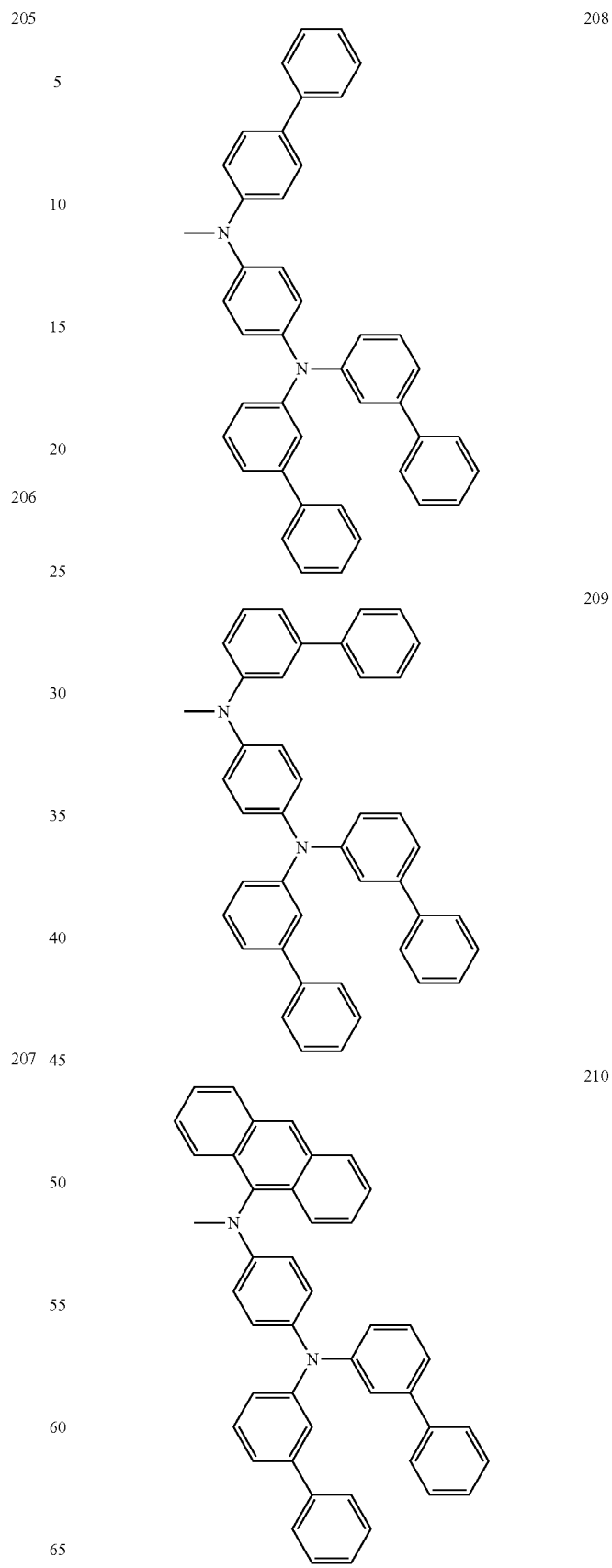
208
209
210

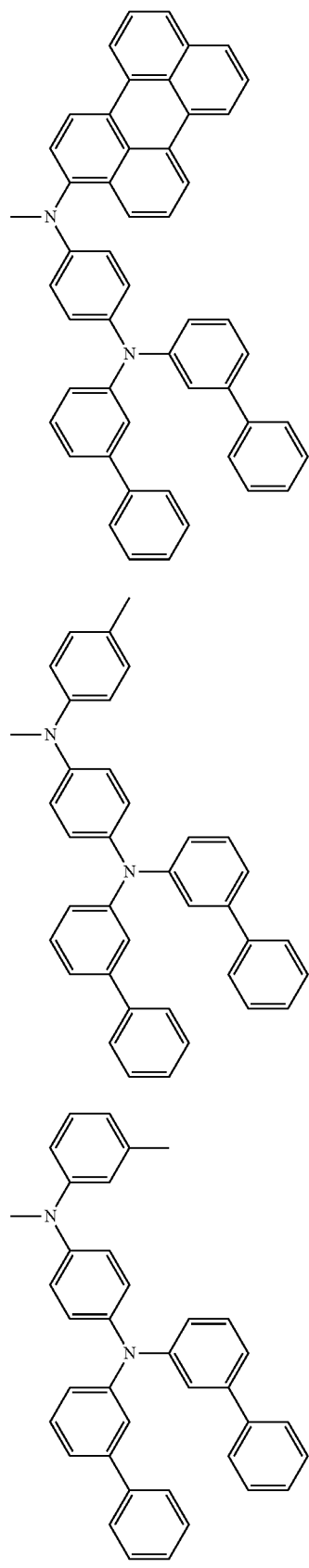

216
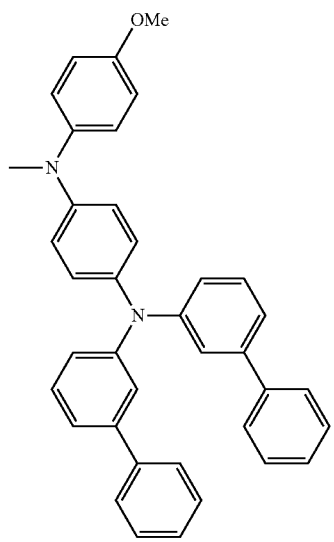
217
218
219
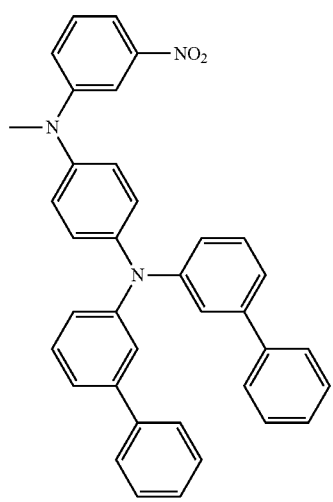
220
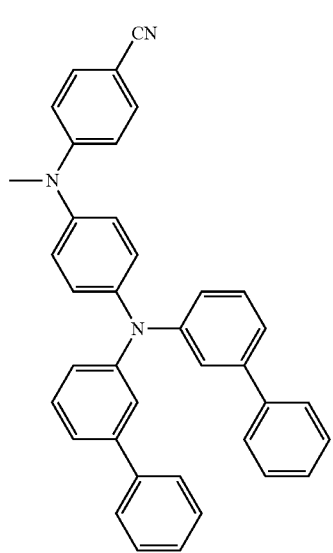
221
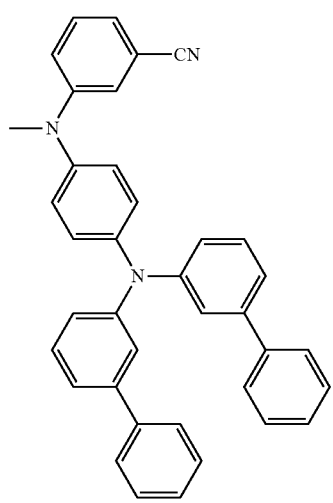

222
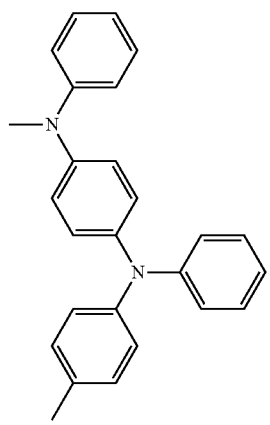
223
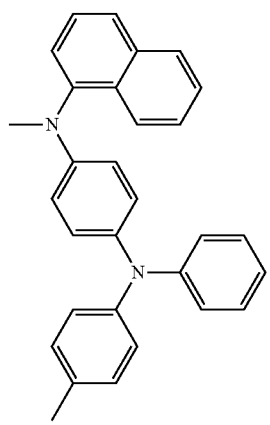
224
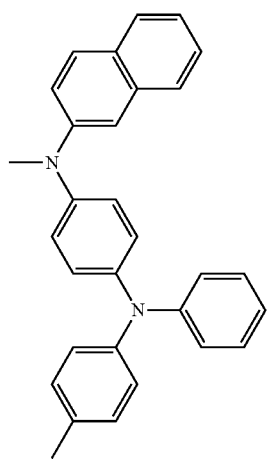
225
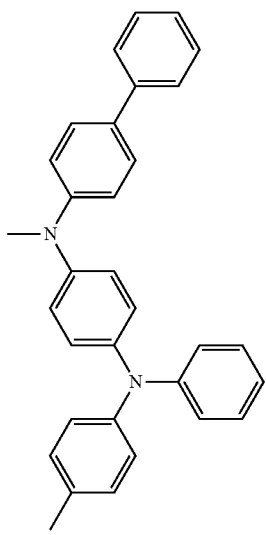
226
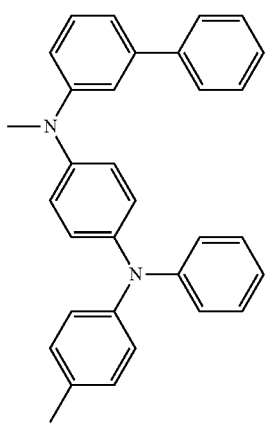
227
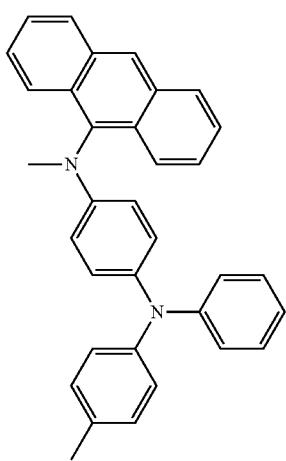

228
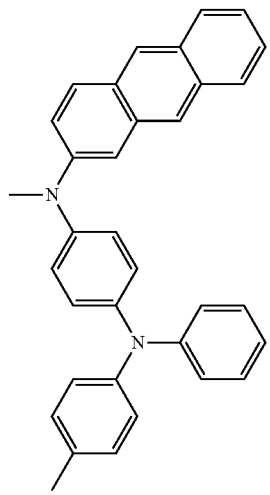
229
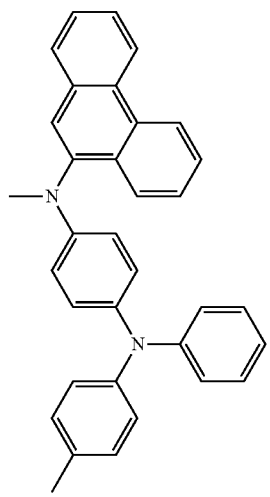
230
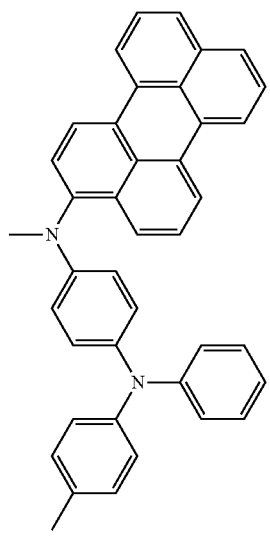
231
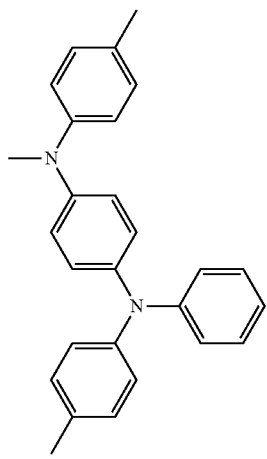
232
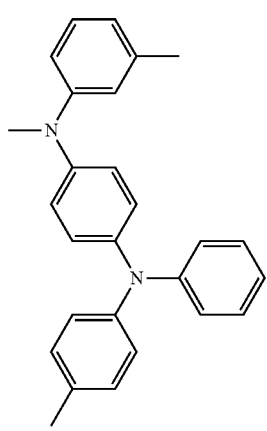
233
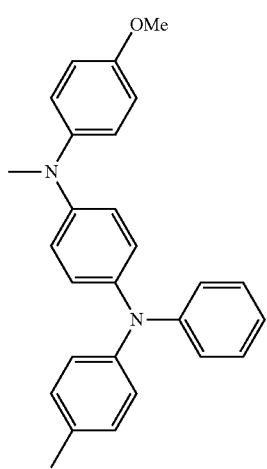

101
-continued
234
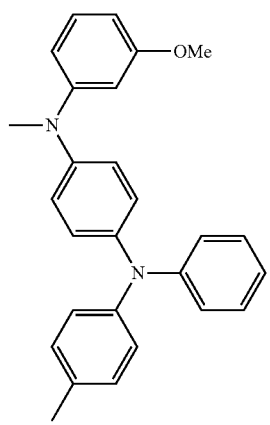
235
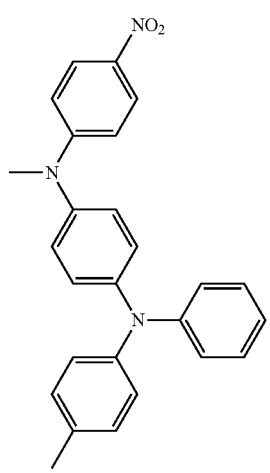
236
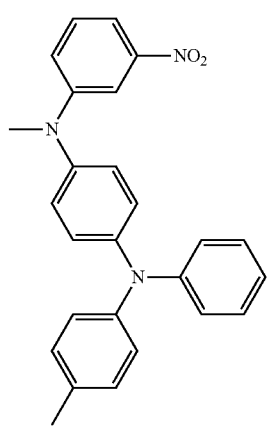
102
-continued
237
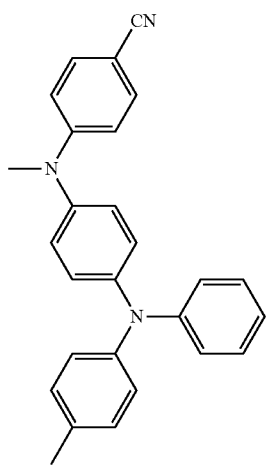
238
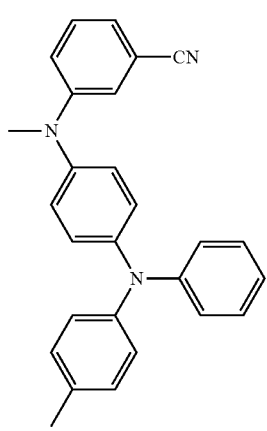
239
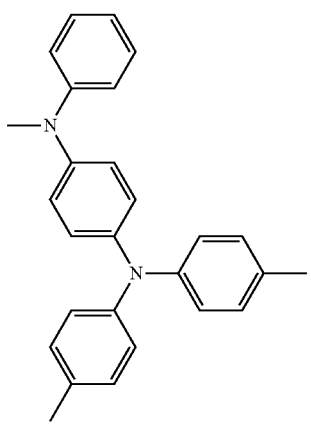

240
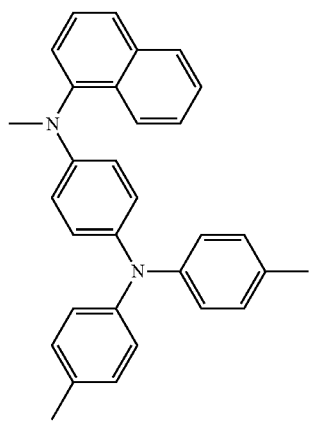
241
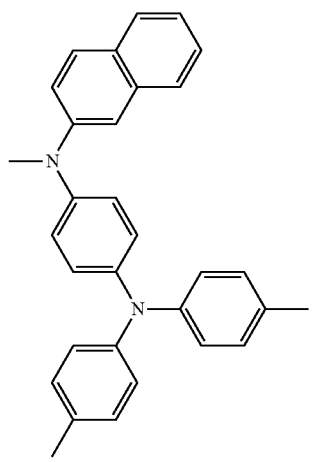
242
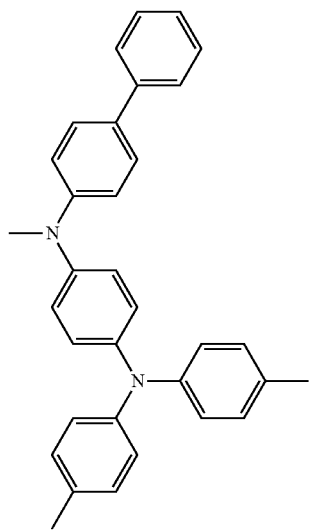
243
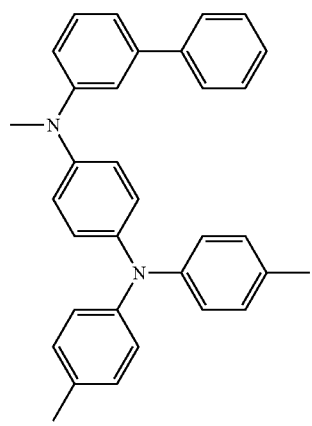
244
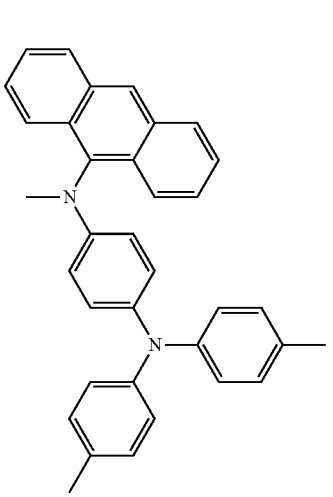
245
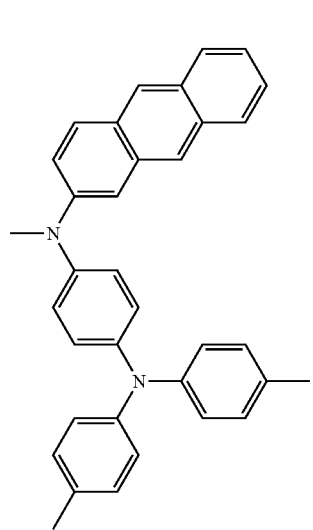

246
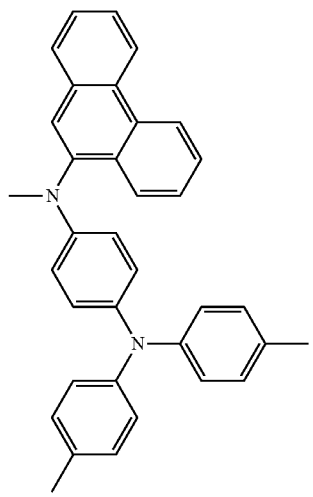
247
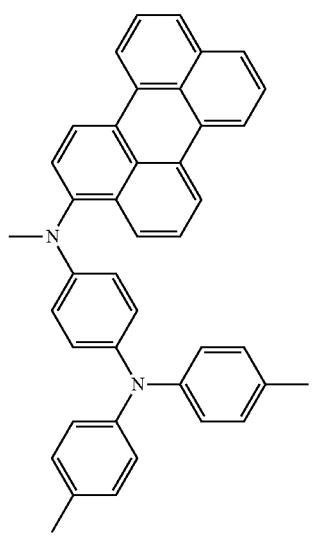
248
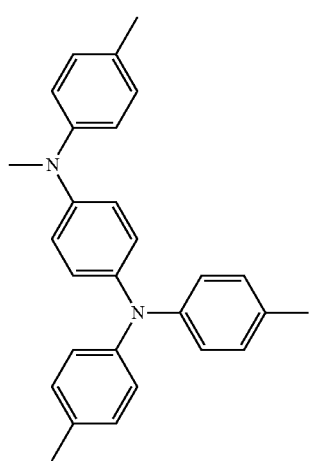
249
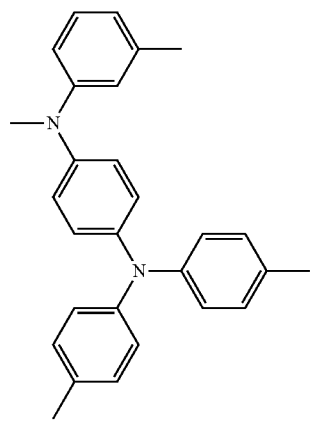
250
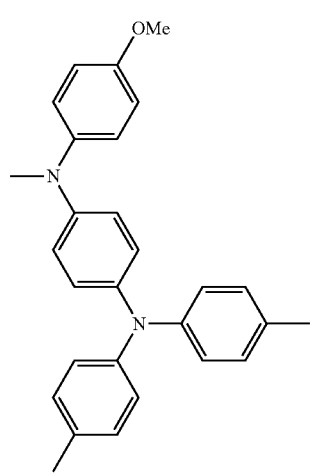
251
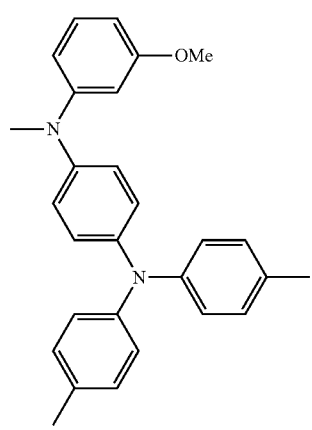

252
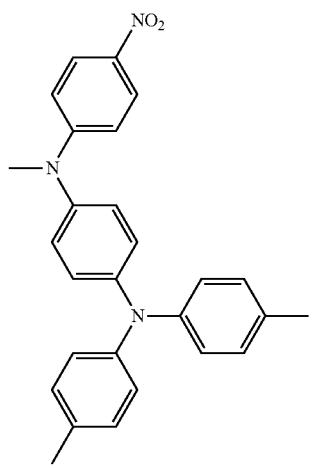
253
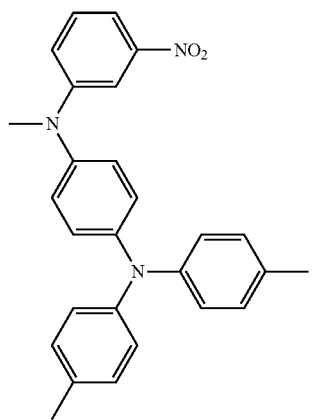
254
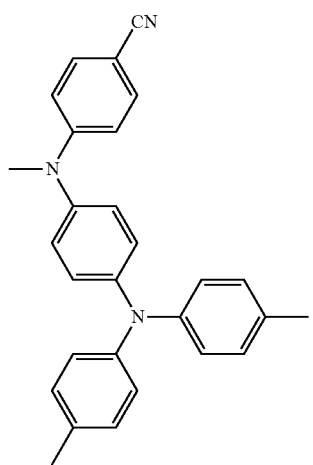
255
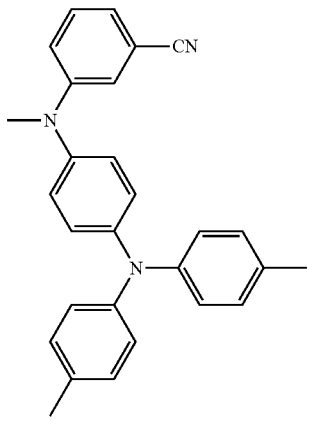
256
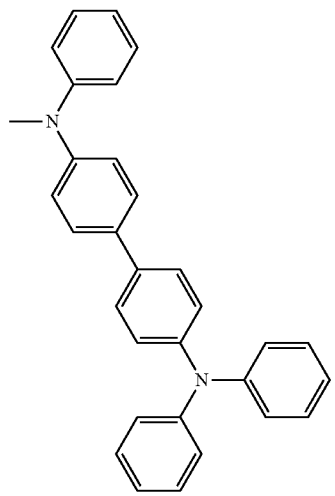
257
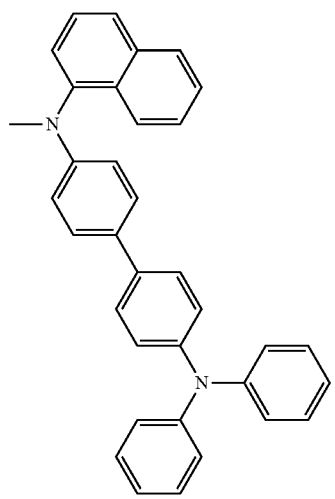

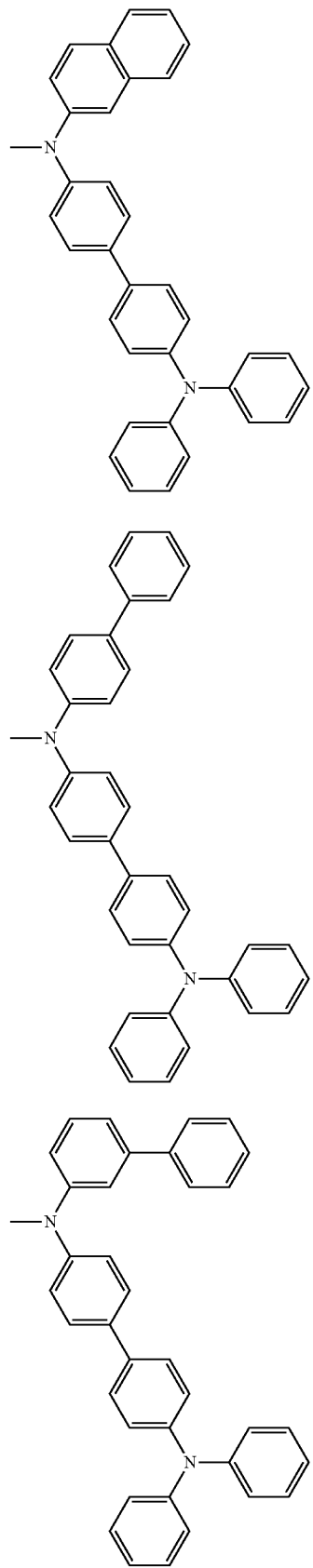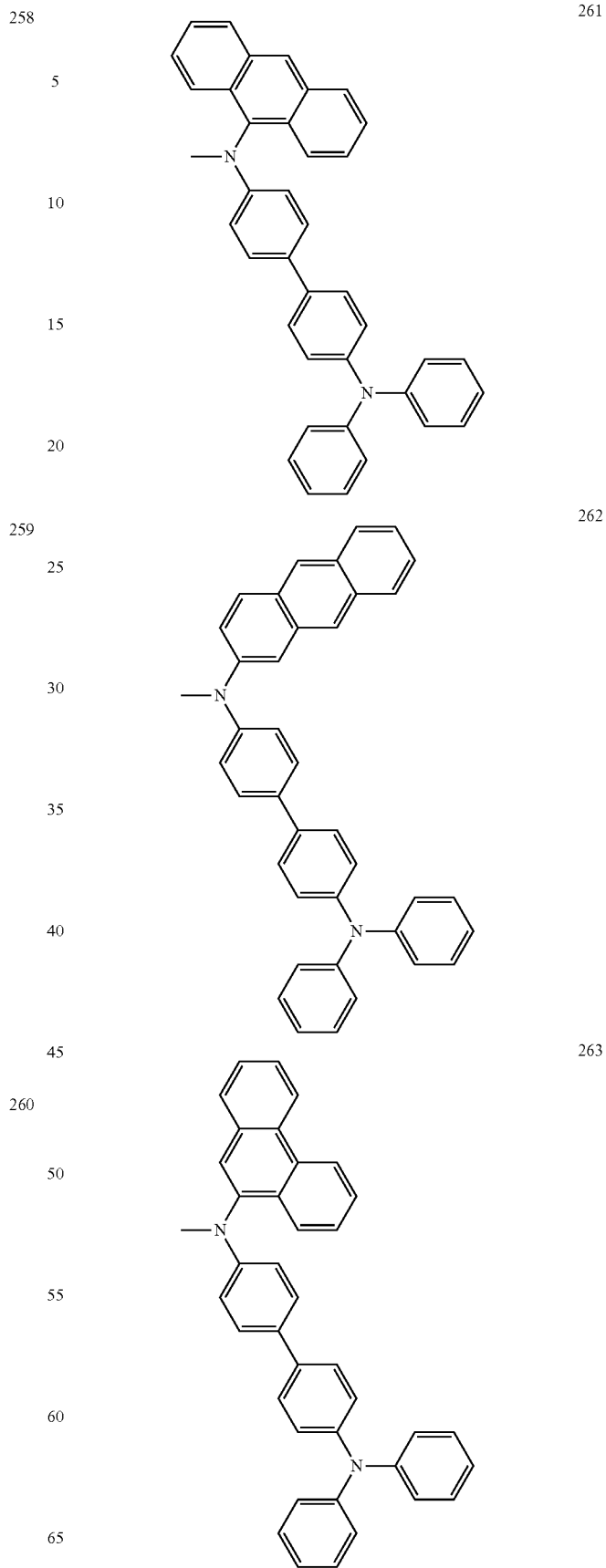

264
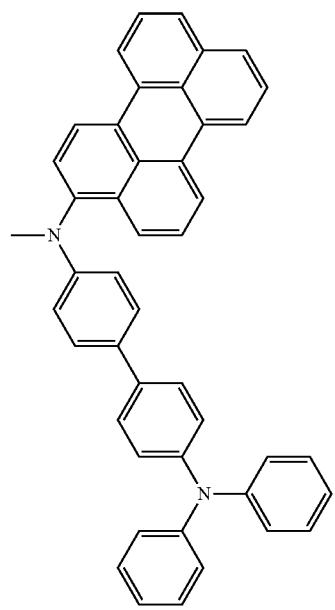
265
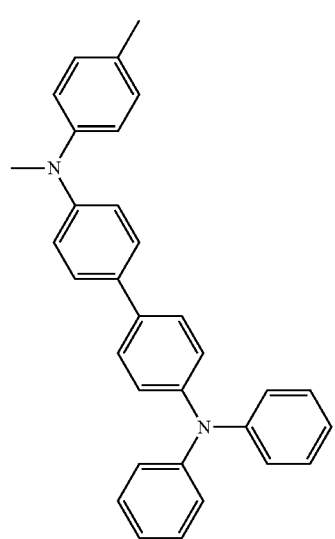
266
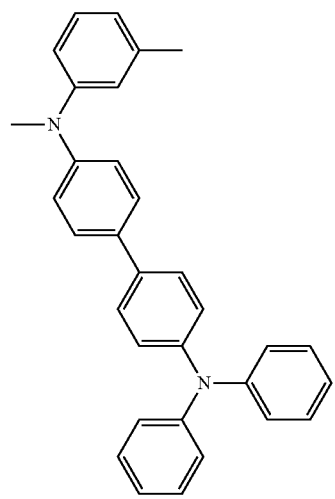
267
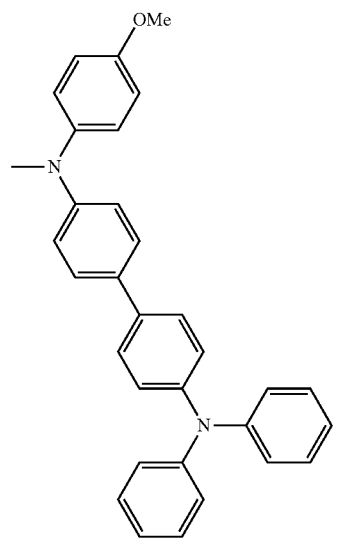
268
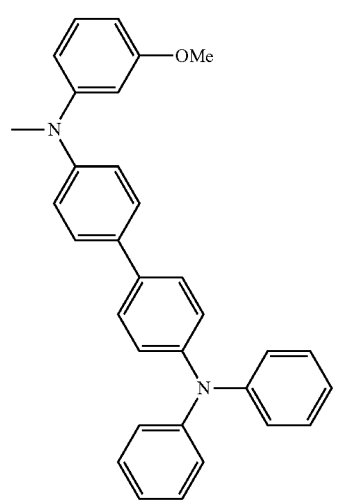
269
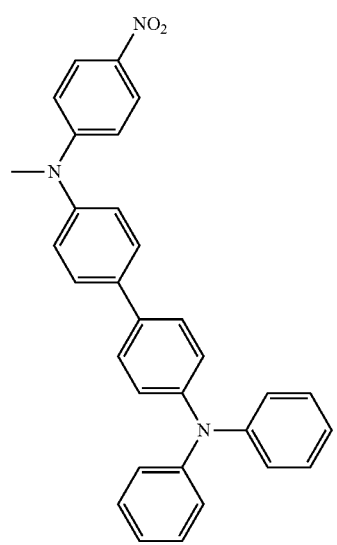

270
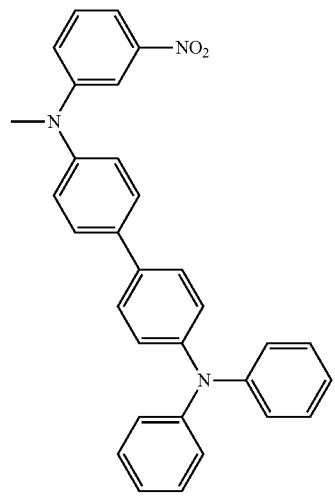
271
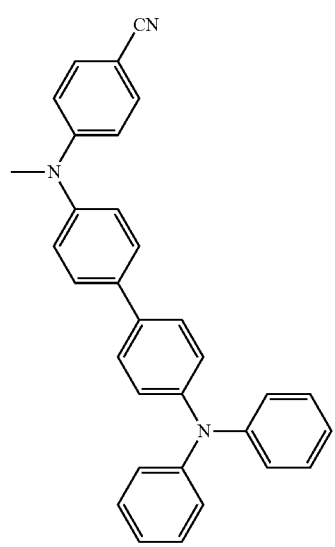
272
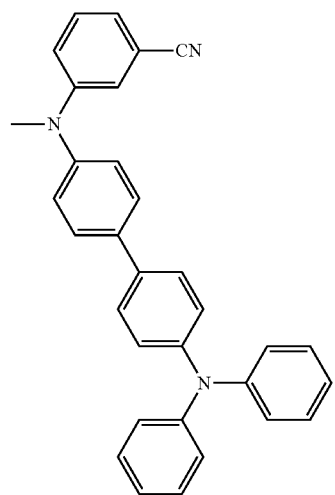
273
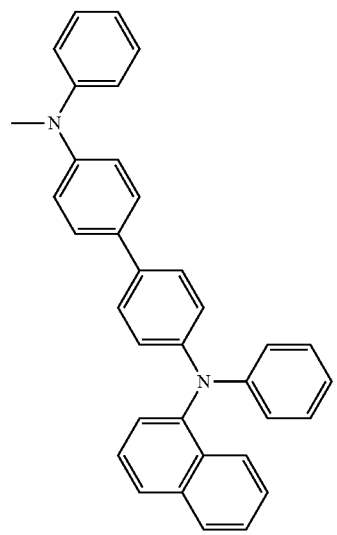
274
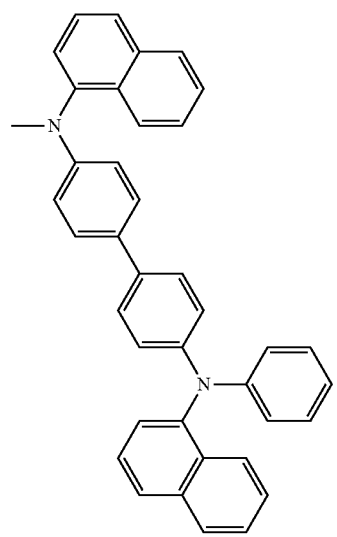
275
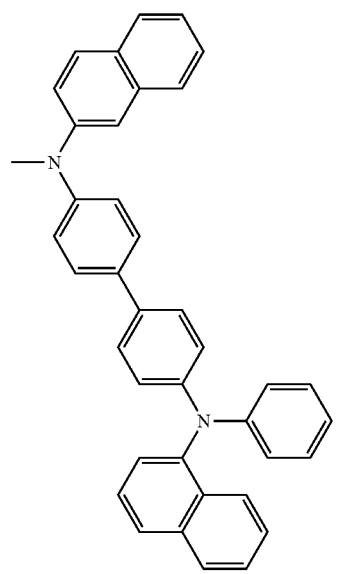

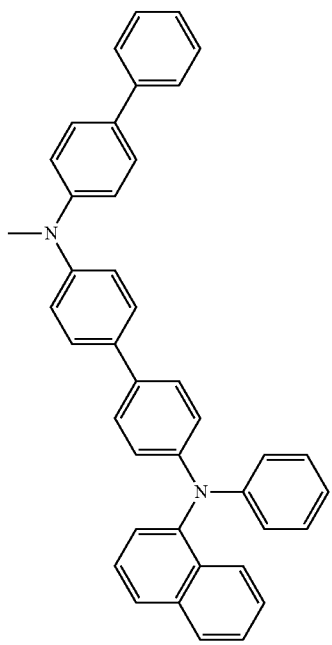
276
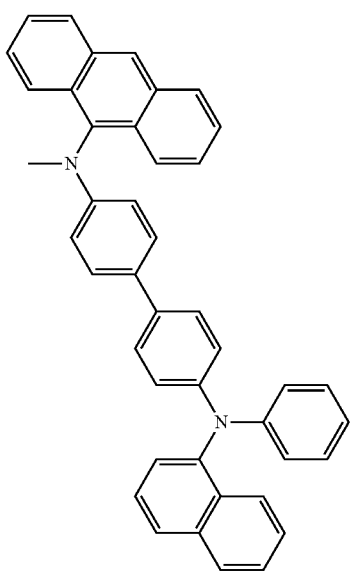
278
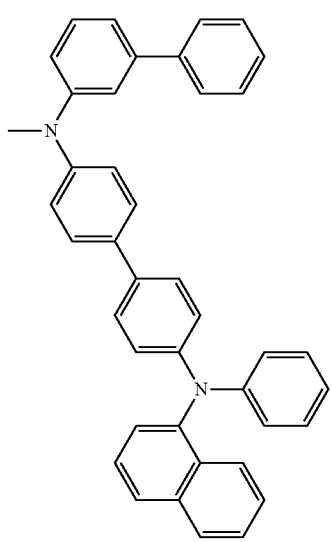
277

117
-continued
280
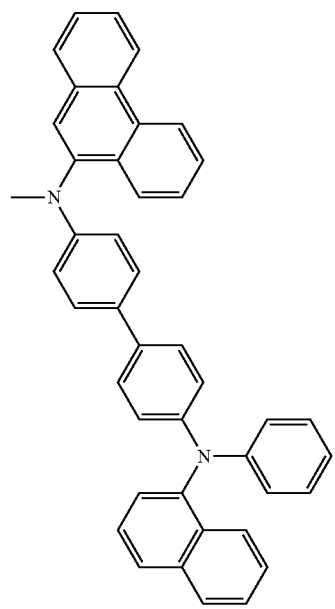
281
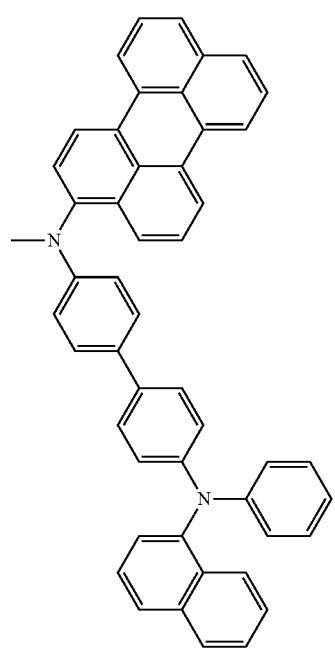
118
-continued
282
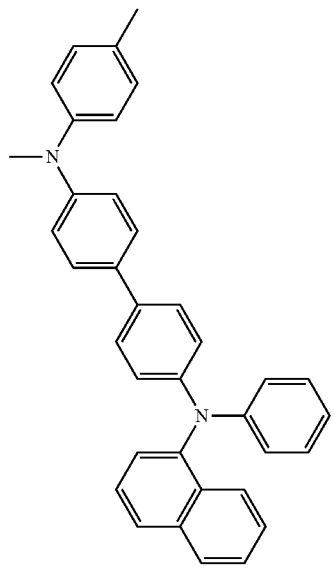
283
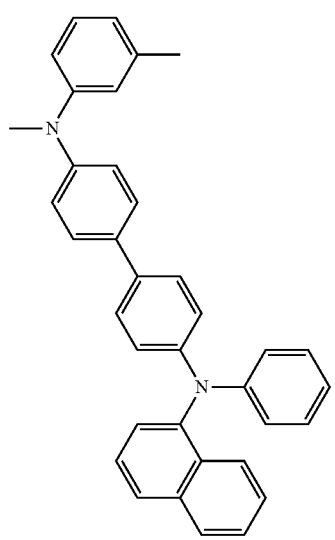
284
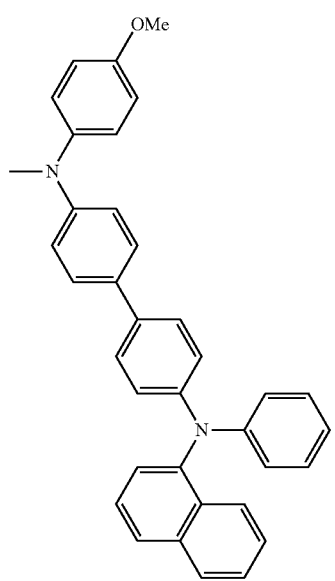

285
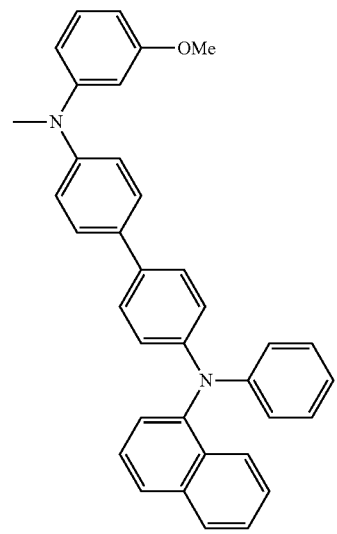
286
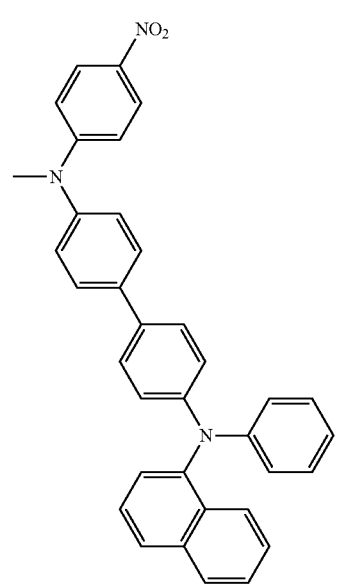
287
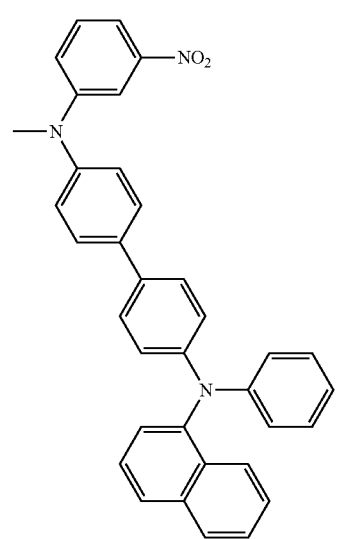
288
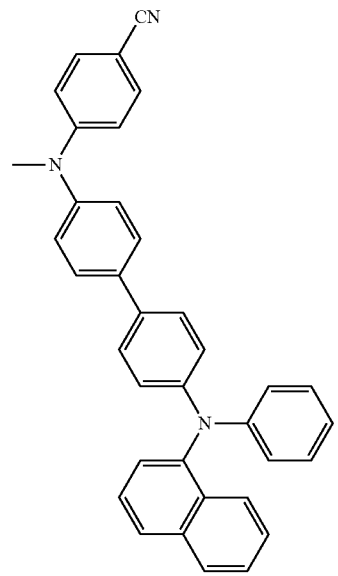
289
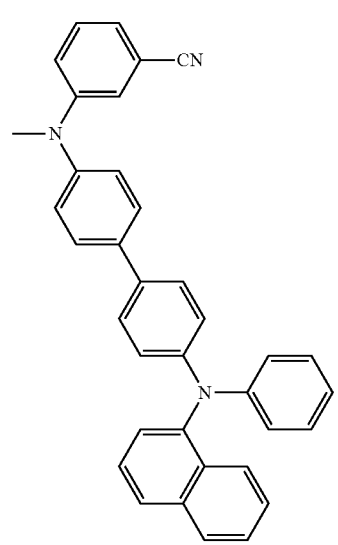
290
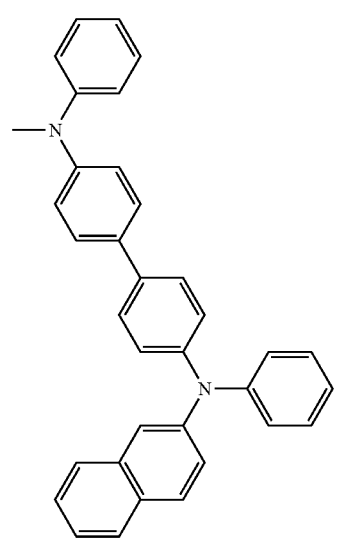

291
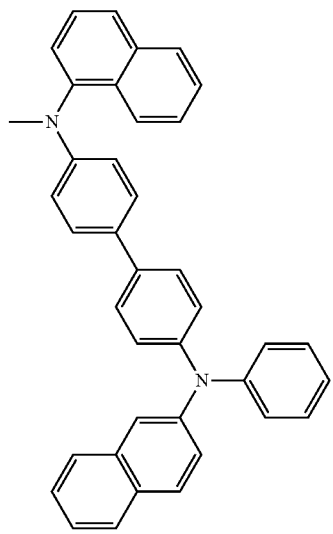
292
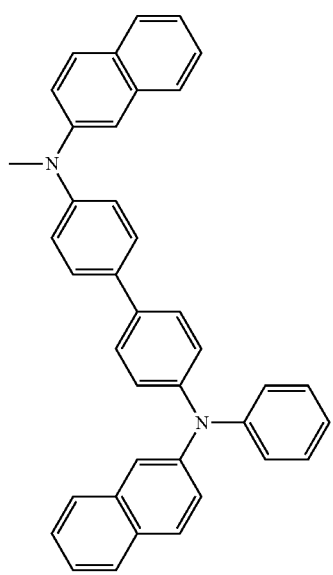
293
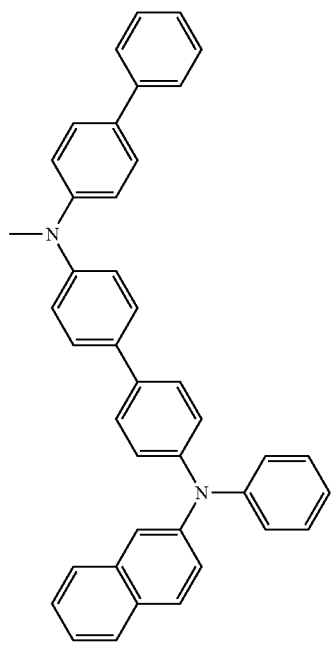
294
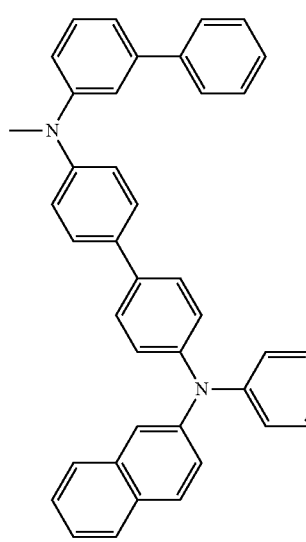

123
-continued
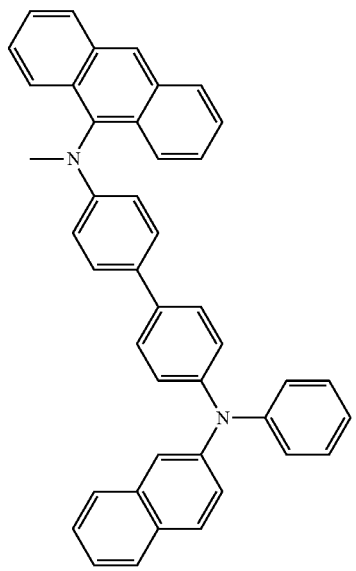
295
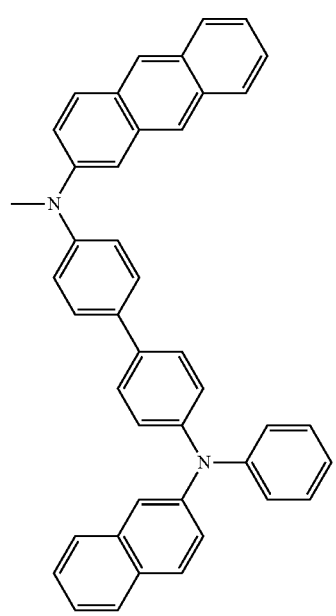
296
124
-continued
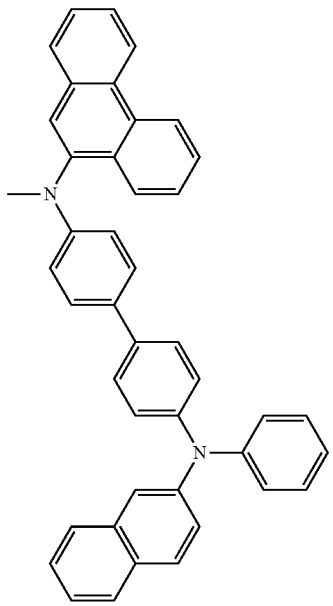
297
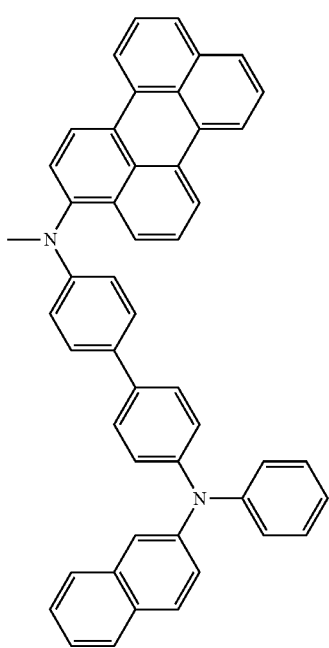
298

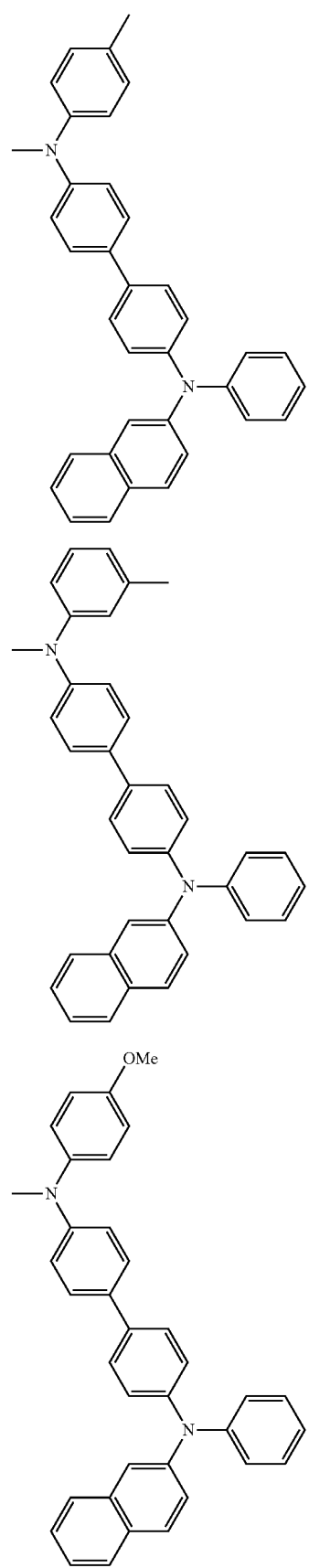
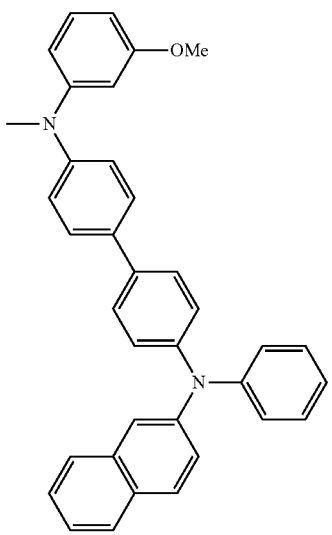
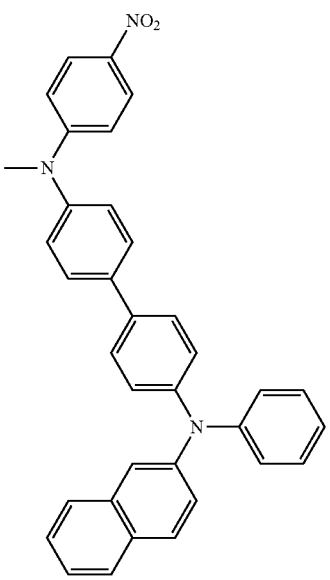

127
-continued
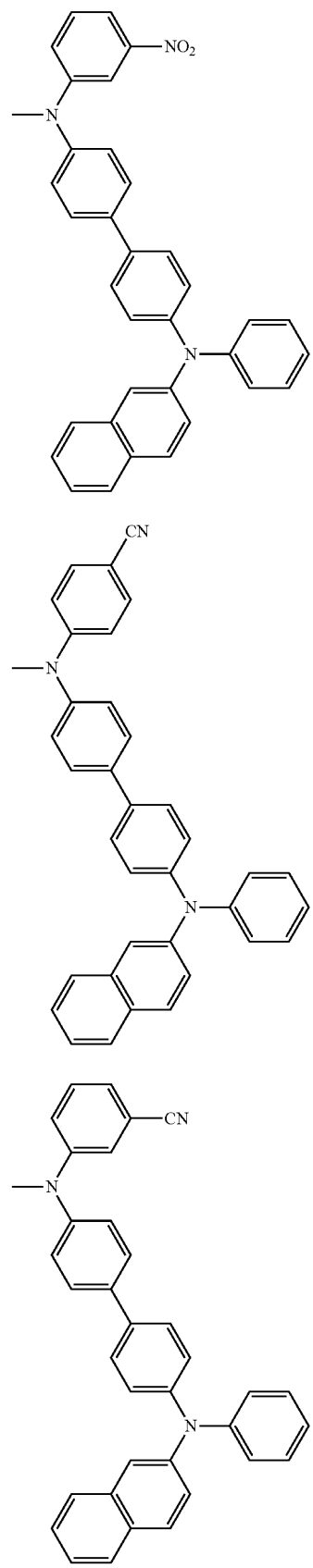
304
305
306
128
-continued
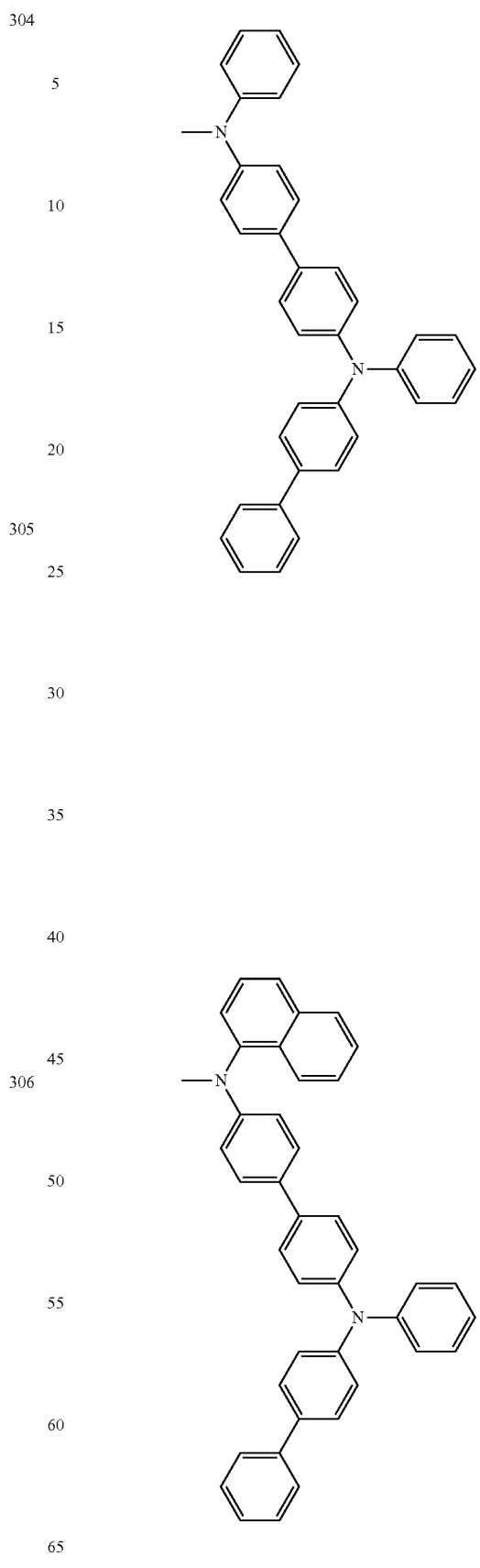
307
308

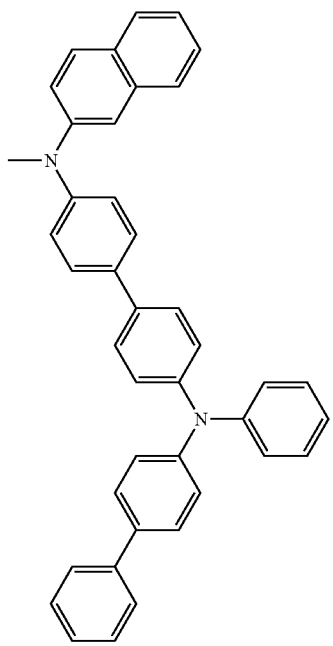
309
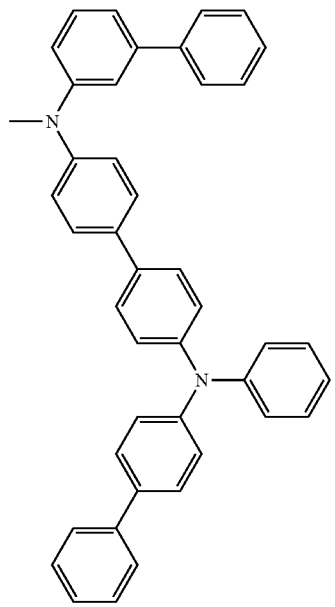
311
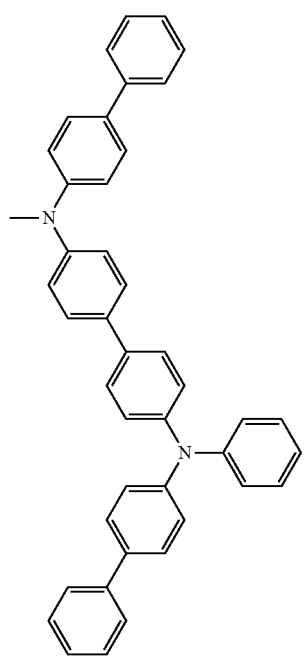
310
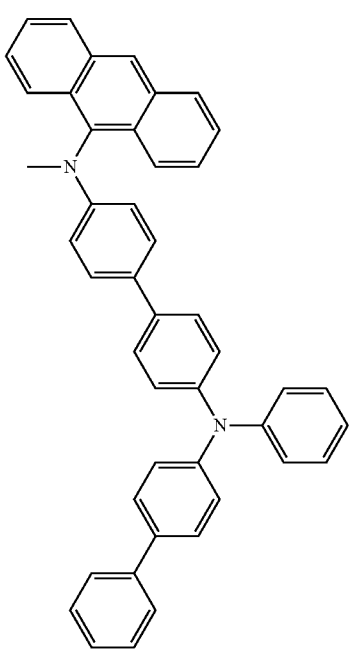
312

131
-continued
313
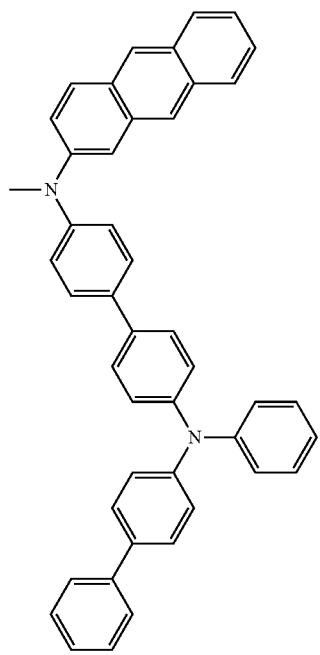
314
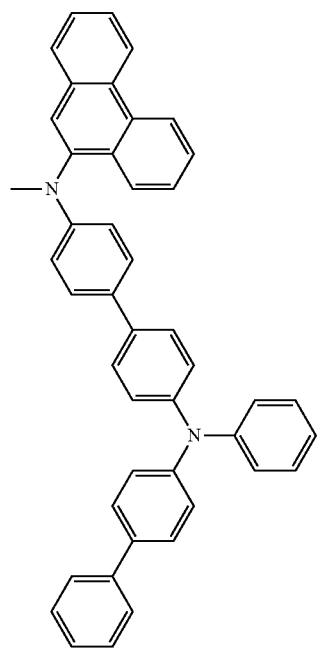
132
-continued
315
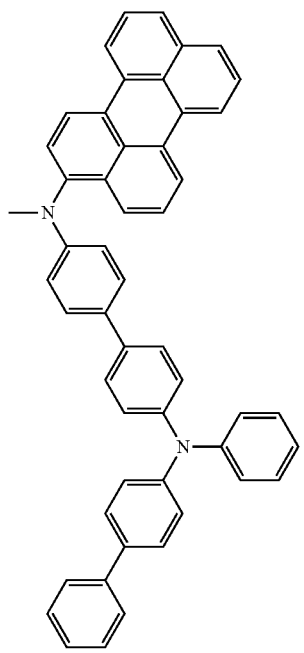
316
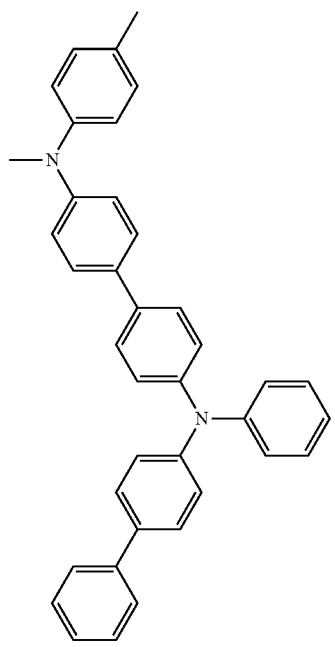

133
-continued
317
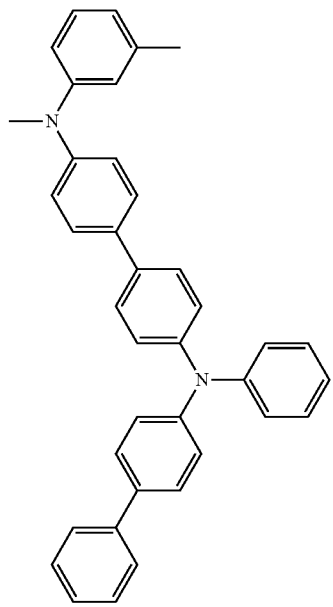
318
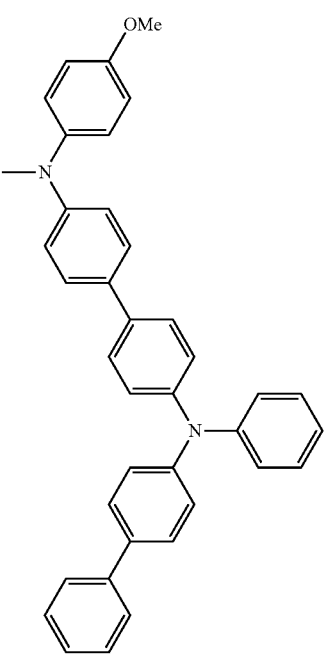
134
-continued
319
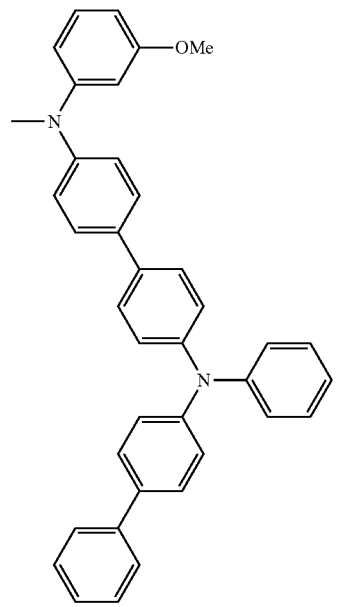
320
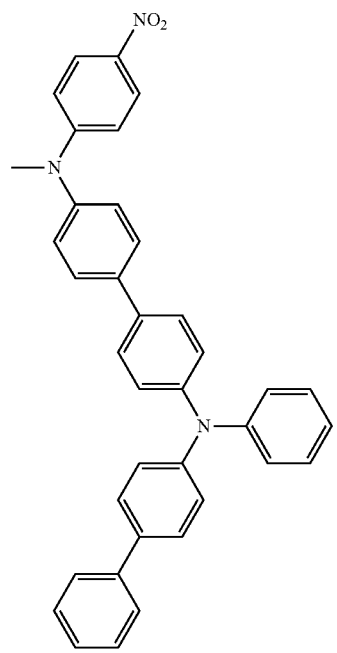

135
-continued
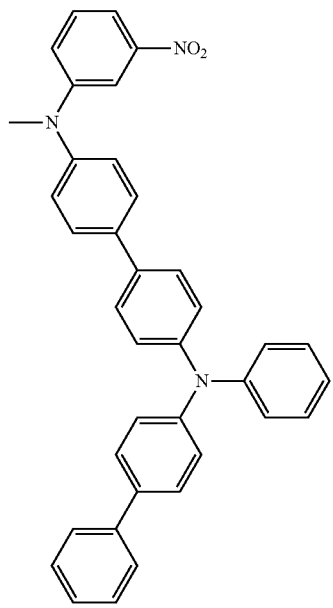
321
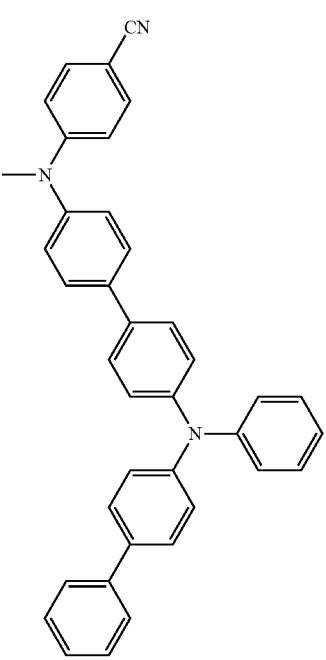
322
136
-continued
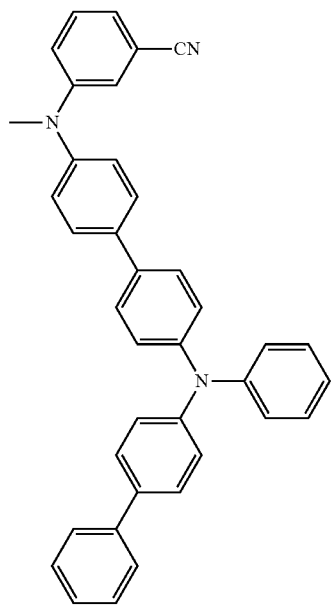
323
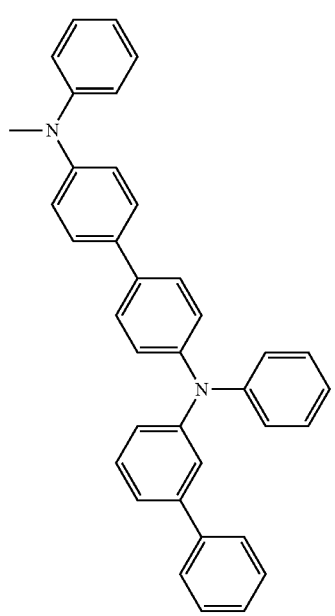
324

137
-continued
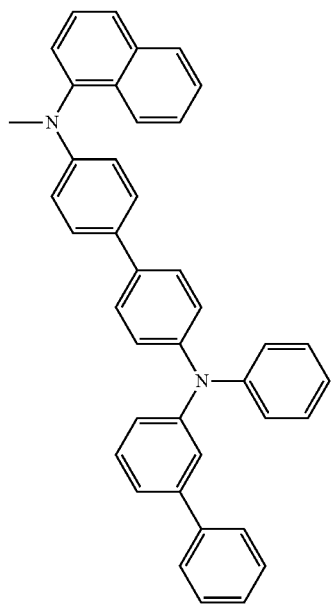
325
326
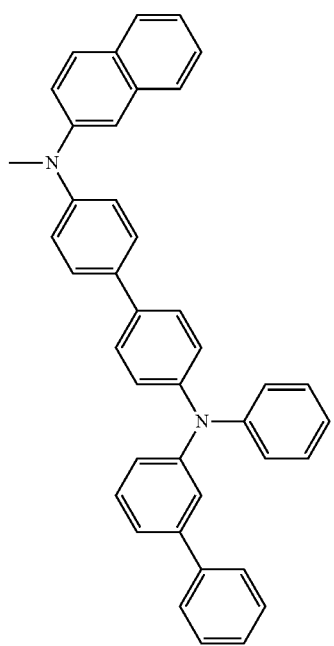
138
-continued
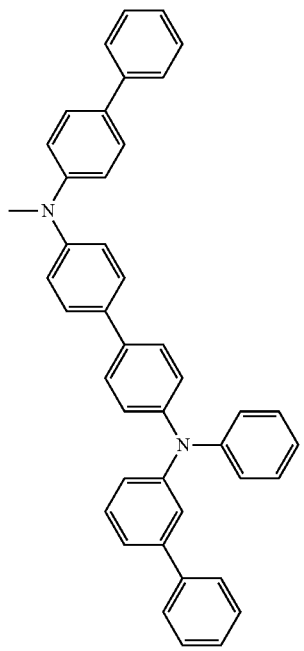
327
328

329
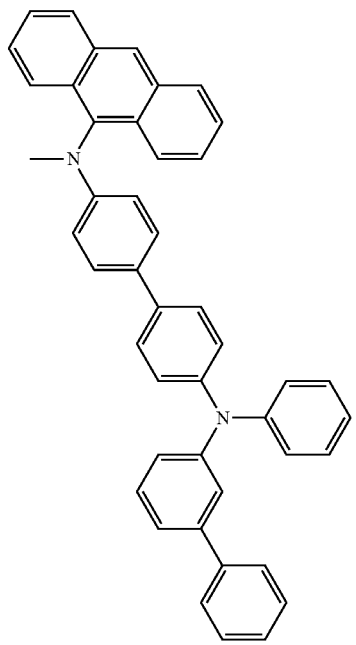
330
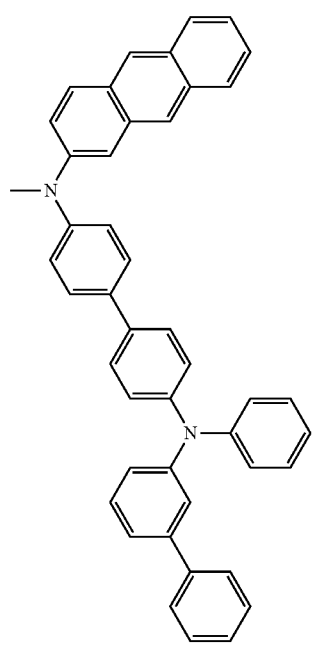
331
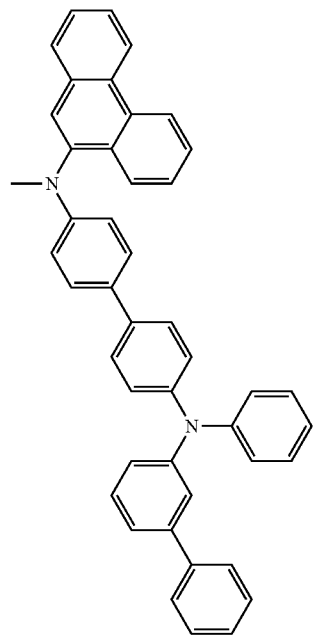
332
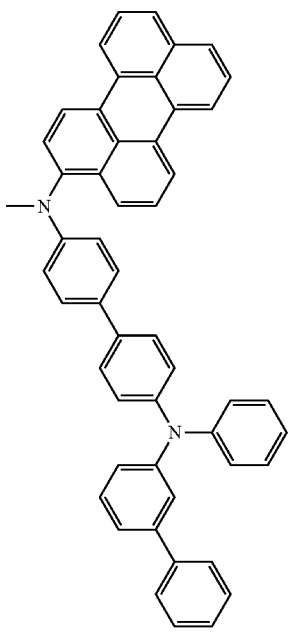

141
-continued
333
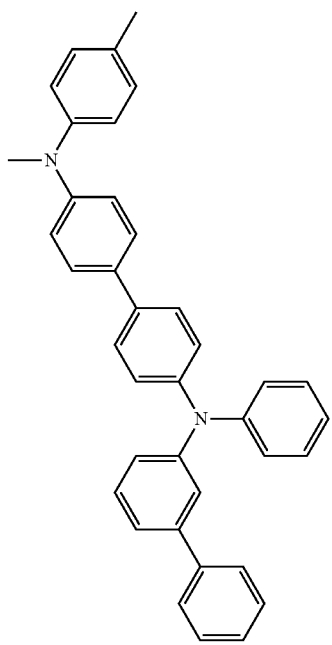
334
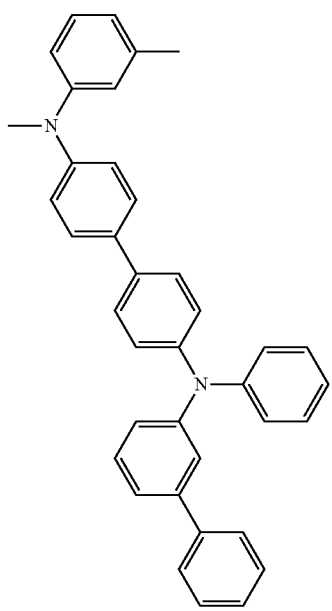
142
-continued
335
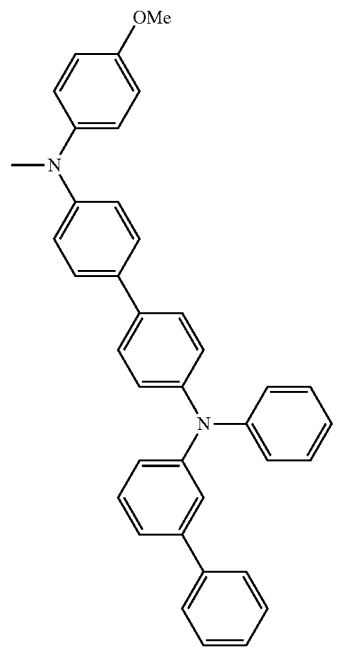
336
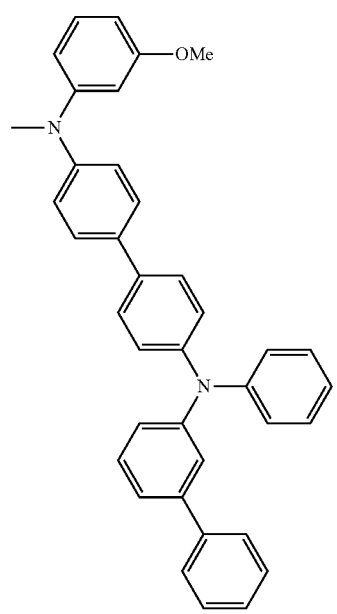

337
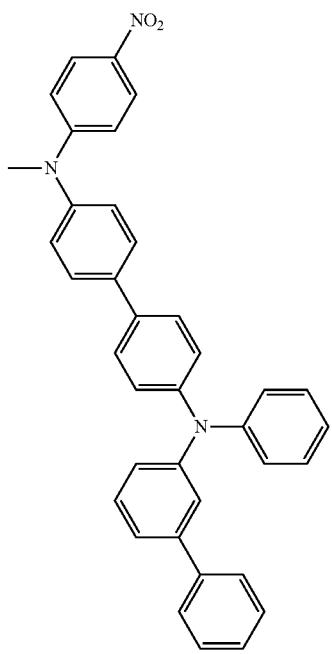
339
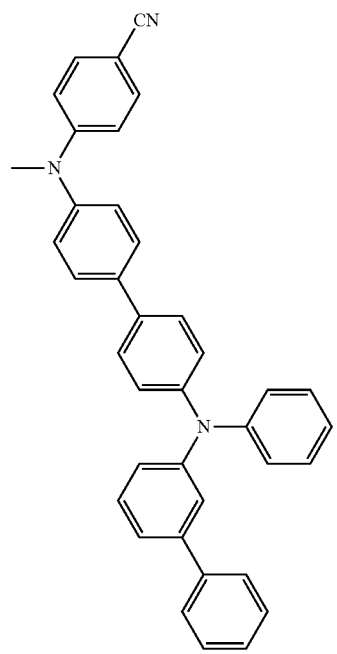
338
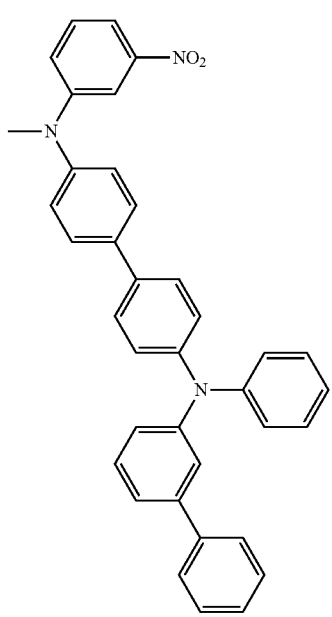
340
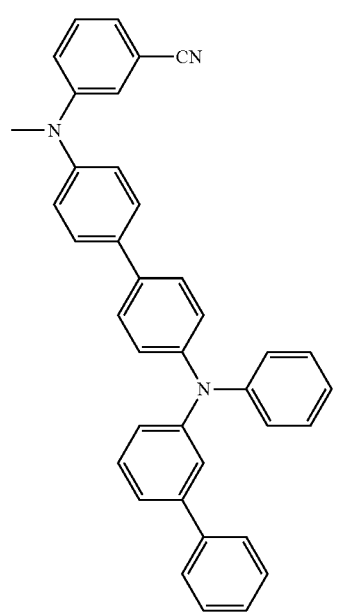

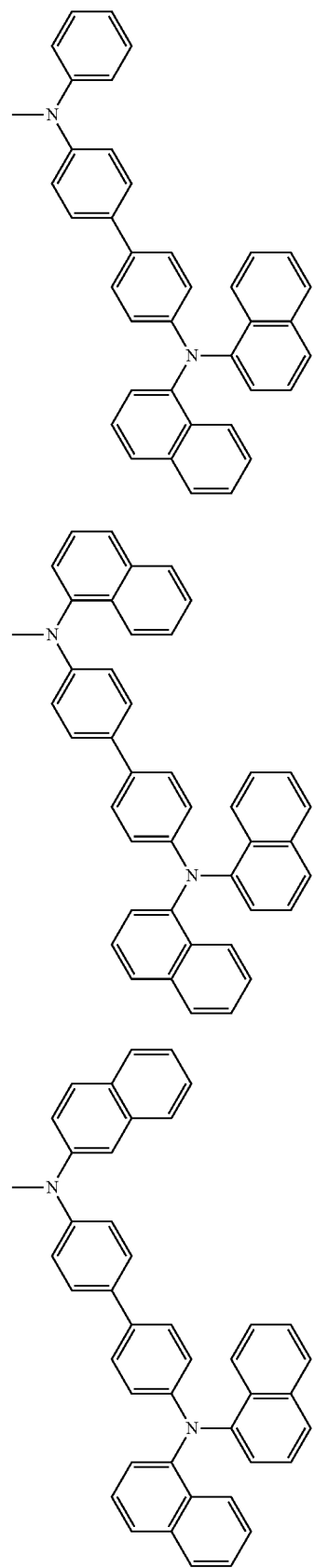
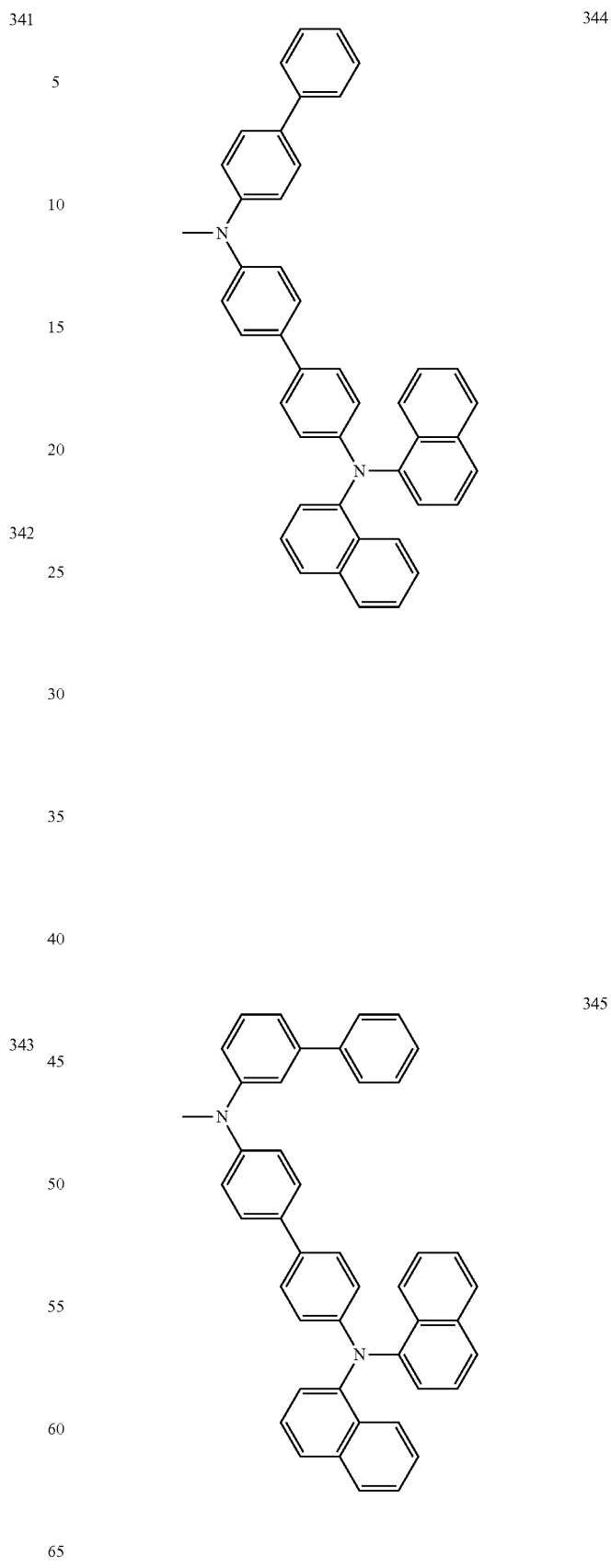

346
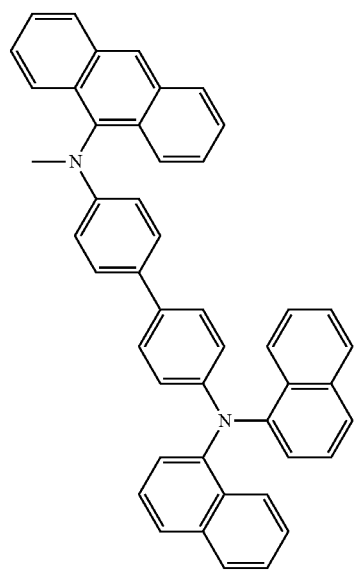
347
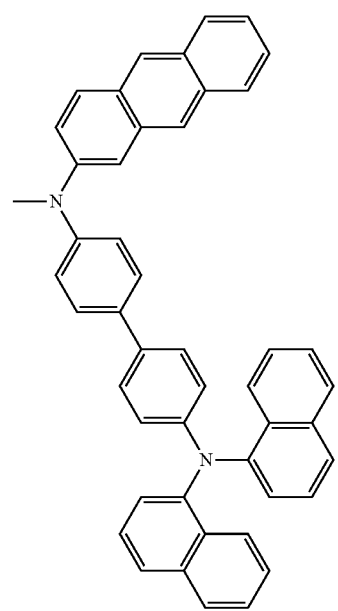
348
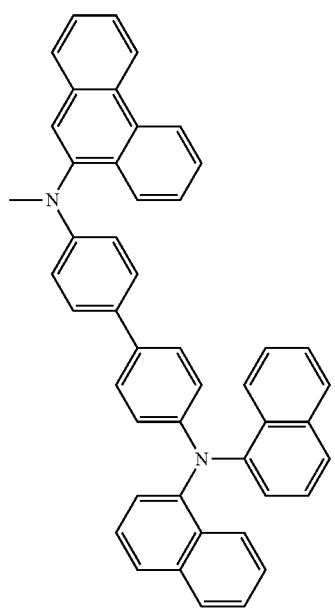
349
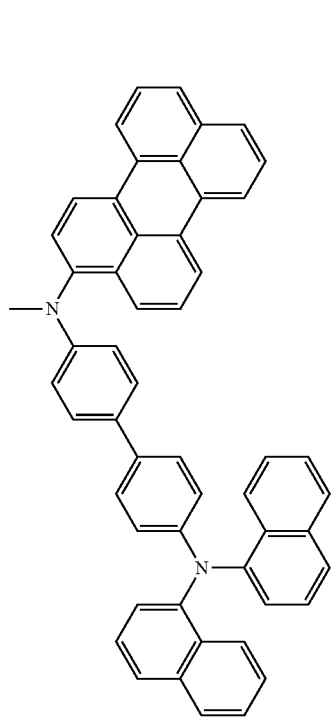

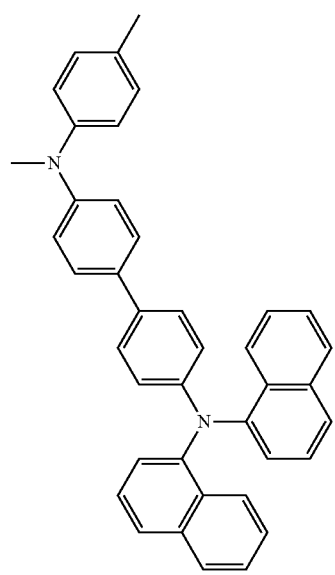
350
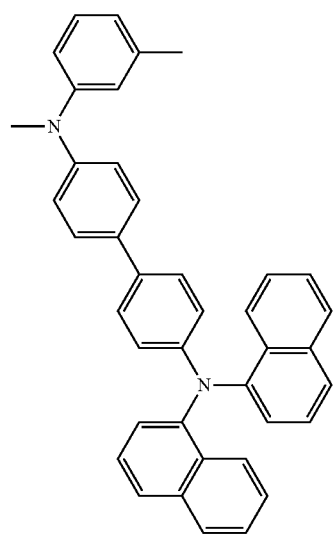
351
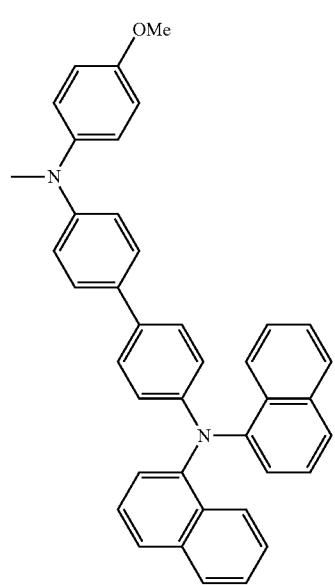
352
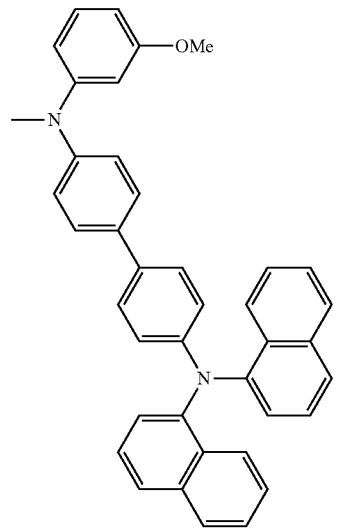
353
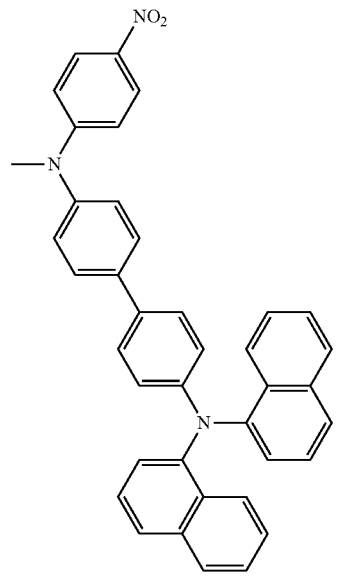
354
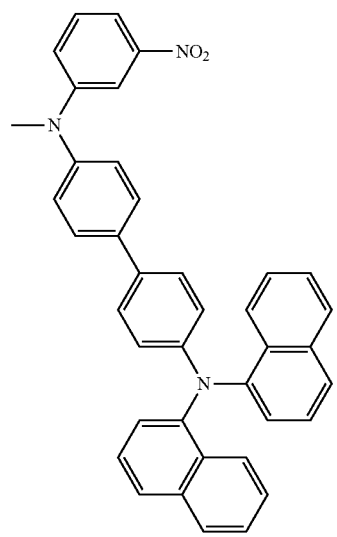
355

356
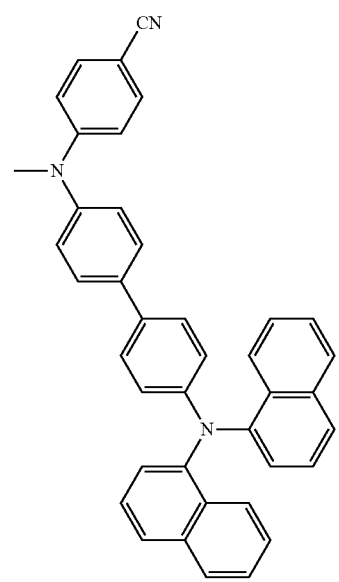
357
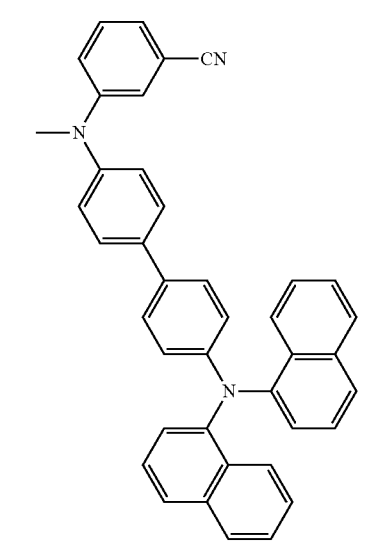
358
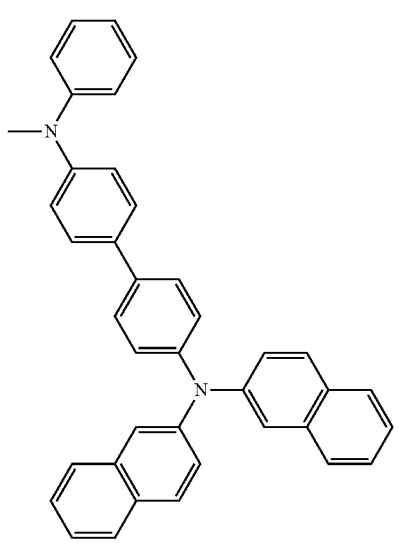
359
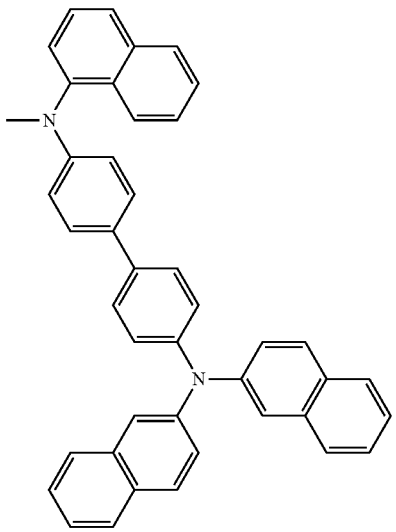
360
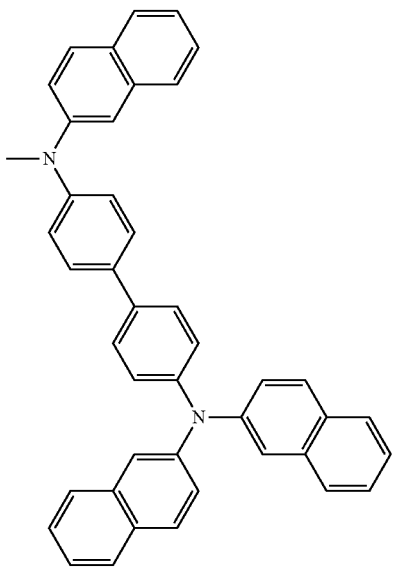

153
-continued
361
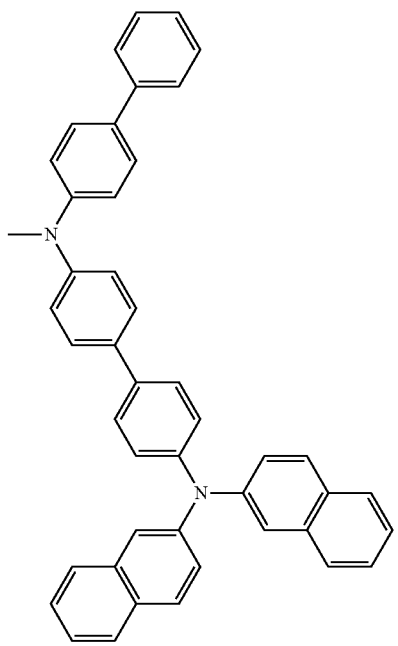
362
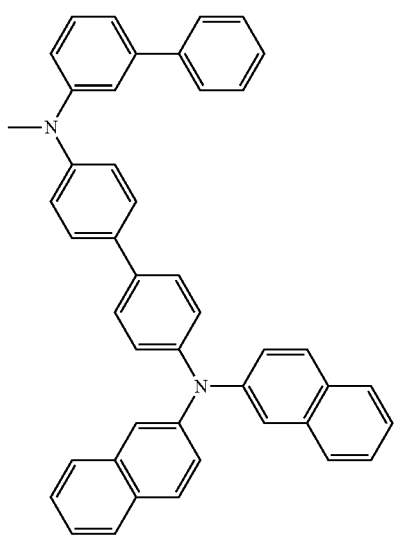
154
-continued
363
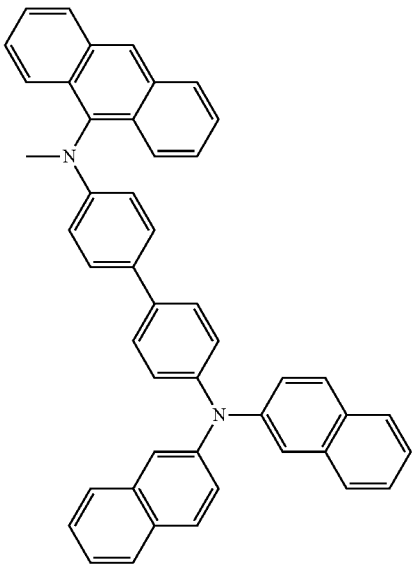
364
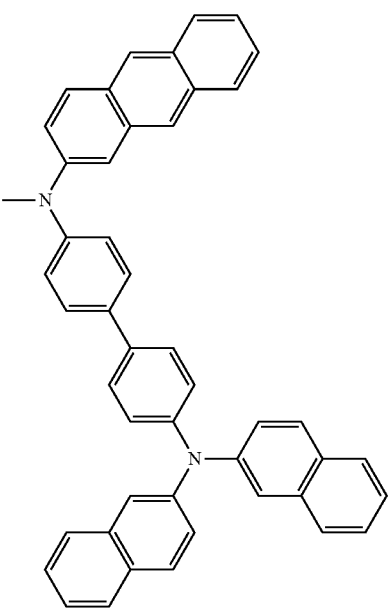

155
-continued
156
-continued
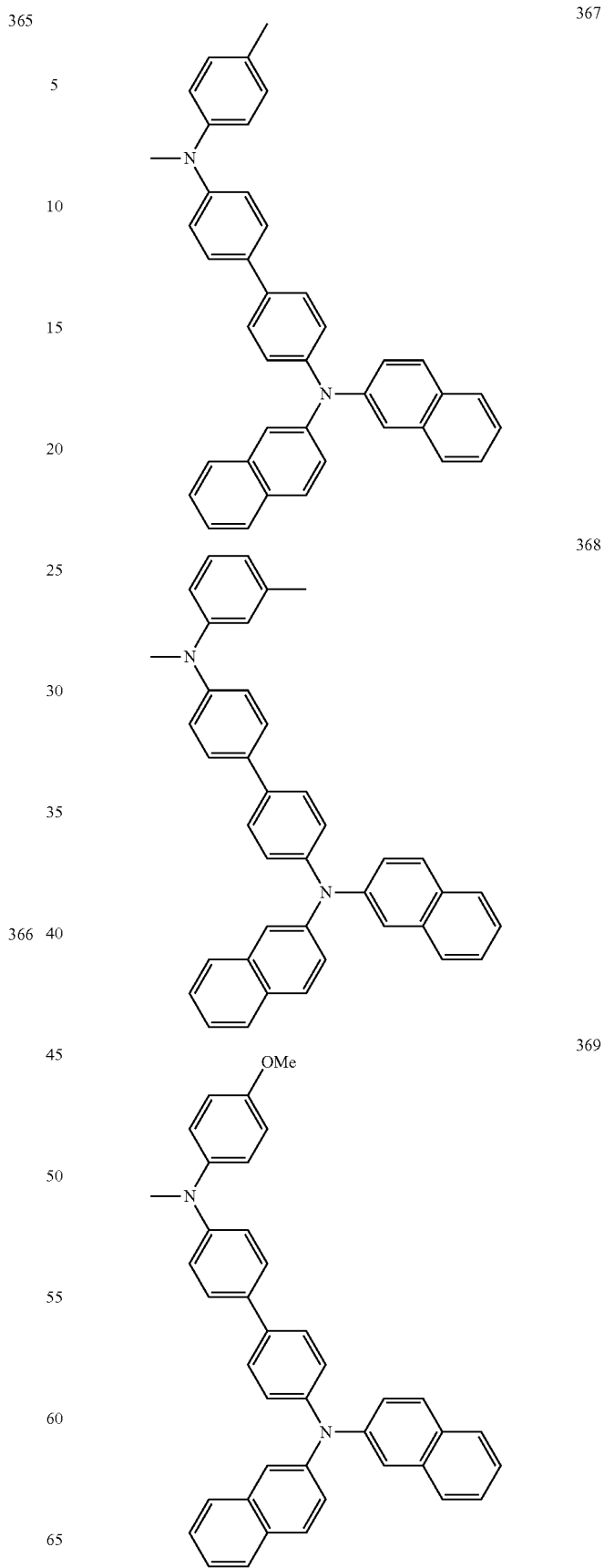

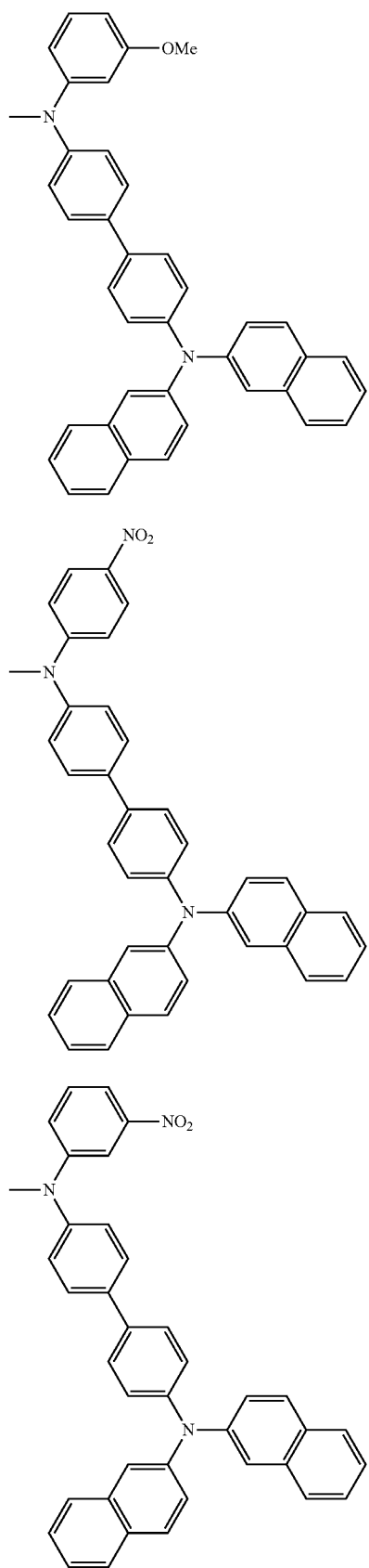
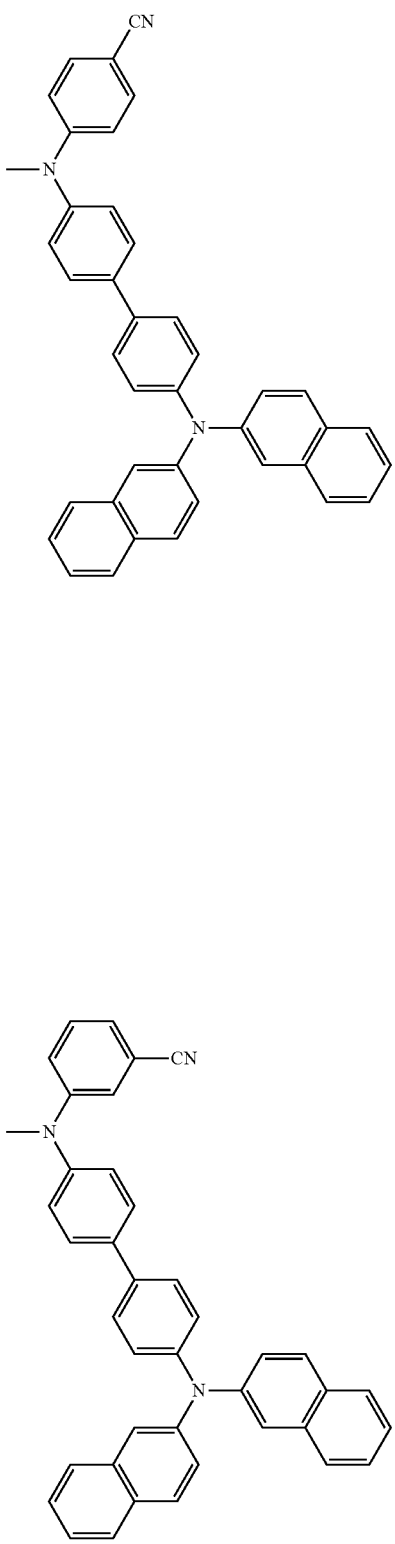

159
-continued
375
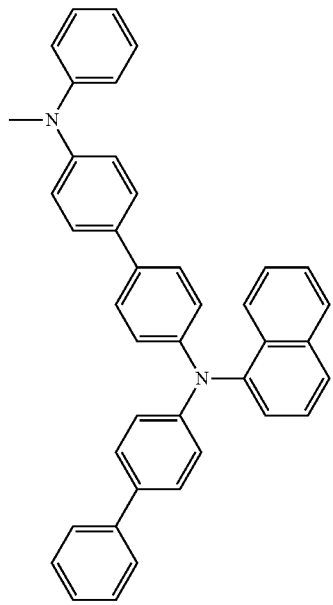
376
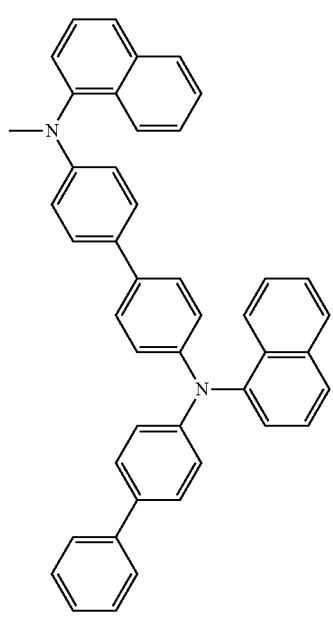
160
-continued
377
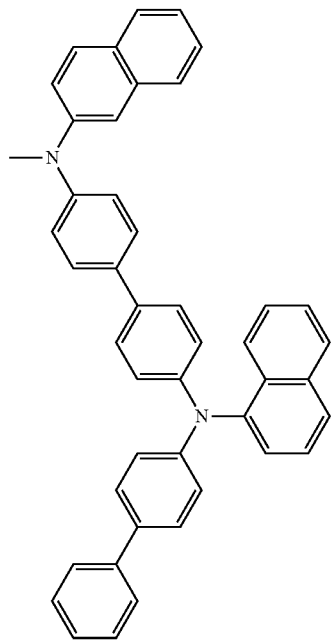
378
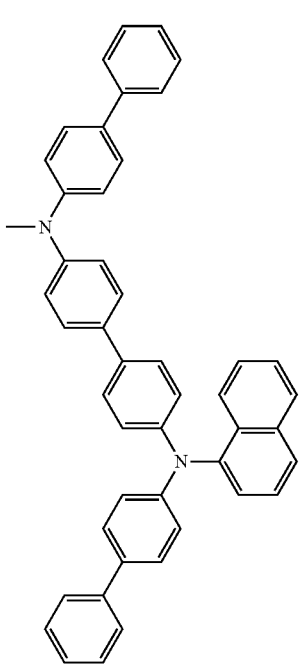

161
-continued
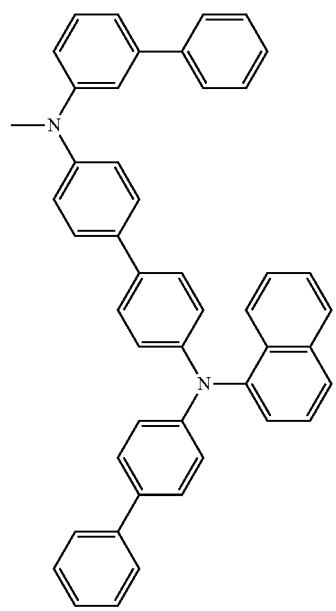
379
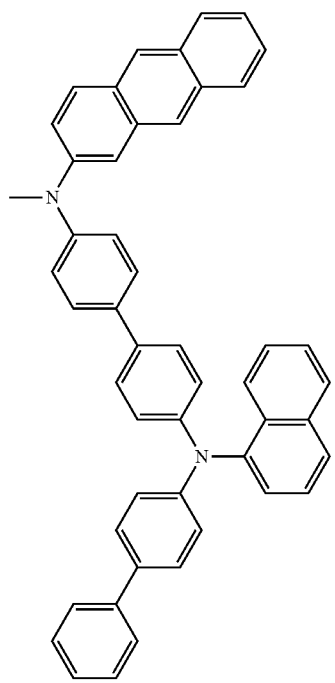
380
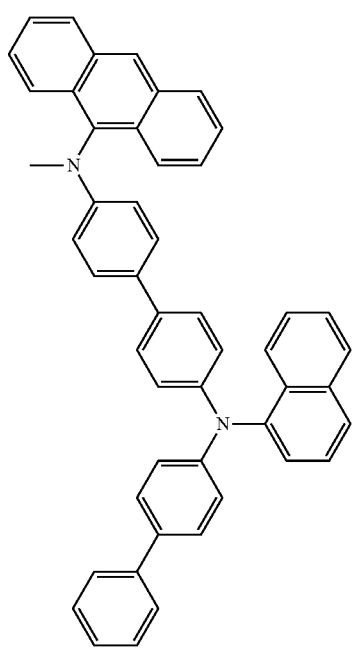
162
-continued
381
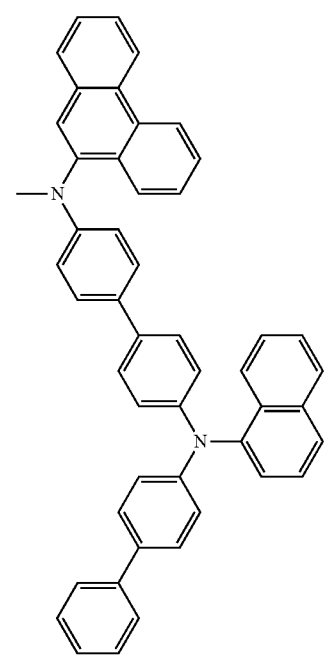
382

163
-continued
383
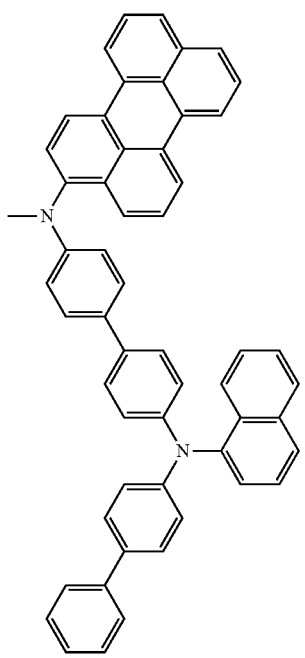
384
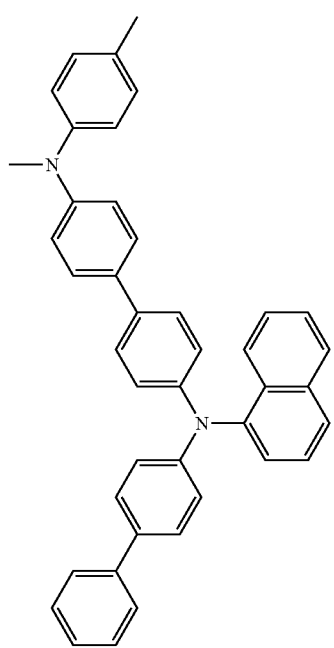
164
-continued
385
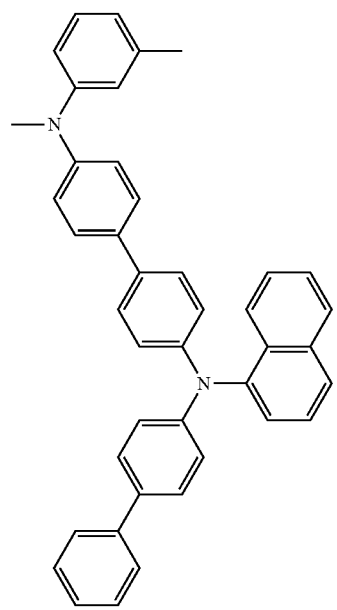
386
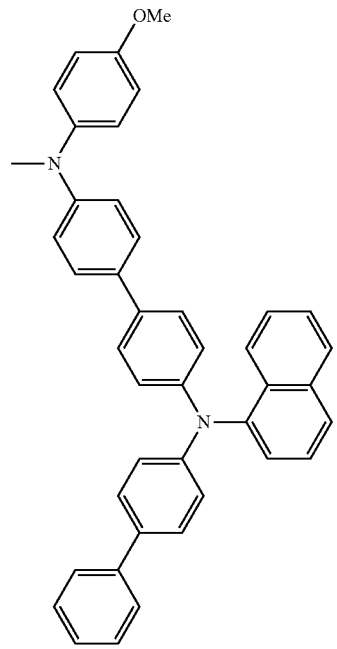

165
-continued
387
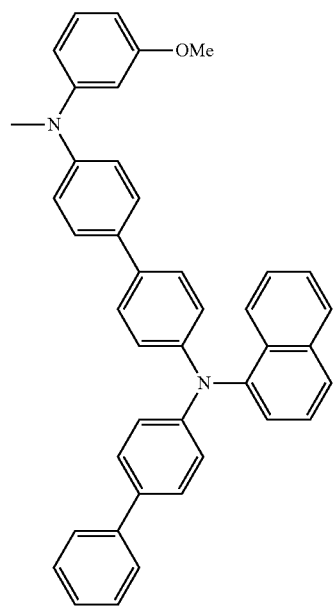
388
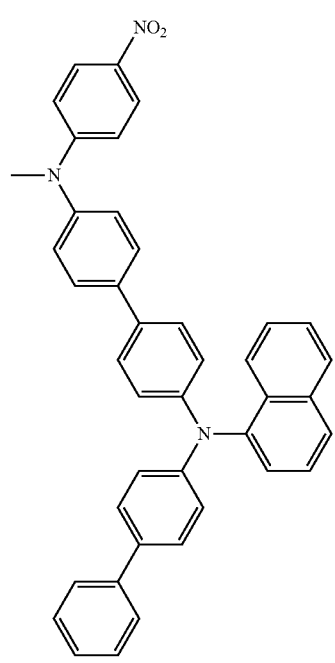
166
-continued
389
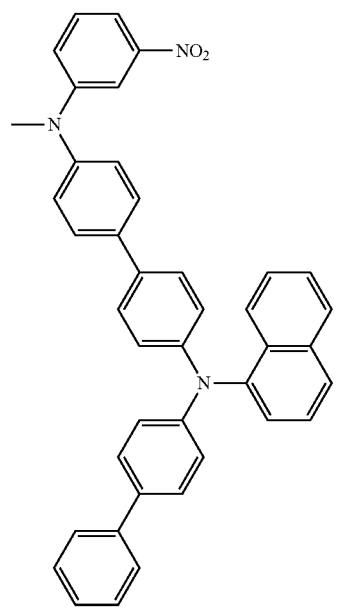
390
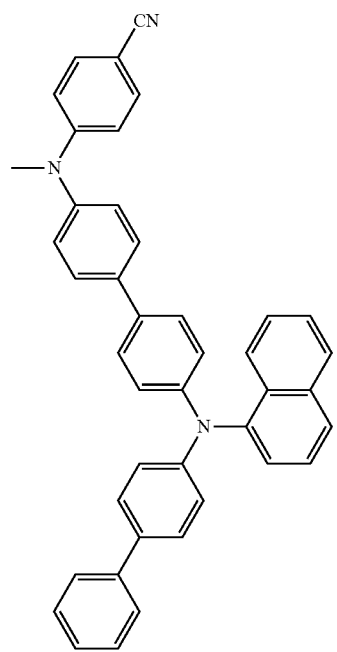

167
-continued
391
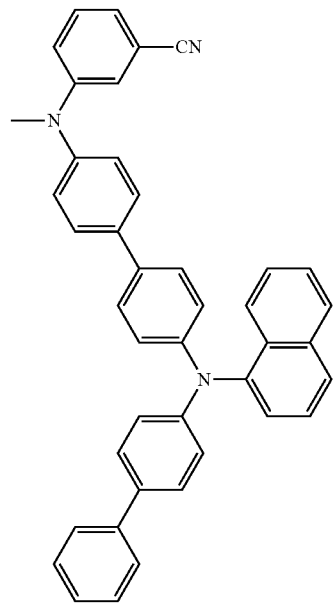
392
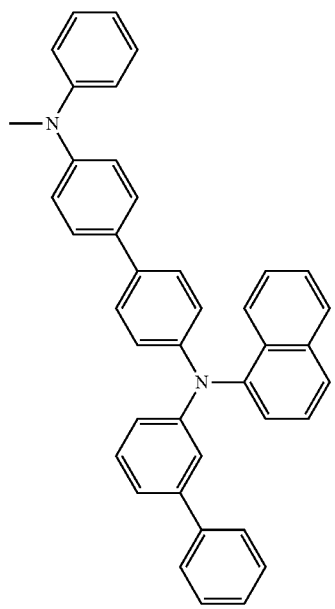
168
-continued
393
394
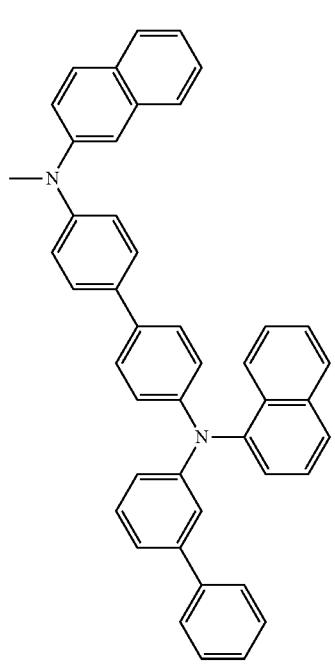

395
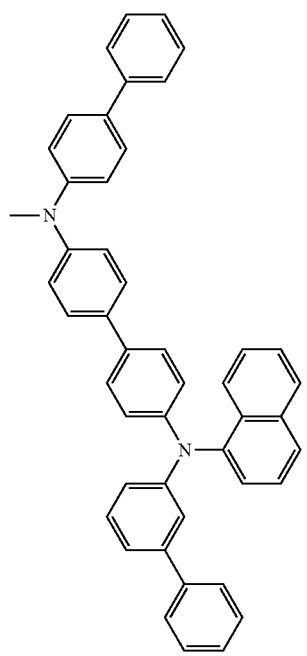
396
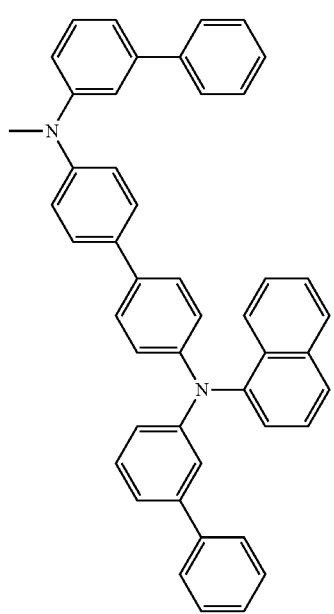
397
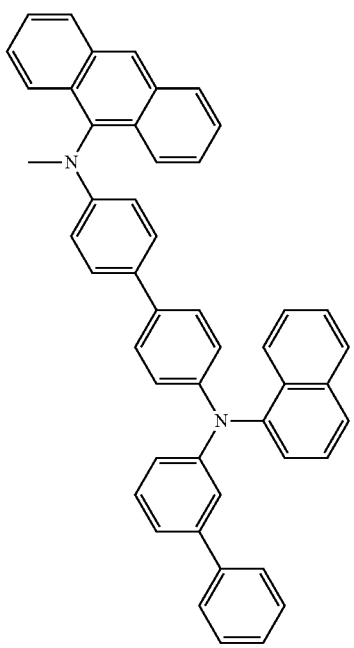
398
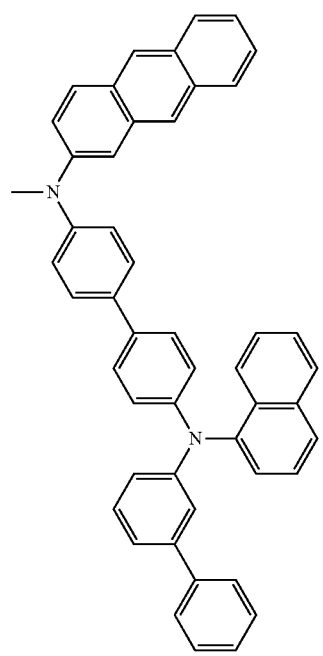

399
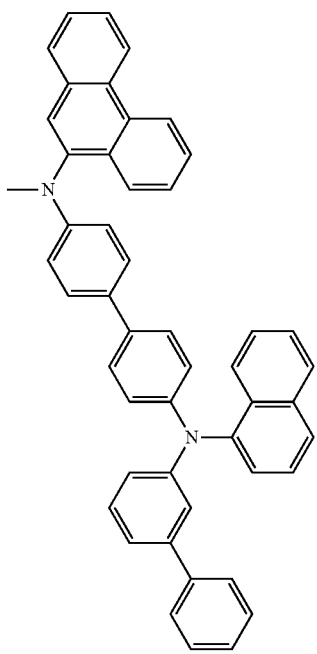
400
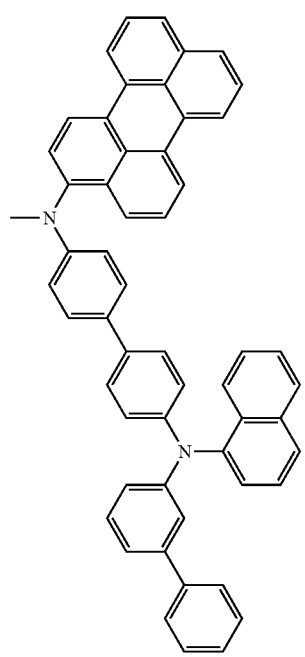
401
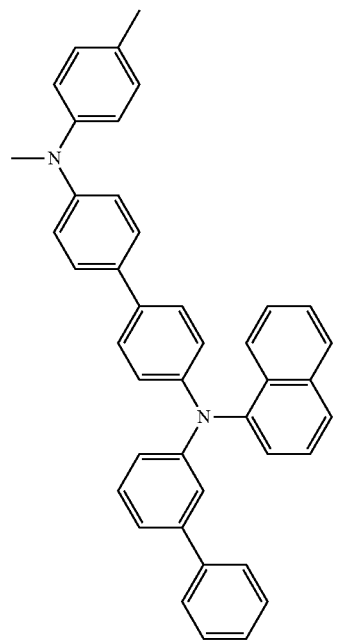
402
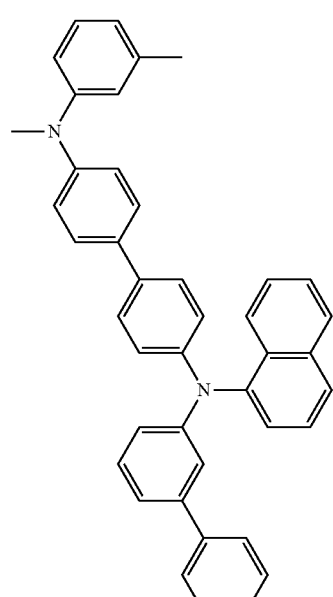

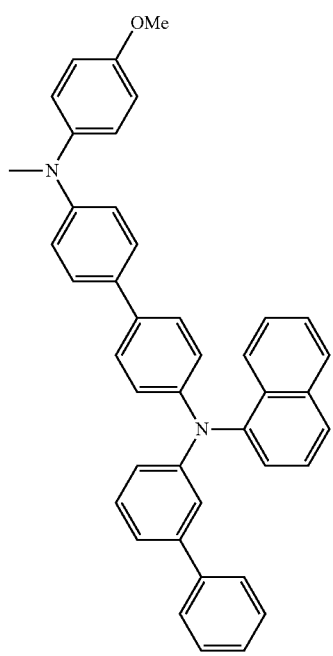
403
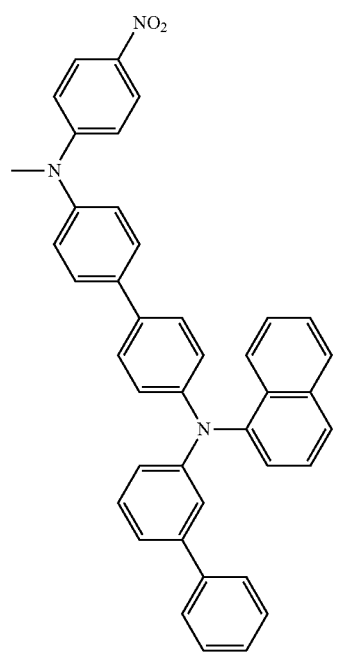
405
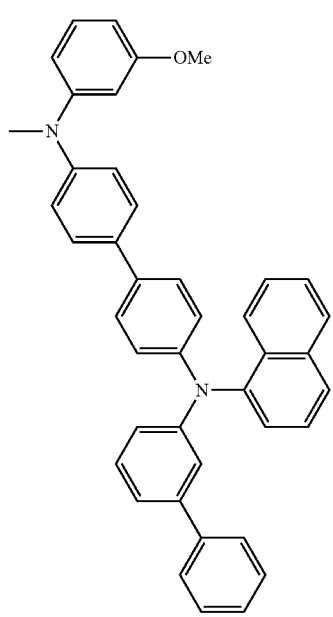
404
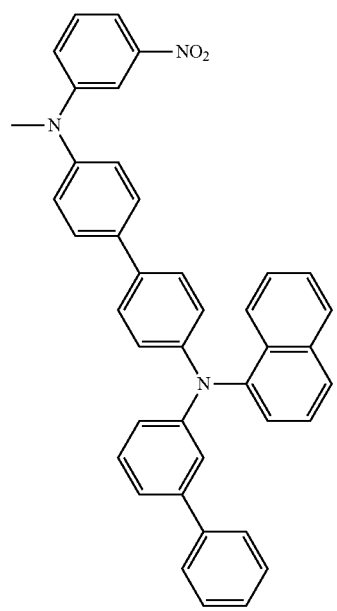
406

175
-continued
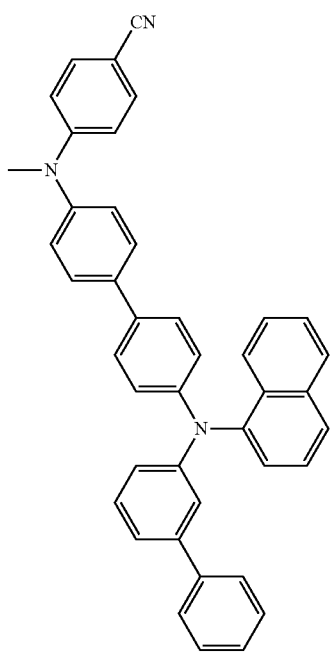
407
176
-continued
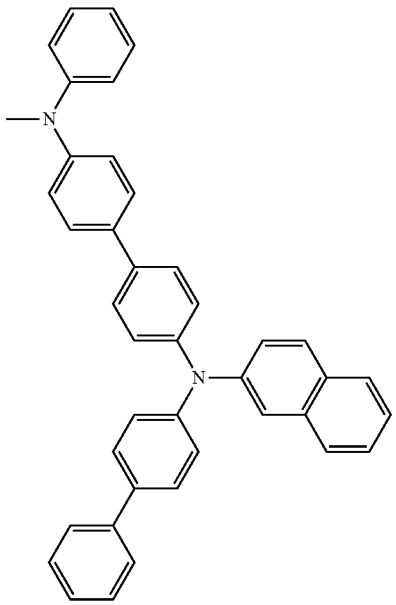
409
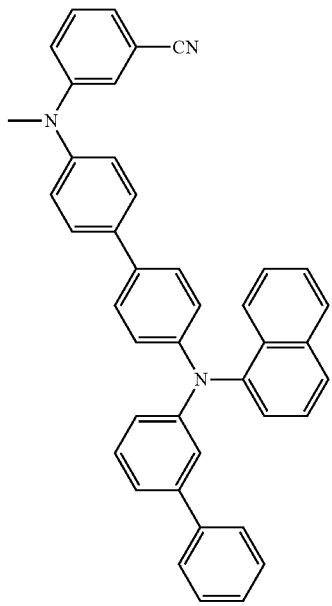
408
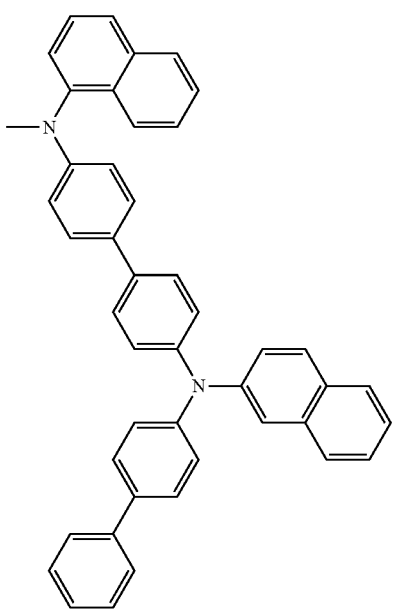
410

411
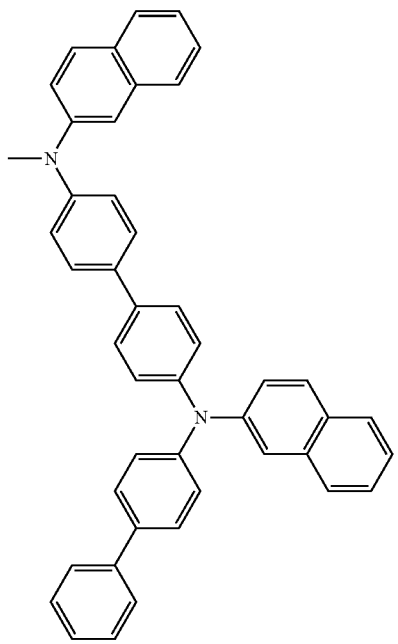
412
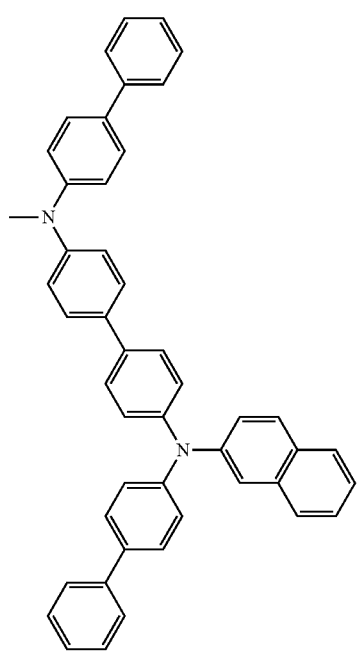
413
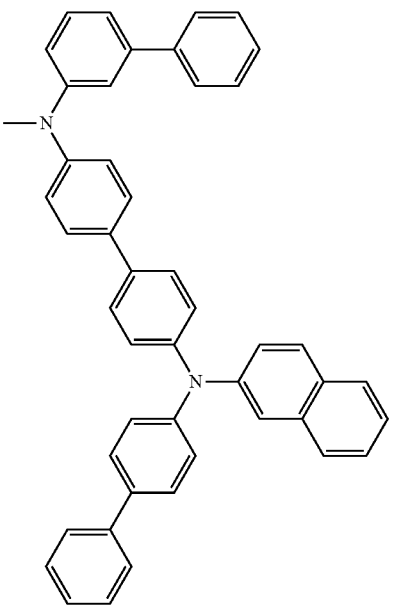
414
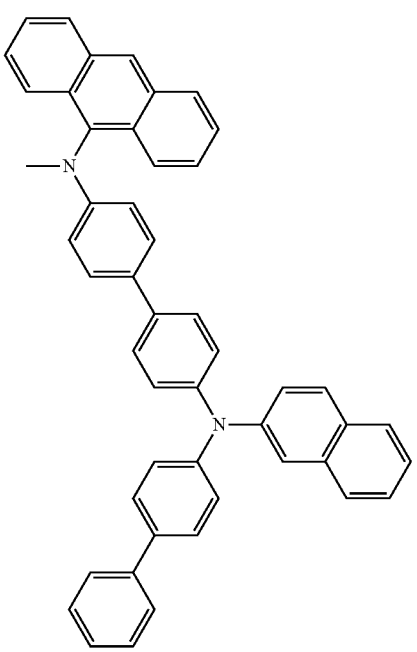

-continued
415
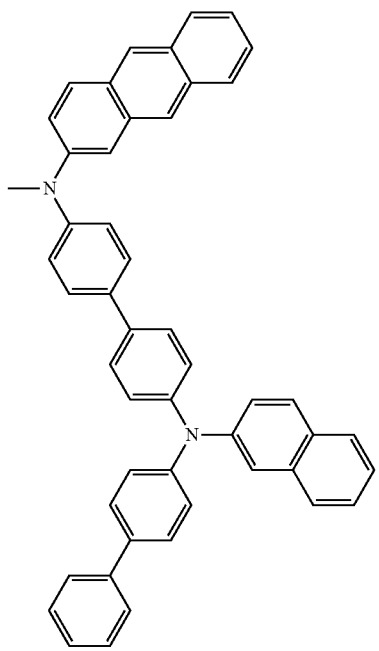
416
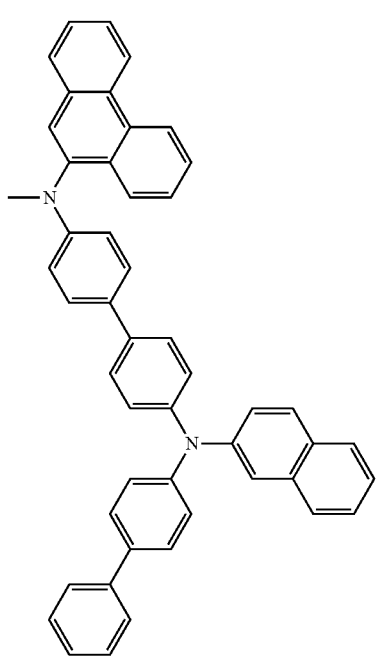
-continued
417
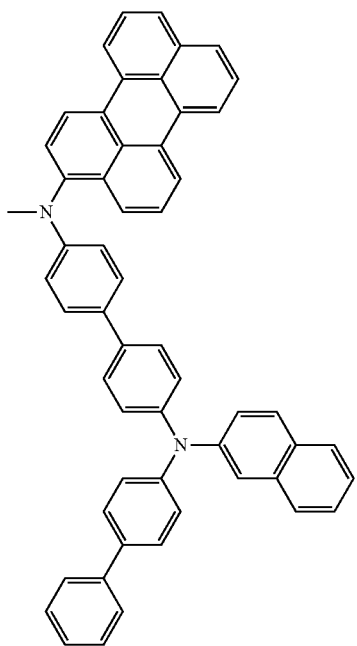
418
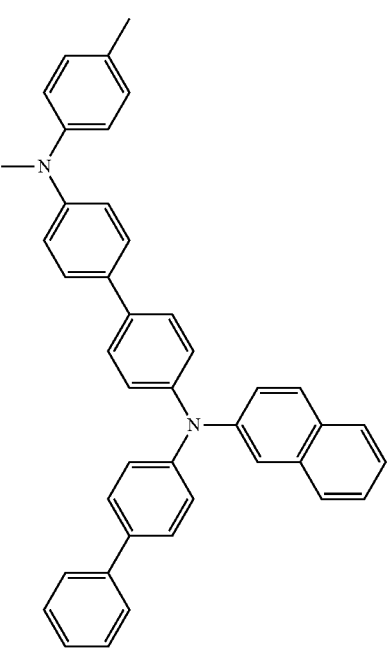

419
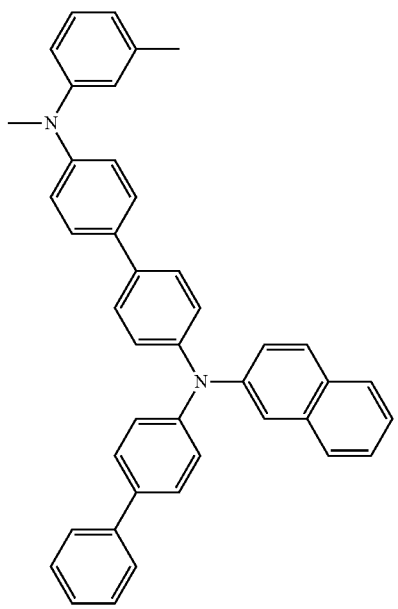
421
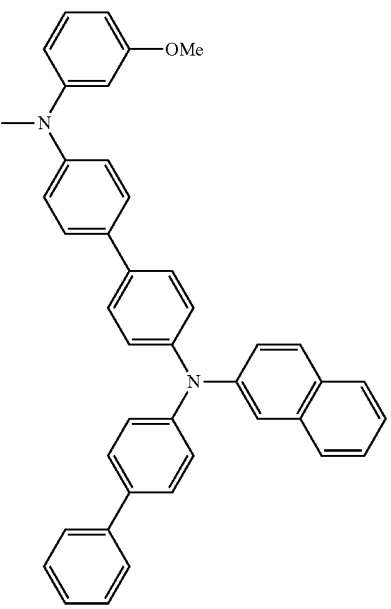
420
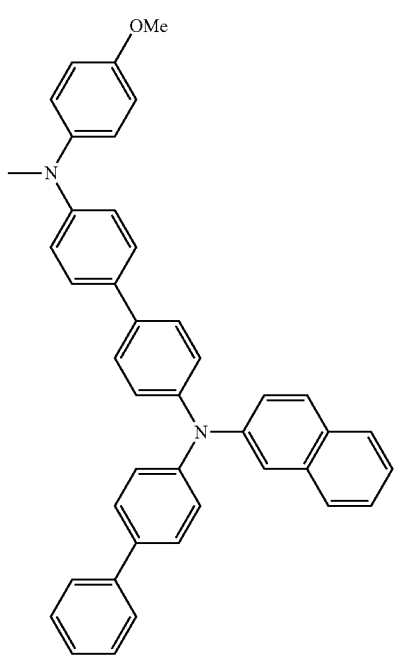
422
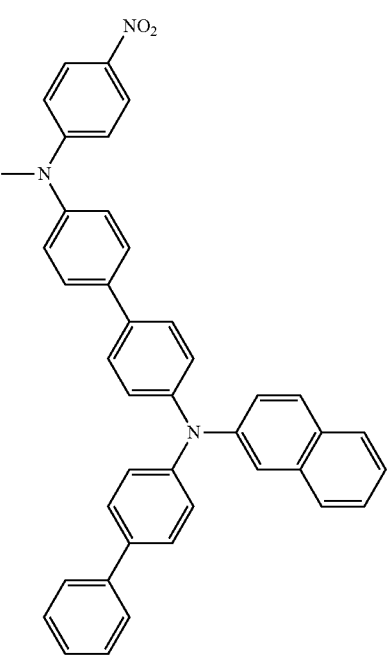

183
-continued
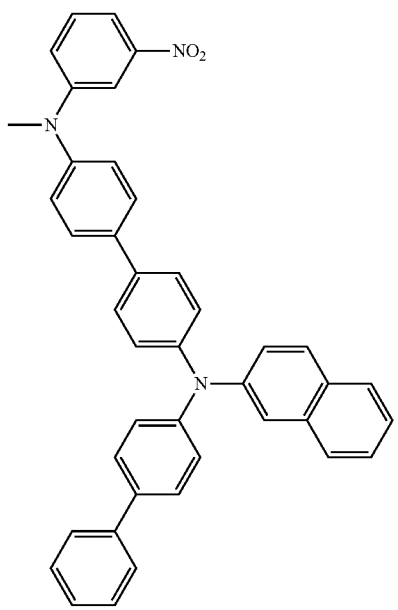
423
184
-continued
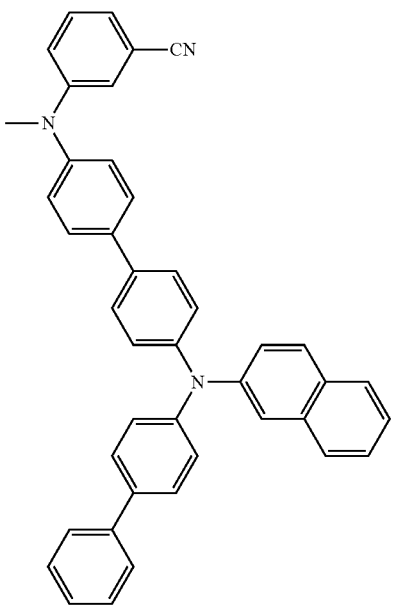
425
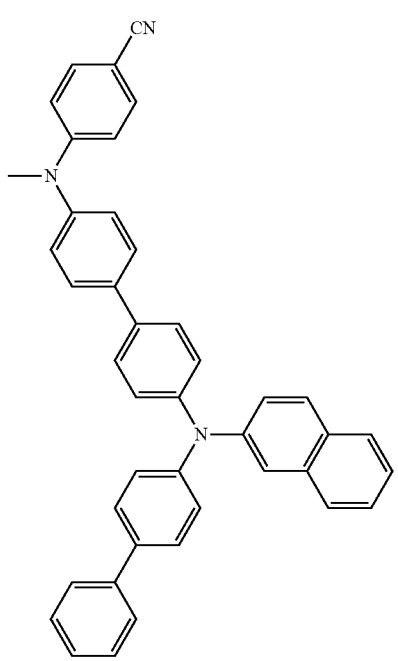
424
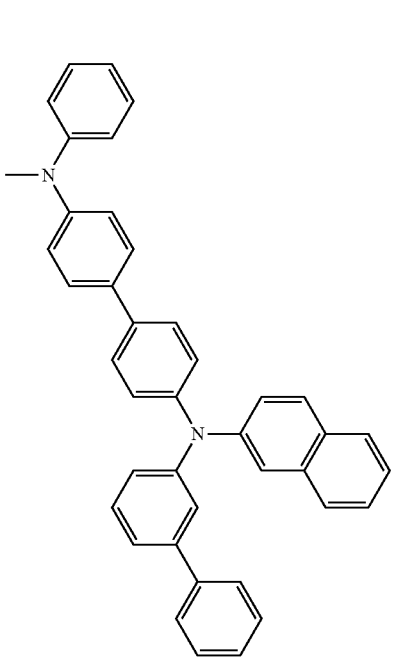
426

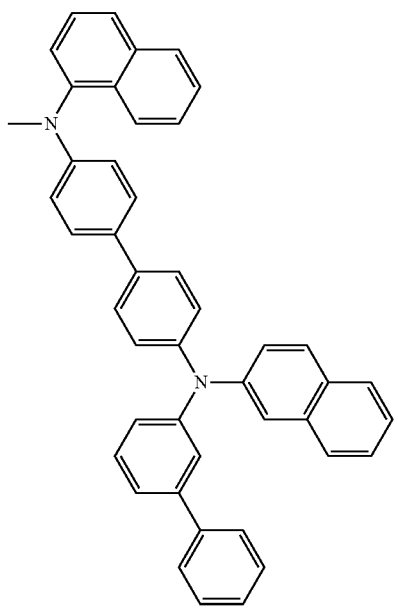
427
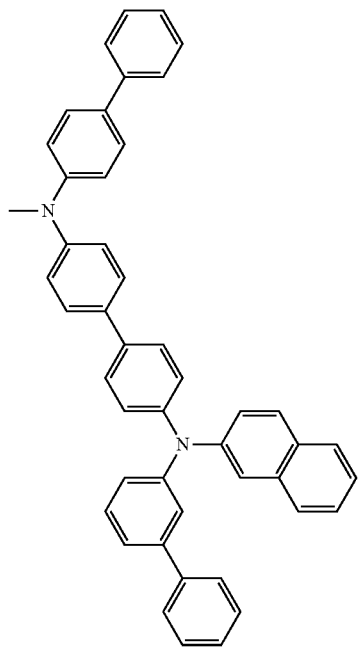
429
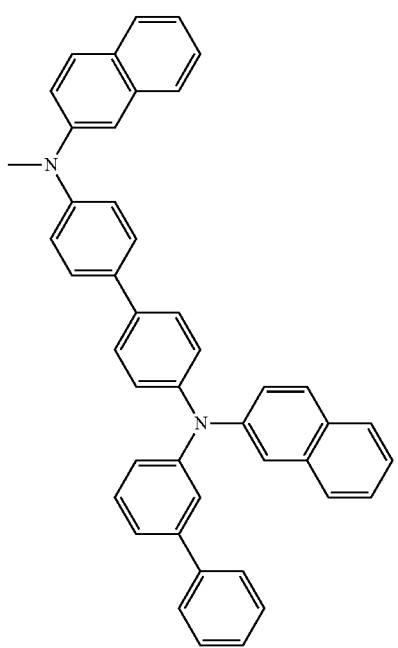
428
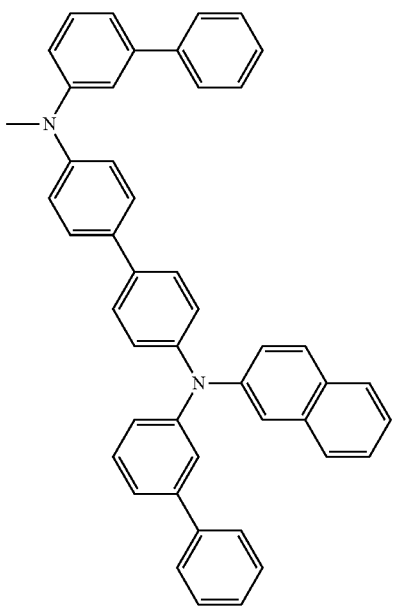
430

187
-continued
431
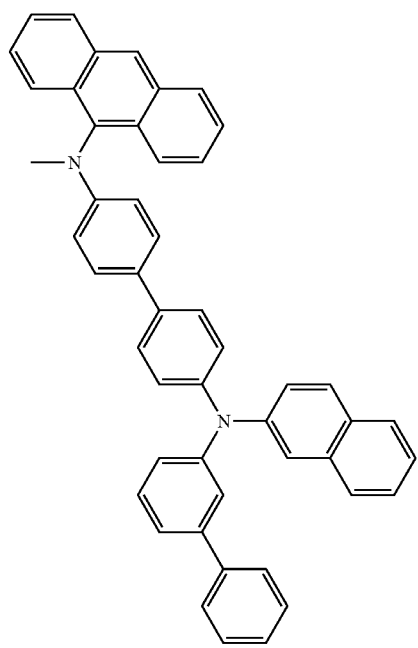
432
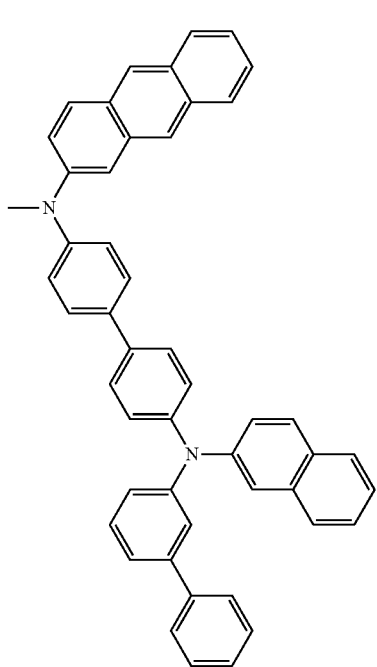
188
-continued
433
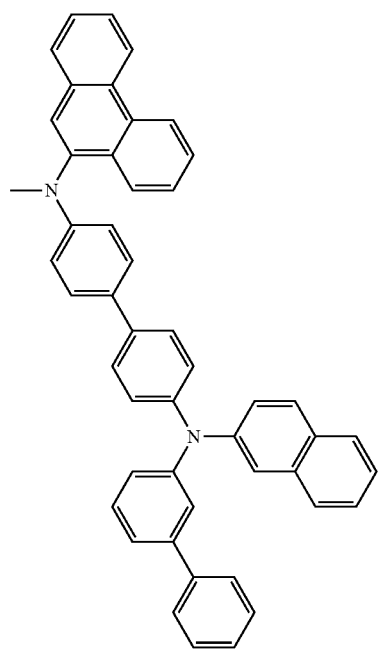
434
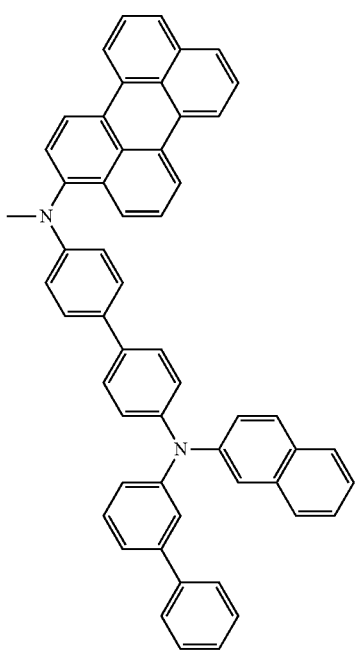

189
-continued
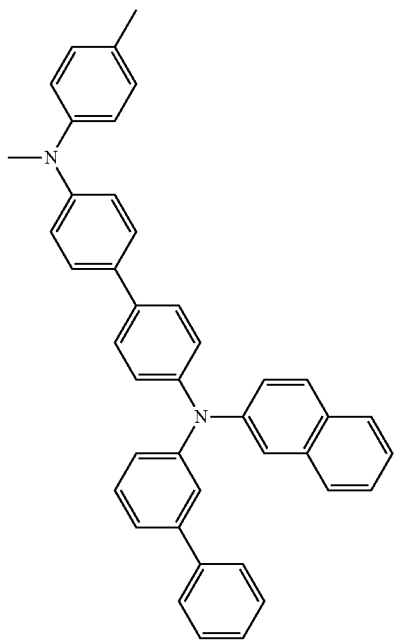
435
190
-continued
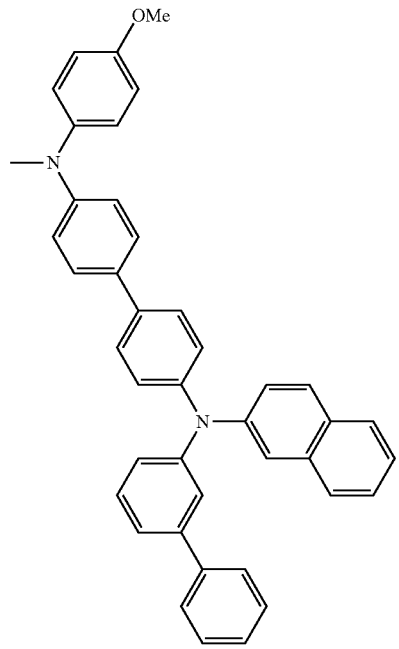
437
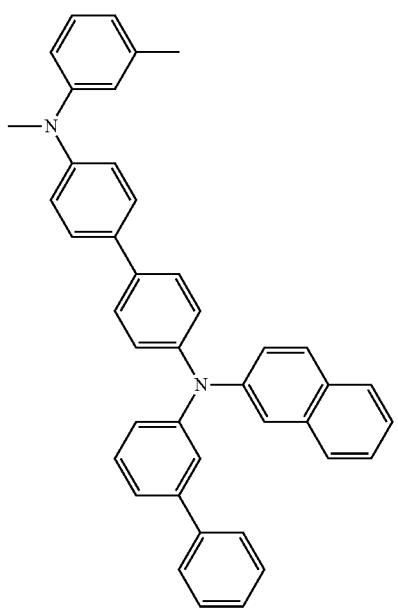
436
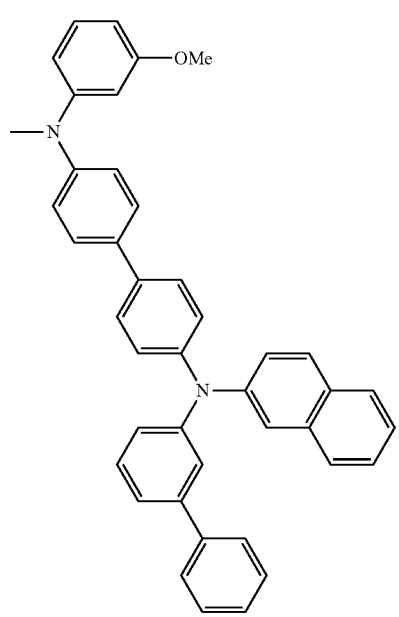
438

439
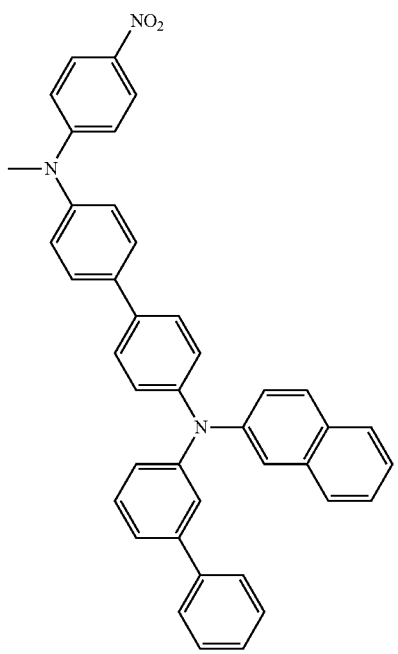
441
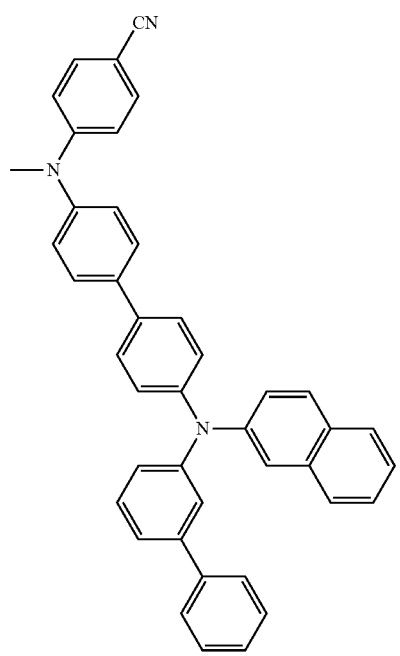
440
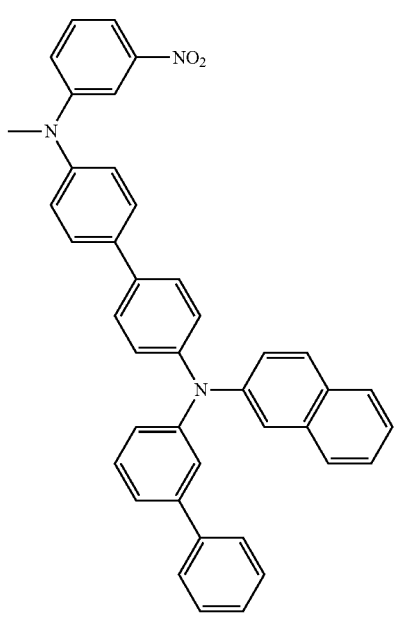
442
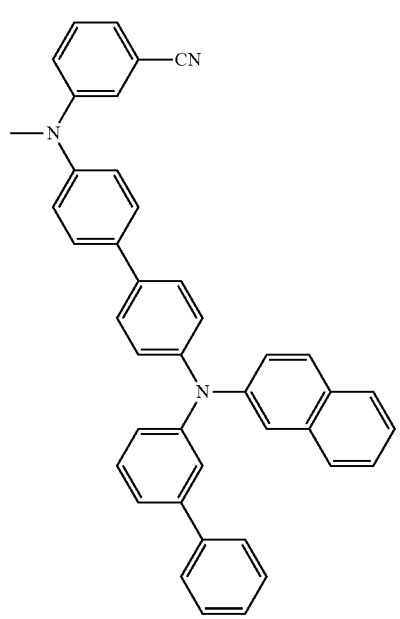

193
-continued
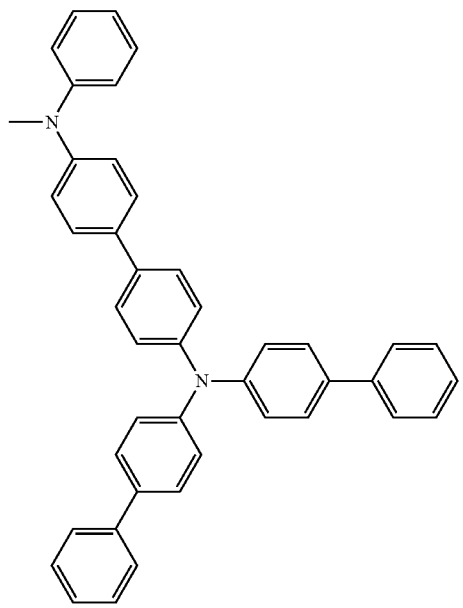
443
194
-continued
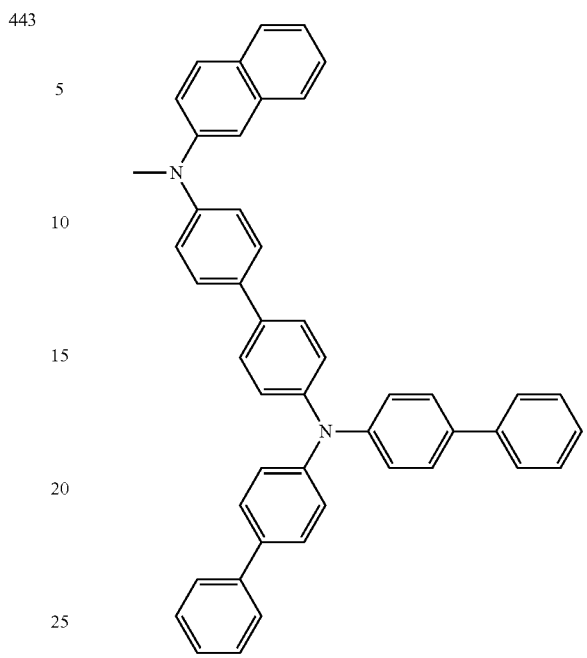
445
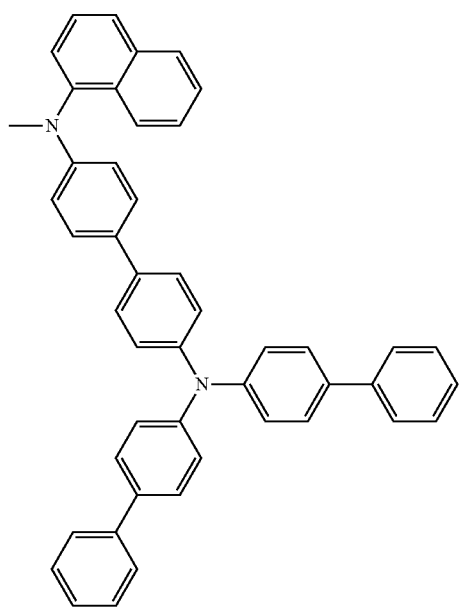
444
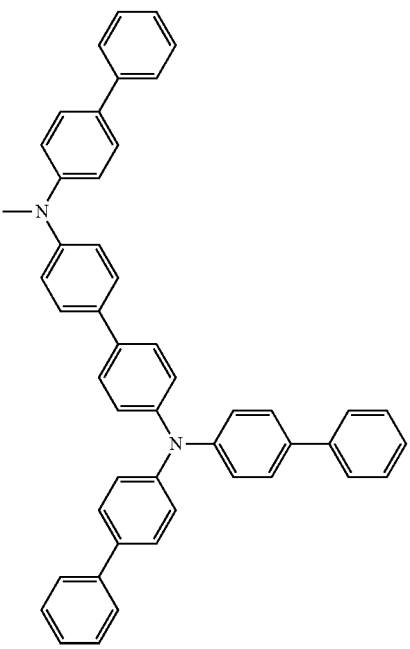
446

195
-continued
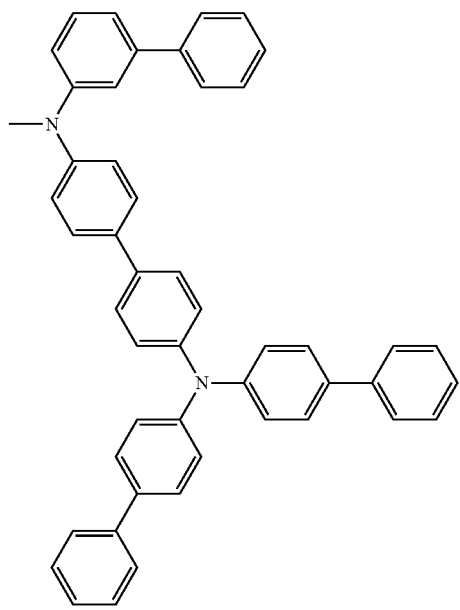
447
196
-continued
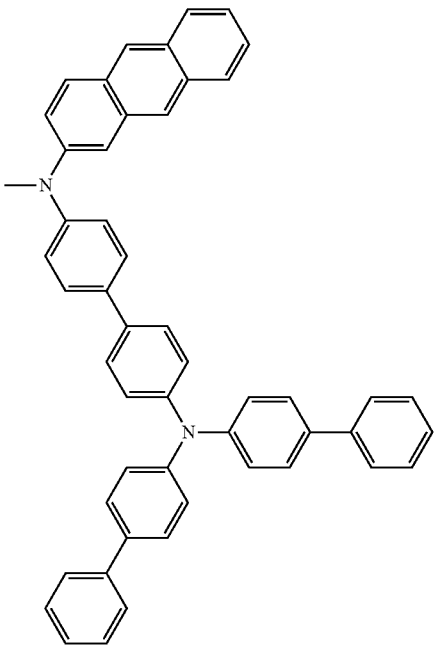
449
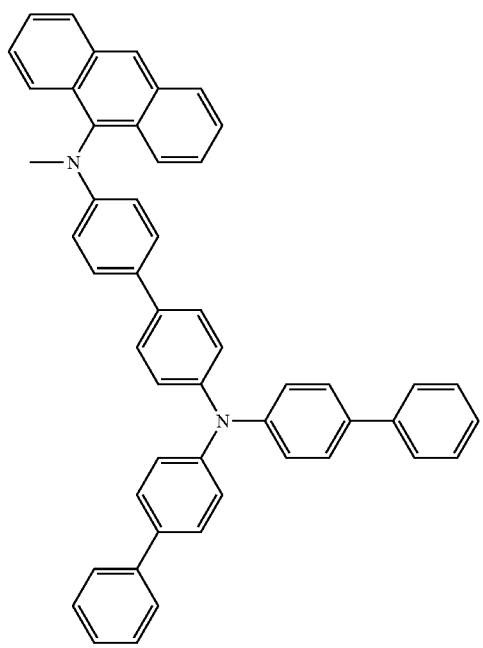
448
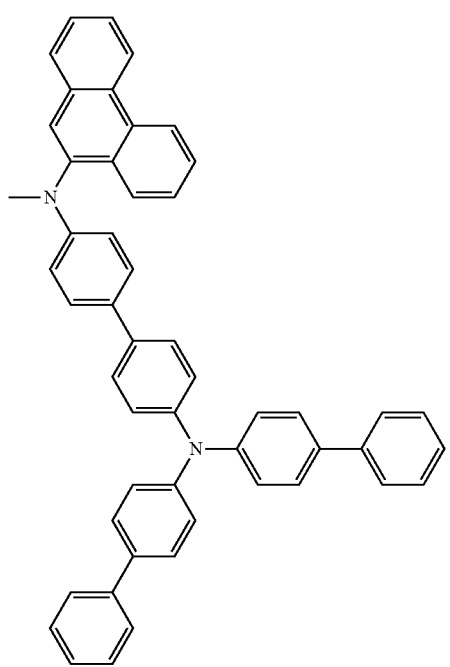
450

451
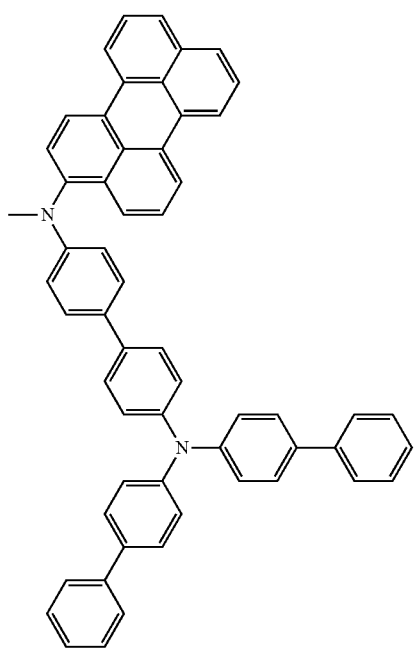
453
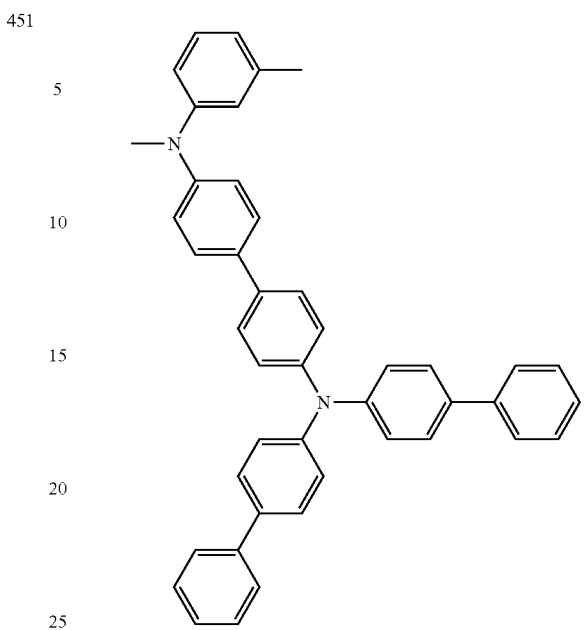
452
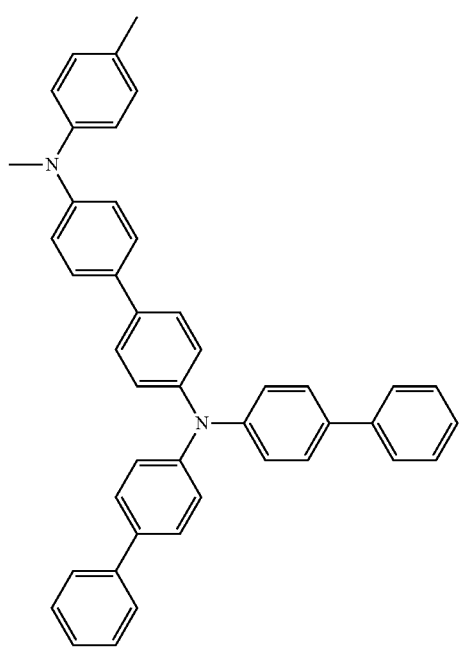
454
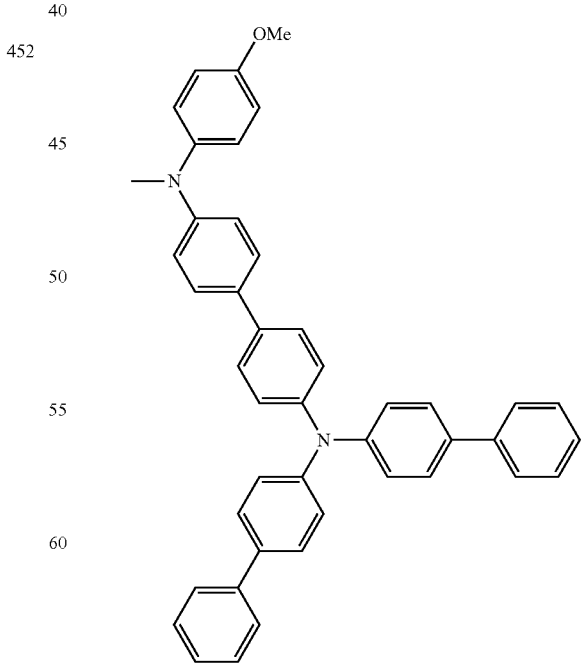

199
-continued
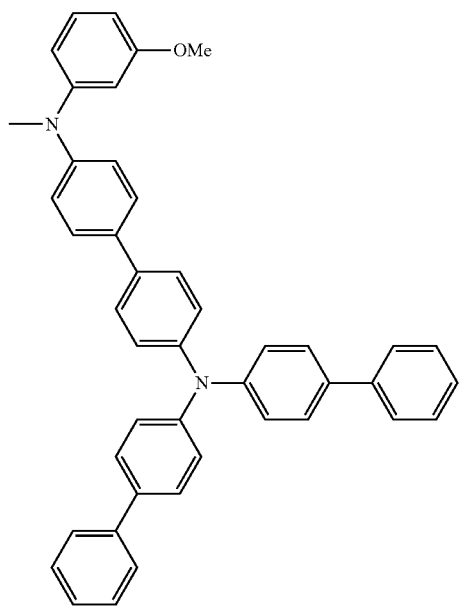
455
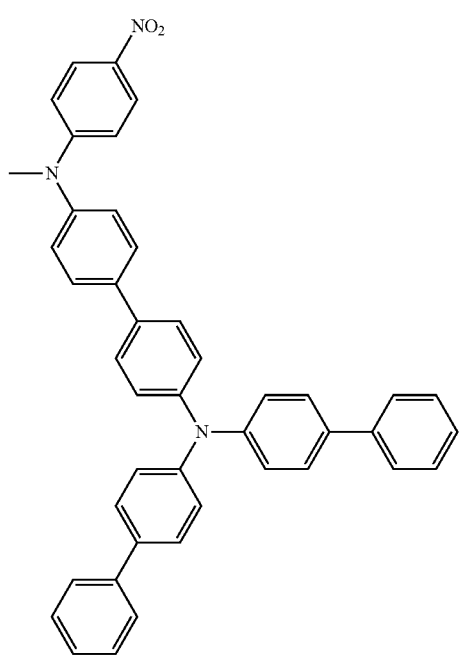
456
200
-continued
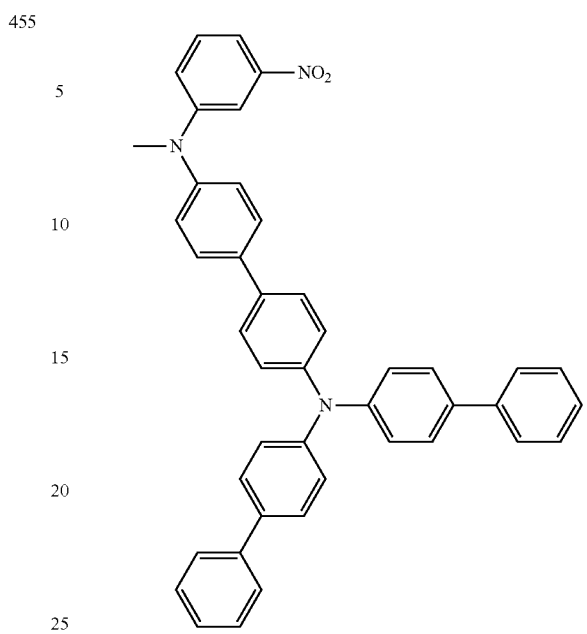
457
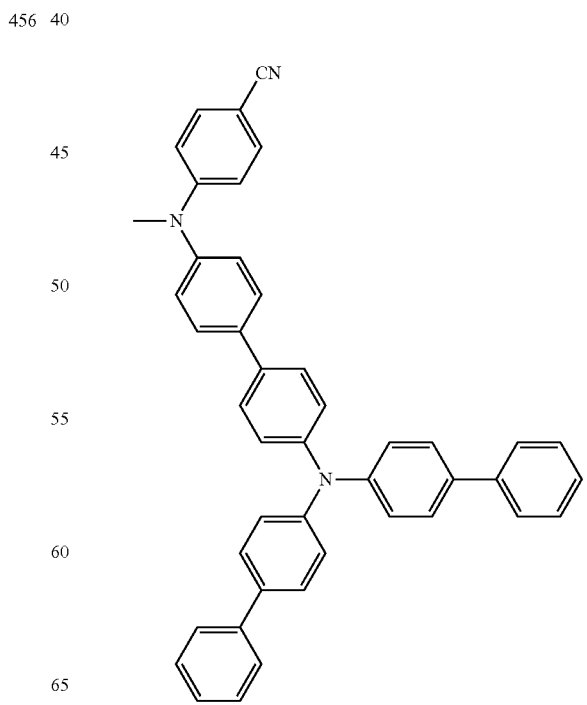
458

201
-continued
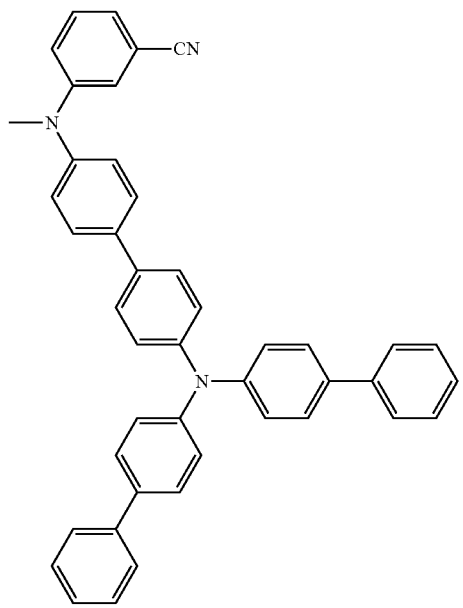
459
202
-continued
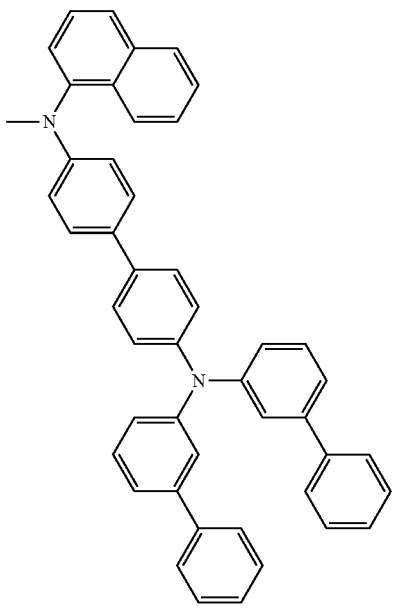
461
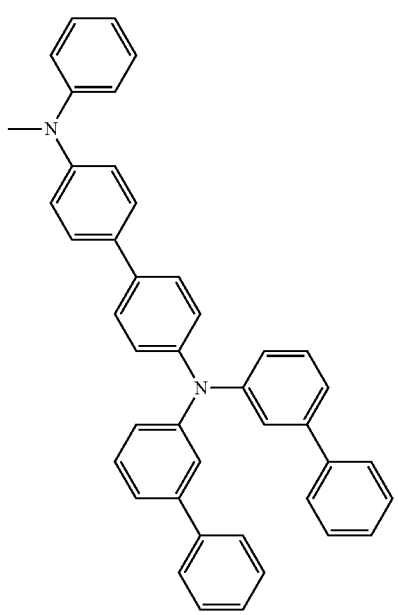
460
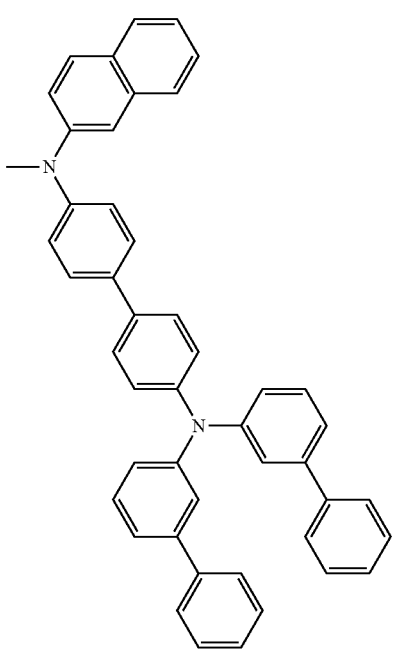
462

203
-continued
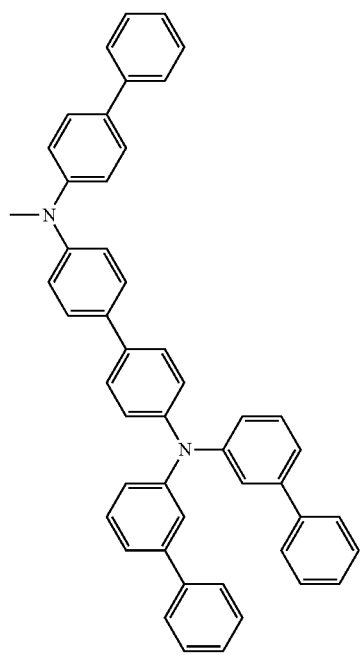
463
204
-continued
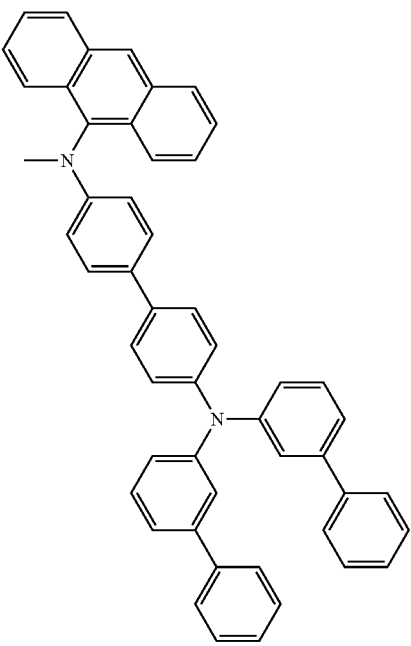
465
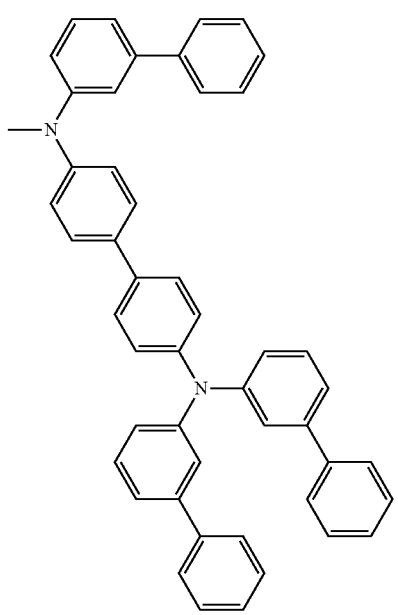
464
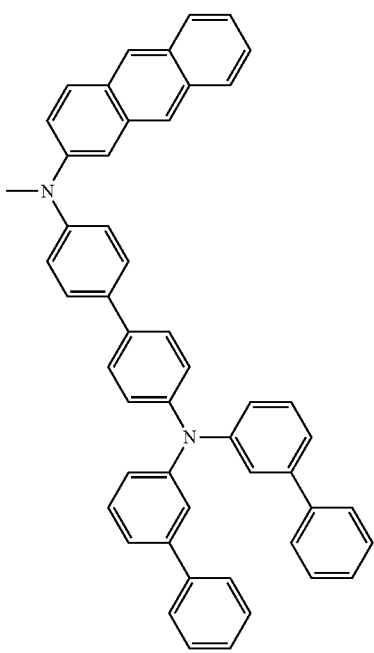
466

205
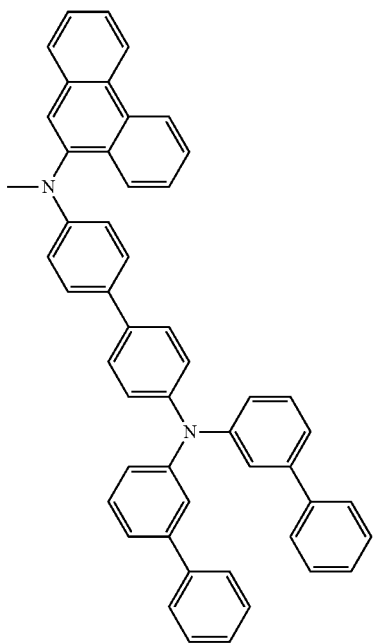
467
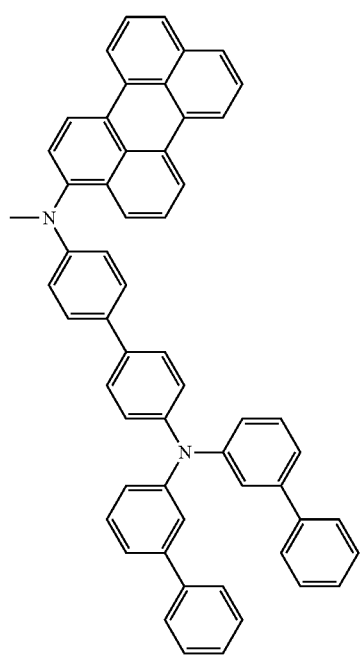
468
206
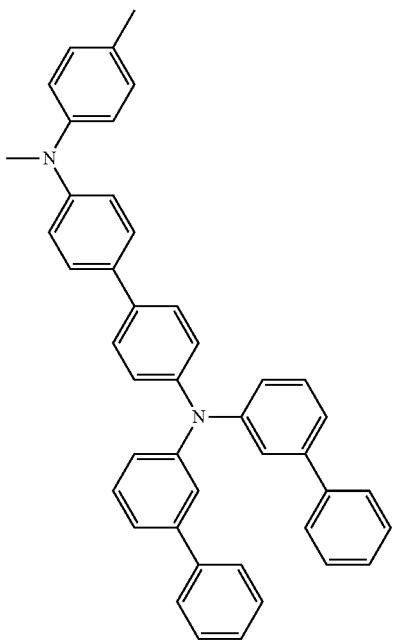
469
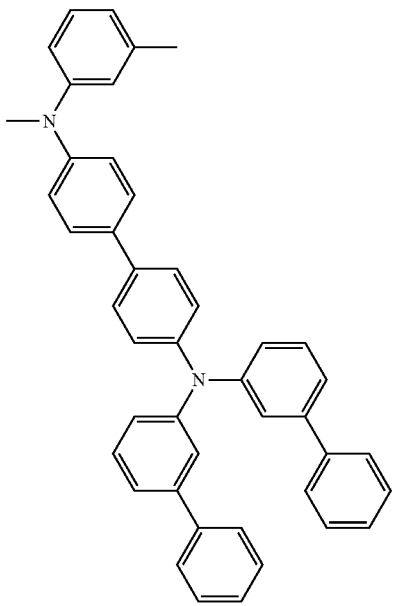
470

207
208
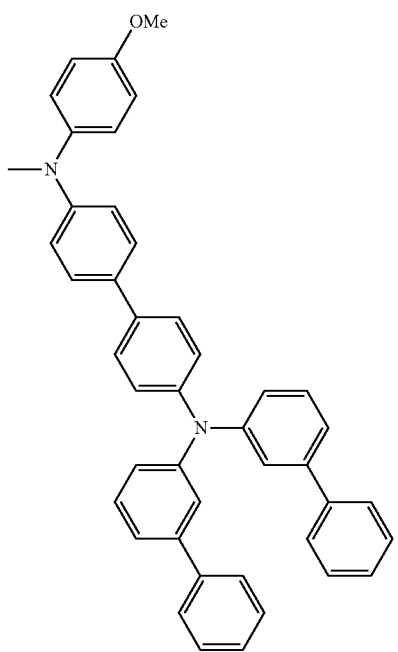
471
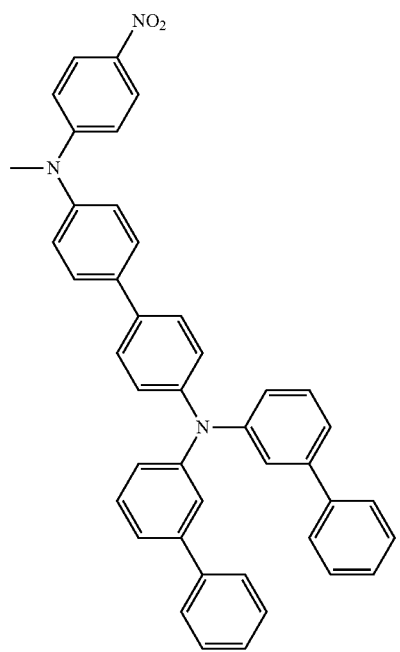
473
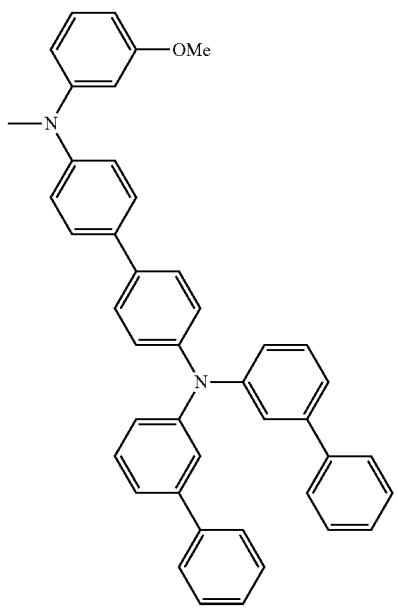
472
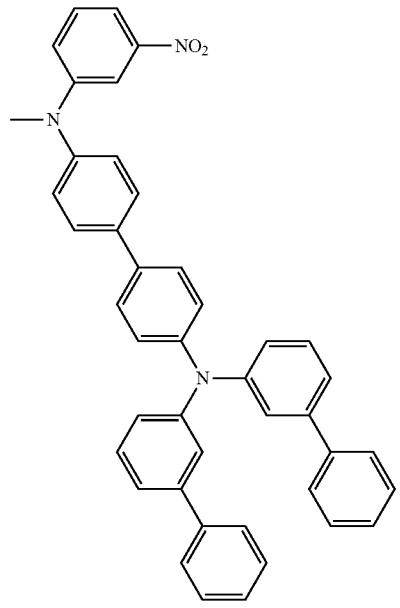
474

209
-continued

475

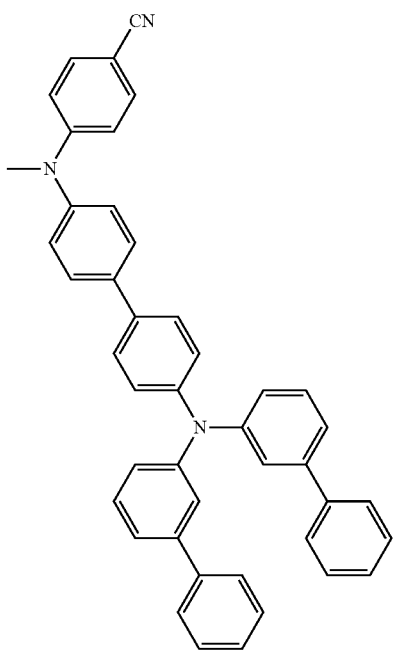

476

[Chemical Formula 1]

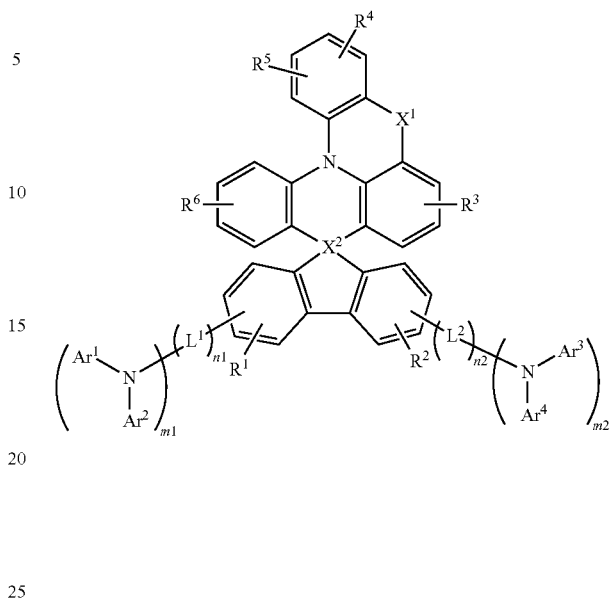

In the above Chemical Formula 1, $X^1$ is —O— or —S—, $X^2$ is —C— or —Si—, $Ar^1$ to $Ar^4$ are independently a substituted or unsubstituted C6 to C30 aryl group, or a substituted or unsubstituted C2 to C30 heteroaryl group. $L^1$ and $L^2$ are independently a substituted or unsubstituted C2 to C10 alkenylene group, a substituted or unsubstituted C2 to C10 arylene group, a substituted or unsubstituted C6 to C30 arylene group, or a substituted or unsubstituted C2 to C30 heteroarylene group, m1 and m2 are independently integers of 0 or 1, one of m1 and m2 is 1, n1 and n2 are independently integers ranging from 0 to 3, $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

The $X^1$ may be —O— or —S—. Since the $X^1$ has a polar group and thus, is able to interact with an electrode, charges may be easily injected.

When the arylamine group (or a hetaroarylamine group) is combined with the core having a spiro structure, charge mobility may be increased, and thus, driving voltage of a device may be deteriorated.

In addition, the compound has steric hindrance and thus, may be suppressed from crystallization due to small interaction among molecules. Accordingly, a yield of manufacturing a device may be improved. In addition, life-span characteristics of the device may be improved.

Furthermore, the compound has a relatively large molecular weight and may be suppressed from decomposition during the deposition.

More specifically, the compound for an organic optoelectronic device may be represented by the following Chemical Formula 1.

More specifically, the above Chemical Formula 1 may be represented by the following Chemical Formula 2. When an aryl amine group (or a heteroaryl amine group) is positioned as shown in the following Chemical formula 2, the compound may be easily synthesized.

[Chemical Formula 2]

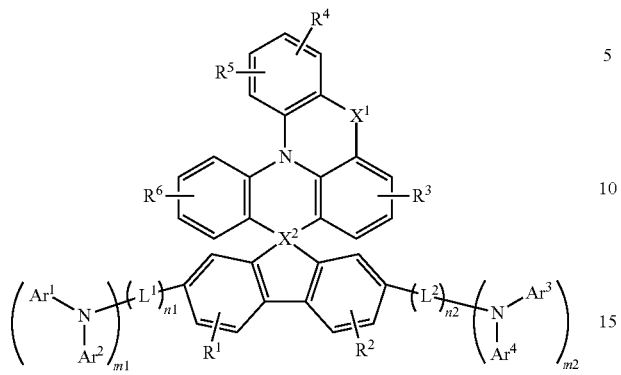

In the above Chemical Formula 2, $X^1$ is —O— or —S—, $X^2$ is —C— or —Si—, $Ar^1$ to $Ar^4$ are independently a substituted or unsubstituted C8 to C30 aryl group, or a substituted or unsubstituted C2 to C30 heteroaryl group, $L^1$ and $L^2$ are independently a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 and m2 are independently integers of 0 or 1, one of m1 and m2 is 1, n1 and n2 are independently integers ranging from 0 to 3, $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

More specifically the compound for an organic optoelectronic device may be represented by the following Chemical Formula 3.

[Chemical Formula 3]

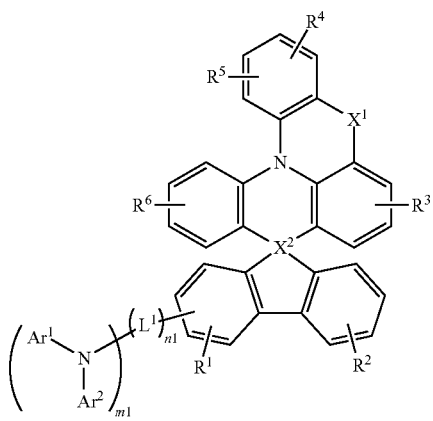

In the above Chemical formula 3, $X^1$ is —O— or —S—, $X^2$ is —C— or —Si—, $Ar^1$ and $Ar^2$ are independently a substituted or unsubstituted C6 to C30 aryl group, or a substituted or unsubstituted C2 to C30 heteroaryl group, $L^1$ is a substituted or unsubstituted C2 to C10 alkenylene group, a substituted or unsubstituted C2 to C10 alkynylene group, a substituted or unsubstituted C8 to C30 arylene group, or a substituted or unsubstituted C2 to C30 heteroarylene group, m1 is 1, n1 is integers ranging from 0 to 3, $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

More specifically, the compound tor an organic optoelectronic device may be represented by the following Chemical Formula 4.

[Chemical Formula 4]

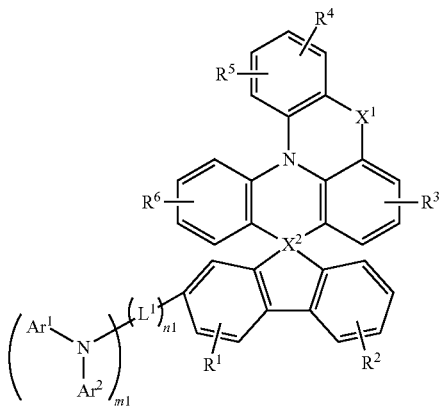

In the above Chemical Formula 4, $X^1$ is —O— or —S—, $X^2$ is —C— or —Si—, $Ar^1$ and $Ar^2$ are independently a substituted or unsubstituted C6 to C30 aryl group, or a substituted or unsubstituted C2 to C30 heteroaryl group, $L^1$ is a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, m1 is 1, n1 is integers ranging from 0 to 3, $R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

The $L^1$ and $L^2$ may be selectively adjusted to determine the entire conjugation length of the compound, and thereby HOMO, LUMO energy band may be adjusted.

Specific examples of the $L^1$ and $L^2$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a thiopheneylene group, a furan group, and the like.

The $Ar^1$ to $Ar^4$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiopheneyl group, a substituted or unsubstituted pyrrolyl group, a substituted or unsubstituted pyrazolyl group, a substituted or unsubstituted imidazolyl groups, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted beozothiopheneyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but is not limited thereto.

The compound for an organic optoelectronic device may have light emission, hole or electron characteristics; film stability; thermal stability; and high triplet exciton energy (T1) due to the substituent.

The $X^2$ may be —C—. Herein, since upper and lower molecules in the center of C are not in the same plane, energy band may be adjusted.

More specifically, the compound for an organic optoelectronic device may be represented by one of the following Chemical Formulae A-1 to A-28, but is not limited thereto.

A-1

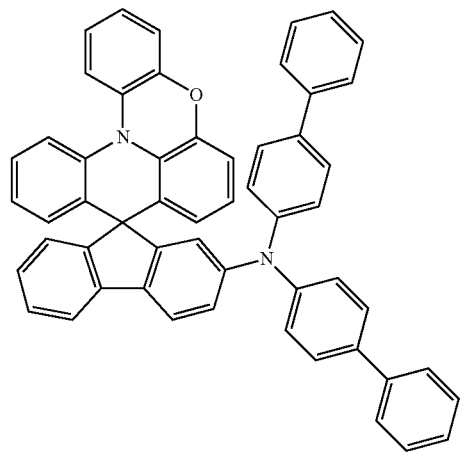

A-2

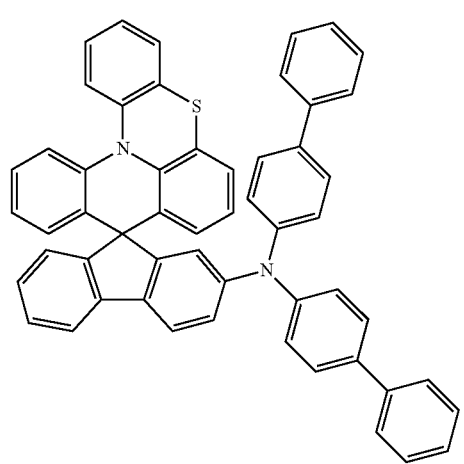

A-3

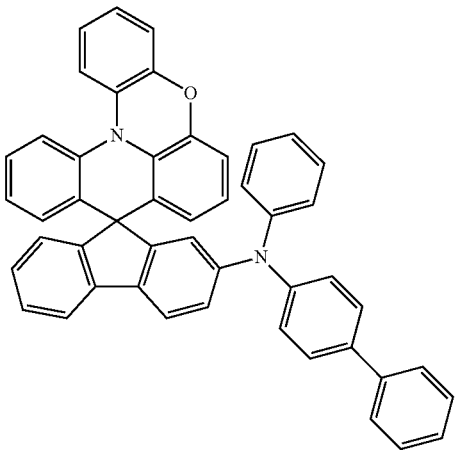

A-4

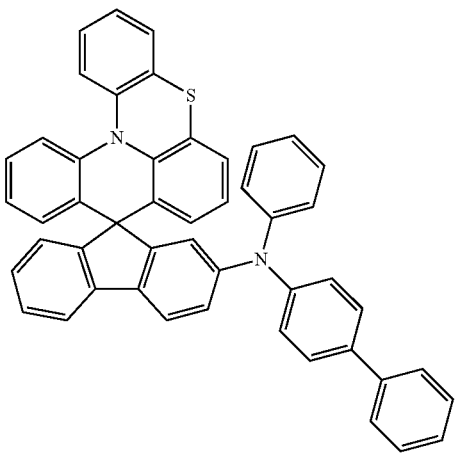

A-5

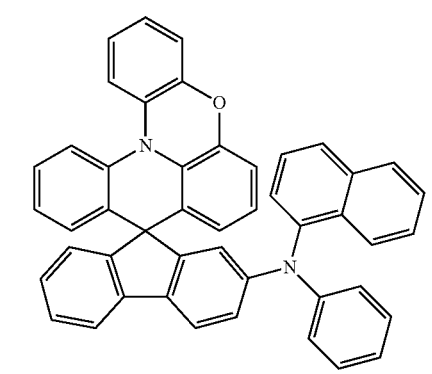

A-6

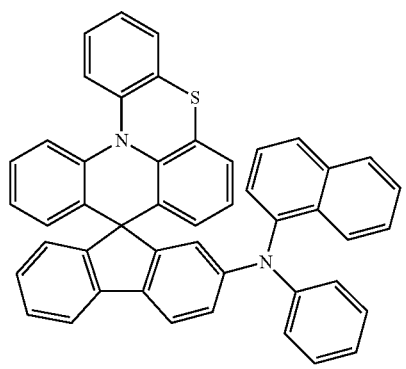

A-7
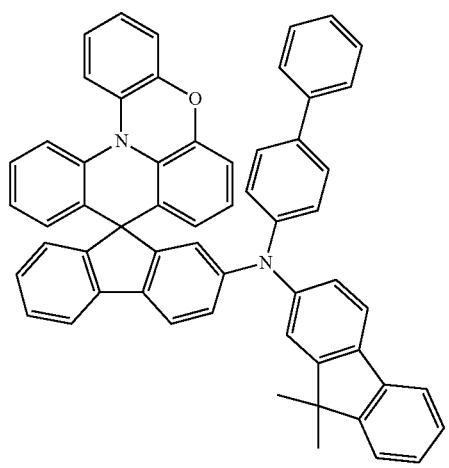
A-8
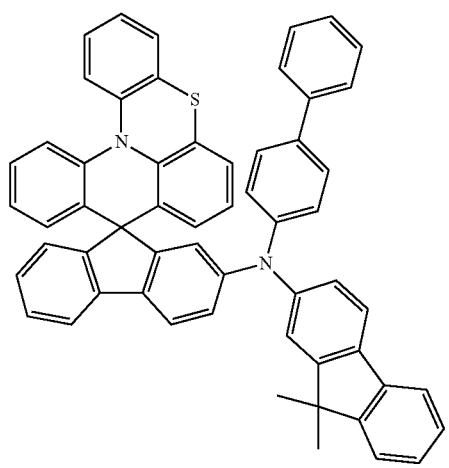
A-9
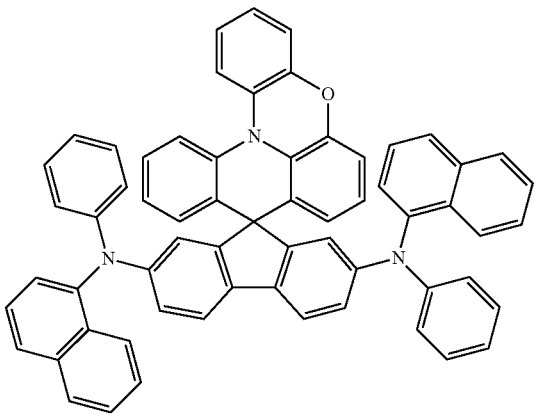
A-10
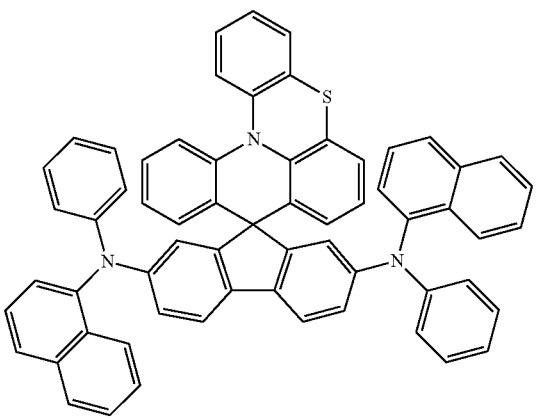
A-11
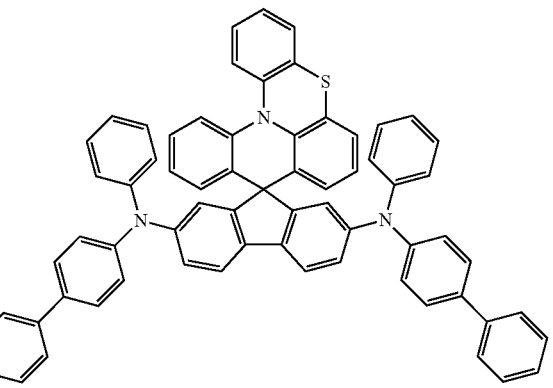
A-12

A-13
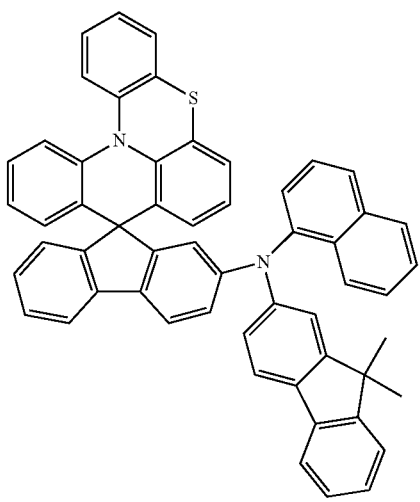
A-16
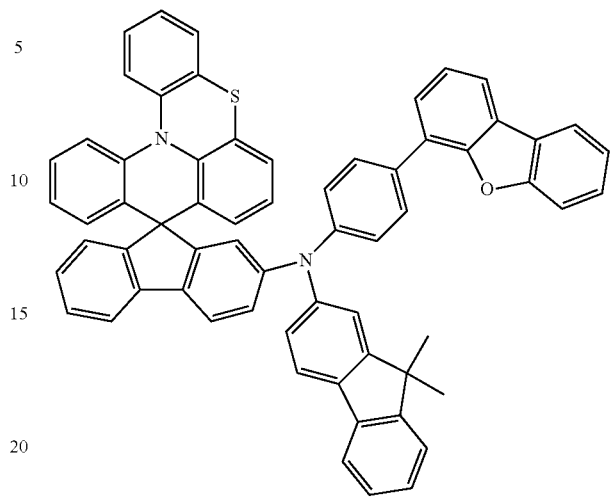
A-14
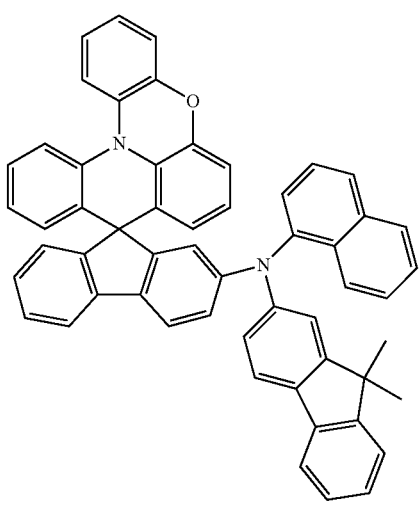
A-17
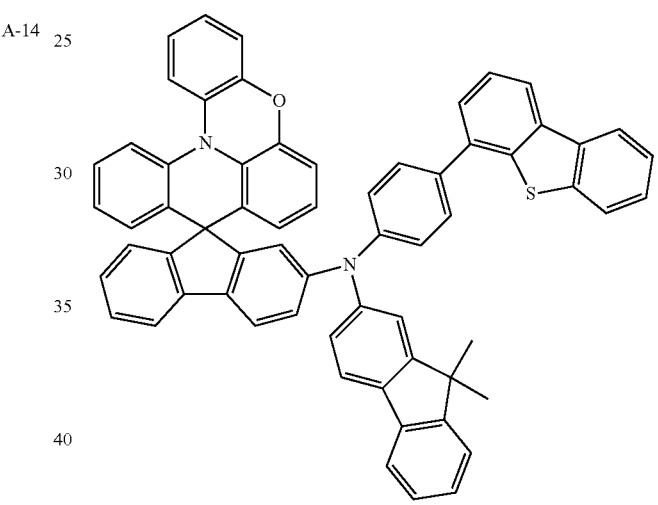
A-15
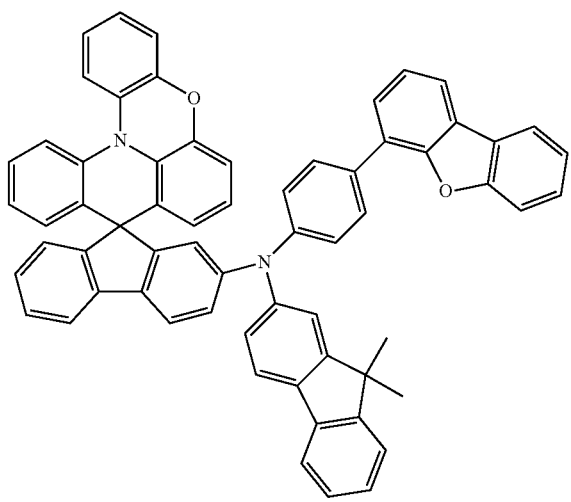
A-18
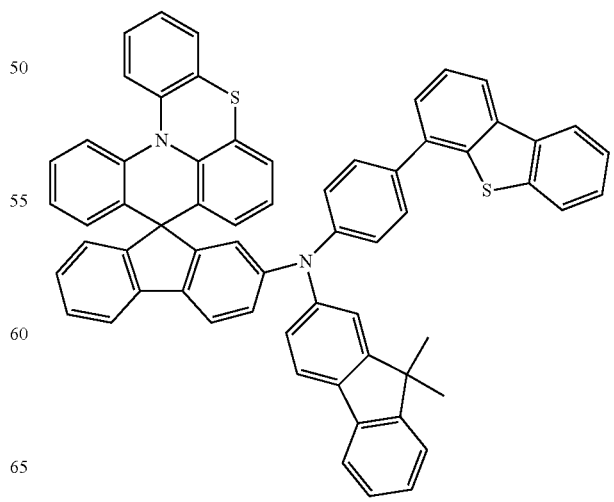

-continued
A-19
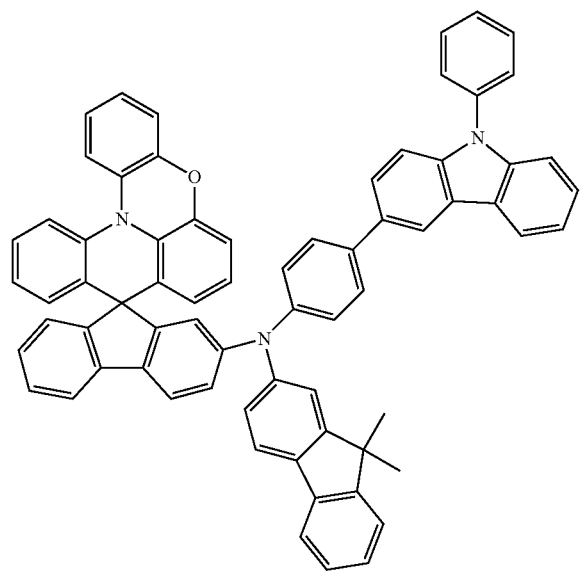
A-21
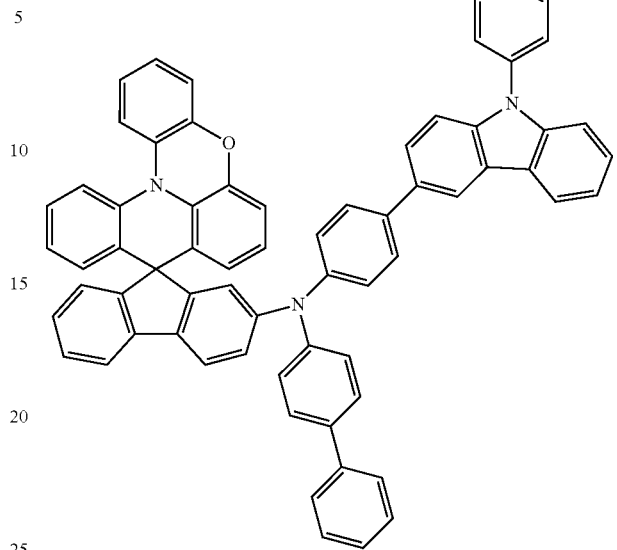
A-20
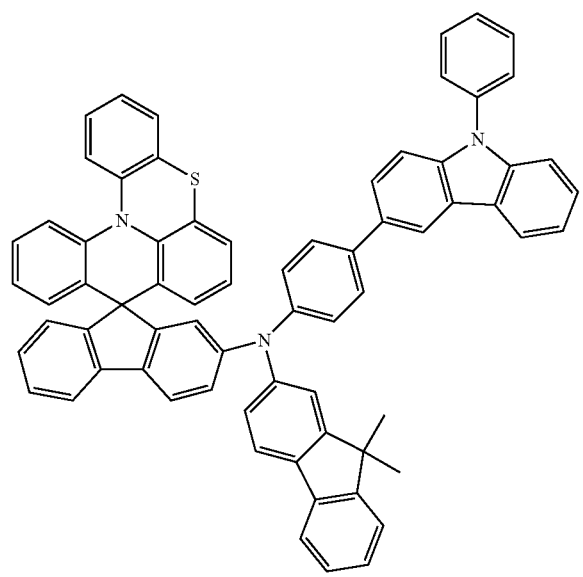
A-22
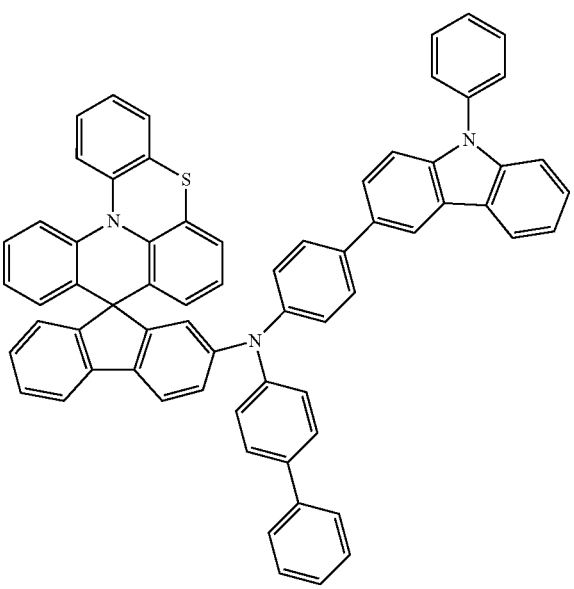

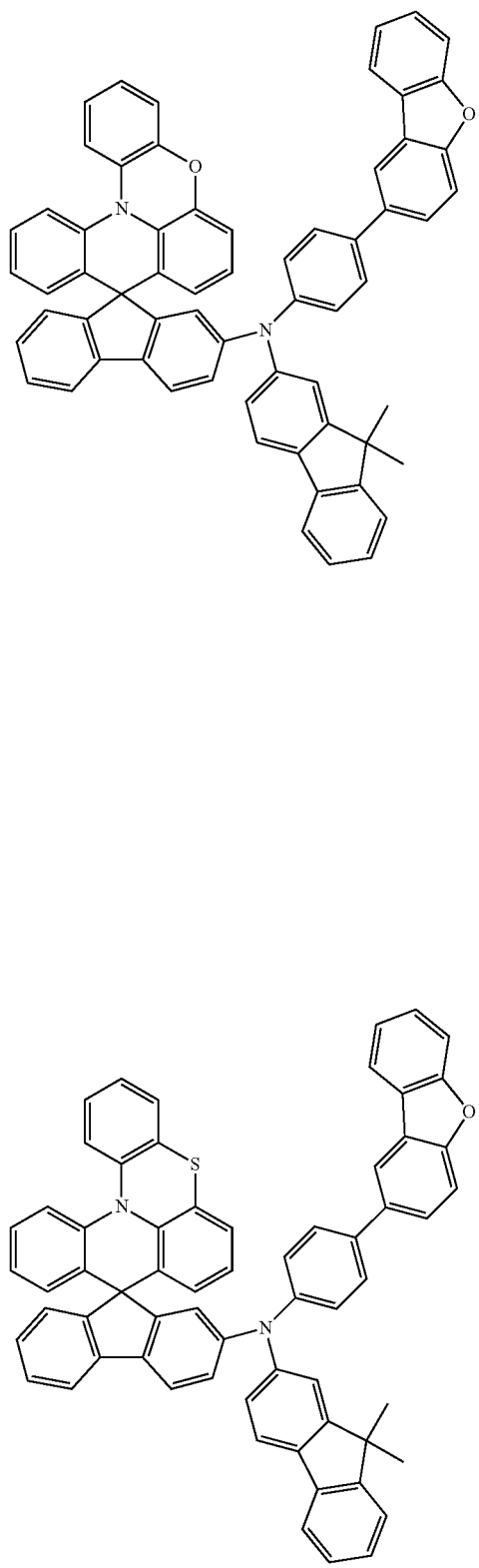
A-23
A-24
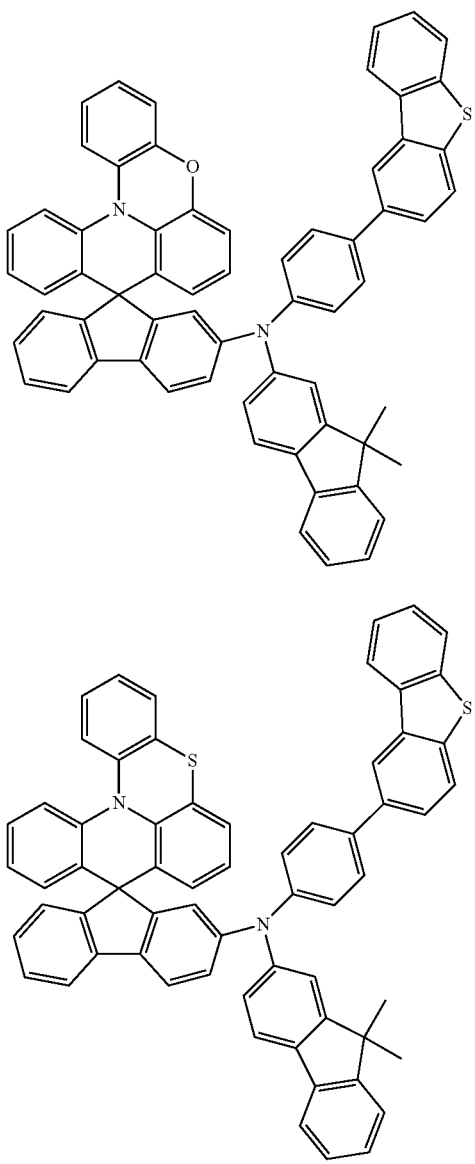
A-25
A-26
More specifically, the compound for an organic optoelectronic device may be represented by one of the following Chemical Formulae B-1 to B-10, but is not limited thereto.
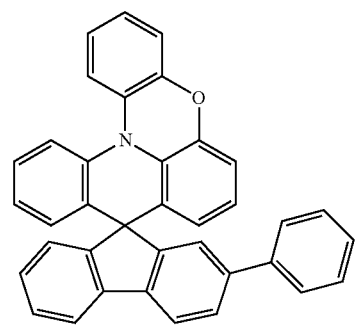
[B-1]

-continued
[B-2]
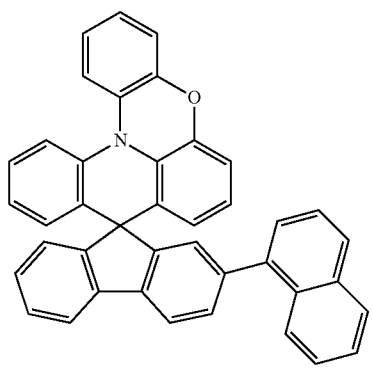
[B-3]
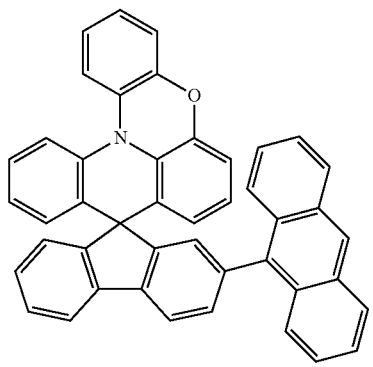
[B-4]
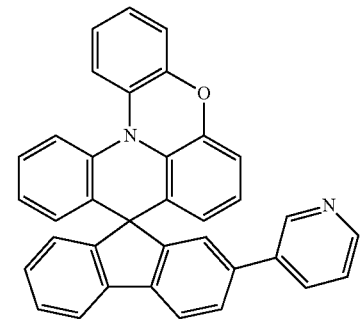
[B-5]
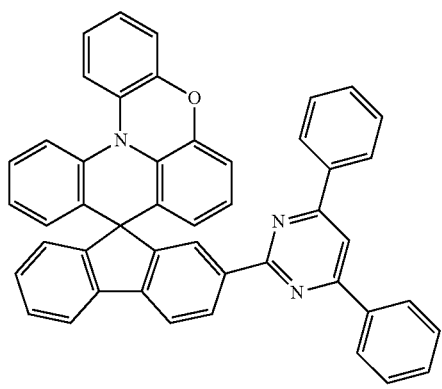
-continued
[B-6]
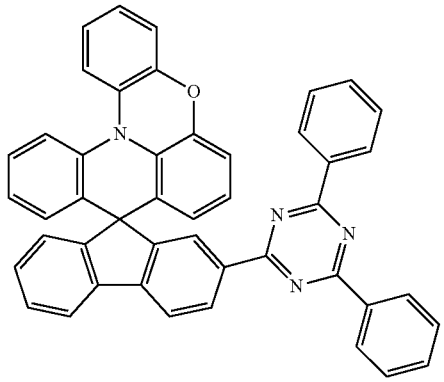
[B-7]
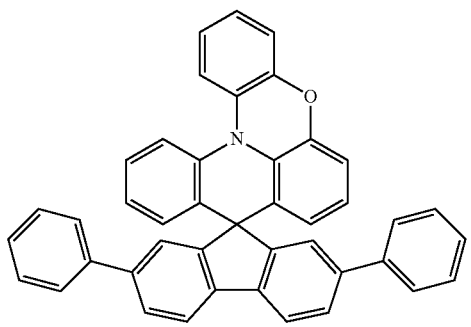
[B-8]
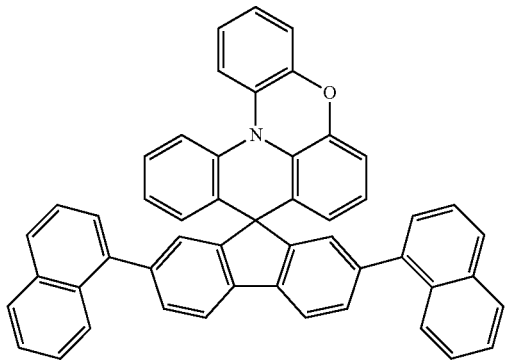
[B-9]
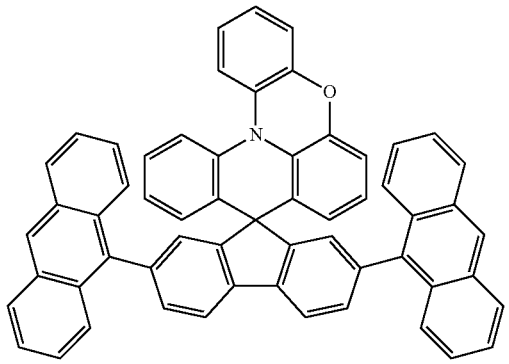

[B-10]

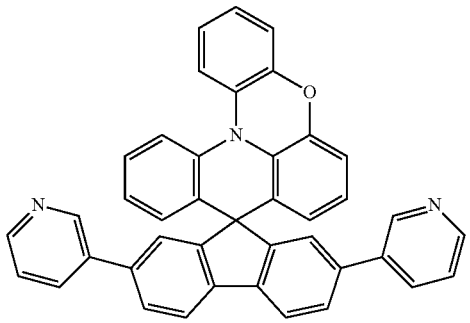

When the above compound according to one embodiment of the present invention requires both electron and hole characteristics, the functional group having electron characteristics may be introduced to effectively improve life-span of an organic light emitting diode, and decreasing its driving voltage.

The above compound for an organic optoelectronic device according to one embodiment of the present invention shows a maximum light emitting wavelength in a range of about 320 to about 500 nm, high triplet exciton energy (T1) of greater than equal to about 2.0 eV and specifically, about 2.0 to about 4.0 eV and thus, has an advantage of increasing luminous efficiency of a dopant by well transporting charges of a host having high triplet exciton energy to the dopant and decreasing a driving voltage by freely adjusting HOMO and LUMO energy levels of a material and accordingly, may be used as a host material or a charge transport material.

In addition, the compound for an organic optoelectronic device has optical and electrical activity and thus, may be used as a non-linear optical material, an electrode material, an electrochromic material, an optical switch, a sensor, a module, a wave guide, an organic transistor, a laser, an optical absorbing material, a dielectric material and a material for a separation membrane and the like.

The compound for an organic optoelectronic device including the above compounds has a glass transition temperature of greater than or equal to about 90° C. and a thermal decomposition temperature of greater than or equal to about 400° C., indicating improved thermal stability. Thereby, it is possible to produce an organic optoelectronic device having a high efficiency.

The compound for an organic optoelectronic device including the above compounds may play a role for emitting light or injecting and/or transporting electrons, and also act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to one embodiment of the present invention is used for an organic thin layer, and it may improve the life-span characteristics, efficiency characteristics, electrochemical stability, and thermal stability of an organic optoelectronic device and decrease the driving voltage.

Therefore, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, and the like. For example, the compound for an organic optoelectronic device according to one embodiment may be included in an electrode or an electrode buffer layer. In the organic solar cell to improve the quantum efficiency, and it may be used as an electrode material for a gate, a source-drain electrode, or the like in the organic transistor.

Hereinafter, en organic light emitting diode is specifically described.

An organic light emitting diode according to another embodiment of the present invention includes an anode, a cathode, and at least one or more organic thin layer between the anode and the cathode, and at least one of the organic thin layers may include the compound for an organic optoelectronic device according to one embodiment of the present invention.

The organic thin layer including the compound for an organic optoelectronic device may include a layer selected from an emission layer, a hole transport layer, a hole injection layer, an electron transport layer, an electron injection layer, a hole blocking layer, and a combination thereof. The at least one layer includes the compound for an organic optoelectronic device according to one embodiment. Particularly, the compound for an organic optoelectronic device according to one embodiment may be included in an electron transport layer or electron injection layer. In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light emitting diodes including the compound for an organic optoelectronic device according to one embodiment of the present invention.

Referring to FIGS. 1 to 6, organic light emitting diodes 100, 200, 300, 400, and 500 according to one embodiment include at least one organic thin layer 105 interposed between an anode 120 and a cathode 110.

The anode 120 includes an anode material having a large work function to help hole injection into an organic thin layer. Specific examples of the anode material include: a metal such as nickel platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or SnO$_2$:Sb or a conductive polymer such as poly(3-methylthiophene), poly[3,4-(ethylene-1,2-dioxy) thiophene] (PEDT), polypyrrole, and polyaniline, but is not limited thereto. It is preferable to include a transparent electrode including indium tin oxide (ITO) as an anode.

The cathode 110 includes a cathode material having a small work function to help electron injection into an organic thin layer. Specific examples of the cathode material include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, LiF/Al, and BaF$_2$/Ca, but is not limited thereto. It is preferable to include a metal electrode including aluminum as a cathode.

First, referring to FIG. 1, the organic light emitting diode 100 includes an organic thin layer 105 including only an emission layer 130.

Figure 2:
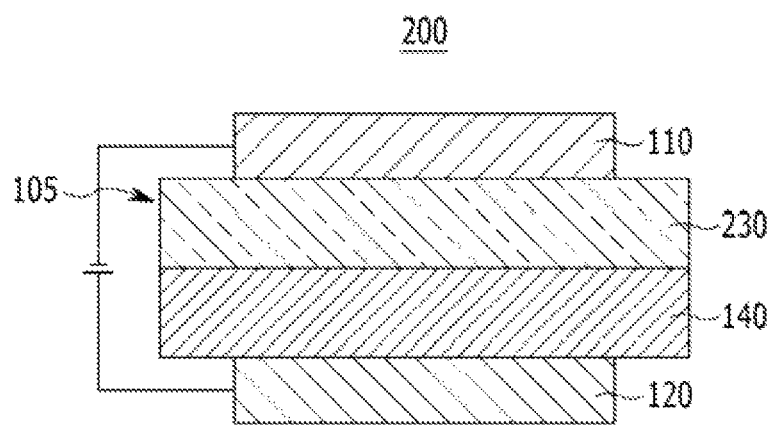

Referring to FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 106 includes a double layer of the emission layer 230 and hole transport layer (HTL) 140. The emission layer 130 also functions as an electron transport layer (ETL), and the hole transport layer (HTL) 140 layer has an excellent binding property with a transparent electrode such as ITO or an excellent hole transport capability.

Figure 3:
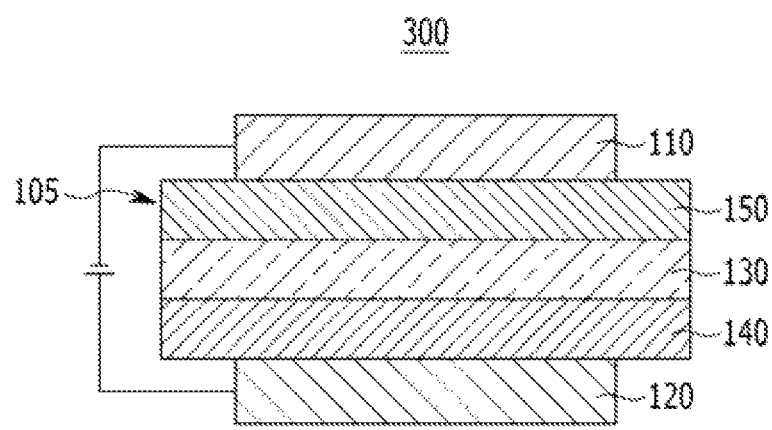

Referring to FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability are separately stacked.

Figure 4:
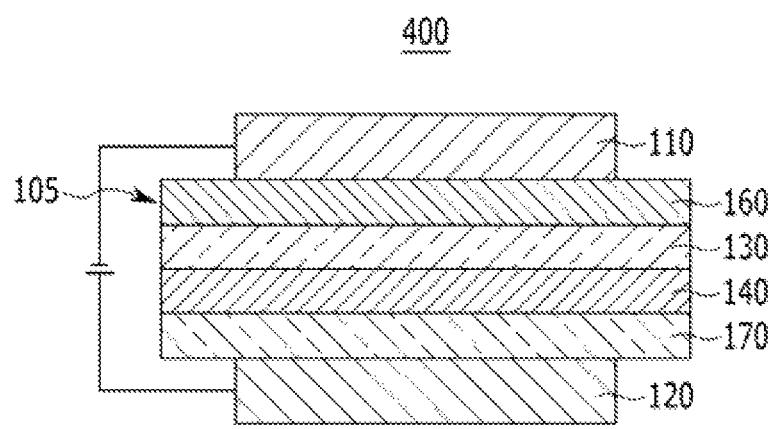

As shown in FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
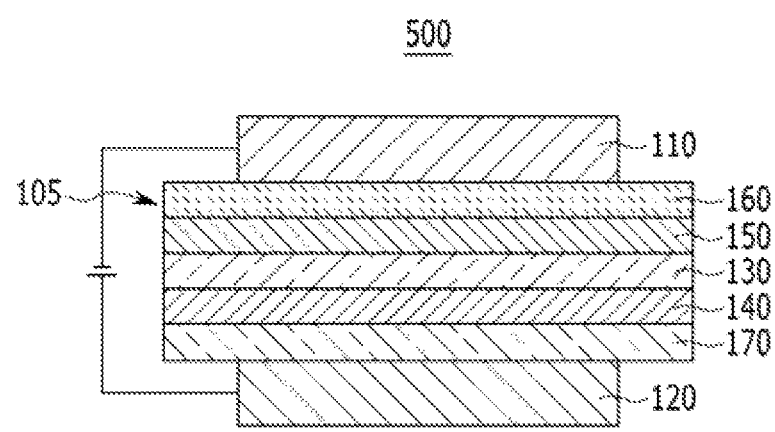

As shown in FIG. 5, a five-layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group consisting of an electron transport layer (ETL) 150, an election infection layer (EIL) 160, emission layers 130 and 230, a hole transport layer (HTL) 140, a hole injection layer (HIL) 170, and combinations thereof includes the compound for an organic optoelectronic device. The compound for an organic optoelectronic device may be used for an electron transport layer (ETL) 150 including the electron transport fever (ETL) 150 or electron infection layer (EL) 160. When it is used for the electron transport layer (ETL), it is possible to provide an organic light emitting diode having a more simple structure because it does not require an additional hole blocking layer (not shown).

Furthermore, when the compound for an organic optoelectronic device is included in the emission layers 130 and 230, the compound for an organic optoelectronic device may be included as a phosphorescent or fluorescent host or a fluorescent blue dopant.

The organic light emitting diode may be manufactured by forming an anode on a substrate; forming an organic thin layer in accordance with a dry coating method such as evaporation, sputtering, plasma plating, and ion plating or a wet coating method such as spin coating, dipping, and low coating; and providing a cathode thereon.

Another embodiment of the present invention provides a display device including: the light emitting diode according to the above embodiment.

MODE FOR THE INVENTION

Hereinafter, embodiments are illustrated in more detail with reference to examples. These examples, however, should not in any sense be interpreted as limiting the scope of the present invention.

Preparation of Compound for Organic Optoelectronic Device

Example 1

Preparation of Compound A-1

A compound re presented by the above Chemical Formula A-1 as specific examples of a compound for m organic optoelectronic device according to one embodiment of the present invention was synthesized through the following Reaction Scheme 1.

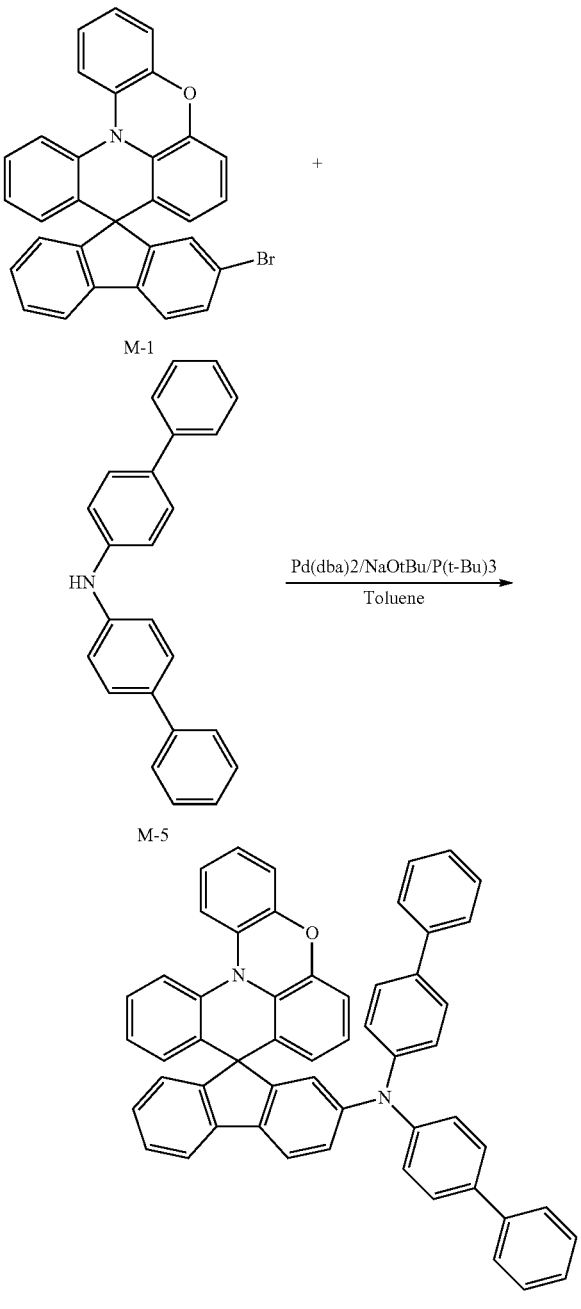

8.36 g (16.71 mmol) of an intermediate M-1, 4.88 g (15.99 mmol) of an intermediate M-5, 4.82 g (50.13 mmol) of sodium t-butoxide, and 0.09 g (0.46 mmol) of tri-tert-butylphosphine were dissolved in 300 ml of toluene, 0.26 g (0.48 mmol) of Pd(dba)$_2$ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was concentrated under a reduced pressure. A product obtained therefrom was purified through silica gel column chromatography by using a normal hexane/dichloromethane mixed solvent, obtaining 8.6 g (76.4%) of a desired compound A-1 as a white solid.

Example 2

Synthesis of Compound A-2

A compound represented by the above Chemical Formula A-2 as specific examples of a compound for an organic optoelectronic device according to one embodiment of the present invention was synthesized through the following Reaction Scheme 2.

[Reaction Scheme 2]

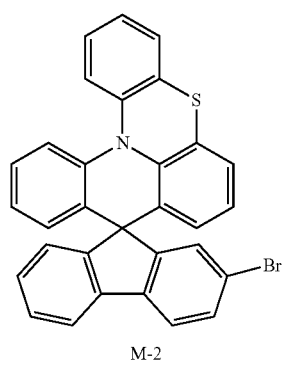

M-2

+

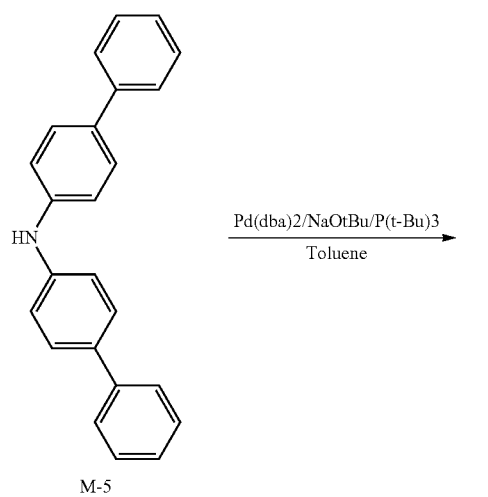

M-5

-continued

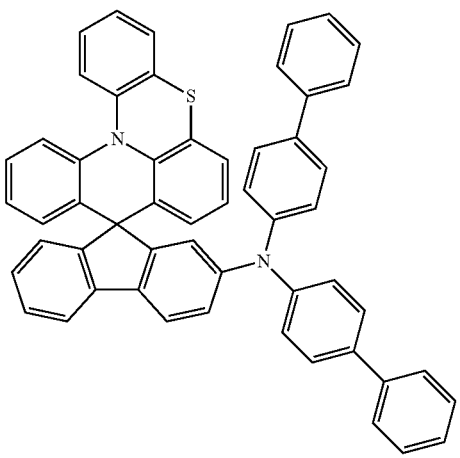

A-2

8.83 g (16.71 mmol) of an intermediate M-2, 4.88 g (15.19 mmol) of an intermediate M-5, 4.82 g (50.13 mmol) of sodium t-butoxide, and 0.99 g (0.46 mmol) of tri-tert-butylphosphine were dissolved in 300 ml of toluene, 0.26 g (0.40 mmol) of Pd(dba)$_2$ was added thereto, and the mixture was refluxed and agitated under a nitrogen atmosphere for 12 hours.

When the reaction was complete, the resultant was extracted with toluene and distilled water, and an organic layer obtained therefrom was dried with anhydrous magnesium sulfate, filtered, and concentrated under a reduced pressure. A product obtained therefrom was purified through silica gel column chromatography by using a normal hexane/dichloromethane mixed solvent. obtaining 8.4 g (73%) of a desired compound A-2 as a white solid.

Example 3

Synthesis of Compound A-3

A compound represented by the above Chemical Formula A-3 as specific examples of a compound for an organic optoelectronic device according to one embodiment of the present invention was synthesized through the following Reaction Scheme 3.

[Reaction Scheme 3]

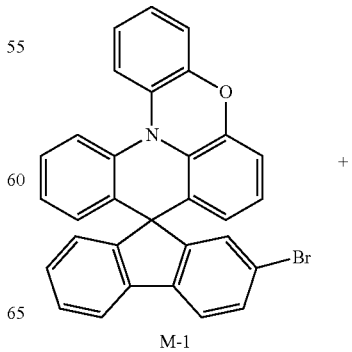

+

M-1

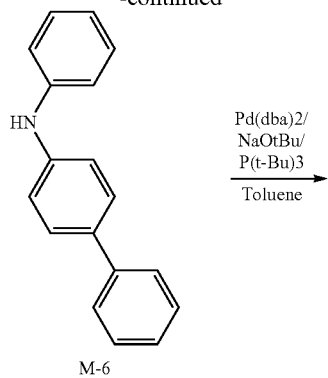

M-6

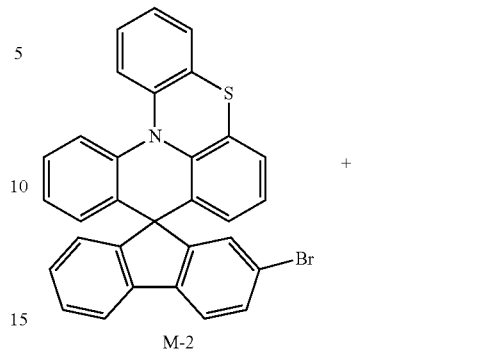

[Reaction Scheme 4]

M-2

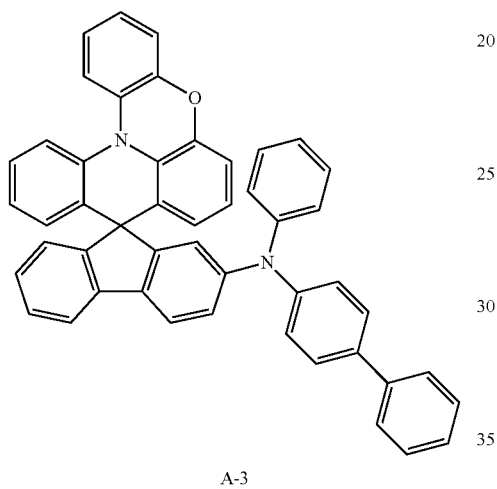

A-3

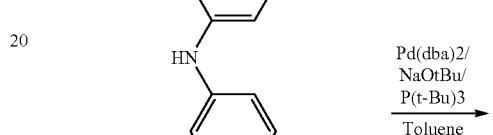

M-6

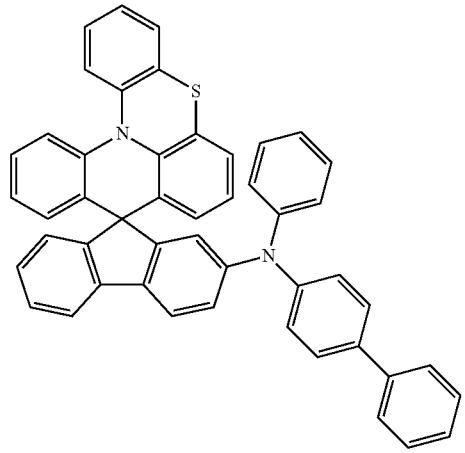

A-4

8.36 g (16.71 mmol) of an intermediate M-1, 3.72 g (15.19 mmol) of art intermediate M-6, 4.82 g (50.13 mmol) of sodium t-butoxide, and 0.09 g (0.46 mmol) of tri-tert-butylphosphine was dissolved in 300 ml of toluene, 0.26 g (0.46 mmol) of Pd(dba)$_2$ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was to concentrated under a reduced pressure. A product obtained therefrom was purified through silica gel column chromatography by using a normal hexane/dichloromethane mixed solvent, obtaining 7.9 g (78.2%) of a desired compound A-3 as a white sold.

Example 4

Synthesis of Compound A-4

A compound represented by the above Chemical Formula A-4 as specific examples of a compound for an organic optoelectronic device according to one embodiment of the present invention was synthesized through the following Reaction Scheme 4.

8.63 g (16.71 mmol) of an intermediate M-2, 3.72 g (15.19 mmol) of an intermediate M-6, 4.82 g (50.13 mmol) of sodium t-butoxide, and 0.09 g (0.46 mmol) of tri-tert-butylphosphine were dissolved in 300 ml of toluene, 0.26 g (0.46 mmol) of Pd(dba)$_2$ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was concentrated under a reduced pressure. A product obtained therefrom was obtained through silica gel column chromatography by using a normal hexane/dichloromethane mixed solvent, obtaining 8.1 g (78.3 %) of a desired compound A-4 as a white sold.

Example 5

Synthesis of Compound A-5

A compound represented by the above Chemical Formula A-5 as specific examples of a compound for an organic optoelectronic device according to one embodiment of the present invention was synthesized through the following Reaction Scheme 5.

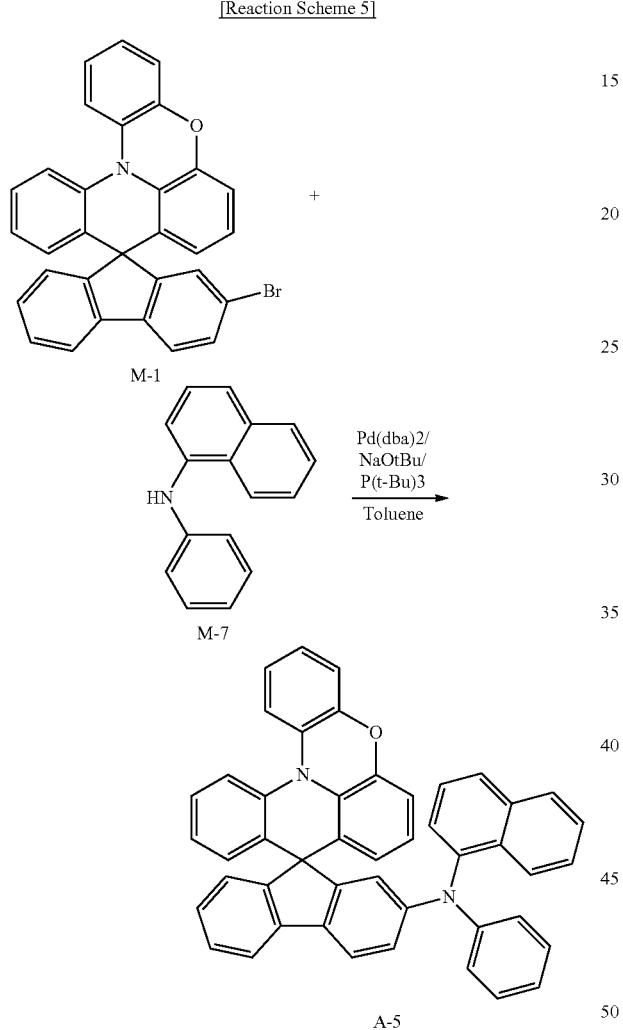

8.36 g (18.71 mmol) of an intermediate 3.33 g (15.19 mmol) of an intermediate M-7, 4.82 g (50.13 mmol) of sodium t-butoxide, and 0.09 g (0.48 mmol) of tri-tert-butylphosphine were dissolved in 300 ml of toluene, 0.26 g (0.46 mmol) of pd(dba)$_2$ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was concentrated under a reduced pressure. A product obtained therefrom was purified through silica gel column chromatography by using a normal hexane/dichloromethane mixed solvent, obtaining 7.8 g (80.4 %) of a desired compound A-5 as a white solid.

Example 6

Synthesis of Compound A-6

A compound represented by the above Chemical Formula A-6 as specific examples of a compound for an organic optoelectronic device according to one embodiment of the present invention was synthesized through the following Reaction Scheme 6.

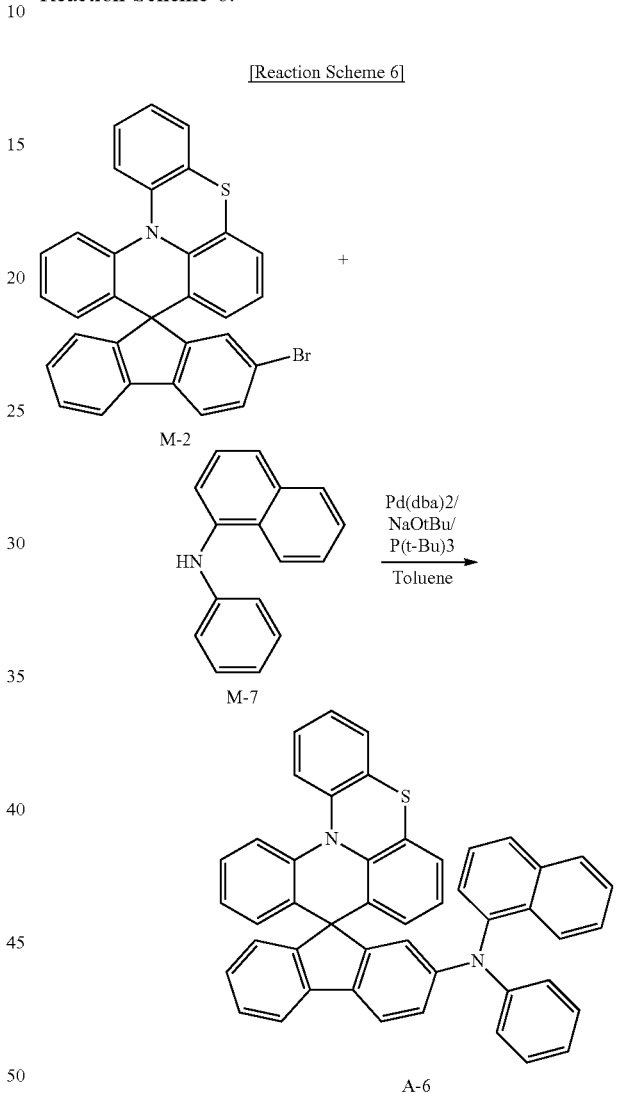

8.63 g. (16.71 mmol) of an intermediate M-2, 3.33 g (15.19 mmol) of an intermediate M-7, 4.82 g (50.13 mmol) of sodium t-butoxide, and 0.09 g (0.46 mmol) of tri-tert-butylphosphine were dissolved in 300 ml of toluene, 0.26 g (0.46 mmol) of Pd(dba)$_2$ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was to concentrated under a reduced pressure. A product obtained therefrom was purified through silica gel column chromatography by using a normal hexane/dichloromethane mixed solvent, obtaining 7.6 g (76.3 %) of a desired compound A-6.

Example 7

Synthesis of Compound A-7

A compound represented by the above Chemical Formula A-7 as specific examples of a compound for an organic optoelectronic device according to one embodiment of the present invention was synthesized through the following Reaction Scheme 7.

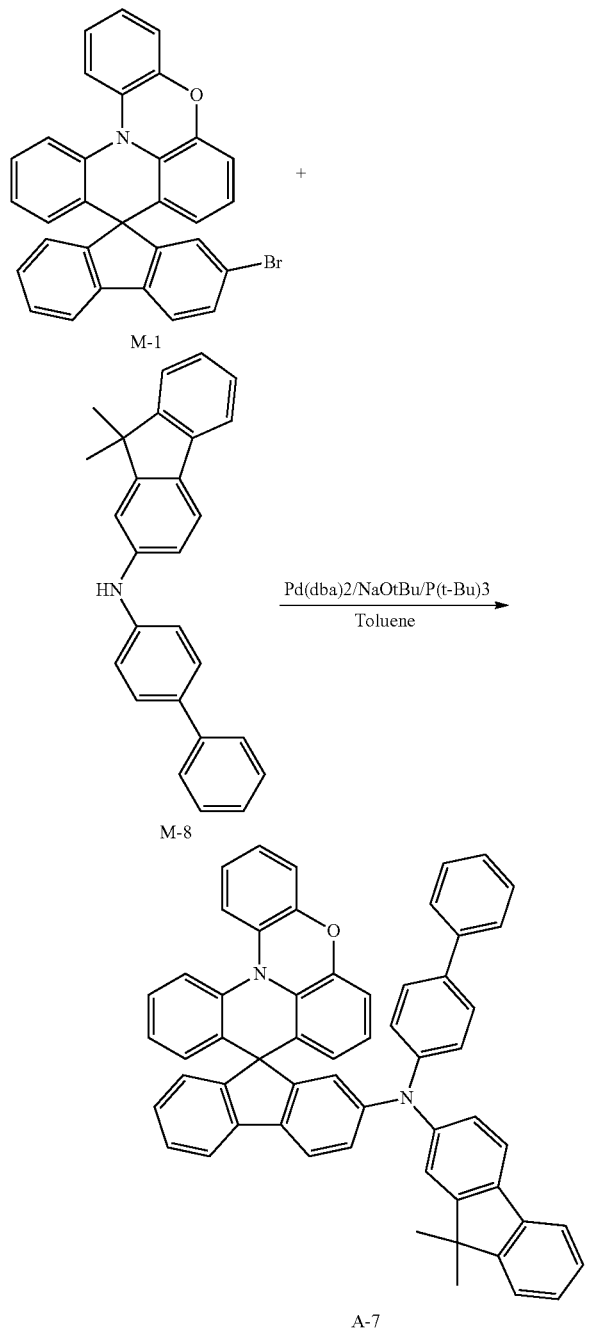

[Reaction Scheme 7]

8.36 g (16.71 mmol) of an intermediate 5.49 g 15.19 mmol) of an intermediate M-8, 4.82 g (50.13 mmol) of sodium t-butoxide, and 0.09 g (0.46 mmol) of tri-tert-butylphosphine were dissolved in 300 ml of toluene, 0.26 g (0.48 mmol) of Pd(dba)₂ was added thereto, and the mixture was refluxed and agitated under a nitrogen atmosphere for 12 hours.

When the reaction was complete, the resultant was extracted with toluene and distilled water, and an organic layer obtained therefrom was dried with anhydrous magnesium sulfate and filtered, and a filtered solution was concentrated under reduced pressure. A product obtained therefrom was purified through silica gel column chromatography by using a normal hexane/dichloromethane mixed solvent, obtaining 8.8 g (74.2 %) of a desired compound A-7 as a white solid.

Example 8

Synthesis of Compound A-8

A compound represented by the above Chemical Formula A-8 as specific examples of a compound for an organic optoelectronic device according to one embodiment of the present invention was synthesized through the following Reaction Scheme 8.

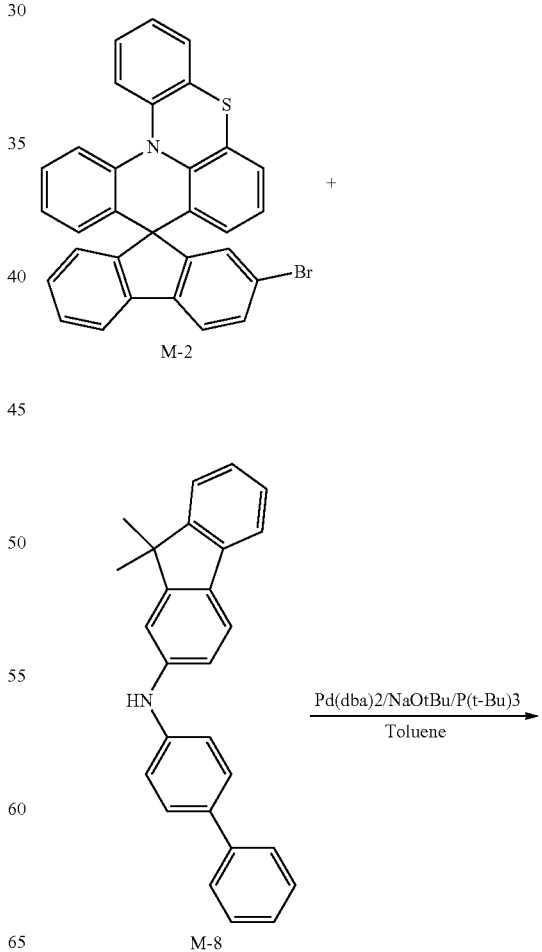

[Reaction Scheme 8]

-continued

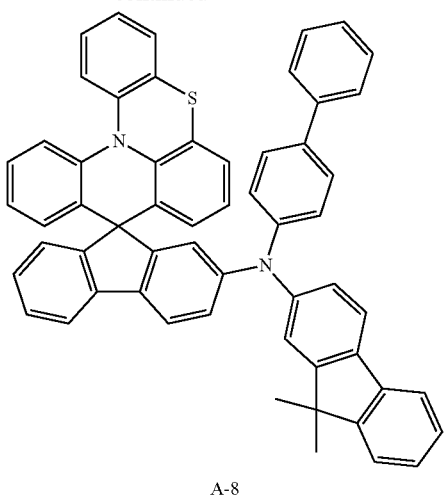

A-8

8.63 g (16.71 mmol) of an intermediate M-2, 5.49 g (15.19 mmol) of an intermediate M-8, 4.82 g (50.13 mmol) of sodium t-butoxide, and 0.09 g (0.46 mmol) of tri-tert-butylphosphine were dissolved in 300 ml of toluene, 0.26 g (0.46 mmol) of Pd(dba)₂ was added thereto, and the mixture was refluxed and agitated under a nitrogen atmosphere for 12 hours.

When the reaction was complete, the resultant was extracted, an organic layer obtained therefrom was dried with anhydrous magnesium sulfate and filtered, and a filtered solution was concentrated under a reduced pressure. A product obtained therefrom was purified through silica gel column chromatography ay using a normal hexane/dichloromethane mixed solvent obtaining 10.1 g (83.5%) of a desired compound A-8 as a white sold.

Example 9

Synthesis of Compound A-9

A compound represented by the above Chemical Formula A-9 as specific examples of a compound for an organic optoelectronic device according to one embodiment of the present invention was synthesized through the following Reaction Scheme 9.

[Reaction Scheme 9]

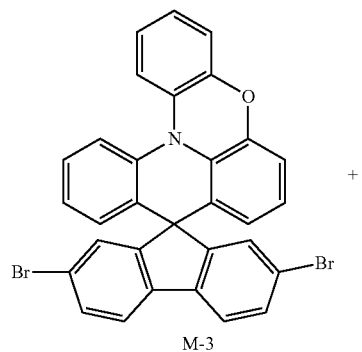

M-3

-continued

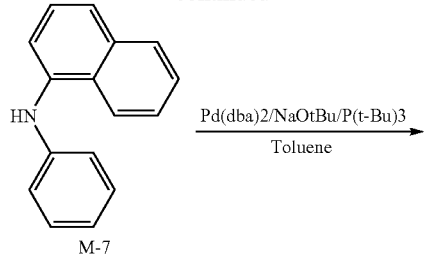

M-7

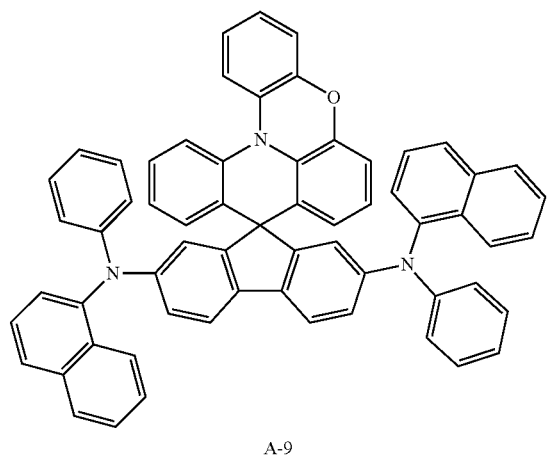

A-9

8 g (13.81 mmol) of so intermediate M-3, 6.36 g (29 mmol) of an intermediate M-7, 9.64 g (100.26 mmol) of sodium t-butoxide, and 0.18 g (0.92 mmol) of tri-tert-butylphosphine were dissolved in 300 ml of toluene, 0.52 g (0.92 mmol) of Pd(dba)₂ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was concentrated under a reduced pressure. A product obtained therefrom was purified through silica gel column chromatography by using a normal hexane/dichloromethane mixed solvent, obtaining 9.3 g (78.7%) of a desired compound A-9 as a white solid.

Example 10

Synthesis of Compound A-10

A compound represented by the above Chemical Formula A-10 as specific examples of a compound for an organic optoelectronic device according to one embodiment of the present invention was synthesized through the following Reaction Scheme 10.

239

[Reaction Scheme 10]

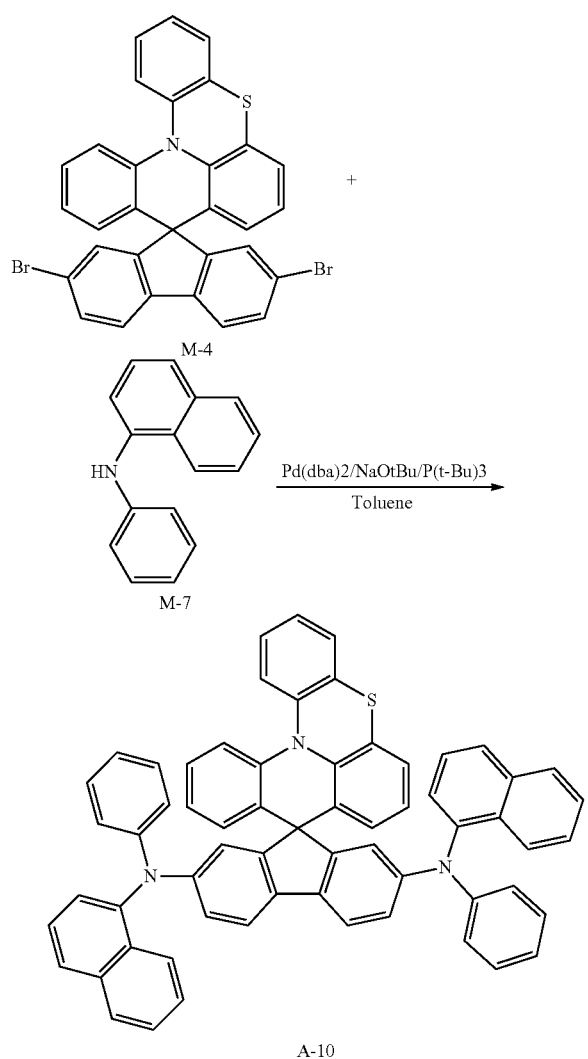

8.22 g (13.81 mmol) of an intermediate M-4, 6.36 g (29 mmol) of an intermediate M-7, 9.64 g (100.26 mmol) of sodium t-butoxide, and 0.18 g (0.92 mmol) of tri-tert-butylphosphine were dissolved in 300 ml of toluene, 0.52 g (0.92 mmol) of Pd(dba)$_2$ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was concentrated under a reduced pressure. A product obtained therefrom was purified through silica gel column chromatography by using a normal hexane/dichloromethene mixed solvent, obtaining 9.5 g (78.9%) of a desired compound A-10 as a white solid.

Example 11

Synthesis of Compound A-11

A compound represented by the above Chemical Formula A-11 as specific examples of a compound for an organic

240 optoelectronic device according to one embodiment of the present invention was synthesized through the following Reaction Scheme 11.

[Reaction Scheme 11]

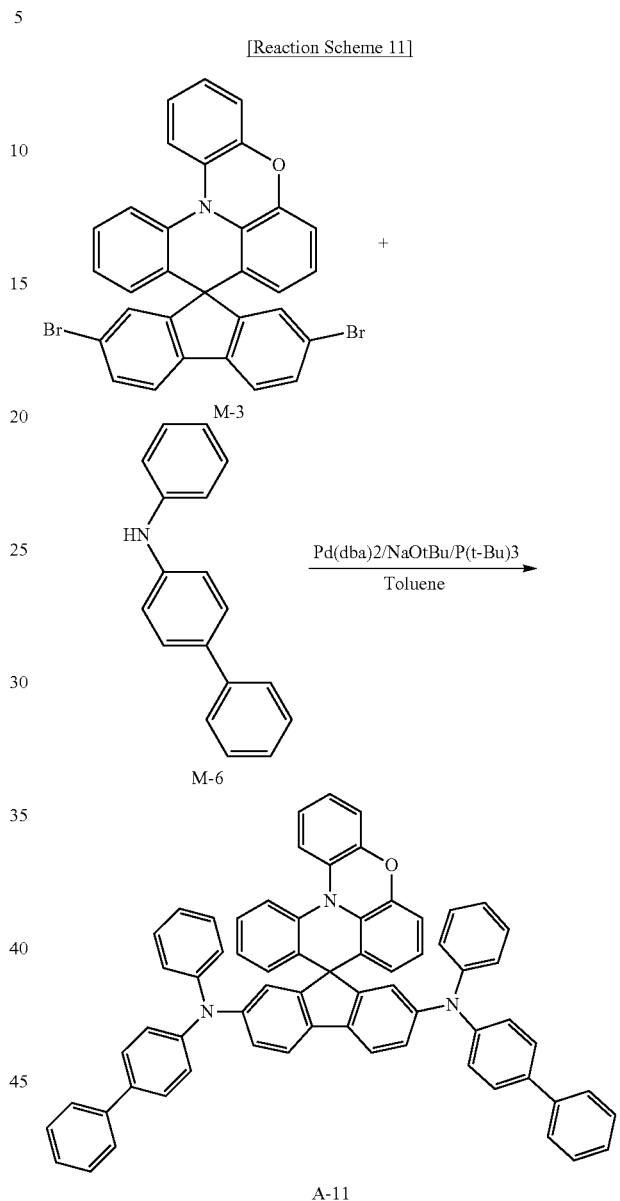

8 g (13.81 mmol) of an intermediate M-3, 7.11 g (29 mmol) of an intermediate M-6, 9.64 g (100.26 mmol) of sodium t-butoxide, and 0.18 g (0.92 mmol) of tri-tert-butylphosphine were dissolved in 300 ml of toluene, 0.52 g (0.92 mmol) of Pd(dba)$_2$ was added thereto, and the mixture was refluxed and agitated under a nitrogen atmosphere for 12 hours.

When the reaction was complete, the resultant was extracted with toluene and distilled water, an organ(c) layer obtained therefrom was dried with anhydrous magnesium sulfate and filtered, and a filtered solution was concentrated under a reduced pressure. A product obtained therefrom was purified through silica gel column chromatography by using a normal hexane/dichloromethane mixed solvent, obtaining 10.5 g (85%) of a desired compound A-11 as a white solid.

Example 12

Synthesis of Compound A-12

A compound represented by the above Chemical Formula A-12 as specific examples of a compound for an organic optoelectronic device according to one embodiment of the present invention was synthesized through the following Reaction Scheme 12.

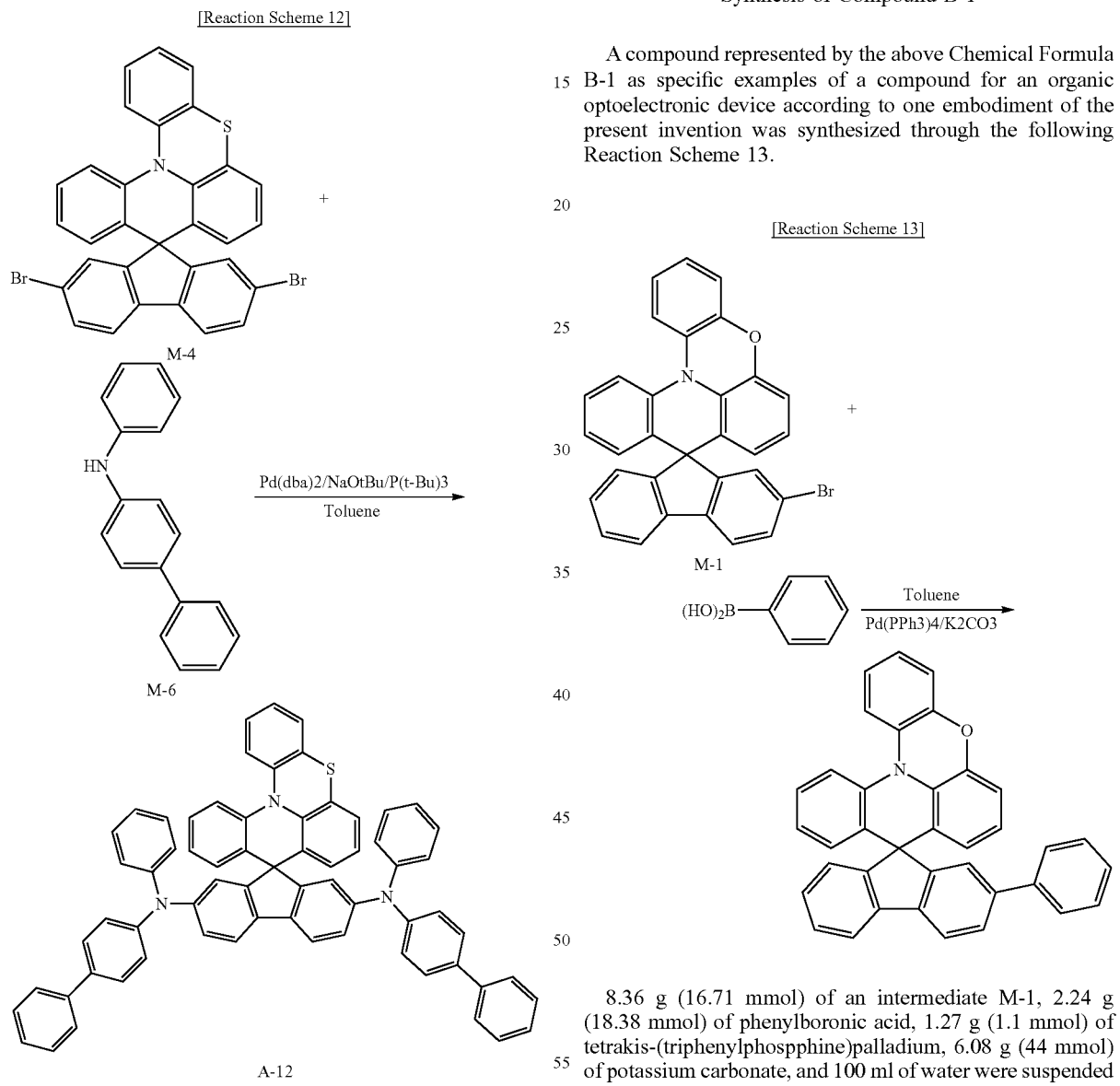

8.22 g (13.81 mmol) of an intermediate M-4, 7.11 g (29 mmol) of an intermediate M-6, 9.64 g (100.26 mmol) of sodium t-butoxide, and 0.18 g (0.92 mmol) of tri-tert-butylphosphine were dissolved in 300 ml of toluene, 0.52 g (0.92 mmol) of Pd(dba)$_2$ was added thereto, and the mixture was refluxed and agitated under a nitrogen atmosphere for 12 hours.

When the reaction was complete, the resultant was extracted with toluene and distilled water, an organic layer obtained therefrom was dried with anhydrous magnesium sulfate and filtered, and a filtered solution was concentrated under a reduced pressure. A product obtained therefrom was purified through silica gel column chromatography by using a normal hexane/dichloromethane a mixed solvent, obtaining 10.3 g (80.7 %) of a desired compound A-12 as a white solid.

Example ad-1

Synthesis of Compound B-1

A compound represented by the above Chemical Formula B-1 as specific examples of a compound for an organic optoelectronic device according to one embodiment of the present invention was synthesized through the following Reaction Scheme 13.

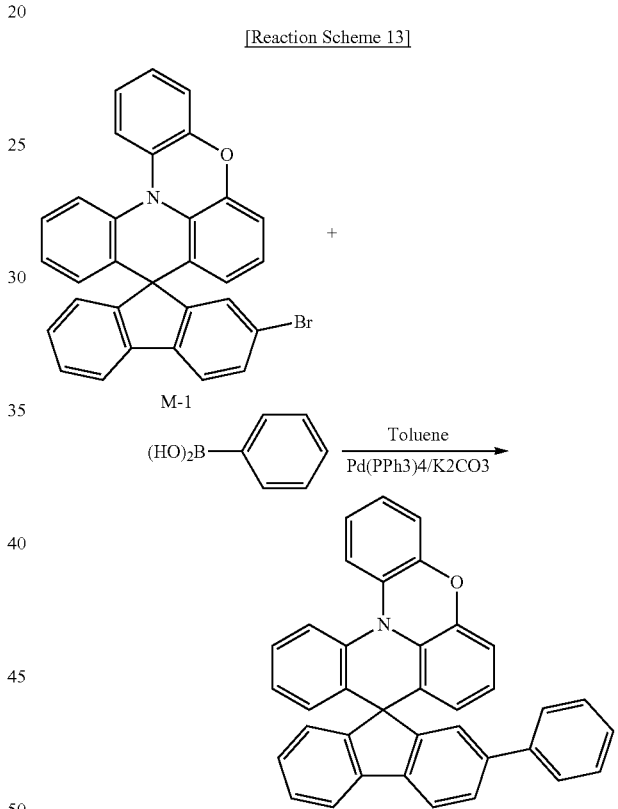

8.36 g (16.71 mmol) of an intermediate M-1, 2.24 g (18.38 mmol) of phenylboronic acid, 1.27 g (1.1 mmol) of tetrakis-(triphenylphospphine)palladium, 6.08 g (44 mmol) of potassium carbonate, and 100 ml of water were suspended in 200 ml of toluene, and the suspended solution was heated and refluxed under a nitrogen atmosphere for 12 hours.

The reaction liquid was separated into two layers, an organic layer out of the two layers was washed with a sodium chloride saturated aqueous solution and dried with anhydrous sodium sulfate.

After distillating and removing an organic solvent therein was under a reduced pressure, its residue was purified through silica gel column chromatography by using a normal hexane/dichloromethane mixed solvent obtaining 7.3 g (87.8%) of a desired compound as a white solid.

Example ad-2

Synthesis of Compound B-4

A compound represented by the above Chemical Formula B-4 as specific examples of a compound for an organic optoelectronic device according to one embodiment of the present invention was synthesized through the following Reaction Scheme 14.

[Reaction Scheme 14]

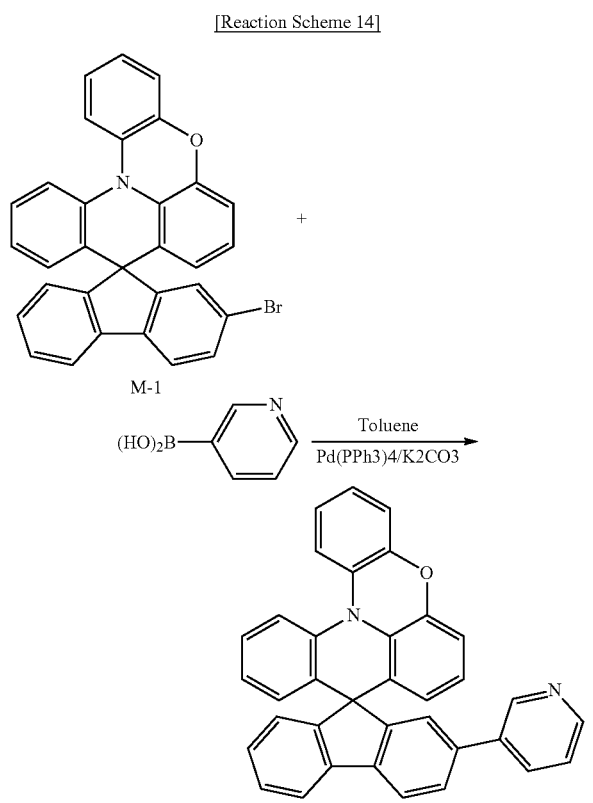

8.36 g (16.71 mmol) of an intermediate M-1, 2.26 g (18.38 mmol) of 3-pyridine boronic acid, 1.27 g (1.1 mmol) of tetrakis-(triphenylphosphine)palladium, 6.08 g (44 mmol) of potassium carbonate, and 100 ml of water were suspended in 200 ml of toluene, and the suspended solution was heated and refluxed under a nitrogen atmosphere for 12 hours.

The reaction liquid was separated into two layers, and an organic layer out of the two layers was washed with a sodium chloride saturated aqueous solution and dried with anhydrous sodium sulfate.

After distilling and removing an organic solvent therein under a reduced pressure, a residue was purified through silica gel column chromatography by using a normal hexane/dichloromethane mixed solvent obtaining 7.1 g (85.2 %) of a desired compound as a white solid.

Example ad-3

Synthesis of Compound B-7

A compound represented by the above Chemical Formula B-7 as specific examples of a compound for an organic optoelectronic device according to one embodiment of the present invention was synthesized through the following Reaction Scheme 15.

[Reaction Scheme 15]

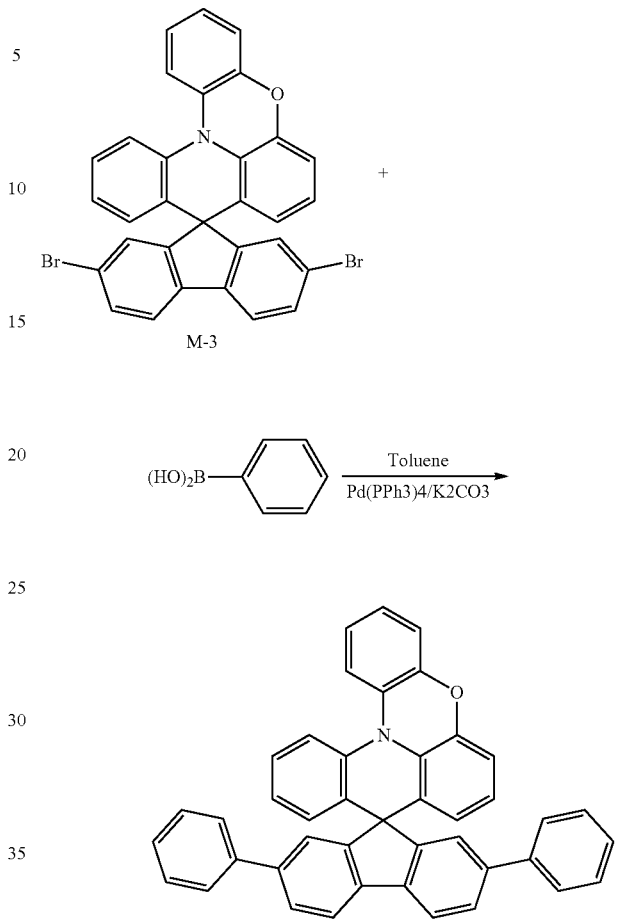

8 g (13.81 mmol) of an intermediate, M-3, 3.53 g (29 mmol) of phenylboronic acid, 1.27 g (1.1 mmol) of tetrakis-(triphenylphosphine)palladium, 6.08 g (44 mmol) of potassium carbonate, and 100 ml of water were suspended in 200 ml of toluene, and the suspended solution was heated and refluxed under a nitrogen atmosphere for 12 hours.

The reaction liquid was separated into two layers, and an organic layer out of the two layers was washed with a sodium chloride saturated aqueous solution and dried with anhydrous sodium sulfate.

After distillating and removing an organic solvent under a reduced pressure, its residue was purified through silica gel column chromatography by using a normal hexane/dichloromethane mixed solvent, obtaining 6.8 g (85.8%) of a desired compound as a white solid.

Example ad-4

Synthesis of Compound B-10

A compound represented by the above Chemical Formula B-10 as specific examples of a compound for an organic optoelectronic device according to one embodiment of the present invention was synthesized through the following Reaction Scheme 16.

[Reaction Scheme 16]

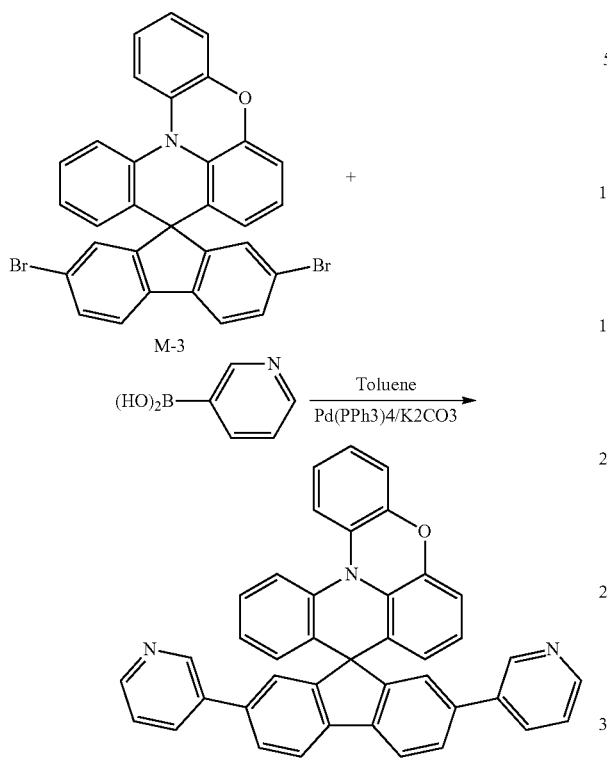

8 g (13.81 mmol) of an intermediate M-3, 3.56 g (29 mmol) of phenylboronic acid, 1.27 g (1.1 mmol) of tetrakis-(triphenylphosphine)palladium, 6.08 g (44 mmol) of potassium carbonate, and 100 ml of water were suspended in 200 ml of toluene, and the suspended solution was heated and refluxed under a nitrogen atmosphere for 12 hours.

The reaction liquid was separated into two layers, and an organic layer out of the two layers was washed with a sodium chloride saturated aqueous solution and dried with anhydrous sodium sulfate.

After distillating and removing an organic solvent therein under a reduced pressure, its residue was purified through silica gel column chromatography by using a normal hexane/dichloromethane mixed solvent, obtaining 6.7 g (84.2%) of a desired compound as a white solid.
(Manufacture of Organic Light Emitting Diode)

Example 13

A glass substrate coated with a 1500 Å-thick ITO (indium tin oxide) thin film was washed with distilled water and ultrasonic wave. When washed with distilled water, the coated substrate was ultrasonic wave-washed by using isopropyl alcohol acetone, methanol, and the like as a solvent and dried, moved to a plasma cleaner, washed by using oxygen plasma for 5 minutes, and moved to a vacuum depositor. This ITO transparent electrode was used as an anode, and a 600 Å-thick hole injection layer (HIL) was formed thereon by vacuum-depositing 4,4'-bis[N-[4-{N,N-bis(3-methylphenyl)amino}-phenyl]-N-phenylamino]biphenyl (DNTPD). Subsequently, the compound according to Example 1 was vacuum-deposited on the hole injection layer (HIL) to form a 300 Å-thick hole transport layer (HTL). On the hole transport layer (HTL), 9,10-di-(2-naphthyl)anthracene (ADN) as a host and 3 wt % of 2,5,8,11-tetra(tert-butyl)perylene (TBPe) as a dopant were vacuum-deposited to form a 250 Å-thick emission layer.

Subsequently, on the emission layer, Alq3 was vacuum-deposited to form a 250 Å-thick electron transport layer (ETL). On the electron transport layer (ETL), a cathode was formed by sequentially vacuum-depositing 10 Å-thick LiF and 1000 Å-thick Al, manufacturing an organic light emitting diode.

The organic light emitting diode has a structure of five-layered organic thin film layers and specifically, a structure of Al 1000 Å/LiF 10 Å/Alq3 250 Å/EML [ADN:TBPe=97:3]250 Å/A-1 300 Å/DNTPD 600 Å/ITO 1500 Å.

Example 14

An organic light emitting diode was manufactured according to the same method as Example 13 except for using the compound A-2 of Example 2 instead of the compound A-1 of Example 1.

Example 15

An organic light emitting diode was manufactured according to the same method as Example 13 except for using the compound A-3 of Example 3 instead of the compound A-1 of Example 1.

Example 16

An organic light emitting diode was manufactured according to the same method as Example 13 except for using the compound A-4 of Example 4 instead of the compound A-1 of Example 1.

Comparative Example 1

An organic light emitting diode was manufactured according to the same method as Example 13 except for using NPB instead of the compound A-1 of Example 1.
(Performance Measurement of Organic Light Emitting Diode)

Current density change, luminance change, and luminous efficiency of each organic light emitting diode according to Examples 13 to 16 and Comparative Example 1 depending on a voltage were measured. Specific measurement methods are as follows, and the results are shown in the following Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The luminance current density, and voltage obtained from the (1) and (2) were used to calculate current efficiency (cd/A) at the same current density (10 mA/cm$^2$).

TABLE 1

| Device | HTL | Voltage (V) | EL color | Efficiency (cd/A) | Half-life life-span (h) @1000 cd/m² |
|---|---|---|---|---|---|
| Example 13 | A-1 | 6.2 | Blue | 6.0 | 1,500 |
| Example 14 | A-2 | 6.2 | Blue | 5.7 | 1,700 |
| Example 15 | A-3 | 6.1 | Blue | 5.9 | 2,000 |
| Example 16 | A-4 | 6.1 | Blue | 5.9 | 1,700 |
| Comparative Example 1 | NPB | 7.1 | Blue | 4.9 | 1,250 |

The organic light emitting diodes according to Examples 13 to 16 showed decreased driving voltage and improved luminance and efficiency compared with the organic light emitting diode according to Comparative Example 1.

Accordingly, an organic light emitting diode having excellent electron injection and electron transport capability and also a low voltage, high efficiency, high luminance, and a long lifespan may be manufactured.

While this invention has been described in connection with what is presently considered to be practical exemplary embodiments. It is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device represented by the following Chemical Formula ad-1:

[Chemical Formula ad-1]

wherein in the above Chemical Formula ad-1,
$X^1$ is —O— or —S—,
$X^2$ is —C— or —Si—,
$L^1$ and $L^2$ are independently a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m1 and m2 are independently integers of 0 or 1,
n1 and n2 are independently integers ranging from 0 to 3,
$R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group, and
$R^a$ and $R^b$ are each independently, hydrogen, deuterium, a substituted or unsubstituted silyl group, a substituted or unsubstituted C4 to C60 amine group, a substituted or unsubstituted C6 to C30 aryl group, or a substituted or unsubstituted C2 to C30 heteroaryl group.

2. The compound for an organic optoelectronic device of claim 1, wherein at least one of the $R^a$ and $R^b$ is a substituted or unsubstituted pyridinyl group, a substituted or unsubstituted pyrimidinyl group, or a substituted or unsubstituted triazinyl group.

3. The compound for an organic optoelectronic device of claim 1, wherein at least one of the $R^a$ and $R^b$ is a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

4. The compound for an organic optoelectronic device of claim 1, wherein the compound for an organic optoelectronic device is represented by the following Chemical Formula 1:

[Chemical Formula 1]

wherein in the above Chemical Formula 1,
$X^1$ is —O— or —S—,
$X^2$ is —C— or —Si—,
$Ar^1$ to $Ar^4$ are independently a substituted or unsubstituted C6 to C30 aryl group, or a substituted or unsubstituted C2 to C30 heteroaryl group,
$L^1$ and $L^2$ are independently a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m1 and m2 are independently integers of 0 or 1, one of m1 and m2 is 1,
n1 and n2 are independently integers ranging from 0 to 3, and
$R^1$ to $R^6$ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

5. The compound for an organic optoelectronic device of claim 1, wherein the compound for an organic optoelectronic device is represented by the following Chemical Formula 2:

[Chemical Formula 2]

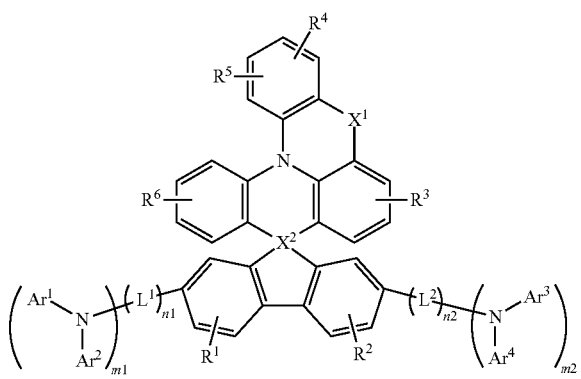

wherein in the above Chemical Formula 2,
X¹ is —O— or —S—,
X² is —C— or —Si—,
Ar¹ to Ar⁴ are independently a substituted or unsubstituted C6 to C30 aryl group, or a substituted or unsubstituted C2 to C30 heteroaryl group,
L¹ and L² are independently a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m1 and m2 are independently integers of 0 or 1, one of m1 and m2 is 1,
n1 and n2 are independently integers ranging from 0 to 3, and
R¹ to R⁶ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

6. The compound for an organic optoelectronic device of claim 1, wherein the compound for an organic optoelectronic device is represented by the following Chemical Formula 3:

[Chemical Formula 3]

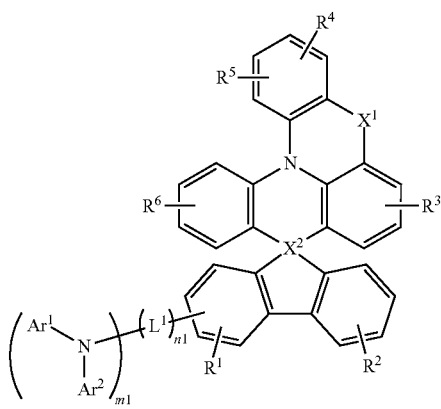

wherein in the above Chemical Formula 3,
X¹ is —O— or —S—,
X² is —C— or —Si—,
Ar¹ and Ar² are independently a substituted or unsubstituted C6 to C30 aryl group, or a substituted or unsubstituted C2 to C30 heteroaryl group, L¹ is a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m1 is 1,
n1 is an integer ranging from 0 to 3, and
R¹ to R⁶ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

7. The compound for an organic optoelectronic device of claim 1, wherein the compound for an organic optoelectronic device is represented by the following Chemical Formula 4:

[Chemical Formula 4]

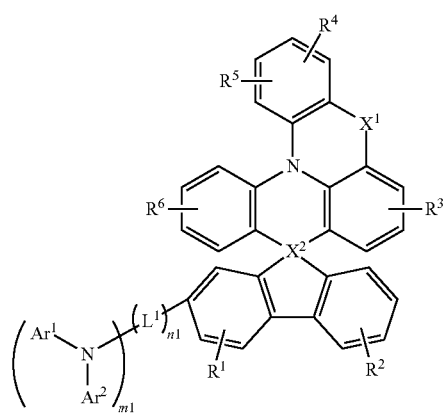

wherein in the above Chemical Formula 4,
X¹ is —O— or —S—,
X² is —C— or —Si—,
Ar¹ and Ar² are independently a substituted or unsubstituted C6 to C30 aryl group, or a substituted or unsubstituted C2 to C30 heteroaryl group,
L¹ is a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group,
m1 is 1,
n1 is an integer ranging from 0 to 3, and
R¹ to R⁶ are independently hydrogen, deuterium, a substituted or unsubstituted C1 to C10 alkyl group, a substituted or unsubstituted C6 to C30 aryl group, or a substituted or unsubstituted C2 to C30 heteroaryl group.

8. The compound for an organic optoelectronic device of claim 1, wherein the X² is —C—.

9. The compound for an organic optoelectronic device of claim 4, wherein the Ar¹ to Ar⁴ are independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiopheneyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiopheneyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

10. The compound for an organic optoelectronic device of claim 1, wherein the compound for an organic optoelectronic device is represented by one of the following Chemical Formulae A-1 to A-26:

A-1
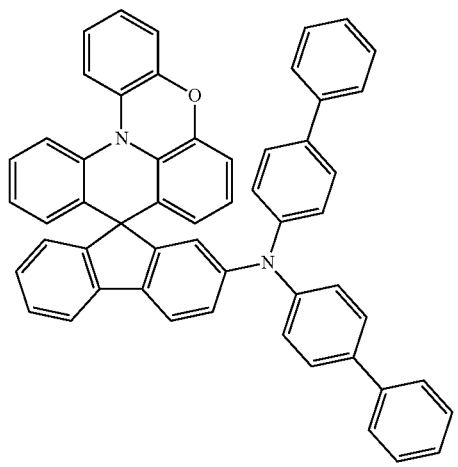

A-2
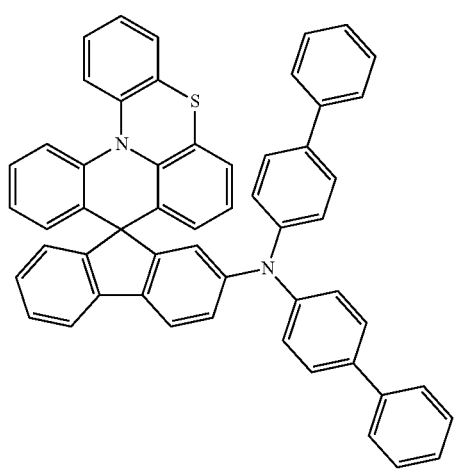

A-3
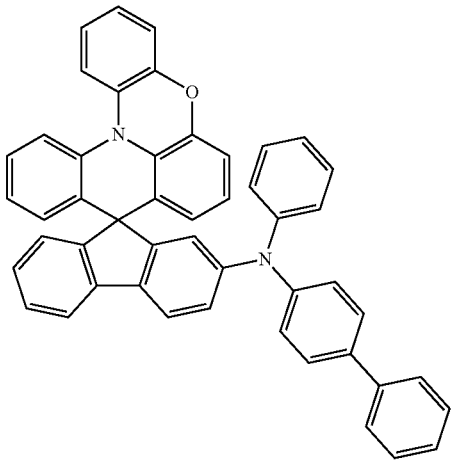

A-4
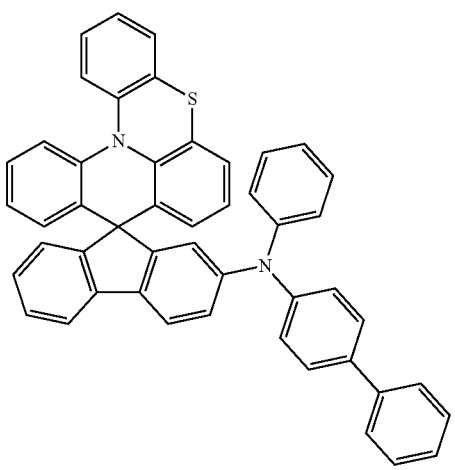

A-5
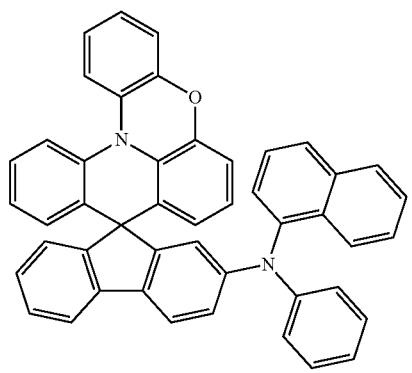

-continued
A-6
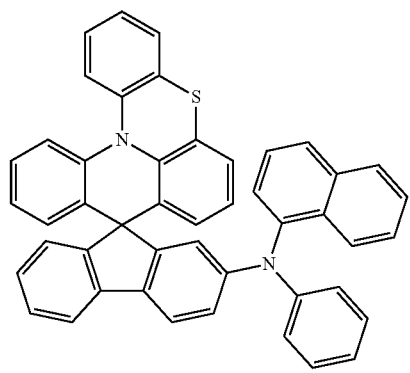
A-7
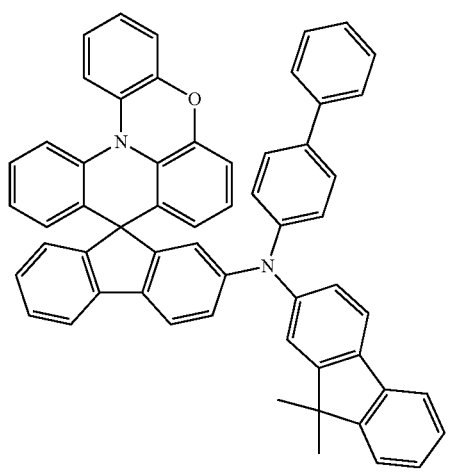
A-8
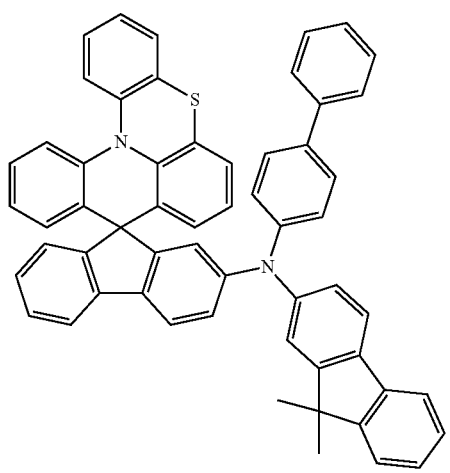
-continued
A-9
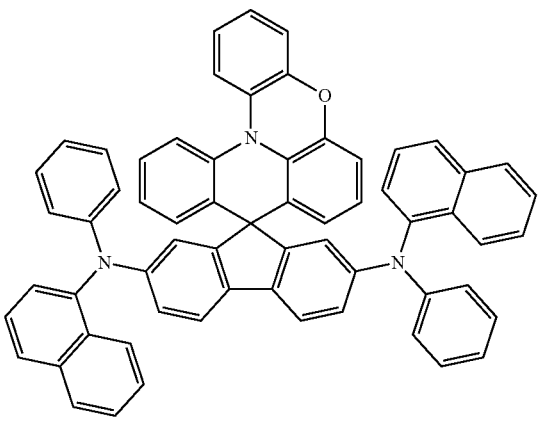
A-10
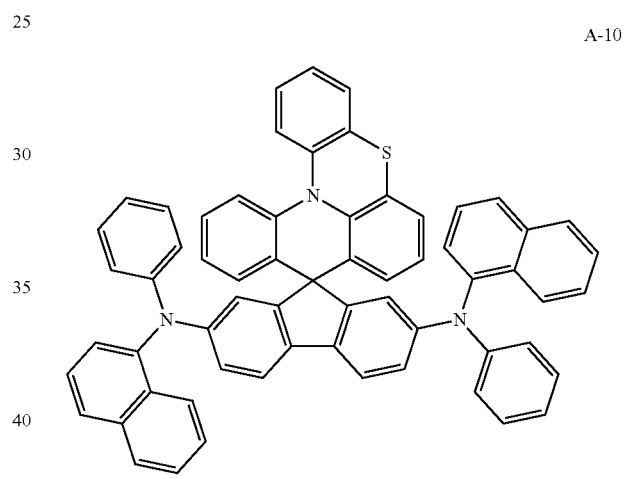
A-11
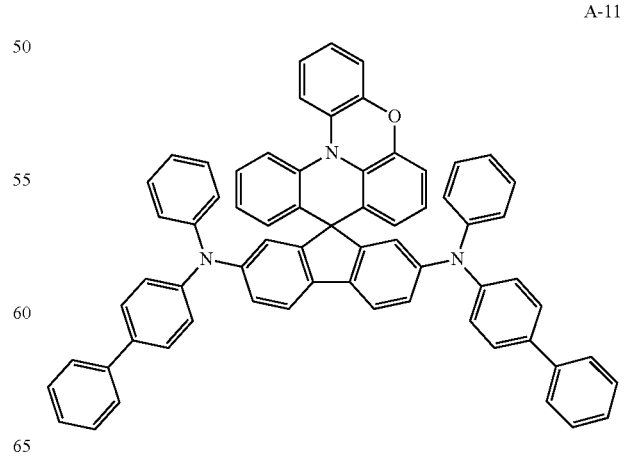

A-12
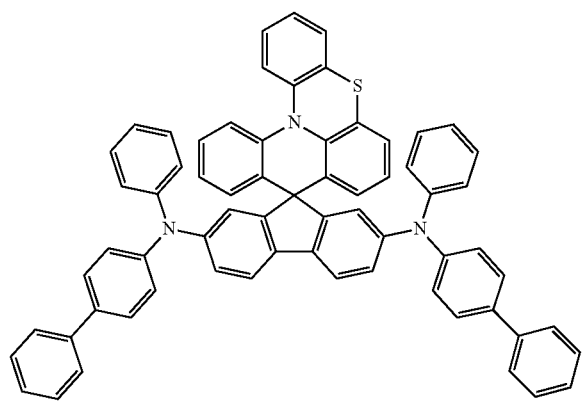
A-13
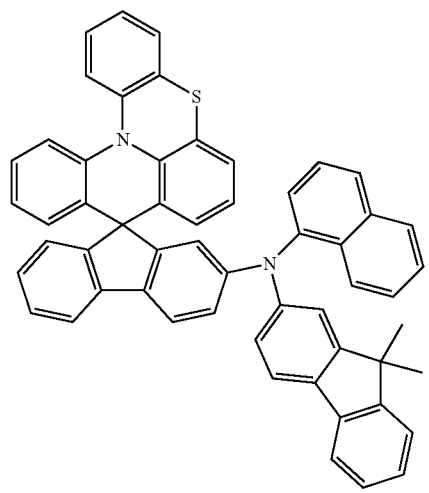
A-14
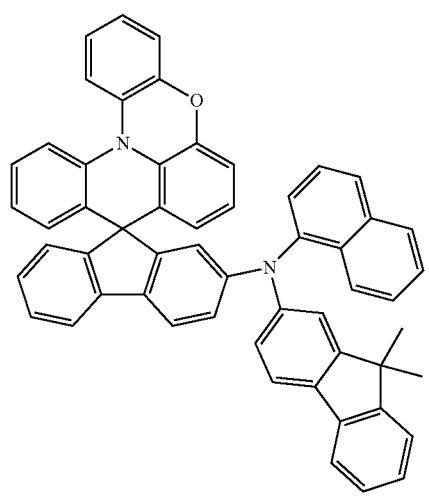
A-15
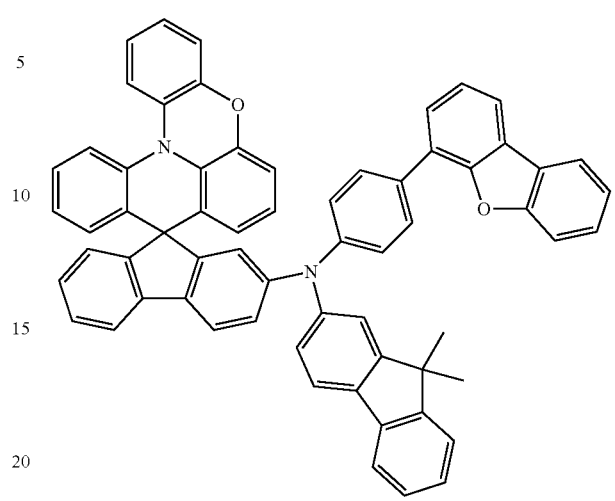
A-16
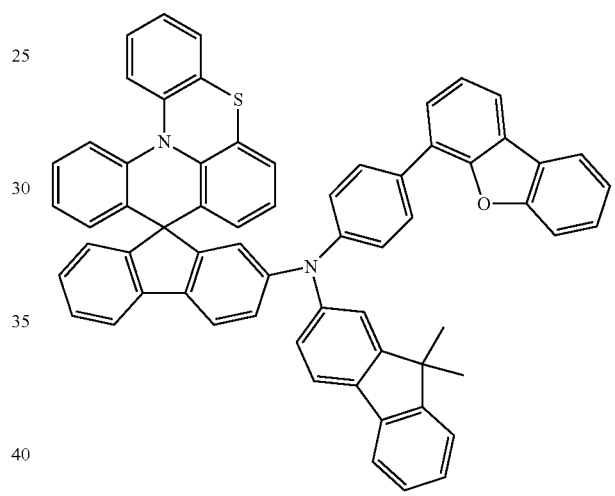
A-17
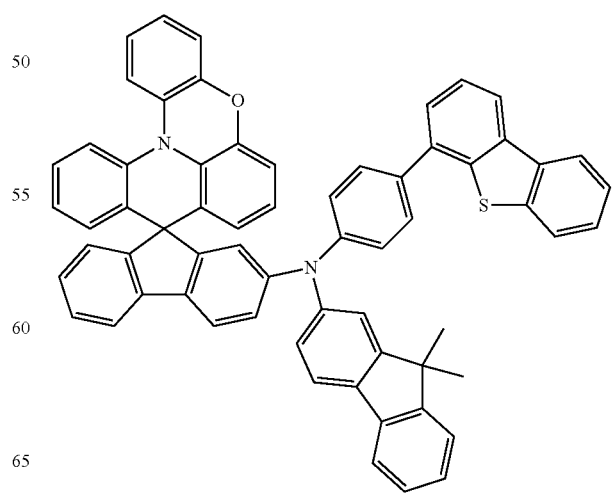

A-18
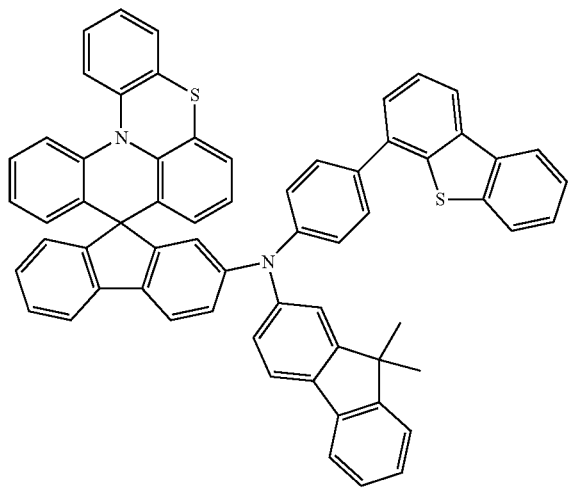
A-20
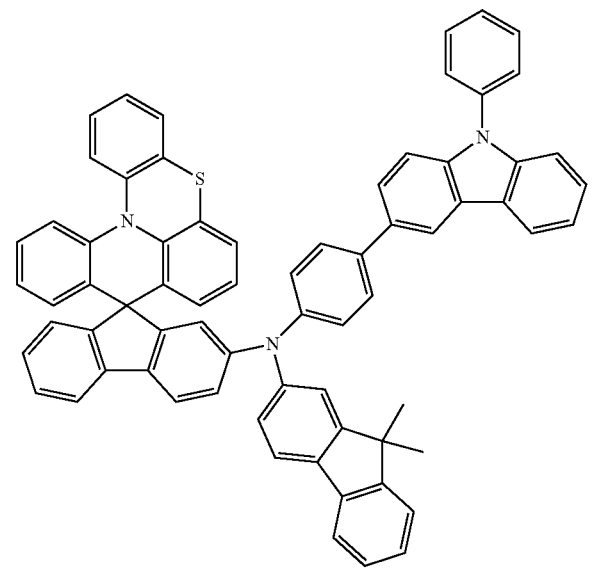
A-19
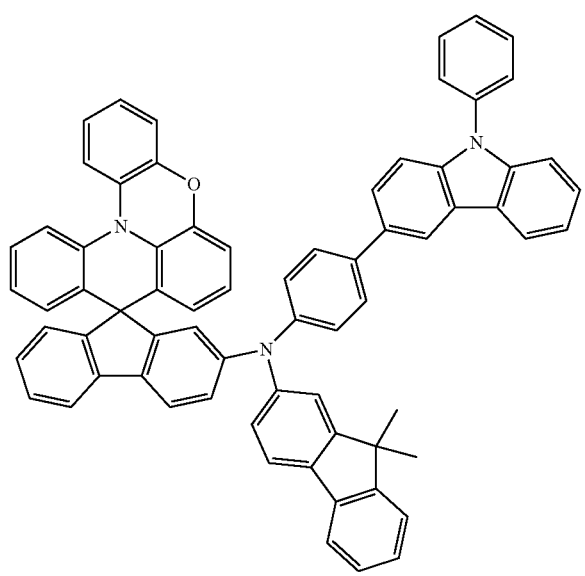
A-21
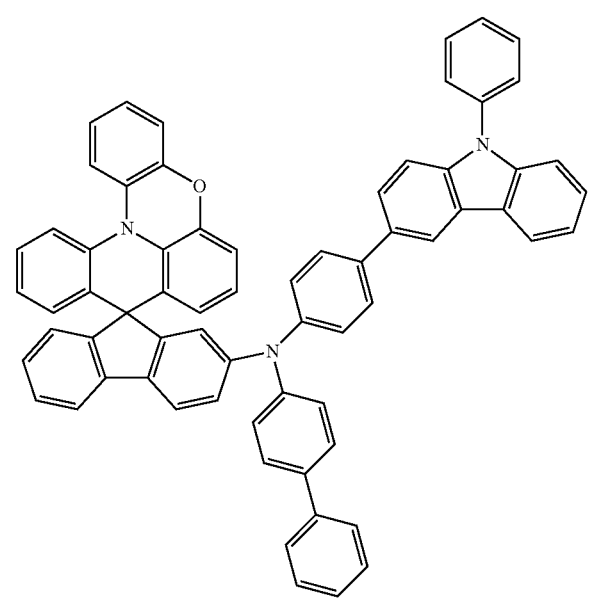

-continued
A-22
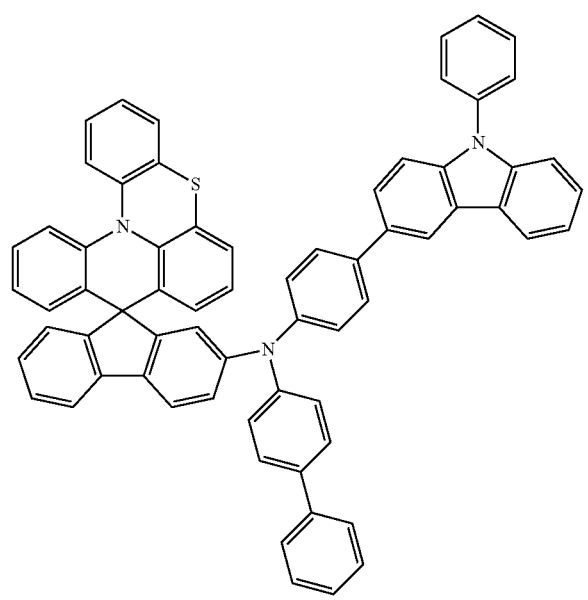
A-23
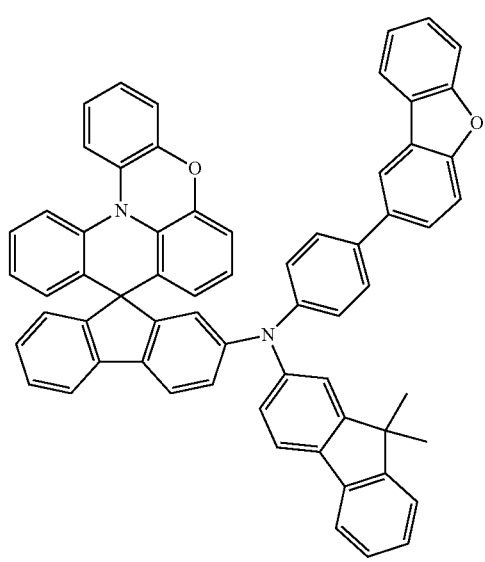
A-24
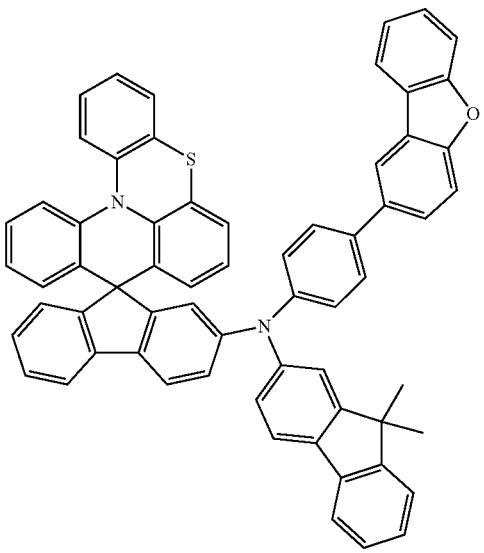
A-25
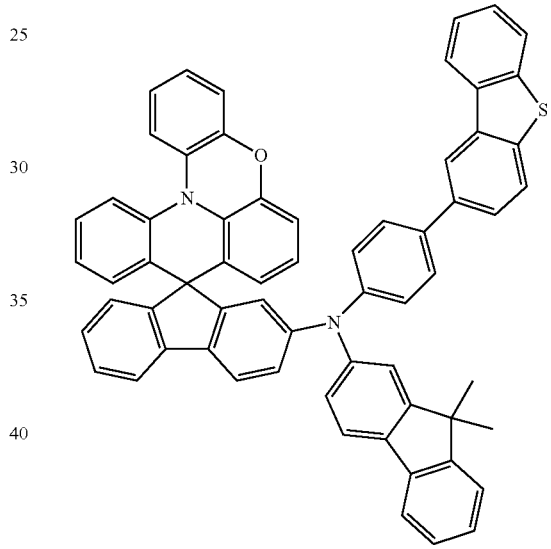
A-26
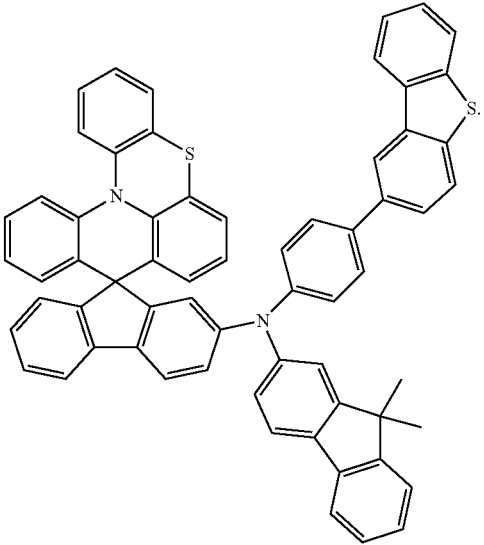

11. The compound for an organic optoelectronic device of claim 1, wherein the compound for an organic optoelectronic device is represented by one of the following Chemical Formulae B-1 to B-10:
[B-1]
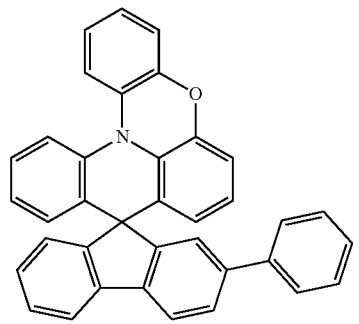
[B-2]
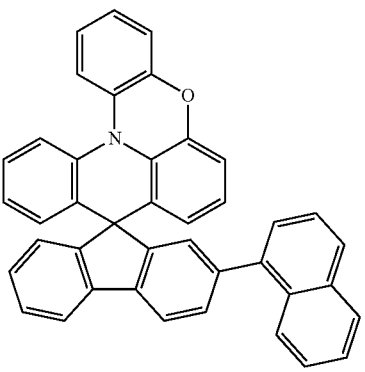
[B-3]
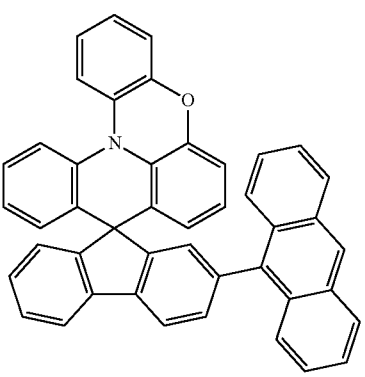
[B-4]
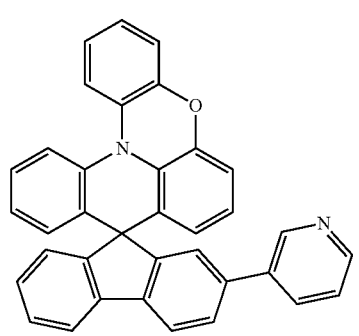
-continued
[B-5]
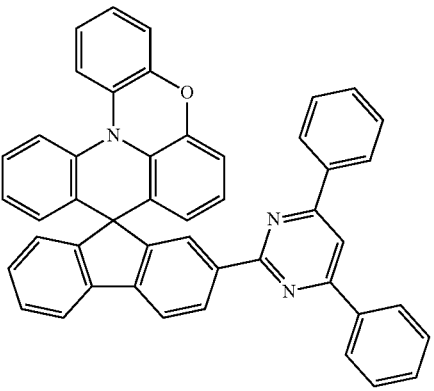
[B-6]
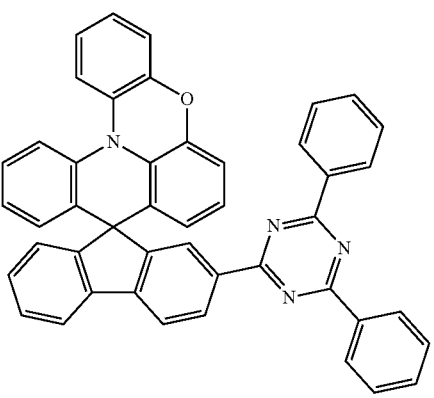
[B-7]
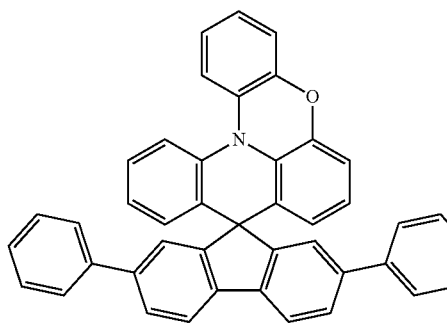
[B-8]
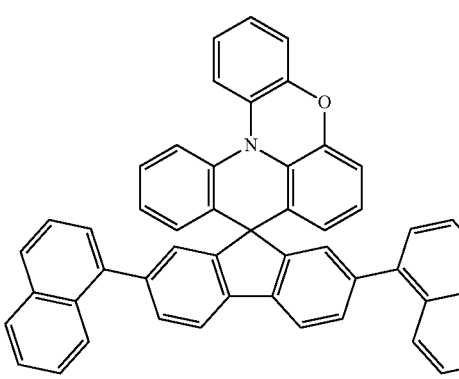

[B-9]

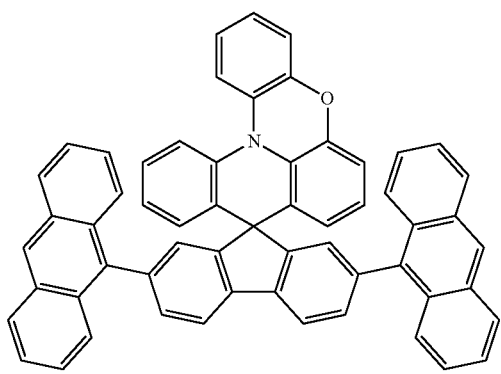

[B-10]

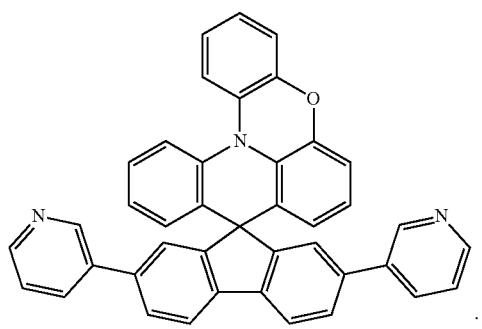

12. The compound for an organic optoelectronic device of claim 1, wherein the compound for an organic optoelectronic device has triplet exciton energy (T1) of greater than or equal to about 2.0 eV.

13. The compound for an organic optoelectronic device of claim 1, wherein the organic optoelectronic device is organic optoelectronic device is selected from an organic photoelectric device, an organic light emitting diode, an organic solar cell, an organic transistor, an organic photo-conductor drum, and an organic memory device.

14. An organic light emitting diode, comprising
an anode, a cathode, and at least one organic thin layer interposed between the anode and cathode,
wherein at least one of the organic thin layers comprises the above compound for an organic optoelectronic device of claim 1.

15. The organic light emitting diode of claim 14, wherein the organic thin layer is selected from an emission layer, a hole transport layer, a hole injection layer, an electron transport layer, an electron injection layer, a hole blocking layer, and a combination thereof.

16. The organic light emitting diode of claim 15, wherein the compound for an organic optoelectronic device is included in a hole transport layer (HTL) or a hole injection layer (HIL).

17. The organic light emitting diode of claim 15, wherein the compound for an organic optoelectronic device is included in an emission layer.

18. The organic light emitting diode of claim 17, wherein the compound for an organic optoelectronic device is used as a phosphorescent or fluorescent host material in an emission layer.

19. A display device comprising the above organic light emitting diode of claim 14.

* * * * *